(12) United States Patent
Salituro et al.

(10) Patent No.: US 11,643,434 B2
(45) Date of Patent: May 9, 2023

(54) NEUROACTIVE STEROIDS AND COMPOSITIONS THEREOF

(71) Applicant: Sage Therapeutics, Inc., Cambridge, MA (US)

(72) Inventors: Francesco G. Salituro, Marlborough, MA (US); Maria Jesus Blanco-Pillado, Arlington, MA (US); Marshall Lee Morningstar, Framingham, MA (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/887,887

(22) Filed: May 29, 2020

(65) Prior Publication Data
US 2020/0377547 A1 Dec. 3, 2020

Related U.S. Application Data

(60) Provisional application No. 62/855,435, filed on May 31, 2019.

(51) Int. Cl.
C07J 43/00 (2006.01)

(52) U.S. Cl.
CPC .................. *C07J 43/003* (2013.01)

(58) Field of Classification Search
CPC ..................................... C07J 31/003
See application file for complete search history.

(56) References Cited

U.S. PATENT DOCUMENTS

| | | | |
|---|---|---|---|
| 2,856,415 | A | 10/1958 | Mihina |
| 3,169,134 | A | 2/1965 | Klimstra et al. |
| 3,206,459 | A | 9/1965 | Cross |
| 3,580,937 | A | 5/1971 | Campbell et al. |
| 3,943,124 | A | 3/1976 | Phillipps et al. |
| 3,983,111 | A | 9/1976 | Phillipps et al. |
| 3,998,829 | A | 12/1976 | Phillips et al. |
| 4,029,777 | A | 6/1977 | Engelfried et al. |
| 4,071,625 | A | 1/1978 | Grunwell et al. |
| 4,179,336 | A | 12/1979 | Weber et al. |
| 4,192,871 | A | 3/1980 | Phillipps et al. |
| 4,389,345 | A | 6/1983 | Lenz |
| 5,593,983 | A | 1/1997 | Campbell |
| 5,721,227 | A | 2/1998 | Melloni et al. |
| 5,925,630 | A | 7/1999 | Upasani et al. |
| 5,935,545 | A | 8/1999 | Leary et al. |

(Continued)

FOREIGN PATENT DOCUMENTS

| | | |
|---|---|---|
| CA | 2831054 A1 | 12/2013 |
| CN | 1190404 A | 8/1998 |

(Continued)

OTHER PUBLICATIONS

Jayakumar et al. (Organic & Medicinal Chem IJ, 2018, 5(3), pp. 001-006).*
Botella et al., "Neuroactive Steroids. 1. Positive Allosteric Modulators of the (g-Aminobutyric Acid)A Receptor: Structure-Activity Relationships of Heterocyclic Substitution at C-21", Journal of Medical Chemistry, 2015, Vo.58(8) pp. 3500-3511.
Adams et al., "The estrogenic activity and enzymic oxidation of 17b-estradiol-17a-d1", Steroids, Elsevier Science Publishers, (1965), pp. 75-84.
Anderson et al., "Anesthetic Activity of Novel Water-Soluble 2b-Morpholinyl Steroids and Their Modulatory Effects at GABA-A Receptors", Journal ofMedicinal Chemistry., 1997, vol. 40, pp. 1668-1681.
Anderson et al., "Conformationally Constrained Anesthetic Steroids That Modulate GABAA Receptors," Journal of Medicinal Chemistry, 2000, vol. 43, No. 22, pp. 4118-4125.
Anonymous: "Archive History for NCT03000530", Aug. 4, 2017, Retrieved from the Internet: <URL:https://www.clinicaltrials.gov/ct2/his>tory/NCTO3000530?V-_6=View#StudyPageTop; [retrieved on Nov. 20, 2018].
Atack, "Development of Subtype-Selective GABAA Receptor Compounds for the Treatment of Anxiety, Sleep Disorders and Epilepsy", GABA and Sleep. Molecular, Functional and Clinical Aspects. 2010, pp. 25-72.
Banday et al., "D-ring substituted 1,2,3-triazolyl 20-keto pregnenanes as potential anticancer agents: Synthesis and biological evaluation", Steroids, (2010), vol. 75, No. 12, pp. 801-804, Abstract.

(Continued)

*Primary Examiner* — Susanna Moore
(74) *Attorney, Agent, or Firm* — Honigman LLP; Andrew N. Weber; Jonathan P. O'Brien

(57) ABSTRACT

Provided herein is a compound of Formula (I):

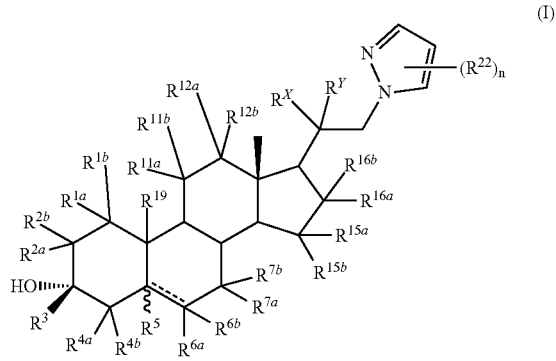

or a pharmaceutically acceptable salt thereof, wherein $R^{1a}$, $R^{1b}$, $R^{2a}$, $R^{2b}$, $R^3$, $R^{4a}$, $R^{4b}$, $R^5$, $R^{6a}$, $R^{6b}$, $R^{7a}$, $R^{7a}$, $R^{11a}$, $R^{11b}$, $R^{12a}$, $R^{12b}$, $R^{16a}$, $R^{16b}$, $R^{19}$, $R^{11a}$, $R^{22}$, $R^X$, $R^Y$ and n are defined herein. Also provided herein are pharmaceutical compositions comprising a compound of Formula (I) and methods of using the compounds, e.g., in the treatment of CNS-related disorders.

25 Claims, No Drawings

(56) References Cited

U.S. PATENT DOCUMENTS

| | | | |
|---|---|---|---|
| 5,939,545 A | 8/1999 | Upasani et al. | |
| 6,133,280 A | 10/2000 | Brodie et al. | |
| 6,143,736 A | 11/2000 | Upasani et al. | |
| 6,277,838 B1 | 8/2001 | Upasani et al. | |
| 6,717,002 B2 | 4/2004 | Yano et al. | |
| 6,844,456 B2 | 1/2005 | Covey | |
| 7,064,116 B2 | 6/2006 | Calogeropoulou et al. | |
| 7,781,421 B2 | 8/2010 | Covey et al. | |
| 8,759,330 B2 | 6/2014 | Covey et al. | |
| 8,939,545 B2 | 1/2015 | Tunmore et al. | |
| 9,156,876 B2 | 10/2015 | Covey | |
| 9,365,611 B2 | 6/2016 | Martinez Botella et al. | |
| 9,512,165 B2 | 12/2016 | Martinez Botella et al. | |
| 9,630,986 B2 | 4/2017 | Covey et al. | |
| 9,725,481 B2 | 8/2017 | Martinez Botella et al. | |
| 9,765,110 B2 | 9/2017 | Covey | |
| 10,246,482 B2 | 4/2019 | Harrison et al. | |
| 11,241,446 B2 | 2/2022 | Martinez Botella et al. | |
| 2002/0091112 A1 | 7/2002 | Menzenbach et al. | |
| 2005/0176976 A1 | 8/2005 | Calogeropoulou et al. | |
| 2006/0094696 A1 | 5/2006 | Leese et al. | |
| 2007/0014719 A1 | 1/2007 | Reading et al. | |
| 2008/0269183 A1 | 10/2008 | Mellon et al. | |
| 2009/0048218 A1 | 2/2009 | Kuhnke et al. | |
| 2009/0131495 A1 | 5/2009 | Kim | |
| 2010/0152840 A1 | 6/2010 | Seguin et al. | |
| 2010/0234335 A1 | 9/2010 | Gravanis et al. | |
| 2010/0317638 A1 | 12/2010 | Covey et al. | |
| 2011/0152840 A1 | 6/2011 | Lee et al. | |
| 2011/0172242 A1 | 7/2011 | Helton et al. | |
| 2014/0017675 A1 | 1/2014 | Ito | |
| 2014/0050789 A1 | 2/2014 | Rogawski et al. | |
| 2014/0094619 A1 | 4/2014 | Runyon et al. | |
| 2014/0148412 A1 | 5/2014 | Hogenkamp | |
| 2014/0235600 A1 | 8/2014 | Covey et al. | |
| 2014/0249120 A1 | 9/2014 | Covey et al. | |
| 2014/0275241 A1 | 9/2014 | Covey | |
| 2015/0291654 A1 | 10/2015 | Upasani et al. | |
| 2015/0315230 A1 | 11/2015 | Covey et al. | |
| 2016/0068563 A1 | 3/2016 | Martinez Botella et al. | |
| 2016/0083418 A1 | 3/2016 | Martinez Botella et al. | |
| 2016/0108080 A1 | 4/2016 | Martinez Botella et al. | |
| 2016/0229887 A1 | 8/2016 | Martinez Botella et al. | |
| 2017/0233433 A1 | 8/2017 | Martinez Botella et al. | |
| 2017/0246191 A1 | 8/2017 | Martinez Botella et al. | |
| 2018/0071315 A1 | 3/2018 | Cashman et al. | |
| 2019/0160078 A1 | 5/2019 | Masuoka et al. | |
| 2019/0177358 A1 | 6/2019 | Martinez Botella et al. | |
| 2019/0337975 A1 | 11/2019 | Bryson et al. | |

FOREIGN PATENT DOCUMENTS

| | | | | |
|---|---|---|---|---|
| CN | 101412742 A | 4/2009 | | |
| CN | 101624414 A | 1/2010 | | |
| CN | 104136452 A | 11/2014 | | |
| CN | 108727453 A | 11/2018 | | |
| DE | 2330342 A1 | 1/1974 | | |
| DE | 2526373 A1 | 12/1976 | | |
| DE | 2700267 A1 | 7/1977 | | |
| DE | 2632677 A1 | 1/1978 | | |
| EP | 0104489 A1 | 4/1984 | | |
| EP | 0554436 B1 | 8/1993 | | |
| EP | 0656365 A1 | 6/1995 | | |
| EP | 0701444 B1 | 3/1996 | | |
| EP | 1038880 A2 | 9/2000 | | |
| EP | 3750908 A1 | 12/2020 | | |
| FR | 2969 M | 7/1904 | | |
| FR | 1994 M | 9/1963 | | |
| GB | 1380246 A | 1/1975 | | |
| GB | 1430942 A | 4/1976 | | |
| GB | 1494097 A | 12/1977 | | |
| GB | 1538869 A | 1/1979 | | |
| GB | 1570394 A | 7/1980 | | |
| GB | 1581234 A | 12/1980 | | |
| GB | 1581235 A | 12/1980 | | |
| RU | 2194712 C2 | 12/2002 | | |
| RU | 2243232 C2 | 12/2004 | | |
| RU | 2010100334 A | 7/2011 | | |
| RU | 2675855 C2 | 12/2018 | | |
| WO | 1991016897 A1 | 11/1991 | | |
| WO | 9303732 A1 | 3/1993 | | |
| WO | 9305786 A1 | 4/1993 | | |
| WO | 9318053 A1 | 9/1993 | | |
| WO | 9427608 A1 | 12/1994 | | |
| WO | 1995021617 A1 | 8/1995 | | |
| WO | 1996003421 A1 | 2/1996 | | |
| WO | 1996016076 A1 | 5/1996 | | |
| WO | 9640043 A2 | 12/1996 | | |
| WO | 9805337 A1 | 2/1998 | | |
| WO | 0066614 A1 | 11/2000 | | |
| WO | 2005051972 A1 | 6/2005 | | |
| WO | 2005105822 A2 | 11/2005 | | |
| WO | 2006037016 A2 | 4/2006 | | |
| WO | 2006131392 A1 | 12/2006 | | |
| WO | 2008151745 A1 | 12/2008 | | |
| WO | 2008157460 A1 | 12/2008 | | |
| WO | 2009142594 A1 | 11/2009 | | |
| WO | WO-2009142594 A1 * | 11/2009 | ............. | A61K 31/00 |
| WO | 2010003391 A2 | 1/2010 | | |
| WO | 2010054158 A2 | 5/2010 | | |
| WO | 2010107815 A1 | 9/2010 | | |
| WO | 2012/013816 A2 | 7/2011 | | |
| WO | 2012083090 A2 | 6/2012 | | |
| WO | 2012109752 A1 | 8/2012 | | |
| WO | 2012110010 A1 | 8/2012 | | |
| WO | 2012116290 A2 | 8/2012 | | |
| WO | 2013019711 A2 | 2/2013 | | |
| WO | 2013036835 A1 | 3/2013 | | |
| WO | 2013056181 A1 | 4/2013 | | |
| WO | 2013188792 A2 | 12/2013 | | |
| WO | 2013192097 A1 | 12/2013 | | |
| WO | 2014058736 A1 | 4/2014 | | |
| WO | 2014071449 A1 | 5/2014 | | |
| WO | 2014100228 A1 | 6/2014 | | |
| WO | 2014108808 A2 | 7/2014 | | |
| WO | 2014122480 A1 | 8/2014 | | |
| WO | 2014169831 A1 | 10/2014 | | |
| WO | 2014169832 A1 | 10/2014 | | |
| WO | 2014169833 A1 | 10/2014 | | |
| WO | 2014169836 A1 | 10/2014 | | |
| WO | WO-2014169833 A1 * | 10/2014 | ............. | A61K 31/57 |
| WO | 2015010054 A2 | 1/2015 | | |
| WO | 2015027227 A1 | 2/2015 | | |
| WO | 2015180679 A1 | 12/2015 | | |
| WO | 2015195962 A1 | 12/2015 | | |
| WO | 2016/134301 A1 | 2/2016 | | |
| WO | 2016036724 A1 | 3/2016 | | |
| WO | 2016061527 A1 | 4/2016 | | |
| WO | 2016061537 A1 | 4/2016 | | |
| WO | 2016082789 A1 | 6/2016 | | |
| WO | 2016123056 A1 | 8/2016 | | |
| WO | 2016131414 A1 | 8/2016 | | |
| WO | 2016209847 A1 | 12/2016 | | |
| WO | 2017/049044 A1 | 3/2017 | | |
| WO | 2017044659 A1 | 3/2017 | | |
| WO | 2017066626 A1 | 4/2017 | | |
| WO | 2017087864 A1 | 5/2017 | | |
| WO | 2017156103 A1 | 9/2017 | | |
| WO | 2017156418 A1 | 9/2017 | | |
| WO | 2018013613 A1 | 1/2018 | | |
| WO | 2018013615 A1 | 1/2018 | | |
| WO | 2018039378 A1 | 3/2018 | | |
| WO | 2018237282 A1 | 12/2018 | | |
| WO | 2019018119 A1 | 1/2019 | | |
| WO | 2019045121 A1 | 3/2019 | | |
| WO | 2019051264 A1 | 3/2019 | | |
| WO | 2019094724 A1 | 5/2019 | | |
| WO | 2019/126761 A1 | 6/2019 | | |
| WO | 2019126741 A1 | 6/2019 | | |
| WO | 2020118060 A1 | 6/2020 | | |
| WO | WO-2020210117 A1 * | 10/2020 | | |

(56) References Cited

FOREIGN PATENT DOCUMENTS

WO 2020/264509 A1 12/2020
WO 2020264512 A1 12/2020

OTHER PUBLICATIONS

Bandyopadhyaya et al., "Neurosteroid Analogs. 15. A Comparative Study of the Anesthetic and GABAergic Actions of Alphaxalone, D16-Alphaxalone and TheirCorresponding 17-Carbonitrile Analogs," Bioorganic & Medicinal Chemistry Letters 20:6680-6684 (2010).
Berge et al., J. Pharmaceutical Sciences, 1977, vol. 66, pp. 1-19.
Bernstein, BE., "Rett Syndrome Medication" [online], Updated Feb. 6, 2017, [retrieved on May 3, 2018]. Retrieved from the website Medscape, using internet URL: <https://emedicine.medscape.com/article/916377-medication>.
Bjorkhem et al., "Steroid hormone metabolism in developing rates", Eur. J.Biochem., 1972, vol. 27, No. 2, pp. 318-326.
Botella et al., "Neuroactive Steroids. 2. 3a-Hydroxy-3b-methyl-21-(4-cyano-1H-pyrazol-1-yl)-19-nor-5b-pregnan-20-one (SAGE-217): A Clinical Next Generation Neuroactive Steroid Positive Allosteric Modulator of the (g-Aminobutyric Acid) A Receptor" Journal of Medical Chemistry, 2017, 10 pp. A-J.
CAS Registry No. 1040410-23-8 [Database Registry in STN]; STN Entry Date: Aug. 12, 2008; Chemical Name: 1-((3S,8R,9S,10S,13S,14S,17S)-3-hydroxy-10,13-dimethyl-2,3,4,5,8,9,10,11,-12,13,14,15,16,17-tetradecahydro-1H-cyclopenta[a]phenanthren-17-yl)ethan-1 - -one.
CAS Registry No. 162882-77-1 [Database Registry in STN]; STN Entry Date: May 11, 1995; Chemical Name: (3a,5b)-3-Hydroxy-3-methyl-19-norpregnan-25b40-one.
CAS Registry No. 162883-68-3 [Database Registry in STN]; STN Entry Date: May 11, 1995; Chemical Name: 19-Norpregnan-20-one, 3-hydroxy-3-methyl-, (3a,5a).
Caspi et al., "Stereochemistry of 19-hydroxy-19alpha-methyl steroids," Chemical Communications, 1966, vol. 7, pp. 209-210.
Cerny et al., "Syntheses of 19-[O-(carboxymethyl)oxime] haptens of epipregnanolone and pregnanolone", Steroids, 2006, vol. 71(2), pp. 120-128.
Cerny et al., "Synthetic approach to 5alpha-pregnanolone 19-[0-(carboxymethyl) oxime] derivatives", Collection of Czechoslovak Chemical Communications, 2004, vol. 69, No. 9, pp. 1805-1817.
Chen et al., "The mechanism investigation in substitution of 21-bromo-3a-hydroxy-3b-methoxymethyl-5a-pregnan-20-one with nucleophiles", Steroids, vol. 71, (2006), pp. 942-948.
Chodounska et al., "Epalons: Synthesis of 3a, 7a-Dihydroxy-5a-Pregnan-20-One", Collection Symposium Series, vol. 63, No. 10, (1998), pp. 1543-1548.
Chisari et al., "The Influence of Neuroactive Steroid Lipophilicity on GABA Receptor Modulation: Evidence for a Low-Affinity Interaction", Journal of Neurophysiology (2009), vol. 102, pp. 1254-1264.
D'hulst et al., "Expression of the GABAergic system in animal models for fragile X syndrome and fragile X associated tremor/ataxia syndrome (FXTAS)", Brain Research, 2008, vol. 1253, pp. 176-183.
Database CAPLUS in STN, Acc. No. 1995:986323, Upasani et al., WO 9521617 A1 (Aug. 17, 1995) (abstract). [Upasani, Ravindra B. "Andro5b4stanes and pregnanes for allosteric modulation of GABA receptor, and preparation and therapeutic uses ofcompounds".].
Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".].
Database Medline, US National Library of Medicine, Bethesda, MD, 1984, Welling: "Intentions affecting drug absorption", Database accession No. NLM6388952, abstract.
Deluca et al., "Synthesis of 3b-Hydroxy[21-14C] -5b-pregn-8(14)-en-20-one from Chenodeoxycholic Acid", Helvetica Chemica Acta, vol. 69, (1986), pp. 1844-1850.
Deniau et al., "Synthesis of fluorinated analogues of the neurosteroid GABA receptor antagonist, 17-PA", Journal of Fluorine Chemistry, (2008), vol. 129, No. 9, pp. 881-887.
Dorwald, "Side Reactions in Organic Synthesis", 2005, Wiley-VCH, Preface, p. IX.
Duran et al., "Synthesis of 6-thia analogs of the natural neurosteroid allopregnanolone", Tetrahedron, Elsevier Science Publishers, 2006, vol. 62, No. 20, pp. 4762-4768.
Dansey et al: "Synthesis and GABAreceptor activity of A-homo analogues of neuroactive steroids", European Journal of Medicinal Chemistry, Elsevier, Amsterdam, NL, vol. 45, No. 7, Mar. 26, 2010 (Mar. 26, 2010), pp. 3063-3069.
Edgar et al., "CCD-3693: An Orally Bioavailable Analog of the Endogenous Neuroactive Steroid, Pregnanolone, Demonstrates Potent Sedative Hypnotic Actions in the Rat" The Journal of Pharmacology and Experimental Therapeutics (1997) vol. 282, No. 1 ,pp. 420-429.
Eimon et al., "Brain activity patterns in high-throughput electrophysiology screen predict both drug efficacies and side effects", Nature Communications, (2018) 9:219, pp. 1-14.
Evers et al., "A Synthetic 18-Norsleroid Distinguishes Between Two Neuroactive Steroid Binding Sites on GABAA Receptors", Journal of Pharmacology and Experimental Therapeutics, 2010, vol. 333, No. 2, pp. 404-413.
Fajkos et al., "Steroids. XXIII. Synthesis and configuration of the two stereoisomeric 3b-hydroxy-16-acetylandrostanes", Chemicke Listy pro Vedu a Prumysl, 1956, vol. 50, pp. 791-799.
Fesik et al., "Geometric Requirements for Membrance Perturbation and Anesthetic Activity", Molecular Pharmacology, 1985, vol. 27, pp. 624-629.
G. Akk et al: "Neurosteroid Access to the GABAA Receptor", The Journal of Neuroscience, vol. 25, No. 50, Dec. 14, 2005, pp. 11605-11613.
Galofre et al., "GABAA receptor and cell membrane potential as functional endpoints in cultured neurons to evaluate chemicals for human acute toxicity", Neurotoxicology and Teratology, (2009), vol. 32, pp. 52-61.
Gasior et al., "Neuroactive steroids: potential therapeutic use in neurological and psychiatric disorders", Trends in Pharmacological Science, (1999), vol. 20, No. 3, pp. 107-112.
Gottesmann, "GABA Mechanisms and Sleep", Neuroscience, (2002), vol. 111, No. 2, pp. 231-239.
Green et al., "The nonfeminizing enantiomer of 17b-estradiol exerts protective effects in neuronal cultures and a rat model of cerebral ischemia", Endocrinology, 2001, vol. 142, pp. 400-406.
Guardia et al., "GABAergic and Glutamatergic Modulation in Binge Eating: Therapeutic Approach", Current pharmaceutical design, 2011, vol. 17, No. 14, pp. 1396-1409.
Gunduz-Bruce et al.,"Sage-217 in Major Depressive Disorder: A Multicenter, Randomized, Double-Blind, Phase 2 Placebo-Controlled Trial", European Nueuropsychopharmacology, vol. 29, 2019, pp. S59-S-60, Abstract.
Gunduz-Bruce et al.,"Sage-217 in Subjects with Major Depressive Disorder: Efficacy and Safety Results from Open-Label Part A of a Phase 2a Study", Poster, (Presented on Sep. 2-5, 2017 at the 30th ECNP Congress, Paris, France.
Gustafsson et al., "Steroid excretion patterns in urine from ovariectomized and adrenalectomized rats", Biochmica ET Biophysica ACTA—Lipids and Lipid Metabolism, Elsevier Science BV, 1972, vol. 280, No. 1, pp. 182-186.
Gustafsson et al., "Steroids in Germfree and Conventional Rats. 7. Identification of C19 and C21 Steroids in faeces from Conventional Rats", European Journal of Biochemistry, 1968, vol. 6, No. 2, pp. 248-255.
Gyermek et al., "Steroids, CCCX. 1 Structure-Activity Relationship of Some Steroidal Hypnotic Agents", Journal of Medicinal Chemistry, 1968, vol. 11, No. 1, pp. 117-125.
Han et al., "Neurosteroid Analogs. 3. The Synthesis and Electrophysiological Evaluation of Benz[e]indene Congeners of Neuroactive Steroids Having the 5b-Configuration", Journal of of Medicinal Chemistry, 1995, vol. 38, No. 22, pp. 4548-4556.
Han et al., "Neurosteroid Analogues. 4. The Effect of Methyl Substitution at the C-5 and C-10 Positions of Neurosteroids on

(56) References Cited

OTHER PUBLICATIONS

Electrophysiological Activity at GABAA Receptors", Journal of Medicinal Chemistry, (1996), vol. 39, pp. 4218-4232.
Harrison et al., "Structure-Activity Relationships for Steroid Interaction with the y-Aminobutyric AcidA Receptor Complex" The Journal of Pharmacology and Experimental Therapeutics (1987) vol. 241, No. 1, pp. 346-353.
Hauser et al., "Steroids. CCV. Fragmentations and intramolecular abstractions of tertiary hydrogen atoms by primary oxy radicals with fixed reaction centers", Helv. Chim. Acta, 1964, vol. 47, pp. 1961-1979.
Hawkins et al., "The synthetic neuroactive steroid SGE-516 reduces seizure burden and improves survival in a Dravet syndrome mouse model", Science Reports, (2017), pp. 1-8.
Hawkinson et al., "3a-Hydroxy-3b-trifluoromethyl-5a-pregnan-20-one (Co Feb. 1970): A Partial Agonist at the Neuroactive Steroid Site of the y-Aminobutyric acidA Receptor" Molecular Pharmacology (1996) vol. 49, pp. 897-906.
Hawkinson et al., "Correlation of Neuroactive Steroid Modulation of [35S]t-Butylbicyclophosphorothionate and [3H] Flunitrazepam Binding and y-Aminobutyric AcidA Receptor Function", Molecular Pharmacology (1994) vol. 46, pp. 977-985.
Hawkinson et al., "Substituted 3b-Phenylethynyl Derivatives of 3a-Hydroxy-5a-pregnan-20-one: Remarkably Potent Neuroactive Steroid Modulators of y-Aminobutyric AcidA Receptors", The Journal of Pharmacology and Experimental Therapeutics(1998), vol. 287, No. 1, pp. 198-207.
Heard et al., "Steroids. VII. Preparation of of androstan-3(b)-ol-7-one from from dehydroisoandrosterone", Journal of Biological Chemistry, 1946, vol. 165, pp. 677-685.
Hewett et al., "Amino steroids. Part III. 2- and 3-Amino-5a-androstanes", Journal of the Chemical Society, 1968, vol. 9, pp. 1134-1140.
Hill et al., "Pholochemische Reaktionen. 32 Milleilung. UV-Bestrahlung von gesattigten und bela,gamma- ngesalligten, homoallylisch konjugierten steroidaldehyden", Helvetica Chimica Acta, 1946, vol. 49, No. 1, pp. 292-311.
Hogenkamp et al., "Pharmacological profile of a 17b-heteroaryl-substituted neuroactive steroid", Psychopharmacology, vol. 231, (2014), pp. 3517-3524.
Hogenkamp et al., "Synthesis and in Vitro Activity of 3b-Substituted-3a-hydroxypregnan-20-ones: Allosteric Modulators of the GABAA Receptor", Journal of Medicinal Chemistry, (1997), vol. 40, pp. 61-72.
Hu et al., "Neurosteroid analogues. Part 5. Enantiomers of neuroactive steroids and benz[e]indenes: total synthesis,18 electrophysiological effects on GABAA receptor function and anesthetic actions in tadpoles", J. Chem. Soc. Perkin Trans 1, 1997, pp. 3665-3671.
Hu et al., "Neurosteroid Analogues: Structure-Activity Studies of Benz[e] indene Modulators of GABAA Receptor Function. 1. The Effect of 6-Melhyl Substitution on the Electrophysiological Activity of 7-Substituted Benz[e]indene-3-carbonitriles", Journal of Medicinal Chemistry, (1993), pp. 3956-3967.
Im et al., "Studies on the Mechanism of Interactions between Anesthetic Steroids and y-Aminobutyric AcidA Receptors", Molecular Pharmacology (1990), 37(3), pp. 429-434.
International Search Report and Written Opinion for Corresponding International Application No. PCT/US2019/064692 dated Feb. 27, 2020.
International Search Report and Written Opinion for Corresponding International Application No. PCT/US2020/035210 dated Aug. 27, 2020.
International Search Report and Written Opinion for Corresponding International Application No. PCT/US2020/40153 dated Sep. 23, 2020.
International Search Report and Written Opinion for Corresponding International Application No. PCT/US2020/40164 dated Sep. 21, 2020.

Katona et al., "Neurosteroid analogues. 12. Potent enhancement of GABA-mediated chloride currents at GABAA receptors by ent-androgens", European Journal of Medicinal Chemistry, 2008, vol. 43, No. 1, pp. 107-113.
Knox et al., "Steroids. CCLXXVIII. Reductions of 19-substituted androst-4-en-3-ones and related compounds", Journal of Organic Chemistry, 1965, vol. 30, No. 7, pp. 2198-2205.
Krafft et al., "Synthesis of the C/D/E and A/B Rings of Xestobergsterol—(A)", Journal of Organic Chemistry, American Chemical Society, vol. 64, No. 7, (1999), pp. 2475-2485.
Krishnan et al., "Neurosteroid Analogues. Chapter 17. Inverted Binding Orientations of Androsterone Enantiomers at the Steroid Potentiation Site on y-Aminobutyric Acid Type A Receptors", Journal of Medicinal Chemistry, 2012, vol. 55, No. 3, pp. 1334-1345.
Lehmann et al., "Schweinegallensauren Der Abbau von Hyocholsaure zu Pregnanderivaten", vol. 32, No. 3-4, (1966), pp. 217-224.
Lewbart et al., "Oxidation of Steroidal a-Ketols to Glyoxals with Cupric Acetate", Journal of Organic Chemistry, (1963), vol. 28, No. 8, pp. 2001-2006.
Li et al., "Neuroactive Steroids and Human Recombinant p1 GABAc Receptors", Journal of Pharmacology and Experimental Therapeutics, (2007), vol. 323, pp. 236-247.
Mangialasche et al., "Alzheimer's disease: clinical trials and drug development", Lance Neurology, vol. 9 (2010), pp. 702-716.
Matsui et al., "Comparative fate of testosterone and testosterone sulfate in female rats: C19O2 and C19O3 steroid metabolites in the bile", Journal of Steroid Biochemistry, 1977, 8(4), pp. 323-328.
Mohler, "The GABA system in anxiety and depression and its therapeutic potential", Neuropharmacology, (2012) 62; pp. 42-53.
Mok et al., "Evidence that 5a-pregnan-3a-ol-20-one is the metabolite responsible for progesterone anesthesia", Brain Research (1990), 533(1), pp. 42-45.
Morrow et al., "Characterization of Steroid Interactions with gamma-Aminobutyric Acid Receptor-Gated Chloride Ion Channels: Evidence for Multiple Steroid Recognition Sites", 1989, Molecular Pharmacology, 37, pp. 263-270.
Nicoletti et al., "Synthesis and GABAA receptor activity of 6-oxa-analogs of neurosteroids", Steroids, Elsevier Science Publishers 2000, vol. 65, No. 6, pp. 349-356.
Nilsson et al., "Neurosteroid analogues. 6. The synthesis and GABAA receptor pharmacology of enantiomers of dehydroepiandrosterone sulfate, pregnenolone sulfate, and (3a,5b)-3-hydroxypregnan-20-one sulfate", Journal of Medicinal Chemistry, 1998, vol. 41, pp. 2604-2613.
Paradiso et al., "Steroid Inhibition of Rat Neuronal Nicotinic a4B2 Receptors Expressed in HEK 293 Cells", Journal of Molecular Pharmacology, (2000), vol. 58, pp. 341-351.
Paul et al., "Neuroactive Steroids", The Journal of the Federation of American Societies for Experimental Biology, (1992), pp. 2311-2322.
Peart et al., "Hydroxylation of steroids by Fusarium oxysporum, Exophiala jeanselmei and Ceratocystis paradoxa", Steroids, vol. 76, No. 12, (2011), pp. 1317-1330.
Pechet et al. "Metabolism of 19-hydroxycorticosterone. Isolation and characterization of three metabolites", Journal of Biological Chemistry, Jan. 1, 1961, vol. 236, No. 10, pp. PC68-PC69.
Phillipps et al., "A New Series of Steroidal Antidysrhythmic Agents," J. Steroid Biochem. 19(1):759-765 (1983).
Phillipps et al., "Water-soluble Steroidal Anaesthetics", Journal of Steroid Biochemistry 11:79-86 (1979).
Phillipps, "Structure-Activity Relationships in Steroidal Anaesthetics", Journal of Steroid Biochemistry, (1975), vol. 6, pp. 607-613.
Phillipps, "Structure-Activity Relationships in Steroidal Anaesthetics", Nol. Mech. Gen. Anaesth. Glaxo Symposium, (1974), pp. 32-47.
PubChem CID: 70249446, [database online], created Dec. 1, 2012 [retrieved on Mar. 21, 2018]. Retrieved from the National Center for Biotechnology Information, PubChem Compound Database, using internet URL:<https://pubchem.ncbi.nlm.nih.gov/compound/70249446>.
Purdy et al., "Synthesis, Metabolism, and Pharmacological Activity of 3a-Hydroxy Steroids Which Potentiate GABA-Receptor-

(56) References Cited

OTHER PUBLICATIONS

Mediated Chloride Ion Uptake in Rat Cerebral Cortical Synaptoneurosomes", Journal of Medicinal Chemistry, (1990), vol. 33, pp. 1572-1581.

Qian et al., "Neurosteroid Analogues, 18. Structure-Activity Studies of ent-Steroid Potentiators of y-Aminobutyric Acid Type A Receptors and Comparison of Their Activities with Those of Alphaxalone and Allopregnanolone", Journal of MedicinalChemistry, 2014, vol. 57, No. 1, pp. 171-190.

Qian et al., "The efficient and enantiospecific total synthesis of cyclopenta[b]phenanthrenes structurally related to neurosteroids". Adv. Syn. & Cata., 2010, vol. 352, Nos. 11-12, pp. 2057-2061.

Rogawski et al., "Neuroactive Steroids for the Treatment of Status Epilepticus", Epilepsia (2013), vol. 54, No. 6, pp. 93-98.

Rongone et al., "In vivo metabolism of d-homotestosterone", Steroids, vol. 1, No. 6, 1963, pp. 664-669.

Runyon et al., "17b-Nitro-5a-androstan-3a-ol and its 3b-methyl derivative: Neurosteroid analogs with potent anticonvulsant and anxiolytic activities", European Journal of Pharmacology 617, (2009), pp. 68-73.

Ruzicka et al., "Steroids and sex hormones. CXXXIX. The relation between constitution and odor of steroids. Methylandrostane and allopregnane derivatives", Helvetica Chimica Acta, 1947, vol. 30, pp. 867-878.

Rychnovsky et al., "Synthesis of ent-cholesterol, the unnatural enantiomer", Journal of Organic Chemistry, 1992, vol. 57, No. 9, pp. 2732-2736.

Sage Therapeutics: "Sage Therapeutics Advances SAGE-217 into Placebo-Controlled Phase 2 Clinical Trial in Major Depressive Disorder", Feb. 13, 2017, Retrieved from the Internet:<URL:https://investor.sagerx.com/static-fil>es/80fflf35-fc4c-4eb2-9- 456-3228ec891a59; [retrieved on Dec. 21, 2018].

Santaniello & Caspi, "Reduction of certain steroidal 19-sulfonic esters with metal hydrides", J. Of Ster. Biochem, 1976, vol. 7, No. 3, pp. 223-227.

Saporito et al., "Intravenously Administered Ganaxolone Blocks Diazepam-Resistant Lithium-Pilocarpine-Induced Status Epilepticus in Rats: Comparison with Allopregnanolone", Journal of Pharmacology Exp. Ther. 2019, 3685b4(3), pp. 326-327.

Sarett., "A new method for the preparation of 17(alpha)-hydroxy-20-ketopregnanes", J. Am. Chem. Soc., 1948, vol. 70, pp. 1454-1458.

Scaglione et al., "Neurosteroid Analogues. 14. Alternative Ring System Scaffolds: GABA Modulatory and Anesthetic Actions of Cyclopenta[b]phenanthrenes and Cyclopenta[b]anthracenes", 2008, Journal of Medicinal Chemistry, vol. 51, pp. 1309-1318.

Shen et al., "Microbial aromatization of 19-hydroxymethylepidehydroandrosterone acetate by Corynebacterium simplex", Huaxue Xuebao, 1983, vol. 41, No. 5, pp. 473-474.

Shu et al., "Characteristics of concatemeric GABM receptors containing alpha4/d subunits expressed in Xenopus oocytes" British Journal of Pharmacology (2012) 165, 2228-2243.

Shu et al., "Photodynamic effects of steroid-conjugated fluorophores on gabaa receptors", Molecular Pharmacology, 2009, vol. 76, No. 4, pp. 754-765.

Slavikova et al., "Allopregnanolone (3a-Hydroxy-5a-pregnan-20-one) Derivatives with a Polar Chain in Position 16a: Synthesis and Activity", Journal of Medicinal Chemistry, vol. 52, No. 7, (2009), 2119-2125.

Spiegel et al., "Use of Nonaqueous Solvents in Parenteral Products", Journal of Pharmaceutical Sciences, 1963, vol. 52, No. 10, pp. 917-927.

Starnes et al., "Thin-Layer Chromatography of 17-Kelosteroid 2,4-Dinitrophenylhydrazones", Journal of Clinical Endocrinology and Metabolism, 1966, vol. 26, No. 11, pp. 1245-1250.

Stastna et al., "Neurosteroid Analogues. 16. A New Explanation for the Lack of Anesthetic Effects in D16—Alphaxalone and Identification of a D17(20) Analogue with Potent Anesthetic Activity", Journal of Medicinal Chemistry, 2011, vol. 54, No. 11, pp. 3926-3934.

Stastna et al., "Stereoselectivity of sodium borohydride reduction of saturated steroidal ketones utilizing conditions of Luche reduction", Steroids, 2010, vol. 75, No. 10, pp. 721-725.

Stastna et al., "Synthesis of C3, C5, and C7 pregnane derivatives and their effect on NMDA receptor responses in cultured rat hippocampal neurons", Steroids, Elsevier Science Publishers, vol. 74, No. 2, (2008), pp. 256-263.

Stastna et al., "The use of symmetry in enantioselective synthesis: Four pairs of chrysene enantiomers prepared from 19-nortestosterone", Org. Biomol. Chem., 2011, vol. 9, pp. 4685-4694.

Sunol et al., "Activity of b-nor analogues of neurosteroids on the gabaa receptor in primary neuronal cultures", Journal of Medicinal Chemistry, 2006, vol. 49, No. 11, pp. 3225-3234.

Supplemental European Search Report, European Patent Application No. 14826212.4, dated Feb. 16, 2017.

Suthoff et al., "Assessment of Health-Related Quality of Life by the SF36V2 in a Phase 2, Randomized Placebo-Controlled Trial of the GABA A Receptor Positive Allosteric Modulator Sage-217 in Major Depressive Disorder", Value in Health, vol. 21, No. Suppl. 3, 2018, Abstract.

Tsai et al., "Synthesis and antiproliferative activity of 3a-hydroxyl-3b-methoxymethyl-5a-pregnan-20-one with a C-21 hydrophilic substituent", Heteroatom Chemistry, (2017), pp. 1-9.

Upasani et al., "3a-Hydroxy-3B-(phenylethynyl)-5ß-pregnan-20-ones: Synthesis and Pharmacological Activity of Neuroactive Steroids with High Affinity for GABAA Receptors", J. Med. Chem. (1997) vol. 40, No. 1, pp. 73-84.

Vanover et al., "Behavioral characterization of Co 134444 (3a-hydroxy-21-(1'-imidazolyl)-3b-methoxymethyl-5a-pregnan-20-one), a novel sedative-hypnotic neuroactive steroid", Psychopharmacology (2001), vol. 155, pp. 285-291.

Vanover et al., "Characterization of the Anxiolytic Properties of a Novel Neuroactive Steroid, Co 2-6749 (GMA-839; WAY-141839; 3a, 21-Dihydroxy-3b-trifluoromethyl-19-nor-5b-pregnan-20-one), a Selective Modulator of y-Aminobutyric AcidA Receptors", The Journal of Pharmacology and Experimental Therapeutics, (2000), vol. 295, No. 1, pp. 337-345.

Vanover et al., "Response-Rate Suppression in Operant Paradigm as Predictor of Soporific Potency in Rats and Identification of Three Novel Sedative-Hypnotic Neuroactive Steroids", The Journal of Pharmacology and Experimental Therapeutics, (1999),vol. 291, No. 3, pp. 1317-1323.

Veleiro et al., "Structure-activity relationships of neuroactive steroids acting on the gabaa receptor", Current Medicinal Chemistry, 2009, vol. 16, No. 4, pp. 455-472.

Veleiro et al., "Synthesis and GABAA Receptor Acitivity of a6, 19-Oxido Analogue of Pregnanolone", Bioorganic & Medicinal Chemistry Letters, (2003), vol. 13, pp. 343-345.

Welling, "Interactions affecting drug absorption", Clinical Pharmacokinetics, vol. 9, No. 5, Sep. 1984 (Sep. 1984), pp. 404-434.

Wicha et al., "Transformations of steroidal neopentyl systems. II. Migration of acetate from the 3beta- to the 19-hydroxyl in delta 5 and A/B-trans steroids", Canadian Journal of Chemistry, 1967, vol. 45, No. 7, pp. 707-711.

Wicha et al., "Transformations of steroidal neopentyl systems. IV. Stereochemistry of Products of Reaction of Methyllithium with Steroidal A5-19-aldehydes", Journal of the Chemical Society (Section) C: Organic, 1968, vol. 14, 1740-1746.

Wicha et al., "Transformations of steroidal neopentyl systems. V. Synthesis and proof of the configuration of 19amethyl-19ß-alcohols", Journal of the Chemical Society [Section] C: Organic, 1969, vol. 6, pp. 947-951.

Wicha et al., "Transformations of steroidal neopentyl systems. VI. Intramolecular Claisen condensation of 19R-acetoxy-19A-methyl-3-ones of the 5alpha series", Tetrahedron, 1969, vol. 25, No. 17, pp. 3961-3968.

Wicha et al., "Transformations of steroidal neopentyl systems. VII. Mechanism of the transformation of (19R)-(19)-hydroxy-19-methyl-3-oxo-5alpha-to 3alpha-hydroxy-19-methyl-19--oxo-5alpha-analogs", Journal of Organic Chemistry, 1973, vol. 38 No. 7, pp. 1280-1283.

(56) References Cited

OTHER PUBLICATIONS

Wu, "A New Classification of Prodrugs: Regulatory Perspectives", Pharmaceuticals, 2009, vol. 2, pp. 77-81.
Zeng et al., "Neurosteroid Analogues. 10. The Effect of Methyl Group Substitution at the C-6 and C-7 Positions on the GABA Modulatory and Anesthetic Actions of (3a,5a) -and (3a, 5b)-3-Hydroxypregnan-20-one", Journal of Medicinal Chemistry, (2005). vol. 48, pp. 3051-3059.
Zonana et al., "The Neurobiology of Postpartum Depression", CNS Spectrums, (2005), pp. 792-799, 805.
Zorumski et al., "Enantioselective Modulation of GABAergic Synaptic Transmission by Steroids and Benz[dindenes in Hippocampal Microcultures", Synapse, (1998), vol. 29, pp. 162-171.

\* cited by examiner

NEUROACTIVE STEROIDS AND COMPOSITIONS THEREOF

CROSS-REFERENCE TO RELATED APPLICATIONS

This application claims the benefit of U.S. Provisional Patent Application No. 62/855,435, filed on May 31, 2019, the entire content of which is incorporated by reference herein.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization (change of potential occurs from −70 mV to −50 mV). This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GABA receptor complex (GRC), the effect on brain excitability is mediated by γ-aminobutyric acid (GABA), a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs, i.e., reduced neuron excitability. In other words, the higher the chloride ion concentration in the neuron, the lower the brain excitability and level of arousal.

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as Valium®) produce their therapeutically useful effects by interacting with specific regulatory sites on the GRC. Accumulated evidence has now indicated that in addition to the benzodiazepine and barbiturate binding site, the GRC contains a distinct site for neuroactive steroids. See, e.g., Lan, N. C. et al., Neurochem. Res. (1991) 16:347-356.

Neuroactive steroids occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., *Science* 232: 1004-1007 (1986); Harrison, N. L. et al., *J Pharmacol. Exp. Ther.* 241:346-353 (1987)).

New and improved compounds are needed that act as modulating agents for brain excitability, as well as agents for the prevention and treatment of CNS-related diseases. The compounds, compositions, and methods described herein are directed toward this end.

SUMMARY OF THE INVENTION

Provided herein are compounds designed, for example, to act as GABA modulators. In some embodiments, such compounds are envisioned to be useful as therapeutic agents for treating a CNS-related disorder.

In an aspect, provided herein is a compound of Formula (I):

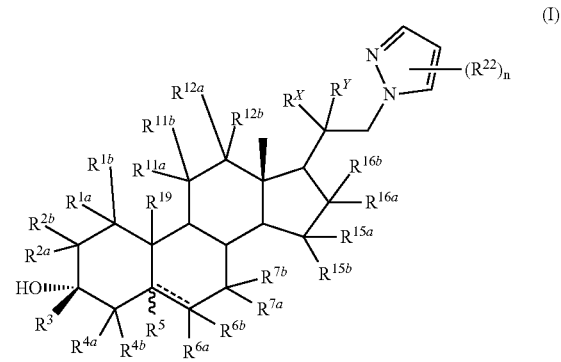

or a pharmaceutically acceptable salt thereof;
wherein:

┄┄┄ represents a single or double bond, provided if a double bond is present, then one of $R^{6a}$ or $R^{6b}$ is absent and $R^5$ is absent;

$R^X$ is selected from the group consisting of halo, —CN, —OH, —$OR^{Q1}$, and substituted or unsubstituted alkyl, wherein $R^{Q1}$ is substituted or unsubstituted alkyl;

$R^Y$ is halo or substituted or unsubstituted alkyl; or $R^Y$ and $R^X$ may join together with the intervening atoms to form a substituted or unsubstituted carbocyclyl or a substituted or unsubstituted heterocyclyl;

$R^3$ is selected from the group consisting of substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl;

$R^5$ is hydrogen or methyl;

each instance of $R^{22}$ is independently selected from the group consisting of halogen, —$NO_2$, —CN, —$OR^{GA}$, —$N(R^{GA})_2$, —C(=O)$R^{GA}$, —C(=O)$OR^{GA}$, —OC(=O)$R^{GA}$, —OC(=O)$OR^{GA}$, —C(=O)N($R^{GA})_2$, —N($R^{GA}$)C(=O)$R^{GA}$, —OC(=O)N($R^{GA})_2$, —N($R^{GA}$)C(=O)$OR^{GA}$, —N($R^{GA}$)C(=O)N($R^{GA})_2$, —$SR^{GA}$, —S(=O) $R^{GA}$, —S(=O)$_2R^{GA}$, —S(=O)$_2OR^{GA}$, —OS(=O)$_2R^{GA}$, —S(=O)$_2$N($R^{GA})_2$, —N($R^{GA}$)S(=O)$_2R^{GA}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, wherein each instance of $R^{GA}$ is independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocyclyl, substituted or unsubstituted aryl, substituted or unsubstituted heteroaryl, an oxygen protecting group when attached to oxygen, and a nitrogen protecting group when attached to nitrogen, or two $R^{GA}$ groups are taken with the intervening atoms to form a substituted or unsubstituted heterocyclyl or heteroaryl ring;

each of $R^{1a}$, $R^{1b}$, $R^{2a}$, $R^{2b}$, $R^{4a}$, $R^{4b}$, $R^{7a}$, $R^{7b}$, $R^{11a}$, $R^{11b}$, $R^{12a}$, and $R^{12b}$ is independently selected from the group consisting of hydrogen, halogen, cyano, —$NO_2$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —$C(=O)R^{A1}$, —$C(=O)OR^{A1}$, —$C(=O)SR^{A1}$, —$C(=O)N(R^{A1})_2$, —$OC(=O)R^{A1}$, —$OC(=O)OR^{A1}$, —$OC(=O)N(R^{A1})_2$, —$OC(=O)SR^{A1}$, —$OS(=O)_2R^{A1}$, —$OS(=O)_2R^{A1}$, —$OS(=O)_2N(R^{A1})_2$, —$N(R^{A1})C(=O)R^{A1}$, —$N(R^{A1})C(=NR^{A1})R^{A1}$, —$N(R^{A1})C(=O)OR^{A1}$, —$N(R^{A1})C(=O)N(R^{A1})_2$, —$N(R^{A1})C(=NR^{A1})N(R^{A1})_2$, —$N(R^{A1})S(=O)_2R^{A1}$, —$N(R^{A1})S(=O)_2OR^{A1}$, —$N(R^{A1})S(=O)_2N(R^{A1})_2$, —$SC(=O)R^{A1}$, —$SC(=O)OR^{A1}$, —$SC(=O)SR^{A1}$, —$SC(=O)N(R^{A1})_2$, —$S(=O)_2R^{A1}$, —$S(=O)_2OR^{A1}$, or —$S(=O)_2N(R^{A1})_2$, wherein each instance of $R^{A1}$ is independently selected from the group consisting of hydrogen, substituted or unsubstituted $C_{1-6}$alkyl, substituted or unsubstituted $C_{2-6}$alkenyl, substituted or unsubstituted $C_{2-6}$alkynyl, substituted or unsubstituted $C_{3-6}$carbocyclyl, or substituted or unsubstituted 3- to 6-membered heterocyclyl, substituted or unsubstituted aryl, substituted or unsubstituted heteroaryl, an oxygen protecting group when attached to oxygen, a nitrogen protecting group when attached to nitrogen, and a sulfur protecting group when attached to sulfur, or two $R^{A1}$ groups are taken with the intervening atoms to form a substituted or unsubstituted heterocyclic ring;

each of $R^{6a}$ and $R^{6b}$ is independently selected from the group consisting of hydrogen, halogen, cyano, —$NO_2$, —OH, substituted or unsubstituted alkyl, substituted or unsubstituted alkenyl, and substituted or unsubstituted alkynyl; or $R^{6a}$ and $R^{6b}$ are joined to form an oxo (=O) group;

each of $R^{15a}$, $R^{15b}$, $R^{16a}$, and $R^{16b}$ is independently selected from the group consisting of hydrogen, halogen, —CN, —$NO_2$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{C3}$, —$N(R^{C3})_2$, —$SR^{C3}$, —$C(=O)R^{C3}$, —$C(=O)OR^{C3}$, —$C(=O)SR^{C3}$, —$C(=O)N(R^3)_2$, —$OC(=O)R^{C3}$, —$OC(=O)OR^{C3}$, —$OC(=O)N(R^{C3})_2$, —$OC(=O)SR^{C3}$, —$OS(=O)_2R^{C3}$, —$OS(=O)_2OR^{C3}$, —$OS(=O)_2N(R^{C3})_2$, —$N(R^{C3})C(=O)R^{C3}$, —$N(R^{C3})C(=NR^{C3})R^{C3}$, —$N(R^{C3})C(=O)OR^{C3}$, —$N(R^{C3})C(=O)N(R^{C3})_2$, —$N(R^{C3})C(=NR^{C3})N(R^{C3})_2$, —$N(R^{C3})S(=O)_2R^{C3}$, —$N(R^{C3})S(=O)_2OR^{C3}$, —$N(R^{C3})S(=O)_2N(R^{C3})_2$, —$SC(=O)R^{C3}$, —$SC(=O)OR^{C3}$, —$SC(=O)SR^{C3}$, —$SC(=O)N(R^{C3})_2$, —$S(=O)_2R^{C3}$, —$S(=O)_2OR^{C3}$, or —$S(=O)_2N(R^3)_2$, wherein each instance of $R^C_3$ is independently selected from the group consisting of hydrogen, substituted or unsubstituted $C_{1-6}$alkyl, substituted or unsubstituted $C_{2-6}$alkenyl, substituted or unsubstituted $C_{2-6}$alkynyl, substituted or unsubstituted aryl, substituted or unsubstituted heteroaryl, substituted or unsubstituted carbocyclyl, or substituted or unsubstituted heterocyclyl, an oxygen protecting group when attached to oxygen, a nitrogen protecting group when attached to nitrogen, and a sulfur protecting group when attached to sulfur, or two $R^{C3}$ groups are taken with the intervening atoms to form a substituted or unsubstituted heterocyclic ring;

$R^{19}$ is hydrogen or substituted or unsubstituted alkyl; and n is selected from the group consisting of 0, 1, 2, and 3.

In some embodiments, the compound is a compound of Formula I-a:

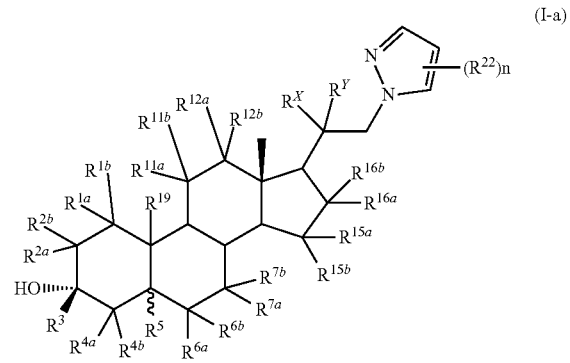

(I-a)

or a pharmaceutically acceptable salt thereof, wherein the variables are as defined above.

In some embodiments, the compound is a compound of Formula I-b1:

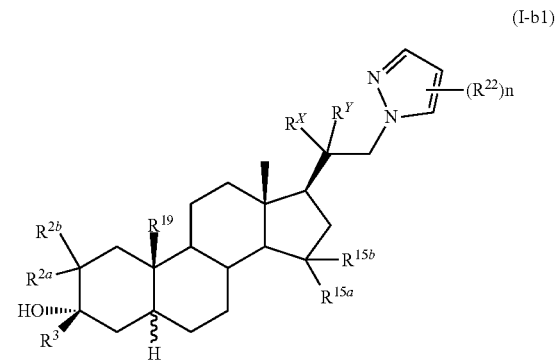

(I-b1)

or a pharmaceutically acceptable salt thereof, wherein the variables are as defined above.

In some embodiments, the compound is a compound of Formula I-c3 or Formula I-c4:

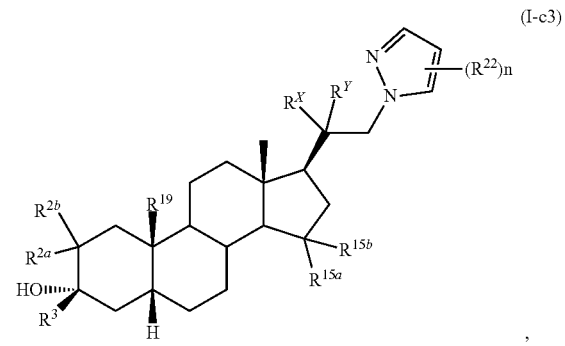

(I-c3)

,

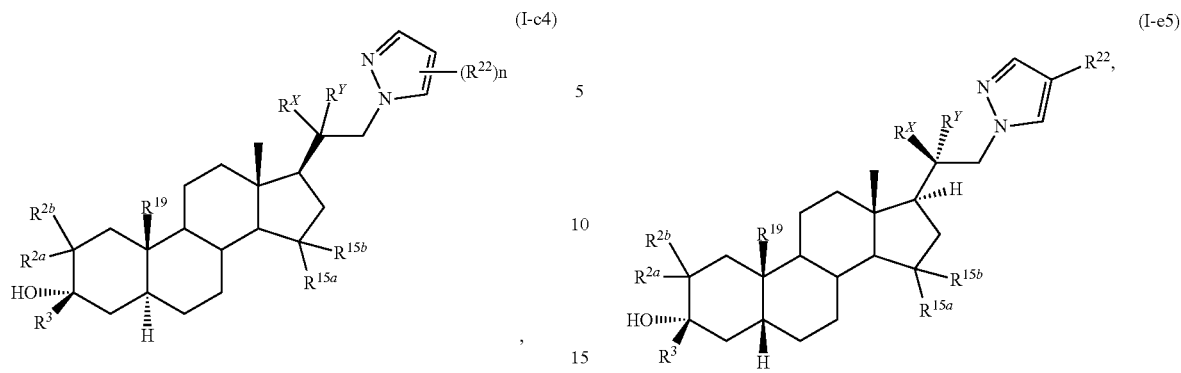

or a pharmaceutically acceptable salt thereof, wherein the variables are as defined above.

In some embodiments, the compound is a compound of Formula I-d3 or Formula I-d4:

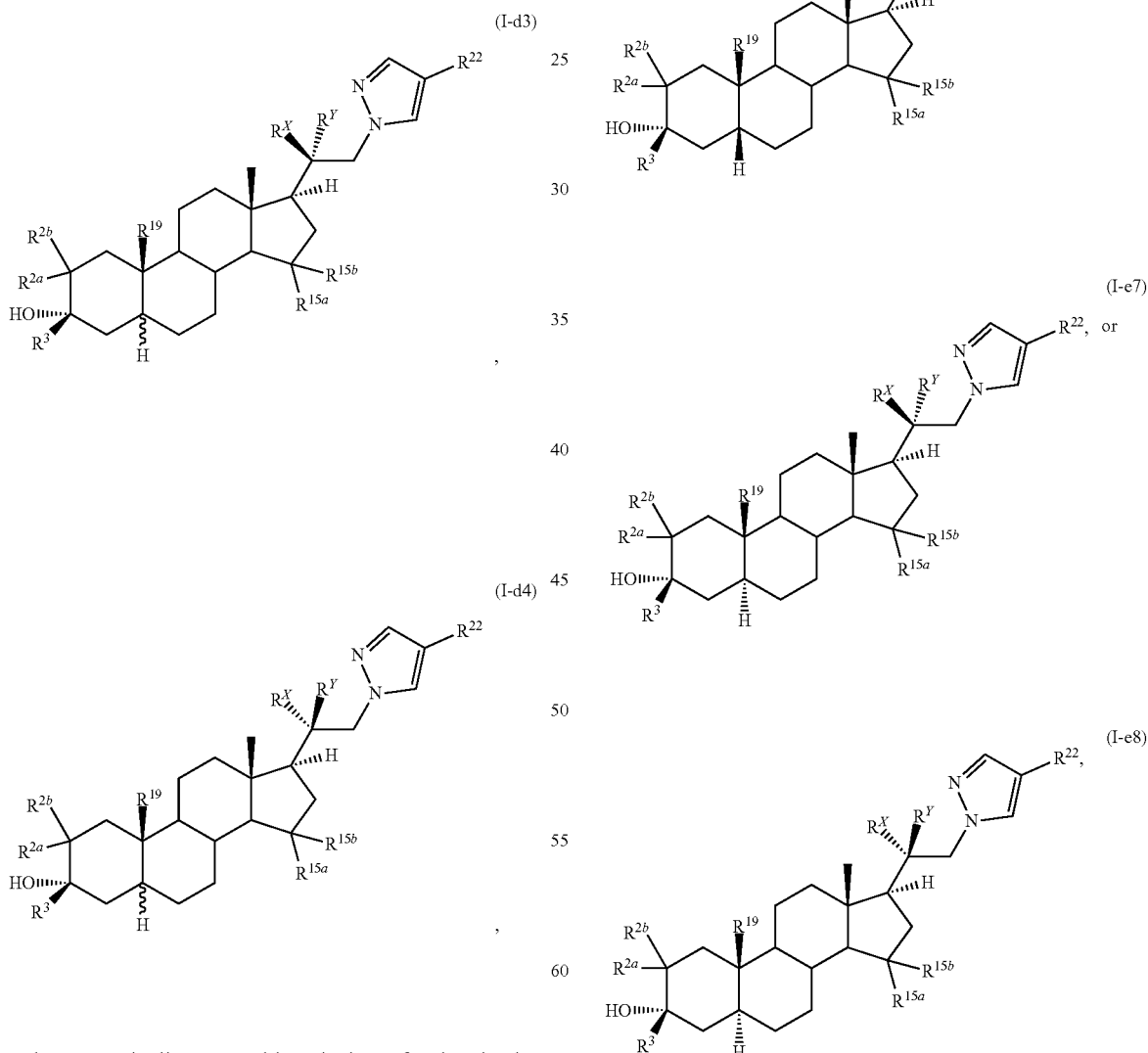

or a pharmaceutically acceptable salt thereof, wherein the variables are as defined above.

In some embodiments, the compound is a compound of Formula I-e5, Formula I-e6, Formula I-e7, or Formula I-e8.

or a pharmaceutically acceptable salt thereof, wherein the variables are as defined above.

In a certain embodiment, the compound is a compound of Formula I-Ib1:

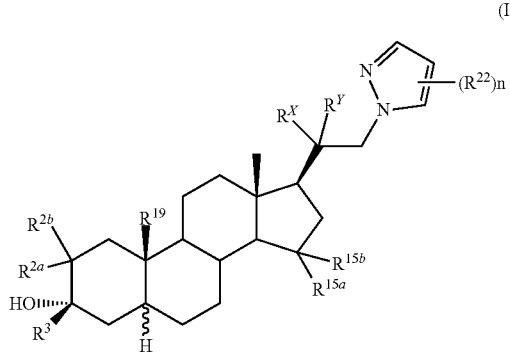
(I-Ib1)

or a pharmaceutically acceptable salt thereof,
wherein $R^{22}$ is CN;
n is 1;
$R^{19}$ is selected from the group consisting of hydrogen, ethyl, and methyl;
$R^{15a}$ and $R^{15b}$ is independently selected from the group consisting of hydrogen, methyl, and cyclopropyl;
$R^{2a}$ and $R^{2b}$ is each independently selected from the group consisting of hydrogen, methyl, ethyl, methoxymethyl, and methoxy;
$R^3$ is selected from the group consisting of unsubstituted $C_{1-3}$ alkyl, —$CH_2OCH_3$, and —$CH_2OCH_2CH_3$;
and $R^X$ and $R^Y$ are as defined herein.

In one embodiment, the compound is a compound of Formula I-Ic1 or Formula I-Ic2:

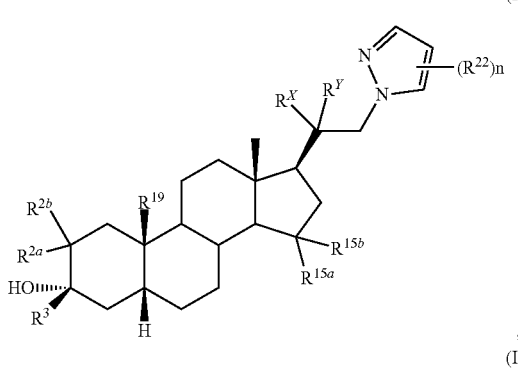
(I-Ic1)

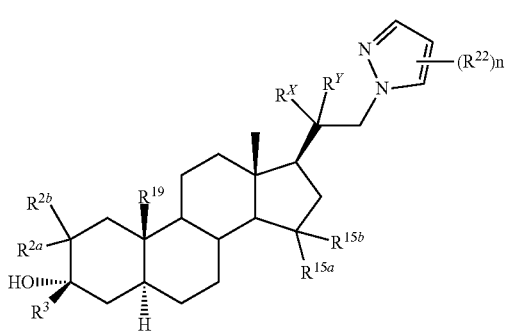
(I-Ic2)

or a pharmaceutically acceptable salt thereof,
wherein $R^{22}$ is CN;
n is 1;
$R^{19}$ is selected from the group consisting of hydrogen, ethyl, and methyl;
$R^{15a}$ and $R^{15b}$ is independently selected from the group consisting of hydrogen, methyl, and cyclopropyl;
$R^{2a}$ and $R^{2b}$ is each independently selected from the group consisting of hydrogen, methyl, ethyl, methoxymethyl, and methoxy;
$R^3$ is selected from the group consisting of unsubstituted $C_{1-3}$ alkyl, —$CH_2OCH_3$, and —$CH_2OCH_2CH_3$; and
$R^X$ and $R^Y$ are as defined herein.

In one embodiment, the compound is a compound of Formula I-Id1 or Formula I-Id2.

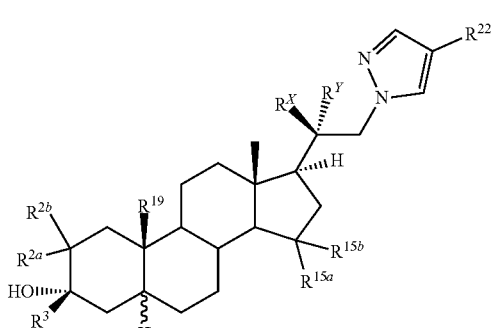
(I-Id1)

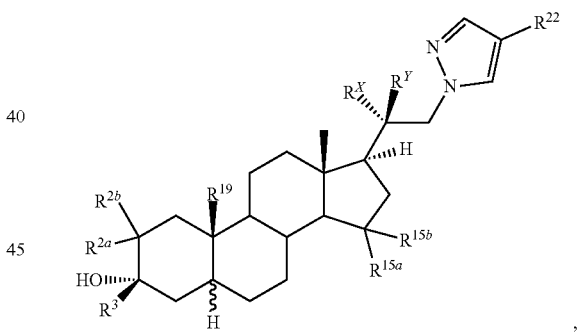
(I-Id2)

or a pharmaceutically acceptable salt thereof,
wherein $R^{22}$ is CN;
$R^{19}$ is selected from the group consisting of hydrogen, ethyl, and methyl;
$R^{15a}$ and $R^{15b}$ is independently selected from the group consisting of hydrogen, methyl, and cyclopropyl;
$R^{2a}$ and $R^{2b}$ is each independently selected from the group consisting of hydrogen, methyl, ethyl, methoxymethyl, and methoxy;
$R^3$ is selected from the group consisting of unsubstituted $C_{1-3}$ alkyl, —$CH_2OCH_3$, and —$CH_2OCH_2CH_3$; and
$R^X$ and $R^Y$ are as defined herein.

In one embodiment, the compound is a compound of Formula I-Ie1, Formula I-Ie2, Formula I-Ie3, or Formula I-Ie4:

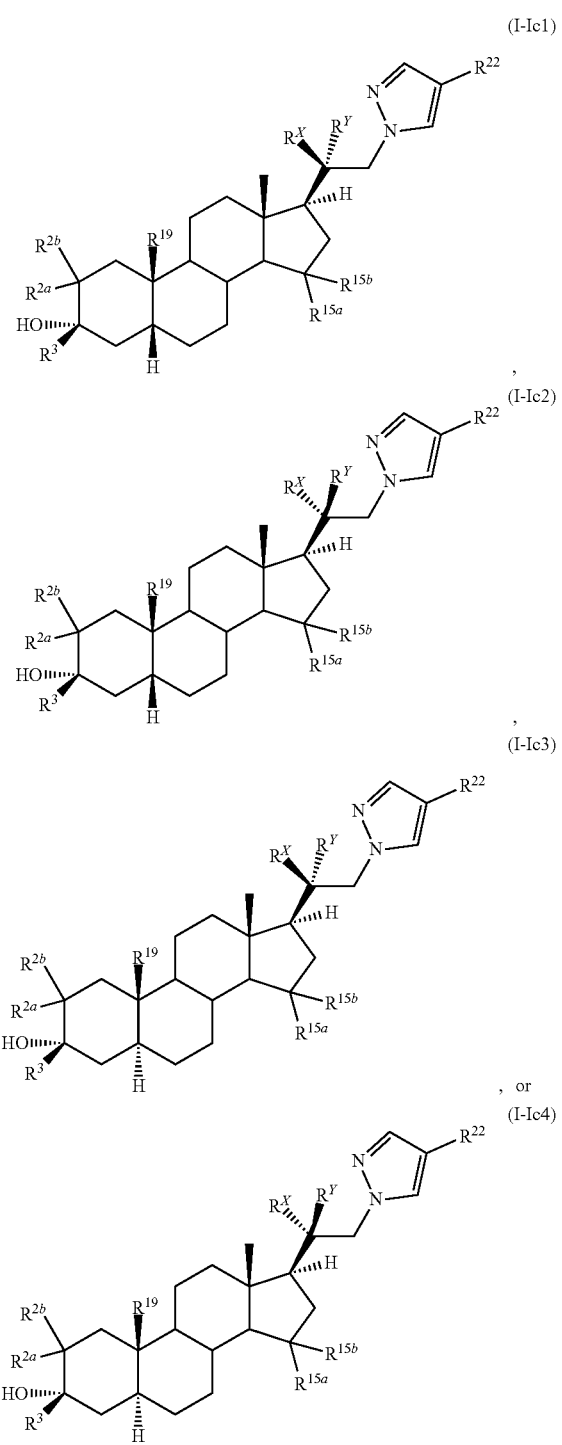

or a pharmaceutically acceptable salt thereof, wherein $R^{22}$ is CN;

$R^{19}$ is selected from the group consisting of hydrogen, ethyl, and methyl;

$R^{15a}$ and $R^{15b}$ is independently selected from the group consisting of hydrogen, methyl, and cyclopropyl;

$R^{2a}$ and $R^{2b}$ is each independently selected from the group consisting of hydrogen, methyl, ethyl, methoxymethyl, and methoxy;

$R^3$ is selected from the group consisting of unsubstituted $C_{1-3}$ alkyl, —$CH_2OCH_3$, and —$CH_2OCH_2CH_3$; and $R^X$ and $R^Y$ are as defined herein.

In one aspect, provided herein is a pharmaceutically acceptable salt of a compound described herein (e.g., a compound of Formula (I)).

In one aspect, provided herein is a pharmaceutical composition comprising a compound described herein (e.g., a compound of Formula (I)) or a pharmaceutically acceptable salt thereof, and a pharmaceutically acceptable excipient. In certain embodiments, the compound of the present invention is provided in an effective amount in the pharmaceutical composition. In certain embodiments, the compound of the present invention is provided in a therapeutically effective amount.

In some embodiments, a method of treating a CNS-related disorder in a subject in need thereof, comprises administering to the subject an effective amount of a compound described herein (e.g., a compound of Formula (I)) or a pharmaceutically acceptable salt thereof. In some embodiments, the CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, tinnitus, or status epilepticus. In some embodiments, the CNS-related disorder is depression. In some embodiments, the CNS-related disorder is postpartum depression. In some embodiments, the CNS-related disorder is major depressive disorder. In some embodiments, the major depressive disorder is moderate major depressive disorder. In some embodiments, the major depressive disorder is severe major depressive disorder.

In some embodiments, the compound is selected from the group consisting of the compounds identified in Table 1 herein.

Compounds of the present invention as described herein, act, in certain embodiments, as GABA modulators, e.g., effecting the $GABA_A$ receptor in either a positive or negative manner. As modulators of the excitability of the central nervous system (CNS), as mediated by their ability to modulate $GABA_A$ receptor, such compounds are expected to have CNS-activity.

Thus, in another aspect, provided are methods of treating a CNS-related disorder in a subject in need thereof, comprising administering to the subject an effective amount of a compound of the present invention. In certain embodiments, CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, tinnitus, or status epilepticus. In certain embodiments, the CNS-related disorder is depression. In certain embodiments, the CNS-related disorder is postpartum depression. In certain embodiments, the CNS-related disorder is major depressive disorder. In certain embodiments, the major depressive disorder is moderate major depressive disorder. In certain embodiments, the major depressive disorder is severe major depressive disorder. In certain embodiments, the compound is administered orally, subcutaneously, intravenously, or intramuscularly. In certain embodiments, the compound is administered orally. In certain embodiments, the compound is administered chronically. In certain embodiments, the compound is administered continuously, e.g., by continuous intravenous infusion.

DETAILED DESCRIPTION OF CERTAIN EMBODIMENTS OF THE INVENTION

As generally described herein, the present invention provides compounds designed, for example, to act as $GABA_A$ receptor modulators. In certain embodiments, such compounds are envisioned to be useful as therapeutic agents for treating a CNS-related disorder (e.g., a disorder as described herein, for example depression, such as post-partum depression or major depressive disorder).

Definitions

Chemical Definitions

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

Isomers, e.g., stereoisomers, can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-position/center/carbon compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The term "diastereomierically pure" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of a single diastereomer. Methods for determining diastereomeric and enantiomeric purity are well-known in the art. Diastereomeric purity can be determined by any analytical method capable of quantitatively distinguishing between a compound and its diastereomers, such as high performance liquid chromatography (HPLC).

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention.

"Alkyl" refers to a radical of a straight-chain or branched saturated hydrocarbon group having from 1 to 20 carbon atoms ("$C_{1-2}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_5$). Additional examples of alkyl groups include n-heptyl ($C_7$), n-octyl ($C_5$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("heteroC$_{1-10}$ alkyl"). In some embodiments, a heteroalkyl group is a saturated group having 1 to 9 carbon atoms and 1, 2, 3, or 4 heteroatoms ("heteroC$_{1-9}$ alkyl"). In some embodiments, a heteroalkyl group is a saturated group having 1 to 8 carbon atoms and 1, 2, 3, or 4 heteroatoms ("heteroC$_{1-8}$ alkyl"). In some embodiments, a heteroalkyl group is a saturated group having 1 to 7 carbon atoms and 1, 2, 3, or 4 heteroatoms ("heteroC$_{1-7}$ alkyl"). In some embodiments, a heteroalkyl group is a group having 1 to 6 carbon atoms and 1, 2, or 3 heteroatoms ("heteroC$_{1-6}$ alkyl"). In some embodiments, a heteroalkyl group is a saturated group having 1 to 5 carbon atoms and 1 or 2 heteroatoms ("heteroC$_{1-5}$ alkyl"). In some embodiments, a heteroalkyl group is a saturated group having 1 to 4 carbon atoms and 1 or 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

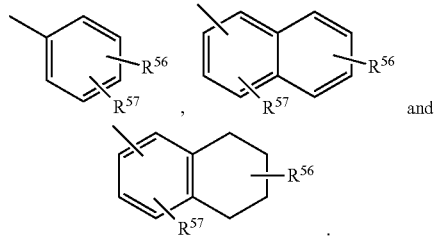

wherein one of R$^{56}$ and R$^{57}$ may be hydrogen and at least one of R$^{56}$ and R$^{57}$ is each independently selected from C$_1$-C$_8$ alkyl, C$_1$-C$_8$ haloalkyl, 4-10 membered heterocyclyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O, or S. R$^{60}$ and R$^{61}$ are independently hydrogen, C$_1$-C$_8$ alkyl, C$_1$-C$_4$ haloalkyl, C$_3$-C$_{10}$ cycloalkyl, 4-10 membered heterocyclyl, C$_6$-C$_{10}$ aryl, substituted C$_6$-C$_{10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

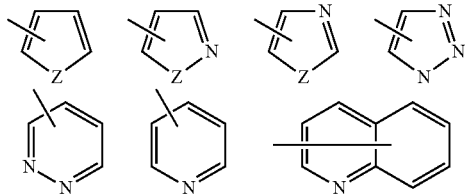

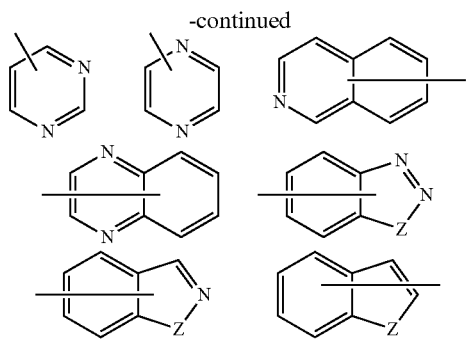

wherein each Z is selected from carbonyl, N, NR$^{65}$, O, and S; and R$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), C(O)—$C_1$-$C_8$ alkyl, —C(O)—(CH$_2$)$_t$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Alkoxy" refers to the group —$OR^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$($C_6$-$C_{10}$ aryl), —O—(CH$_2$)$_t$(5-10 membered heteroaryl), —O—(CH$_2$)$_t$($C_3$-$C_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Oxo group" refers to —C(=O)—.

"Substituted amino" refers to an amino group of the formula —N($R^{38}$)$_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or an amino protecting group, wherein at least one of $R^{38}$ is not a hydrogen. In certain embodiments, each $R^{38}$ is independently selected from hydrogen, $C_1$-$C_7$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), or —(CH$_2$)$_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, —$NR^{39}$—$C_1$-$C_8$ alkyl, —$NR^{39}$—(CH$_2$)$_t$($C_6$-$C_{10}$ aryl), —$NR^{39}$—(CH$_2$)$_t$(5-10 membered heteroaryl), —$NR^{39}$—(CH$_2$)$_t$($C_3$-$C_{10}$ cycloalkyl), and —$NR^{39}$—(CH$_2$)$_t$(4-10 membered heterocyclyl), wherein t is an integer from 0 to 4, for instance 1 or 2, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Haloalkyl" refers to an alkyl radical in which the alkyl group is substituted with one or more halogens. Typical haloalkyl groups include, but are not limited to, trifluoromethyl, difluoromethyl, fluoromethyl, chloromethyl, dichloromethyl, dibromoethyl, tribromomethyl, tetrafluoroethyl, and the like.

"Hydroxy" refers to the radical —OH.

"Nitro" refers to the radical —NO$_2$.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —$OR^{aa}$, —ON($R^{bb}$)$_2$, —N($R^{bb}$)$_2$, —N($R^{bb}$)$_3$$^+$X$^-$, —N($OR^{cc}$)$R^{bb}$, —SH, —$SR^{aa}$, —$SSR^{cc}$, —C(=O)$R^{aa}$, —CO$_2$H, —CHO, —C($OR^{cc}$)$_2$, —CO$_2R^{aa}$, —OC(=O)$R^{aa}$, —OCO$_2R^{aa}$, —C(=O)N($R^{bb}$)$_2$, —OC(=O)N($R^{bb}$)$_2$, —$NR^{bb}$C(=O)$R^{aa}$, —$NR^{bb}$CO$_2R^{aa}$, —$NR^{bb}$OC(=O)N($R^{bb}$)$_2$, —C(=$NR^{bb}$)$R^{aa}$, —C(=$NR^{bb}$)OR—, —OC(=$NR^{bb}$)$R^{aa}$, —OC(=$NR^{bb}$)$OR^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R—, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$—OP(=O)(NR$^{bb}$)$_2$—NR$^{bb}$P(=O)(OR$^{cc}$)$_2$—NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^d$d groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{cc}$, =NR$^{bb}$, or =NOR$^{cc}$;

each instance of R$^{aa}$ is, independently, selected from C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^d$d groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^d$d is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(RE)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ee}$C(=NR$^{ff}$)N(R$^{ff}$)$_2$,—NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^d$d substituents can be joined to form =O or =S;

each instance of R$^{ee}$ is, independently, selected from C$_{1-6}$ alkyl, C$_{1-6}$ haloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl),—OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ haloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{99}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

These and other exemplary substituents are described in more detail in the Detailed Description, and Claims. The invention is not intended to be limited in any manner by the above exemplary listing of substituents.

Other Definitions

As used herein, the term "modulation" refers to the inhibition or potentiation of GABA$_A$ receptor function. A "modulator" (e.g., a modulator compound) may be, for example, an agonist, partial agonist, antagonist, or partial antagonist of the $GABA_A$ receptor.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are nontoxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like. See, e.g., Berge, et al., *J. Pharm. Sci.* (1977) 66(1): 1-79.

The term "prodrug" is intended to encompass therapeutically inactive compounds that, under physiological conditions, are converted into the therapeutically active agents of the present invention. One method for making a prodrug is to design selected moieties that are hydrolyzed or cleaved at a targeted in vivo site of action under physiological conditions to reveal the desired molecule which then produces its therapeutic effect. In certain embodiments, the prodrug is converted by an enzymatic activity of the subject.

In an alternate embodiment, the present invention provides prodrugs of compound of Formula (I), wherein the prodrug includes a cleavable moiety on the $C_3$ hydroxy as depicted in Formula (I).

"Tautomers" refer to compounds that are interchangeable forms of a particular compound structure, and that vary in the displacement of hydrogen atoms and electrons. Thus, two structures may be in equilibrium through the movement of 7 electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human ("human subject"). In certain embodiments, the subject is a non-human animal.

In certain embodiments, the substituent present on an oxygen atom is an oxygen protecting group (also referred to as a hydroxyl protecting group). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), 2-methoxyethoxymethyl (MEM), benzyl (Bn), triisopropylsilyl (TIPS), t-butyldimethylsilyl (TBDMS), t-butylmethoxyphenylsilyl (TBMPS), methanesulfonate (mesylate), and tosylate (Ts).

In certain embodiments, the substituent present on a sulfur atom is a sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

In certain embodiments, the substituent present on a nitrogen atom is an amino protecting group (also referred to herein as a nitrogen protecting group). Amino protecting groups include, but are not limited to, $-OH$, $-OR^{aa}$, $-N(R^{cc})$, $-C(=O)R^{aa}$, $-C(=O)OR^{aa}$, $-C(=O)N(R^{cc})$, $-S(=O)_2R^{aa}$, $-C(=NR^{cc})R^{aa}$, $-C(=NR^{cc})OR^{aa}$, $-C(=NR^{cc})N(R^{cc})$, $-SO_2N(R^{cc})_2$, $-SO_2R^{cc}$, $-SO_2OR^{cc}$, $-SOR^{aa}$, $-C(=S)N(R^{cc})$, $-C(=O)SR^{cc}$, $-C(=S)SR^{cc}$, $C_{1-10}$ alkyl, $C_{2-10}$ alkenyl, $C_{2-10}$ alkynyl, $C_{3-10}$ carbocyclyl, 3-14-membered heterocyclyl, $C_{6-14}$ aryl, and 5-14-membered heteroaryl groups, wherein each alkyl, alkenyl, alkynyl, carbocyclyl, heterocyclyl, aryl, and heteroaryl is independently substituted with 0, 1, 2, 3, 4, or 5 $R^d$d groups, and wherein $R^{aa}$, $R^{bb}$, $R^{cc}$ and $R^{dd}$ are as defined herein. Amino protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary amino protecting groups include, but are not limited to amide groups (e.g., —C(=O)$R^{aa}$), which include, but are not limited to, formamide and acetamide; carbamate groups (e.g., —C(=O)O$R^{aa}$), which include, but are not limited to, 9-fluorenylmethyl carbamate (Fmoc), t-butyl carbamate (BOC), and benzyl carbamate (Cbz); sulfonamide groups (e.g., —S(=O)$_2R^{aa}$) which include, but are not limited to, p-toluenesulfonamide (Ts), methanesulfonamide (Ms), and N-[2-(trimethylsilyl)ethoxy]methylamine (SEM).

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition.

In general, the "effective amount" of a compound refers to an amount sufficient to elicit the desired biological response, e.g., to treat a CNS-related disorder, is sufficient to induce anesthesia or sedation. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

In an alternate embodiment, the present invention contemplates administration of the compounds of the present invention or a pharmaceutically acceptable salt or a pharmaceutically acceptable composition thereof, as a prophylactic before a subject begins to suffer from the specified disease, disorder or condition. As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein, an "episodic dosing regimen" is a dosing regimen wherein a compound of Formula (I) or a composition comprising a compound of Formula (I) is administered to a subject for a finite period of time in response to the diagnosis of a disorder or symptom thereof, e.g, a diagnosis or symptom of depression. an episode of major depressive disorder, bipolar depression, anxiety, or postpartum depression. In some embodiments, the major depressive disorder is moderate major depressive disorder. In some embodiments, the major depressive disorder is severe major depressive disorder. In some embodiments, the compound is formulated as individual dosage units, each unit comprising a compound of Formula (I) and one or more suitable pharmaceutical excipients. In some embodiments, the episodic dosing regimen has a duration of a plurality of weeks, e.g. about 8 weeks. In contrast with chronic administration as defined herein, episodic dosing of a compound occurs over a finite period of time, e.g., from about 2 weeks to about 8 weeks, in response to a diagnosis of a disorder, e.g., depression, or a symptom thereof. In some embodiments, episodic dosing occurs once per day across a plurality of weeks, e.g., from about 2 weeks to about 6 weeks. In one embodiment, the episodic dosing has a duration of two weeks. In some embodiments, more than one episodic dosing regimen is administered to the subject, e.g., two or more episodic regimens throughout the subject's life.

Compounds

It should be appreciated that formulas described herein may reference particular carbon atoms, such as C17, C3, C19, etc. These references are based on the position of carbon atoms according to steroid nomenclature known and used in the industry, as shown below:

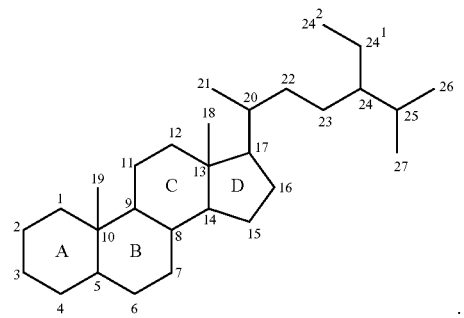

For example, C17 refers to the carbon at position 17 and C3 refers to the carbon at position 3.

In an aspect, provided herein is a compound of Formula (I):

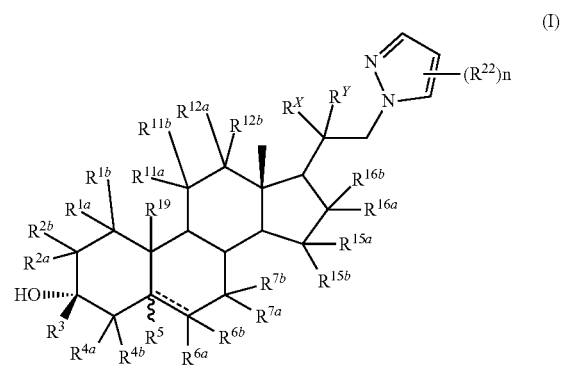

(I)

or a pharmaceutically acceptable salt thereof;
wherein:

===== represents a single or double bond, provided if a double bond is present, then one of $R^{6a}$ or $R^{6b}$ is absent and $R^5$ is absent;

$R^X$ is selected from the group consisting of halo, —CN, —OH, —OR$^{Q1}$, and substituted or unsubstituted alkyl, wherein R$^{Q1}$ is substituted or unsubstituted alkyl;

$R^Y$ is halo or substituted or unsubstituted alkyl; or $R^Y$ and $R^X$ may join together with the intervening atoms to form a substituted or unsubstituted carbocyclyl or a substituted or unsubstituted heterocyclyl;

$R^3$ is selected from the group consisting of substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl;

$R^5$ is hydrogen or methyl;

each instance of $R^{22}$ is independently selected from the group consisting of halogen, —NO$_2$, —CN, —OR$^{GA}$, —N(R$^{GA}$)$_2$, —C(=O)R$^{GA}$, —C(=O)OR$^{GA}$, —OC(=O)R$^{GA}$, —OC(=O)OR$^{GA}$, —C(=O)N(R$^{GA}$)$_2$, —N(R$^{GA}$)C(=O)R$^{GA}$, —OC(=O)N(R$^{GA}$)$_2$, —N(R$^{GA}$)C(=O)OR$^{GA}$, —N(R$^{GA}$)C(=O)N(R$^{GA}$)$_2$, —SR$^{GA}$, —S(=O) R$^{GA}$, —S(=O)$_2$R$^{GA}$, —S(=O)$_2$OR$^{GA}$, —OS(=O)$_2$R$^{GA}$, —S(=O)$_2$N(R$^{GA}$)$_2$, —N(R$^{GA}$)S(=O)$_2$R$^{GA}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, wherein each instance of R$^{GA}$ is independently selected from the group consisting of hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ carbocylyl, substituted or unsubstituted 3- to 6-membered heterocyclyl, substituted or unsubstituted aryl, substituted or unsubstituted heteroaryl, an oxygen protecting group when attached to oxygen, and a nitrogen protecting group when attached to nitrogen, or two R$^{GA}$ groups are taken with the intervening atoms to form a substituted or unsubstituted heterocyclyl or heteroaryl ring;

each of $R^{1a}$, $R^{1b}$, $R^2$, $R^{2b}$, $R^{4a}$, $R^{4b}$, $R^{7a}$, $R^{7b}$, $R^{1a}$, $R^{1b}$, $R^{12a}$, and $R^{12b}$ is independently selected from the group consisting of hydrogen, halogen, cyano, —NO$_2$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{41}$, —N(R$^{41}$)$_2$, —SR$^{41}$, —C(=O)R$^{41}$, —C(=O)OR$^{41}$, —C(=O)SR$^{41}$, —C(=O)N(R$^{41}$)$_2$, —OC(=O)R$^{41}$, —OC(=O)OR$^{41}$, —OC(=O)N(R$^{41}$)$_2$, —OC(=O)SR$^{41}$, —OS(=O)$_2$R$^{41}$, —OS(=O)$_2$R$^{41}$, —OS(=O)$_2$N(R$^{41}$)$_2$, —N(R$^{41}$)C(=O)R$^{41}$, —N(R$^{41}$)C(=NR$^{41}$) R$^{41}$, —N(R$^{41}$)C(=O)OR$^{41}$, —N(R$^{41}$)C(=O)N(R$^{41}$)$_2$, —N(R$^{41}$)C(=NR$^{41}$) N(R$^{41}$)$_2$, —N(R$^{41}$)S(=O)$_2$R$^{41}$, —N(R$^{41}$)S(=O)$_2$OR$^{41}$, —N(R$^{41}$)S(=O)$_2$N(R$^{41}$)$_2$, —SC(=O)R$^{41}$, —SC(=O)OR$^{41}$, —SC(=O)SR$^{41}$, —SC(=O)N(R$^{41}$)$_2$, —S(=O)$_2$R$^{41}$, —S(=O)$_2$OR$^{41}$, or —S(=O)$_2$N(R$^{41}$)$_2$, wherein each instance of R$^{41}$ is independently selected from the group consisting of hydrogen, substituted or unsubstituted C$_{1-6}$alkyl, substituted or unsubstituted C$_{2-6}$alkenyl, substituted or unsubstituted C$_{2-6}$alkynyl, substituted or unsubstituted C$_{3-6}$carbocyclyl, or substituted or unsubstituted 3- to 6-membered heterocyclyl, substituted or unsubstituted aryl, substituted or unsubstituted heteroaryl, an oxygen protecting group when attached to oxygen, a nitrogen protecting group when attached to nitrogen, and a sulfur protecting group when attached to sulfur, or two R$^{41}$ groups are taken with the intervening atoms to form a substituted or unsubstituted heterocyclic ring; each of R$^{6a}$ and R$^{6b}$ is independently selected from the group consisting of hydrogen, halogen, cyano, —NO$_2$, —OH, substituted or unsubstituted alkyl, substituted or unsubstituted alkenyl, and substituted or unsubstituted alkynyl; or R$^{6a}$ and R$^{6b}$ are joined to form an oxo (=O) group;

each of $R^{15a}$, $R^{15b}$, $R^{16a}$, and $R^{16b}$ is independently selected from the group consisting of hydrogen, halogen, —CN, —NO$_2$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{C3}$, —N(R$^3$)$_2$, —SR$^{C3}$, —C(=O)R$^{C3}$, —C(=O)OR$^{C3}$, —C(=O)SR$^{C3}$, —C(=O)N(R$^3$)$_2$, —OC(=O)R$^{C3}$, —OC(=O)OR$^{C3}$, —OC(=O)N(R$^{C3}$)$_2$, —OC(=O)SR$^{C3}$, —OS(=O)$_2$R$^{C3}$, —OS(=O)$_2$OR$^{C3}$, —OS(=O)$_2$N(R$^{C3}$)$_2$, —N(R$^{C3}$)C(=O) R$^{C3}$, —N(R$^{C3}$)C(=NR$^{C3}$)R$^{C3}$, —N(R$^{C3}$)C(=O)OR$^{C3}$, —N(R$^{C3}$)C(=O)N(R$^{C3}$)$_2$, —N(R$^{C3}$)C(=NR$^{C3}$) N(R$^{C3}$)$_2$, —N(R$^{C3}$)S(=O)$_2$R$^{C3}$, —N(R$^{C3}$)S(=O)$_2$OR$^{C3}$, —N(R$^{C3}$)S(=O)$_2$N(R$^{C3}$)$_2$, —SC(=O)R$^{C3}$, —SC(=O)OR$^{C3}$, —SC(=O)SR$^{C3}$, —SC(=O)N(R$^{C3}$)$_2$, —S(=O)$_2$R$^{C3}$, —S(=O)$_2$OR$^{C3}$, or —S(=O)$_2$N(R$^3$)$_2$, wherein each instance of R$^C_3$ is independently selected from the group consisting of hydrogen, substituted or unsubstituted C$_{1-6}$alkyl, substituted or unsubstituted C$_{2-6}$alkenyl, substituted or unsubstituted C$_{2-6}$alkynyl, substituted or unsubstituted aryl, substituted or unsubstituted heteroaryl, substituted or unsubstituted carbocyclyl, or substituted or unsubstituted heterocyclyl, an oxygen protecting group when attached to oxygen, a nitrogen protecting group when attached to nitrogen, and a sulfur protecting group when attached to sulfur, or two R$^{C3}$ groups are taken with the intervening atoms to form a substituted or unsubstituted heterocyclic ring;

$R^{19}$ is hydrogen or substituted or unsubstituted alkyl; and n is selected from the group consisting of 0, 1, 2, and 3.

In some embodiments, the compound of Formula (I) is a compound of Formula (I-a), Formula (I-b), Formula (I-c1), Formula (I-c2), Formula (I-d1), Formula (I-d2), Formula (I-e1), Formula (I-e2), Formula (I-e3), Formula (I-e4), Formula (I-b1), Formula (I-c3), Formula (I-c4), Formula (I-d3), Formula (I-d4), Formula (I-e5), Formula (I-e6), Formula (I-e7), or Formula (I-e8).

In some embodiments, the compound of Formula I is a compound of Formula I-a:

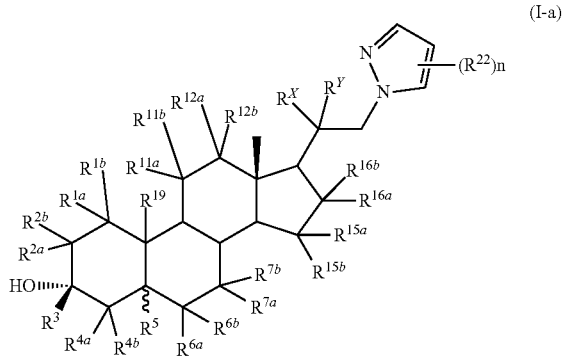

(I-a)

or a pharmaceutically acceptable salt thereof.

In some embodiments, the compound is a compound of Formula (I) and each $R^{1a}$, $R^{1b}$, $R^{2a}$, $R^{2b}$, $R^{4a}$, $R^{4b}$, $R^{7a}$, $R^{7b}$, $R^{11a}$, $R^{11b}$, $R^{12a}$, $R^{12b}$, $R^{6a}$, $R^{6b}$, $R^{15a}$, $R^{15b}$, $R^{16a}$, and $R^{16b}$ is hydrogen.

In some embodiments, the compound is a compound of Formula (I) and n is 1, $R^{22}$ is —CN, $R^5$ is hydrogen, and $R^{19}$ is selected from the group consisting of hydrogen, methyl, and ethyl.

In some embodiments, the compound is a compound of Formula (I) and n is 1, $R^{22}$ is —CN, $R^5$ is hydrogen, and $R^{19}$ is hydrogen.

Groups $R^{1a}$ and $R^{1b}$

In some embodiments, each $R^{1a}$ and $R^{1b}$ is independently selected from the group consisting of hydrogen, halogen, cyano, substituted or unsubstituted $C_{1-6}$alkyl, substituted or unsubstituted $C_{3-6}$carbocyclyl, substituted or unsubstituted 3- to 6-membered heterocyclyl, substituted or unsubstituted aryl, substituted or unsubstituted heteroaryl, —$OR^{A1}$, —$N(R^{A1})_2$, —$C(\!\!=\!\!O)R^{A1}$, —$C(\!\!=\!\!O)OR^{A1}$, and —$C(\!\!=\!\!O)N(R^{A1})_2$, wherein each instance of $R^{A1}$ is independently selected from the group consisting of hydrogen, substituted or unsubstituted $C_{1-6}$alkyl, substituted or unsubstituted $C_{2-6}$alkenyl, substituted or unsubstituted $C_{2-6}$alkynyl, substituted or unsubstituted $C_{3-6}$carbocyclyl, substituted or unsubstituted 3- to 6-membered heterocyclyl, substituted or unsubstituted aryl, and substituted or unsubstituted heteroaryl.

In some embodiments, each $R^{1a}$ and $R^{1b}$ is independently selected from the group consisting of hydrogen, halogen, cyano, substituted or unsubstituted $C_{1-6}$alkyl, and —$OR^{A1}$ wherein $R^{A1}$ is selected from the group consisting of hydrogen, substituted or unsubstituted $C_{1-6}$alkyl, substituted or unsubstituted $C_{3-6}$carbocyclyl, substituted or unsubstituted 3- to 6-membered heterocyclyl, substituted or unsubstituted aryl, and substituted or unsubstituted heteroaryl.

In some embodiments, each $R^{1a}$ and $R^{1b}$ is independently selected from the group consisting of hydrogen, substituted or unsubstituted $C_{1-6}$ alkyl, and —$OR^{A1}$, wherein $R^{A1}$ is hydrogen or unsubstituted $C_{1-6}$alkyl.

In some embodiments, each of $R^{1a}$ and $R^{1b}$ is independently hydrogen or substituted or unsubstituted $C_{1-6}$ alkyl.

In some embodiments, $R^{1a}$ and $R^{1b}$ are both hydrogen.

Groups $R^{2a}$ and $R^{2b}$

In some embodiments, each $R^2$ and $R^{2b}$ is independently selected from the group consisting of hydrogen, halogen, cyano, substituted or unsubstituted $C_{1-6}$ alkyl, substituted or unsubstituted $C_{3-6}$ carbocyclyl, substituted or unsubstituted 3- to 6-membered heterocyclyl, substituted or unsubstituted aryl, substituted or unsubstituted heteroaryl, —$OR^{A1}$, $N(R^{A1})_2$, —$C(\!\!=\!\!O)R^{A1}$, —$C(\!\!=\!\!O)OR^{A1}$, and —$C(\!\!=\!\!O)N(R^{A1})_2$, wherein each instance of $R^{A1}$ is independently selected from the group consisting of hydrogen, substituted or unsubstituted $C_{1-6}$ alkyl, substituted or unsubstituted $C_{2-6}$ alkenyl, substituted or unsubstituted $C_{2-6}$alkynyl, substituted or unsubstituted $C_{3-6}$ carbocyclyl, or substituted or unsubstituted 3- to 6-membered heterocyclyl, substituted or unsubstituted aryl, and substituted or unsubstituted heteroaryl.

In some embodiments, each $R^2$ and $R^{2b}$ is independently selected from the group consisting of hydrogen, halogen, cyano, substituted or unsubstituted $C_{1-6}$ alkyl, and —$OR^{A1}$, wherein $R^{A1}$ is selected from the group consisting of hydrogen, substituted or unsubstituted $C_{1-6}$ alkyl, substituted or unsubstituted $C_{3-6}$ carbocyclyl, substituted or unsubstituted 3- to 6-membered heterocyclyl, substituted or unsubstituted aryl, and substituted or unsubstituted heteroaryl.

In some embodiments, each $R^2$ and $R^{2b}$ is independently selected from the group consisting of hydrogen, substituted or unsubstituted $C_{1-6}$ alkyl, and —$OR^{A1}$, wherein $R^{A1}$ is hydrogen or unsubstituted $C_{1-6}$ alkyl.

In some embodiments, each $R^2$ and $R^{2b}$ is independently selected from the group consisting of hydrogen, methyl, ethyl, methoxymethyl, and methoxy.

In some embodiments, $R^{2a}$ and $R^{2b}$ are both hydrogen.

Groups $R^{4a}$ and $R^{4b}$

In some embodiments, each $R^{4a}$ and $R^{4b}$ is independently selected from the group consisting of hydrogen, halogen, cyano, substituted or unsubstituted $C_{1-6}$ alkyl, substituted or unsubstituted $C_{3-6}$ carbocyclyl, substituted or unsubstituted 3- to 6-membered heterocyclyl, substituted or unsubstituted aryl, substituted or unsubstituted heteroaryl, —$OR^{A1}$,—$N(R^{A1})_2$, —$C(\!\!=\!\!O)R^{A1}$, —$C(\!\!=\!\!O)OR^{A1}$, and —$C(\!\!=\!\!O)N(R^{A1})_2$, wherein each instance of $R^{A1}$ is independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, or substituted or unsubstituted 3- to 6-membered heterocyclyl, substituted or unsubstituted aryl, and substituted or unsubstituted heteroaryl.

In some embodiments, each $R^{4a}$ and $R^{4b}$ is independently selected from the group consisting of hydrogen, halogen, cyano, substituted or unsubstituted $C_{1-6}$ alkyl, and —$OR^{A1}$ wherein $R^{A1}$ is selected from the group consisting of from hydrogen, substituted or unsubstituted $C_{1-6}$ alkyl, substituted or unsubstituted $C_{3-6}$ carbocyclyl, or substituted or unsubstituted 3- to 6-membered heterocyclyl, substituted or unsubstituted aryl, and substituted or unsubstituted heteroaryl.

In some embodiments, each $R^{4a}$ and $R^{4b}$ is independently selected from the group consisting of hydrogen, substituted or unsubstituted $C_{1-6}$ alkyl, and —$OR^{A1}$, wherein $R^{A1}$ is hydrogen or unsubstituted $C_{1-6}$ alkyl.

In some embodiments, each $R^{4a}$ and $R^{4b}$ is independently hydrogen or substituted or unsubstituted $C_{1-6}$ alkyl.

In some embodiments, $R^{4a}$ and $R^{4b}$ are both hydrogen.

Groups $R^{7a}$ and $R^{7b}$

In some embodiments, each $R^{7a}$ and $R^{7b}$ is independently selected from the group consisting of hydrogen, halogen, cyano, substituted or unsubstituted $C_{1-6}$ alkyl, substituted or unsubstituted $C_{3-6}$ carbocyclyl, substituted or unsubstituted 3- to 6-membered heterocyclyl, substituted or unsubstituted aryl, substituted or unsubstituted heteroaryl, —$OR^{A1}$, —$N(R^{A1})_2$, —$C(\!\!=\!\!O)R^{A1}$, —$C(\!\!=\!\!O)OR^{A1}$, and —$C(\!\!=\!\!O)N(R^{A1})_2$, wherein each instance of $R^{A1}$ is independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, or substituted or unsubstituted 3- to 6-membered heterocyclyl, substituted or unsubstituted aryl, and substituted or unsubstituted heteroaryl.

In some embodiments, each $R^{7a}$ and $R^{7b}$ is independently selected from the group consisting of hydrogen, halogen, cyano, substituted or unsubstituted $C_{1-6}$ alkyl, and —$OR^{A1}$ wherein $R^{A1}$ is selected from the group consisting of from hydrogen, substituted or unsubstituted $C_{1-6}$ alkyl, substituted or unsubstituted $C_{3-6}$ carbocyclyl, or substituted or unsubstituted 3- to 6-membered heterocyclyl, substituted or unsubstituted aryl, and substituted or unsubstituted heteroaryl.

In some embodiments, each $R^{7a}$ and $R^{7b}$ is independently selected from the group consisting of hydrogen, substituted or unsubstituted $C_{1-6}$ alkyl, and —$OR^{A1}$, wherein $R^{A1}$ is hydrogen or unsubstituted $C_{1-6}$ alkyl.

In some embodiments, each $R^{7a}$ and $R^{7b}$ is independently hydrogen or substituted or unsubstituted $C_{1-6}$ alkyl.

In some embodiments, $R^{7a}$ and $R^{7b}$ are both hydrogen.
Groups $R^{11a}$ and $R^{11b}$ In some embodiments, each $R^{11a}$ and $R^{11b}$ is independently selected from the group consisting of hydrogen, halogen, cyano, substituted or unsubstituted $C_{1-6}$ alkyl, substituted or unsubstituted $C_{3-6}$ carbocyclyl, substituted or unsubstituted 3- to 6-membered heterocyclyl, substituted or unsubstituted aryl, substituted or unsubstituted heteroaryl, —$OR^{41}$, —$N(R^{41})_2$, —$C(=O)R^{41}$, —$C(=O)OR^{41}$, and —$C(=O)N(R^{41})_2$, wherein each instance of $R^{41}$ is independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, or substituted or unsubstituted 3- to 6-membered heterocyclyl, substituted or unsubstituted aryl, and substituted or unsubstituted heteroaryl.

In some embodiments, each $R^{11a}$ and $R^{11b}$ is independently selected from the group consisting of hydrogen, halogen, cyano, substituted or unsubstituted $C_{1-6}$ alkyl, and —$OR^{41}$ wherein $R^{41}$ is independently selected from the group consisting of hydrogen, substituted or unsubstituted $C_{1-6}$ alkyl, substituted or unsubstituted $C_{3-6}$ carbocyclyl, or substituted or unsubstituted 3- to 6-membered heterocyclyl, substituted or unsubstituted aryl, and substituted or unsubstituted heteroaryl.

In some embodiments, each $R^{11a}$ and $R^{11b}$ is independently selected from the group consisting of hydrogen, substituted or unsubstituted $C_{1-6}$ alkyl, and —$OR^{41}$, wherein $R^{41}$ is hydrogen or unsubstituted $C_{1-6}$ alkyl.

In some embodiments, each $R^{11a}$ and $R^{11b}$ is independently hydrogen or substituted or unsubstituted $C_{1-6}$ alkyl.

In some embodiments, $R^{11a}$ and $R^{11b}$ are both hydrogen.
Groups $R^{12a}$ and $R^{12b}$ In some embodiments, each $R^{12a}$ and $R^{12b}$ is independently selected from the group consisting of hydrogen, halogen, cyano, substituted or unsubstituted $C_{1-6}$ alkyl, substituted or unsubstituted $C_{3-6}$ carbocyclyl, substituted or unsubstituted 3- to 6-membered heterocyclyl, substituted or unsubstituted aryl, substituted or unsubstituted heteroaryl, —$OR^{41}$, —$N(R^{41})_2$, —$C(=O)R^{41}$, —$C(=O)OR^{41}$, and —$C(=O)N(R^{41})_2$, wherein each instance of $R^{41}$ is independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, or substituted or unsubstituted 3- to 6-membered heterocyclyl, substituted or unsubstituted aryl, and substituted or unsubstituted heteroaryl.

In some embodiments, each $R^{12a}$ and $R^{12b}$ is independently selected from the group consisting of hydrogen, halogen, cyano, substituted or unsubstituted $C_{1-6}$ alkyl, and —$OR^{41}$, wherein $R^{41}$ is independently selected from the group consisting of hydrogen, substituted or unsubstituted $C_{1-6}$ alkyl, substituted or unsubstituted $C_{3-6}$ carbocyclyl, or substituted or unsubstituted 3- to 6-membered heterocyclyl, substituted or unsubstituted aryl, and substituted or unsubstituted heteroaryl.

In some embodiments, each $R^{12a}$ and $R^{12b}$ is independently selected from the group consisting of hydrogen, substituted or unsubstituted $C_{1-6}$ alkyl, and —$OR^{41}$, wherein $R^{41}$ is hydrogen or unsubstituted $C_{1-6}$ alkyl.

In some embodiments, each $R^{12a}$ and $R^{12b}$ is independently hydrogen or substituted or unsubstituted $C_{1-6}$ alkyl.

In some embodiments, $R^{12a}$ and $R^{12b}$ are both hydrogen.
Groups $R^{6a}$ and $R^{6b}$ In some embodiments, each $R^{6a}$ and $R^{6b}$ is independently selected from the group consisting of hydrogen, halogen, substituted or unsubstituted $C_{1-6}$ alkyl, substituted or unsubstituted $C_{2-6}$ alkenyl, and substituted or unsubstituted $C_{2-6}$ alkynyl.

In some embodiments, each $R^{6a}$ and $R^{6b}$ is independently hydrogen or substituted or unsubstituted $C_{1-6}$ alkyl.

In some embodiments, each $R^{6a}$ and $R^{6b}$ is independently hydrogen or unsubstituted $C_{1-6}$ alkyl.

In some embodiments, $R^{6a}$ and $R^{6b}$ are both hydrogen.
Groups $R^{15a}$ and $R^{15b}$ In some embodiments, each $R^{15a}$ and $R^{15b}$ is independently selected from the group consisting of hydrogen, halogen, substituted or unsubstituted $C_{1-6}$ alkyl, substituted or unsubstituted $C_{3-6}$ carbocyclyl, and substituted or unsubstituted heteroaryl.

In some embodiments, each $R^{15a}$ and $R^{15b}$ is independently selected from the group consisting of hydrogen, unsubstituted $C_{1-6}$ alkyl, and unsubstituted $C_{3-6}$ carbocyclyl.

In some embodiments, each $R^{15a}$ and $R^{15b}$ is independently selected from the group consisting of hydrogen, methyl, and cyclopropyl.

In some embodiments, $R^{15a}$ and $R^{15b}$ are both hydrogen.
Groups $R^{16a}$ and $R^{16b}$ In some embodiments, each $R^{16a}$ and $R^{16b}$ is independently selected from the group consisting of hydrogen, halogen, substituted or unsubstituted $C_{1-6}$ alkyl, substituted or unsubstituted $C_{3-6}$ carbocyclyl, and substituted or unsubstituted heteroaryl.

In some embodiments, each $R^{16a}$ and $R^{16b}$ is independently hydrogen or substituted or unsubstituted $C_{1-6}$ alkyl.

In some embodiments, each $R^{16a}$ and $R^{16b}$ is independently hydrogen or unsubstituted $C_{1-6}$ alkyl.

In some embodiments, each $R^{16a}$ and $R^{16b}$ are both hydrogen.
Group $R^3$ In some embodiments, $R^3$ is selected from the group consisting of substituted or unsubstituted $C_{1-6}$ alkyl, substituted or unsubstituted $C_{2-6}$ alkenyl, and substituted or unsubstituted $C_{2-6}$ alkynyl.

In some embodiments, $R^3$ is substituted or unsubstituted $C_1$-$C_6$alkyl.

In some embodiments, $R^3$ is $C_{1-3}$ alkyl optionally substituted with $C_{1-3}$ alkoxy.

In some embodiments, $R^3$ is selected from the group consisting of methyl, ethyl, n-propyl, —$CH_2OCH_3$, and —$CH_2OCH_2CH_3$.

In some embodiments, $R^3$ is methyl.
Group $R^{19}$

In some embodiments, $R^{19}$ is hydrogen or substituted or unsubstituted $C_{1-6}$alkyl.

In some embodiments, $R^{19}$ is hydrogen or unsubstituted $C_{1-3}$alkyl.

In some embodiments, $R^{19}$ is selected from the group consisting of hydrogen, methyl, and ethyl.

In some embodiments, $R^{19}$ is hydrogen.

In some embodiments, $R^{19}$ is unsubstituted $C_1$-$C_3$alkyl.

In some embodiments $R^{19}$ is methyl or ethyl.

In some embodiments $R^{19}$ is methyl.

In some embodiments, $R^{19}$ is ethyl.
Group $R^X$ and/or Group $R^Y$

In some embodiments, $R^X$ is selected from the group consisting of halo, —CN, —OH, —$OR^{Q1}$, and substituted or unsubstituted $C_{1-3}$alkyl.

In some embodiments, $R^X$ is selected from the group consisting of halo, —CN, —OH, —$OR^{Q1}$, and unsubstituted $C_{1-3}$alkyl.

In some embodiments, $R^X$ is selected from the group consisting of fluoro, —CN, —OH, —OCH$_3$, and methyl.

In some embodiments, $R^X$ is —OH.

In some embodiments, $R^X$ is fluoro.

In some embodiments, $R^X$ is unsubstituted C$_1$-C$_3$alkylene-OR$^{Q1}$

In some embodiments, $R^Y$ is halo or unsubstituted C$_{1-6}$alkyl.

In some embodiments, $R^Y$ is halo or unsubstituted C$_{1-3}$alkyl.

In some embodiments, $R^Y$ is selected from the group consisting of methyl, ethyl, and n-propyl.

In some embodiments, $R^Y$ is methyl.

In some embodiments, $R^Y$ is fluoro.

In some embodiments, $R^Y$ and $R^X$ join together with the intervening atoms to form a substituted or unsubstituted C$_{3-6}$carbocyclyl or a substituted or unsubstituted 3- to 6-membered heterocyclyl.

In some embodiments $R^Y$ and $R^X$ join together with the intervening atoms to form an unsubstituted C$_{3-6}$ carbocyclyl or an unsubstituted 3- to 6-membered heterocyclyl.

In some embodiments, $R^Y$ and $R^X$ join together with the intervening atoms to forma substituted or unsubstituted 4-membered carbocyclyl.

In some embodiments, $R^Y$ and $R^X$ join together with the intervening atoms to forma substituted or unsubstituted 4-membered heterocyclyl.

In some embodiments, the 4-membered heterocyclic ring contains a heteroatom selected from N, O, and S.

In some embodiments, $R^Y$ and $R^X$ join together to form an oxetane.

Group R$^{Q1}$

In some embodiments, R$^{Q1}$ is unsubstituted C$_{1-6}$alkyl.

In some embodiments, R$^{Q1}$ is unsubstituted C$_{1-3}$alkyl.

In some embodiments, R$^{Q1}$ is selected from the group consisting of methyl, ethyl, and n-propyl.

In some embodiments, R$^{Q1}$ is methyl.

Group R$^{22}$

In some embodiments, each R$^{22}$ is independently selected from the group consisting of halogen, —NO$_2$, —CN, —OR$^{GA}$, —N(R$^{GA}$)$_2$, —C(=O)R$^{GA}$, —C(=O)OR$^{GA}$, —N(R$^{GA}$)C(=O)R$^{GA}$, —SR$^{GA}$, —S(=O) R$^{GA}$, —S(=O)$_2$R$^{GA}$, —S(=O)$_2$R$^{GA}$, —OS(=O)$_2$R$^{GA}$, —S(=O)$_2$N(R$^{GA}$)$_2$, substituted or unsubstituted C$_{1-6}$ alkyl, substituted or unsubstituted C$_{3-6}$ carbocylyl, and substituted or unsubstituted 3- to 6-membered heterocyclyl, wherein each instance of R$^{GA}$ is independently selected from the group consisting of hydrogen, substituted or unsubstituted C$_{1-6}$ alkyl, substituted or unsubstituted C$_{3-6}$ carbocylyl, substituted or unsubstituted 3- to 6-membered heterocyclyl, substituted or unsubstituted aryl, and substituted or unsubstituted heteroaryl.

In some embodiments, each R$^{22}$ is independently selected from the group consisting of halogen, —CN, substituted or unsubstituted C$_{1-3}$ alkyl, substituted or unsubstituted 3- to 6-membered heterocyclyl, and —OR$^{GA}$, wherein R$^{GA}$ is hydrogen or substituted or unsubstituted C$_{1-3}$ alkyl.

In some embodiments, R$^{22}$ is —CN or C$_{1-3}$ alkyl optionally substituted with oxo.

In some embodiments, R$^{22}$ is located at the 4-position of the pyrazolyl. In some embodiments, R$^{22}$ is located at the 3-position of the pyrazolyl. In another embodiment, R$^{22}$ is located at the 5-position of the pyrazolyl.

In some embodiments, R$^{22}$ is —CN.

In another embodiment, R$^{22}$ is —CN located at the 4-position of the pyrazolyl.

Integer n

In some embodiments n is 1, 2, or 3.

In some embodiments, n is 1 or 2.

In some embodiments n is 0 or 1.

In some embodiments n is 0. In some embodiments n is 1. In some embodiments n is 2. In some embodiments n is 3.

Group R$^5$

In some embodiments, R$^5$ is hydrogen.

In some embodiments, R$^5$ is a hydrogen in the alpha or beta configuration.

In some embodiments, R$^5$ is a hydrogen in the alpha configuration.

In some embodiments, R$^5$ is a hydrogen in the beta configuration.

In some embodiments, the compound of Formula I is a compound of Formula I-b1:

(I-b1)

or a pharmaceutically acceptable salt thereof.

In some embodiments, the compound of Formula I is a compound of Formula I-c3 or Formula I-c4:

(I-c3)

(I-c4)

or a pharmaceutically acceptable salt thereof.

In some embodiments, the compound of Formula I is a compound of Formula I-d3 or Formula I-d4:

(I-d3)

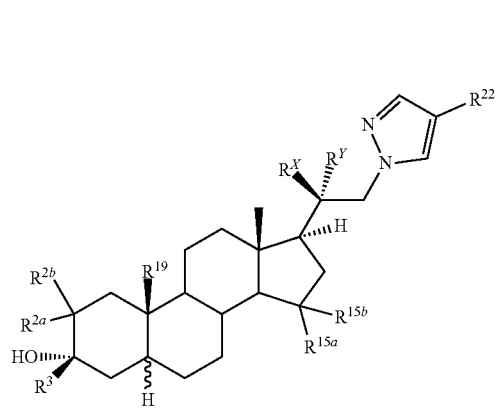

(I-d4)

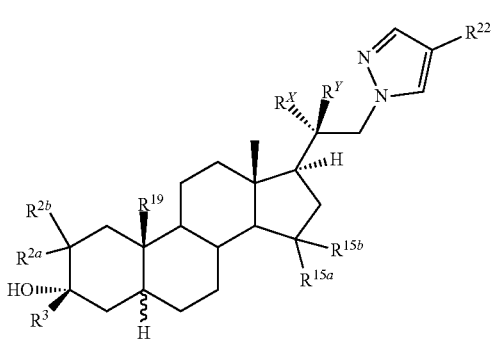

or a pharmaceutically acceptable salt thereof.

In some embodiments, the compound of Formula I is a compound of Formula I-e5, Formula I-e6, Formula I-e7, or Formula I-e8:

(I-e5)

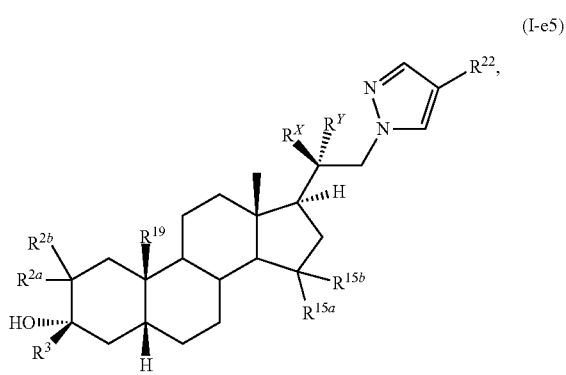

-continued (I-e6)

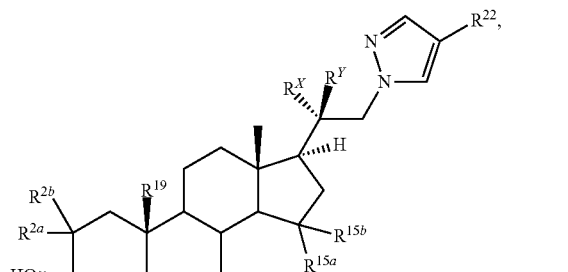

(I-e7)

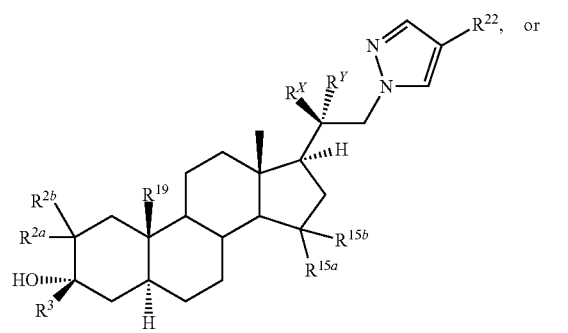

(I-e8)

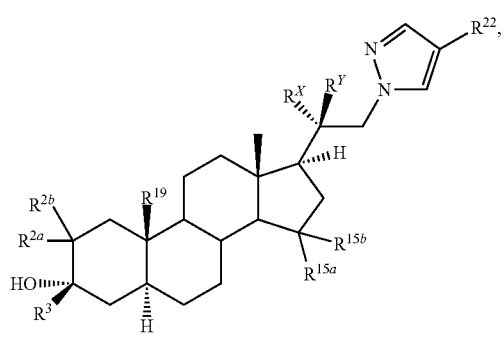

or a pharmaceutically acceptable salt thereof.

In some embodiment, the compound of Formula I is a compound of Formula I-e5, (I-Ib1)

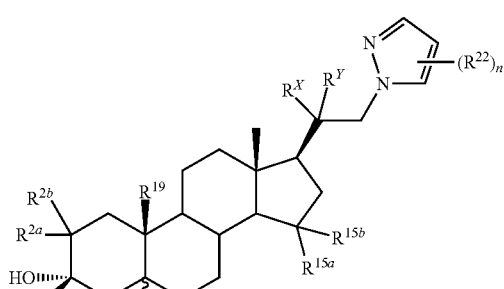

or a pharmaceutically acceptable salt thereof,
wherein $R^{22}$ is CN;
n is 1;
$R^{19}$ is selected from the group consisting of hydrogen, ethyl, and methyl;
$R^{15a}$ and $R^{15b}$ is independently selected from the group consisting of hydrogen, methyl, and cyclopropyl;
$R^{2a}$ and $R^{2b}$ is each independently selected from the group consisting of hydrogen, methyl, ethyl, methoxymethyl, and methoxy;
$R^3$ is selected from the group consisting of unsubstituted $C_{1-3}$ alkyl, —$CH_2OCH_3$, and —$CH_2OCH_2CH_3$; and
$R^X$ and $R^Y$ are as defined herein.

In one embodiment, the compound is a compound of Formula I-Ic1 or Formula I-Ic2:

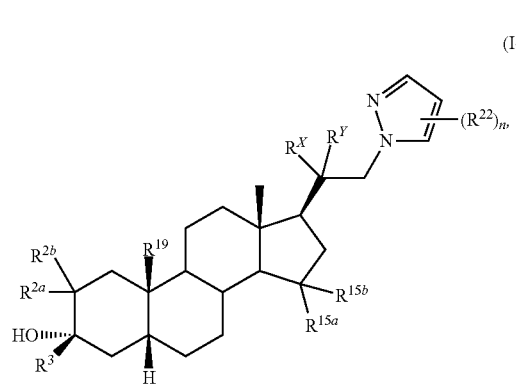
(I-Ic1)

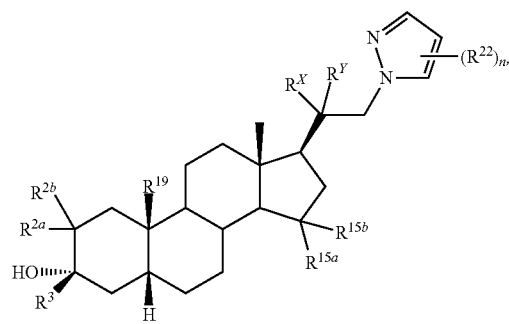
(I-Ic2)

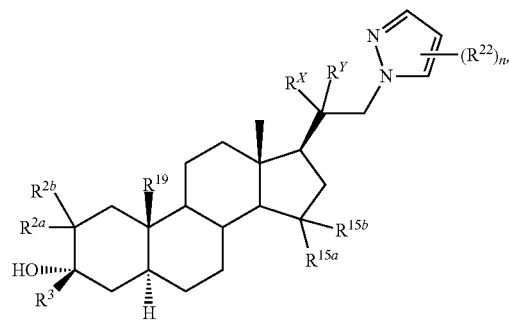

or a pharmaceutically acceptable salt thereof,
wherein $R^{22}$ is CN;
n is 1;
$R^{19}$ is selected from the group consisting of hydrogen, ethyl, and methyl;
$R^{15a}$ and $R^{15b}$ is independently selected from the group consisting of hydrogen, methyl, and cyclopropyl;
$R^{2a}$ and $R^{2b}$ is each independently selected from the group consisting of hydrogen, methyl, ethyl, methoxymethyl, and methoxy;
$R^3$ is selected from the group consisting of unsubstituted $C_{1-3}$ alkyl, —$CH_2OCH_3$, and —$CH_2OCH_2CH_3$; and
$R^X$ and $R^Y$ are as defined herein.

In one embodiment, the compound is a compound of Formula I-Id1 or Formula I-Id2:

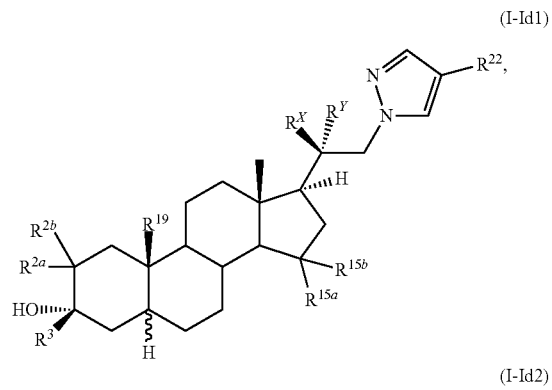
(I-Id1)

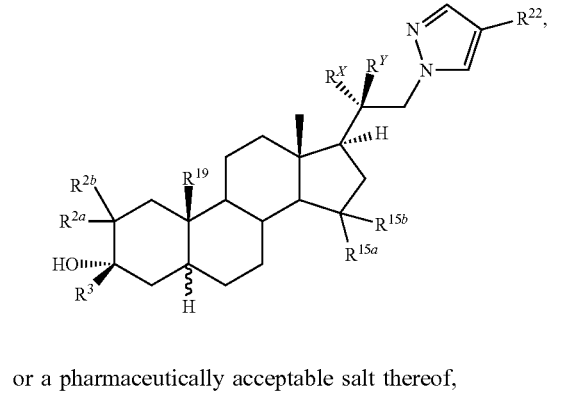
(I-Id2)

or a pharmaceutically acceptable salt thereof,
wherein $R^{22}$ is CN;
$R^{19}$ is selected from the group consisting of hydrogen, ethyl, and methyl;
$R^{15a}$ and $R^{15b}$ is independently selected from the group consisting of hydrogen, methyl, and cyclopropyl;
$R^{2a}$ and $R^{2b}$ is each independently selected from the group consisting of hydrogen, methyl, ethyl, methoxymethyl, and methoxy;
$R^3$ is selected from the group consisting of unsubstituted $C_{1-3}$alkyl, —$CH_2OCH_3$, and —$CH_2OCH_2CH_3$; and
$R^X$ and $R^Y$ are as defined herein.

In one embodiment, the compound is a compound of Formula I-Ie1, Formula I-Ie2, Formula I-e3, or Formula I-e4:

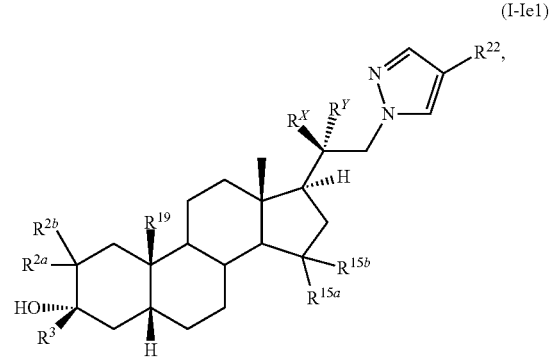
(I-Ie1)

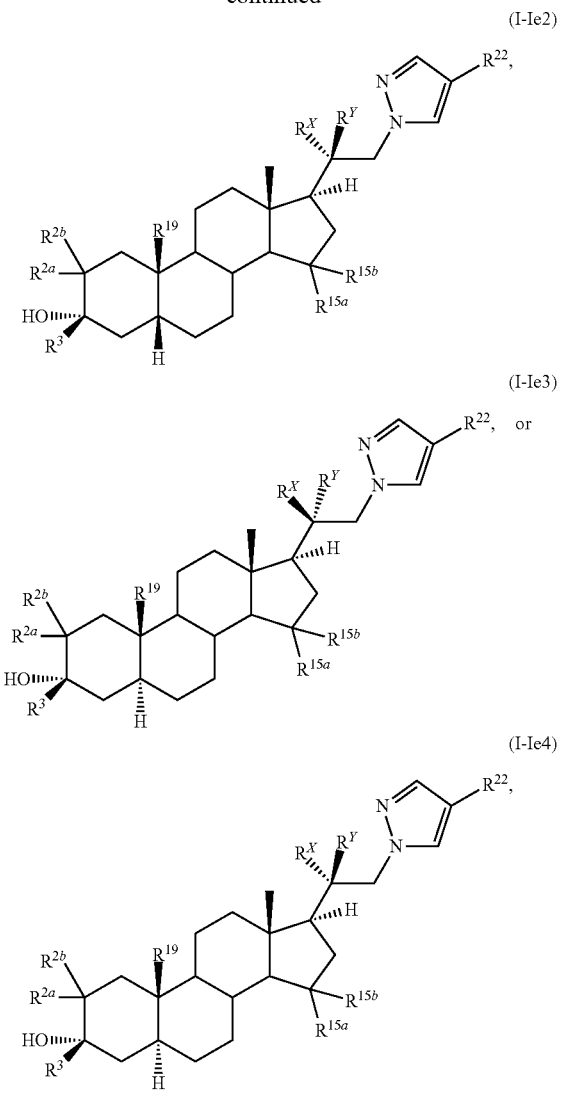

or a pharmaceutically acceptable salt thereof,
wherein $R^{22}$ is CN $R^{19}$ is selected from the group consisting of hydrogen, ethyl, and methyl;

$R^{15a}$ and $R^{15b}$ is independently selected from the group consisting of hydrogen, methyl, and cyclopropyl;

$R^{2a}$ and $R^{2b}$ is each independently selected from the group consisting of hydrogen, methyl, ethyl, methoxymethyl, and methoxy;

$R^3$ is selected from the group consisting of unsubstituted $C_{1-3}$alkyl, —$CH_2OCH_3$, and —$CH_2OCH_2CH_3$; and $R^X$ and $R^Y$ are as defined herein.

In some embodiments, a pharmaceutical composition comprises a compound described herein or pharmaceutically acceptable salt thereof, and a pharmaceutically acceptable excipient.

In some embodiments, a method of treating a CNS-related disorder in a subject in need thereof, comprises administering to the subject an effective amount of a compound described herein or a pharmaceutically acceptable salt thereof. In some embodiments, the CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, tinnitus, or status epilepticus. In some embodiments, the CNS-related disorder is depression. In some embodiments, the CNS-related disorder is postpartum depression. In some embodiments, the CNS-related disorder is major depressive disorder. In some embodiments, the major depressive disorder is moderate major depressive disorder. In some embodiments, the major depressive disorder is severe major depressive disorder.

In some embodiments, the compound is selected from the group consisting of the compounds identified in Table 1 below:

TABLE 1

| Compound No. | Structure |
|---|---|
| 1 | 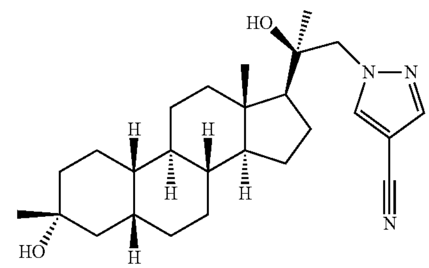 |
| 2 | 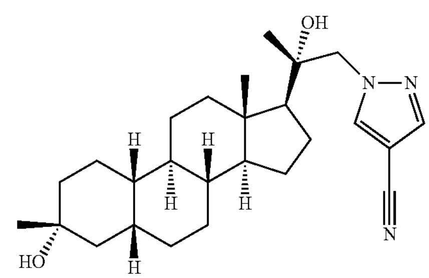 |
| 3 | 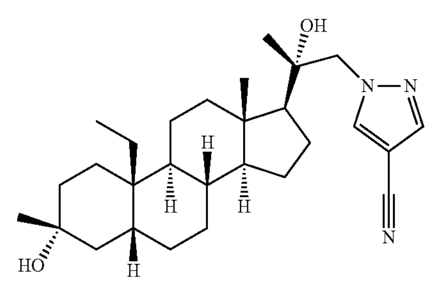 |
| 4 | 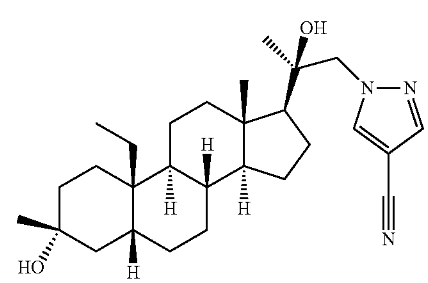 |

TABLE 1-continued
| Compound No. | Structure |
|---|---|
| 5 | 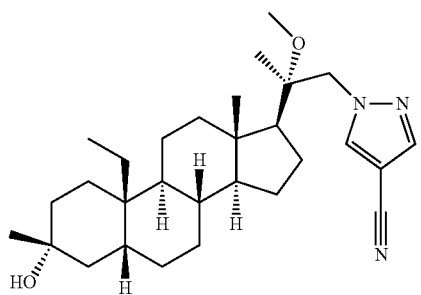 |
| 6 | 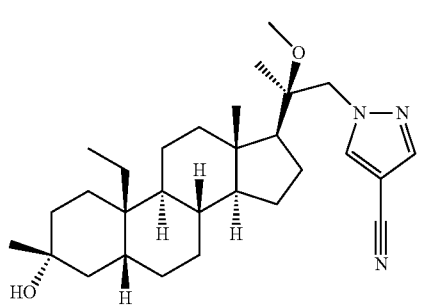 |
| 7 | 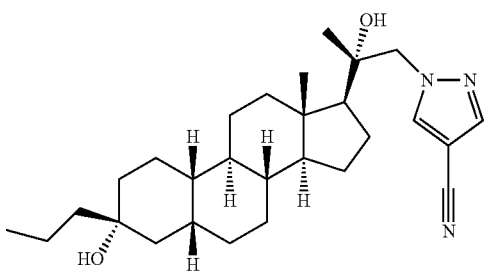 |
| 8 | 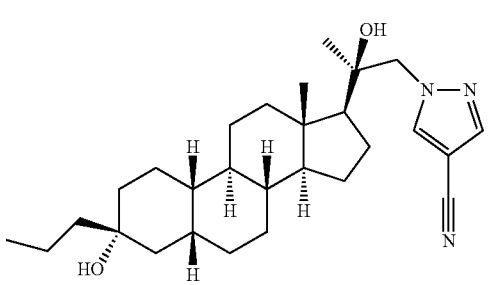 |
| 9 | 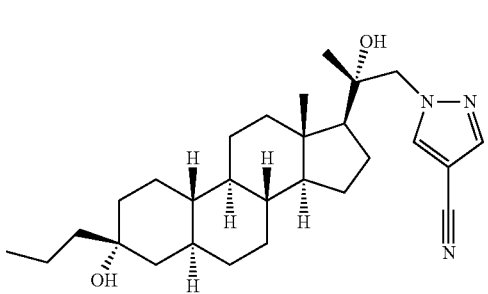 |
| 10 | 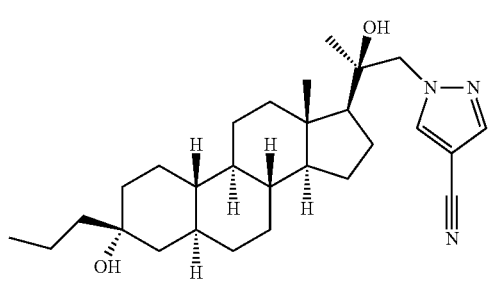 |
| 11 | 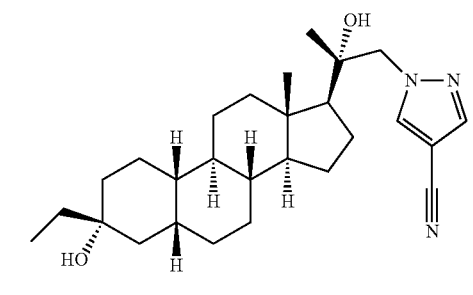 |
| 12 | 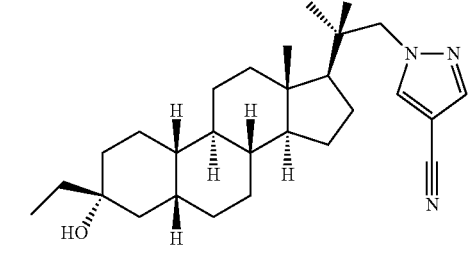 |
| 13 | 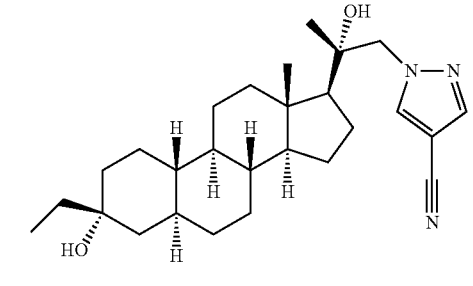 |
| 14 | 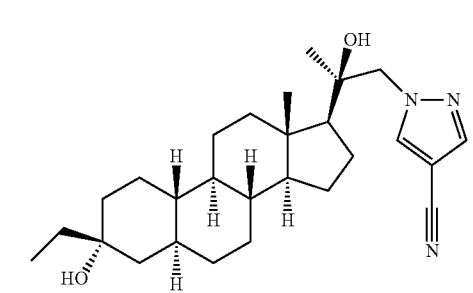 |

TABLE 1-continued

| Compound No. | Structure |
|---|---|
| 15 | 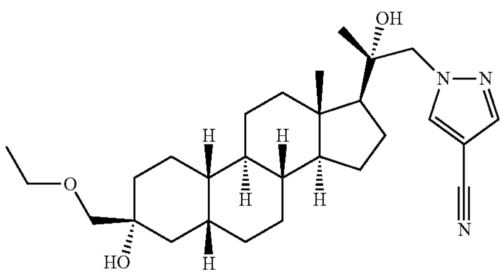 |
| 16 | 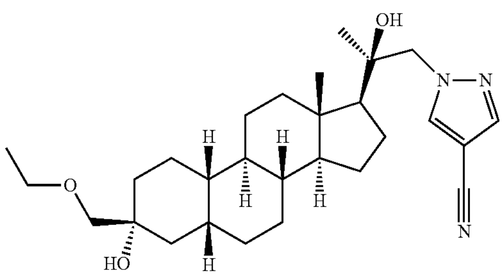 |
| 17 | 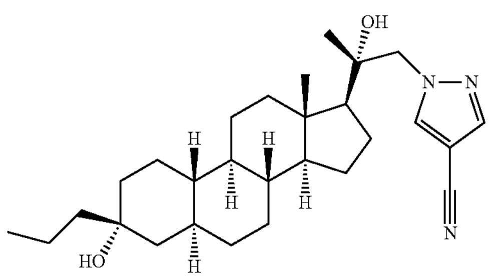 |
| 18 | 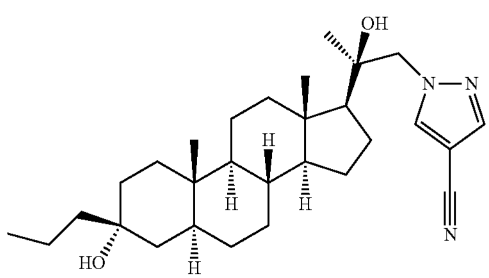 |
| 19 | 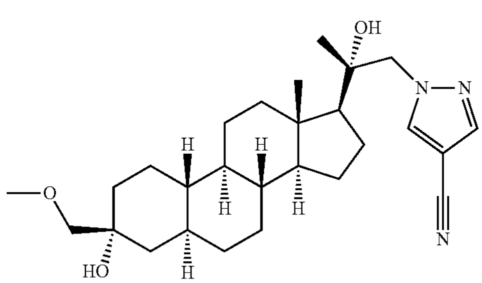 |
| 20 | 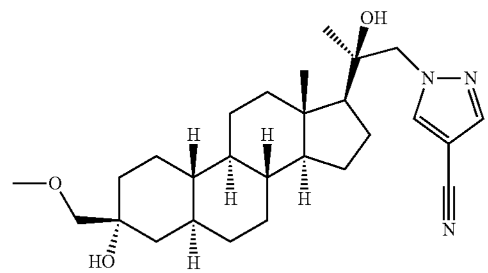 |
| 21 | 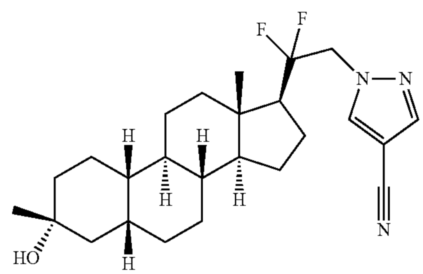 |
| 22 | 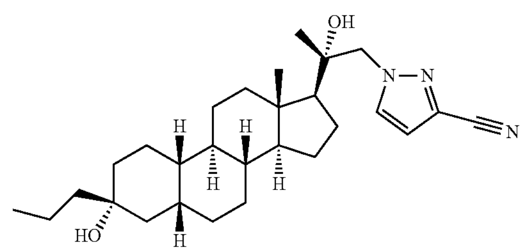 |
| 23 | 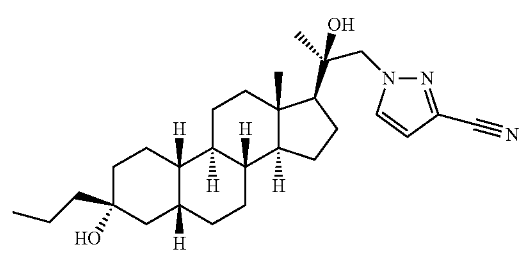 |
| 24 | 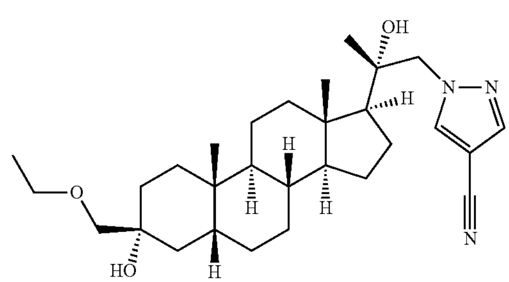 |

TABLE 1-continued

| Compound No. | Structure |
|---|---|
| 25 | 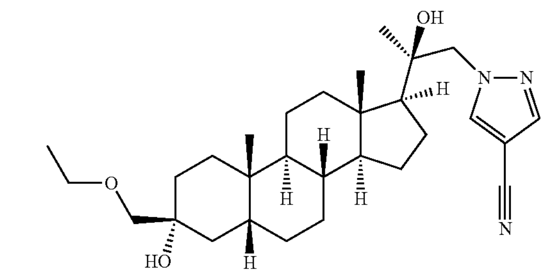 |
| 26 | 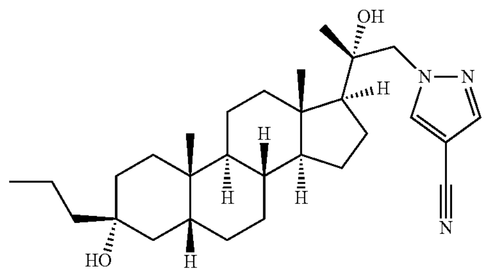 |
| 27 | 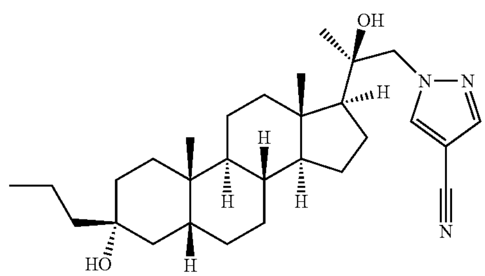 |
| 28 | 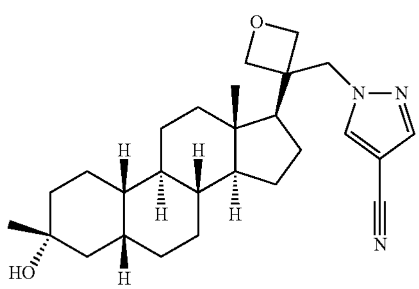 |
| 29 | 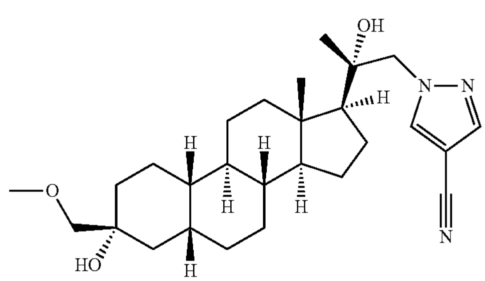 |
| 30 | |
| 31 | |
| 32 | |
| 33 | |
| 34 | |

TABLE 1-continued

| Compound No. | Structure |
|---|---|
| 35 | (structure) |
| 36 | (structure) |
| 37 | (structure) |
| 38 | (structure) |
| 39 | (structure) |
| 40 | (structure) |
| 41 | (structure) |
| 42 | (structure) |
| 43 | (structure) |
| 44 | (structure) |

TABLE 1-continued

| Compound No. | Structure |
|---|---|
| 45 | 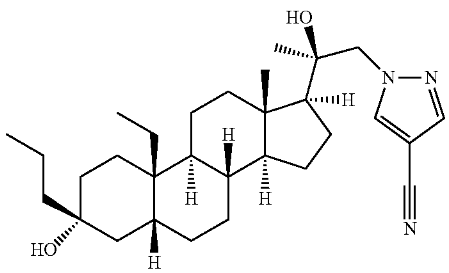 |
| 46 | 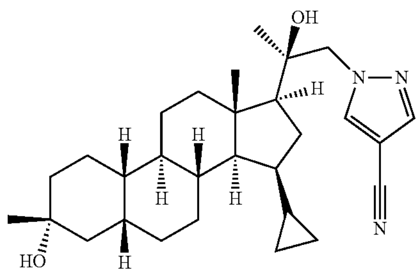 |
| 47 | 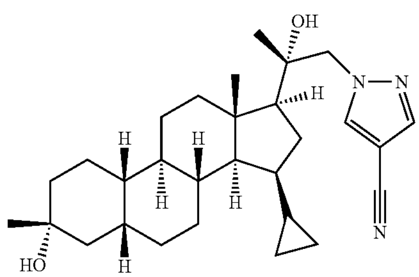 |
| 48 | 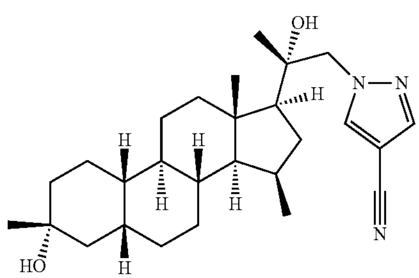 |
| 49 | 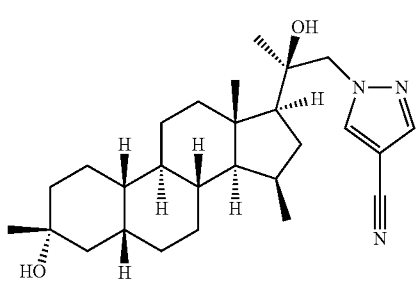 |
| 50 | |
| 51 | |
| 52 | |
| 53 | |
| 54 | |

TABLE 1-continued

| Compound No. | Structure |
|---|---|
| 55 | 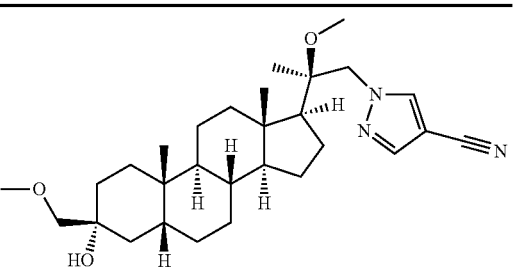 |
| 56 | 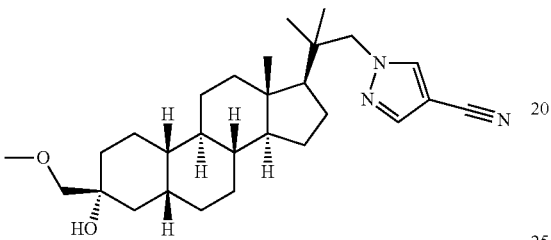 |
| 57 | 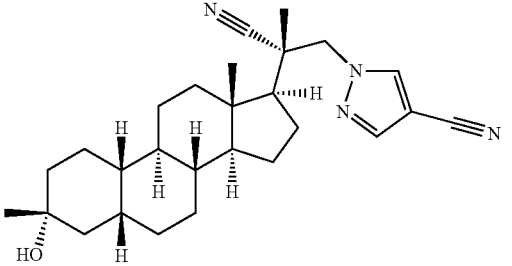 |
| 58 | 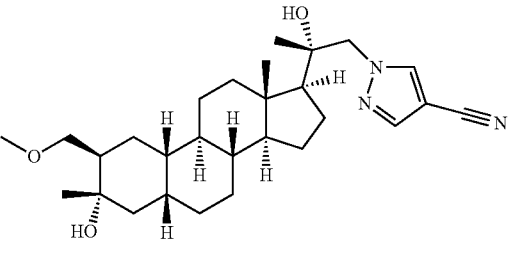 |
| 59 | 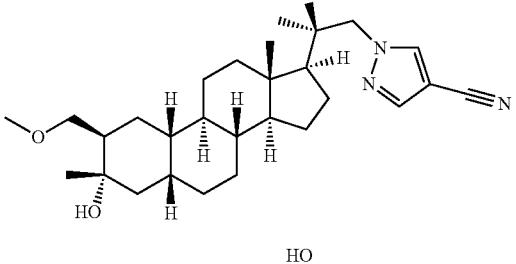 |
| 58A | 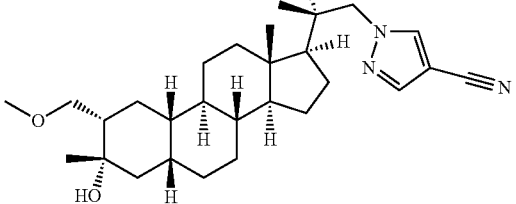 |
| 59A | 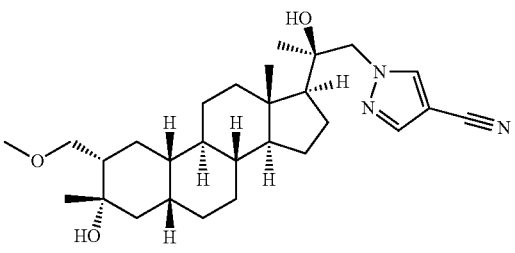 |
| 60 | 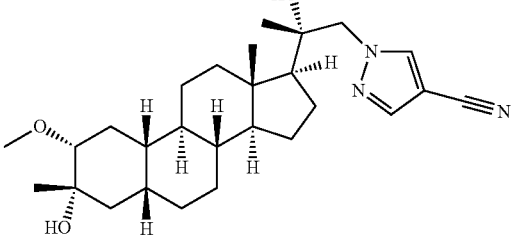 |
| 61 | 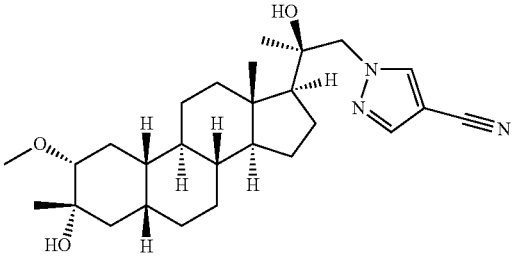 |

In one aspect, provided herein is a pharmaceutically acceptable salt of a compound described herein (e.g., a compound of Formula (I)).

In one aspect, provided herein is a pharmaceutical composition comprising a compound described herein (e.g., a compound of Formula (I)) or a pharmaceutically acceptable salt thereof, and a pharmaceutically acceptable excipient. In certain embodiments, the compound of the present invention is provided in an effective amount in the pharmaceutical composition. In certain embodiments, the compound of the present invention is provided in a therapeutically effective amount.

Compounds of the present invention as described herein, act, in certain embodiments, as GABA modulators, e.g., effecting the $GABA_A$ receptor in either a positive or negative manner. As modulators of the excitability of the central nervous system (CNS), as mediated by their ability to modulate $GABA_A$ receptor, such compounds are expected to have CNS-activity.

Thus, in another aspect, provided are methods of treating a CNS-related disorder in a subject in need thereof, comprising administering to the subject an effective amount of a compound of the present invention. In certain embodiments, CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, tinnitus, or status epilepticus. In certain embodiments, the CNS-related disorder is depression. In certain embodiments, the CNS-related disorder is postpartum depression. In certain embodiments, the CNS-related disorder is major depressive disorder. In certain embodiments, the major depressive disorder is moderate major depressive disorder. In certain embodiments, the major depressive disorder is severe major depressive disorder. In certain embodiments, the compound is administered orally, subcutaneously, intravenously, or intramuscularly. In certain embodiments, the compound is administered orally. In certain embodiments, the compound is administered chronically. In certain embodiments, the compound is administered continuously, e.g., by continuous intravenous infusion.

Exemplary compounds of the invention may be synthesized from the following known starting materials using methods known to one skilled in the art or certain references, In one aspect, provided herein is a pharmaceutically acceptable salt of a compound described herein (e.g., a compound of Formula (I)).

Alternative Embodiments

In an alternative embodiment, compounds described herein may also comprise one or more isotopic substitutions. For example, hydrogen may be 2H (D or deuterium) or 3H (T or tritium); carbon may be, for example, $^{13}$C or 14C; oxygen may be, for example, 18O; nitrogen may be, for example, $^{15}$N, and the like. In other embodiments, a particular isotope (e.g., 3H, $^{13}$C, 14C, $^{18}$O, or $^{15}$N) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Pharmaceutical Compositions

In one aspect, provided herein is a pharmaceutical composition comprising a compound described herein (e.g., a compound of Formula (I)) or a pharmaceutically acceptable salt thereof, and a pharmaceutically acceptable excipient. In certain embodiments, the compound of the present invention is provided in an effective amount in the pharmaceutical composition. In certain embodiments, the compound of the present invention is provided in a therapeutically effective amount.

In certain embodiments, the pharmaceutical composition comprises an effective amount of the active ingredient. In certain embodiments, the pharmaceutical composition comprises a therapeutically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 20 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 5 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The compounds of the present invention can also be administered in sustained release forms or from sustained release drug delivery systems. A description of representative sustained release materials can be found in *Remington's Pharmaceutical Sciences*.

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{st}$ Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as CAPTISOL. See, e.g., U.S. Pat. No. 5,376,645. In certain embodiments, the composition comprises hexapropyl-β-cyclodextrin. In a more particular embodiment, the composition comprises hexapropyl-β-cyclodextrin (10-50% in water).

The injectable composition can be sterilized, for example, by filtration through a bacterial-retaining filter, or by incorporating sterilizing agents in the form of sterile solid compositions which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* $21^{st}$ ed., Lippincott Williams & Wilkins, 2005.

In one aspect, provided is a kit comprising a composition (e.g., a solid composition) comprising a compound of Formula (I).

Combination Therapy

A compound or composition described herein (e.g., a compound of Formula I, or a pharmaceutical salt thereof, or a composition comprising a compound of Formula I, or a pharmaceutically acceptable salt thereof) may be administered in combination with an additional agent or therapy. A subject to be administered a compound disclosed herein may have a disease, disorder, or condition, or a symptom thereof, that would benefit from treatment with another agent or therapy. Combination therapy may be achieved by administering two or more agents, each of which is formulated and administered separately, or by administering two or more agents in a single formulation. In some embodiments, the two or more agents in the combination therapy can be administered simultaneously. In other embodiments, the two or more agents in the combination therapy are administered separately. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination using different sequencing of the component agents. For example, if agent X and agent Y are used in a combination, one could administer them sequentially in any combination one or more times, e.g., in the order X-Y-X, X-X-Y, Y-X-Y, Y-Y-X, X-X-Y-Y, etc. Exemplary additional agents are described below.

Selective Serotonin Reuptake Inhibitor (SSRI)

In some embodiments, the compound or composition described herein (e.g., a compound of Formula I, or a pharmaceutical salt thereof, or a composition comprising a compound of Formula I, or a pharmaceutically acceptable salt thereof) is administered in combination with an SSRI(s). SSRIs include antidepressants that increase the level of serotonin in the brain. Exemplary SSRIs include, but are not limited to, Citalopram (Celexa), Escitalopram (Lexapro), Fluoxetine (Prozac), Fluvoxamine (Luvox), Paroxetine (Paxil), and Sertraline (Zoloft).

Norepinephrine Reuptake Inhibitor (NERI)

In some embodiments, the compound or composition described herein (e.g., a compound of Formula I, or a pharmaceutical salt thereof, or a composition comprising a compound of Formula I, or a pharmaceutically acceptable salt thereof) is administered in combination with an NERI(s). Exemplary NERIs include, but are not limited to, Atomoxetine (Strattera), Reboxetine (Edronax, Vestra), Bupropion (Wellbutrin, Zyban), Duloxetine, Desipramine (Norpramin), Amedalin (UK-3540-1), Daledalin (UK-3557-15), Edivoxetine (LY-2216684), Esreboxetine, Lortalamine (LM-1404), Nisoxetine (LY-94,939), Talopram (tasulopram) (Lu 3-010), Talsupram (Lu 5-005), Tandamine (AY-23,946), and Viloxazine (Vivalan).

Antipsychotics

In some embodiments, the compound or composition described herein (e.g., a compound of Formula I, or a pharmaceutical salt thereof, or a composition comprising a compound of Formula I, or a pharmaceutically acceptable salt thereof) is administered in combination with an antipsychotic agent(s). Antipsychotics include D2 antagonists, lowering dopaminergic neurotransmission in the dopamine pathways. Exemplary antipsychotics include, but are not limited to, Asenapine (Saphris), Aripiprazole (Abilify), Cariprazine (Vrayar), Clozapine (Clozaril), Droperidol, Fluperlapine, Mesoridazine, Quetiapine Hemifumarate, Raclopride, Spiperone, Sulpiride, Trimethobenzamide hydrochloride, Trifluoperazine Dihydrochloride, lurasidone (Latuda), Olanzapine (Zyprexa), Quetiapine (Seroquel), Zotepine, Risperidone (Risperdal), Ziprasidone (Geodon), Mesotidazine, Chlorpromazine hydrochloride, and Haloperidol (Haldol).

Cannabinoids

In some embodiments, the compound or composition described herein (e.g., a compound of Formula I, or a pharmaceutical salt thereof, or a composition comprising a compound of Formula I, or a pharmaceutically acceptable salt thereof) is administered in combination with a cannabinoid(s). Exemplary cannabinoids include, but are not limited to, Cannabidiol (Epidiolex), Tetrahydrocannabinolic Acid, Tetrahydrocannabinol, Cannabidolic Acid, Cannabinol, Cannabigerol, Cannabichromene, Tetrahydrocannabivarin, and Cannabidivarin.

NMDA Receptor Antagonists

In some embodiments, the compound or composition described herein (e.g., a compound of Formula I, or a pharmaceutical salt thereof, or a composition comprising a compound of Formula I, or a pharmaceutically acceptable salt thereof) is administered in combination with an NMDA receptor antagonist(s). NMDA receptor antagonists are a class of drugs that inhibit the action of the N-methyl-d-aspartate receptor. Exemplary NMDA antagonists include, but are not limited to, Ketamine, Esketamine, Ketobemidone, Ifendopril, 5,7-Dichlorokynurenic Acid, Licostinel, Memantine, Gavestinel, Phencyclidine, Dextromethorphan, Remacemide, Selfotel, Tiletamine, Dextropropoxyphene, Aptiganel, Dexanabinol, and Amantadine. NMDA receptor antagonists also include opioids such as Methadone, Dextropropoxyphene, Pethidine, Levorphanol, Tramadol, Neramexane, and Ketobemidone.

GABA Receptor Agonists

In some embodiments, the compound or composition described herein (e.g., a compound of Formula I, or a pharmaceutical salt thereof, or a composition comprising a compound of Formula I, or a pharmaceutically acceptable salt thereof) is administered in combination with GABA receptor agaonist(s). GABA receptor agonist are a class of drugs that are agonists for one or more of the GABA receptors. Exemplary GABA receptor agonists include, but are not limited to, Clobazam, Topiramate, Muscimol, Progabide, Riluzole, Baclofen, Gabapentin, Vigabatrin, Valproic Acid, Tiagabine, Lamotrigine, Pregabalin, Phenyloin, Carbamazepine, Thiopental, Thiamylal, Pentobarbital, Secobarbital, Hexobarbital, Butobarbital, Amobarbital, Barbital, Mephobarbital, Phenobarbital, Primidone, Midazolam, Triazolam, Lometazepam, Flutazolam, Nitrazepam, Fluritrazepam, Nimetazepam, Diazepam, Medazepam, Oxazolam, Prazeam, Tofisopam, Rilmazafonoe, Lorazepam, Temazepam, Oxazepam, Fluidazepam, Chlordizaepoxide, Cloxazolam, Flutoprazepam, Alprazolam, Estazolam, Bromazepam, Flurazepam, Clorazepate Potassium, Haloxazolam, Ethyl Loflazepate, Qazepam, Clonazepam, Mexazolam, Etizolam, Brotizolam, Clotizaepam, Propofol, Fospropofol, Zolpidem, Zopiclone, Exzopiclone, Muscimol, TFQP/gaboxadol, Isoguvacine, Kojic amine, GABA, Homotaurine, Homohypotaurine, Trans-aminocyclopentane-3-carboxylic acid, Trans-amino-4-crotonic acid, b-guanidinopropionic acid, homo-b-proline, Isonipecotic acid, 3-((aminoiminomethyl) thio)-2-propenoic acid (ZAP A), Imidazoleacetic acid, and Piperidine-4-sulfonic acid (P4S).

Cholinesterase Inhibitors

In some embodiments, the compound or composition described herein (e.g., a compound of Formula I, or a pharmaceutical salt thereof, or a composition comprising a compound of Formula I, or a pharmaceutically acceptable salt thereof) is administered in combination with a cholinesterase inhibitor(s). In general, cholinergics are compounds which mimic the action of acetylcholine and/or butyrylcholine. Cholinesterase inhibitors are a class of drugs that prevent the breakdown of acetylcholine. Exemplary cholinesterase inhibitors include, but are not limited to, Donepizil (Aricept), Tacrine (Cognex), Rivastigmine (Exelon, Exelon Patch), Galantamine (Razadyne, Reminyl), Memantine/ Donepezil (Namzaric), Ambenonium (Mytelase), Neostigmine (Bloxiverz), Pyridostigmine (Mestinon Timespan, Regonol), and Galantamine (Razadyne).

The present disclosure also contemplates, among other things administration of a compound or pharmaceutical composition described herein (e.g., a compound of Formula I, or a pharmaceutical salt thereof, or a composition comprising a compound of Formula I, or a pharmaceutically acceptable salt thereof) to a subject has been previously administered an agent selected from the group consisting of a bronchial muscle/airway relaxant, an antiviral, oxygen, an antibody, and an antibacterial. In some embodiments an additional agent is administered to a subject prior to administration of a compound or pharmaceutical composition described herein (e.g., a compound of Formula I, or a pharmaceutical salt thereof, or a composition comprising a compound of Formula I, or a pharmaceutically acceptable salt thereof) and an additional agent is selected from the group consisting of a bronchial muscle/airway relaxant, an antiviral, oxygen, an antibody, and an antibacterial. In some embodiments, a compound or pharmaceutical composition described herein (e.g., a compound of Formula I, or a pharmaceutical salt thereof, or a composition comprising a compound of Formula I, or a pharmaceutically acceptable salt thereof) is co-administered with to a subject with an agent selected from a bronchial muscle/airway relaxant, an antiviral, oxygen, and an antibacterial.

Methods of Use and Treatment

In an aspect, compounds described herein, e.g., compounds of Formula (I), are envisioned to be useful as therapeutic agents for treating a CNS-related disorder (e.g., sleep disorder, a mood disorder such as depression, a schizophrenia spectrum disorder, a convulsive disorder, epileptogenesis, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome). Exemplary CNS conditions related to GABA-modulation include, but are not limited to, sleep disorders [e.g., insomnia], mood disorders [e.g., depression depression (e.g., major depressive disorder (MDD)), dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In certain embodiments, CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, tinnitus, or status epilepticus. In certain embodiments, the CNS-related disorder is depression. In certain embodiments, the CNS-related disorder is postpartum depression. In certain embodiments, the CNS-related disorder is major depressive disorder. In certain embodiments, the major depressive disorder is moderate major depressive disorder. In certain embodiments, the major depressive disorder is severe major depressive disorder.

In an aspect, provided is a method of alleviating or preventing seizure activity in a subject, comprising administering to the subject in need of such treatment an effective amount of a compound of the present invention. In some embodiments, the method alleviates or prevents epileptogenesis.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing premenstrual syndrome (PMS) or postnatal depression (PND) in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is depression.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

Inflammation of the central nervous system (CNS) (neuroinflammation) is recognized to be a feature of all neurological disorders. Major inflammatory neurological disorders include multiple sclerosis (characterized by an immune-mediated response against myelin proteins), and meningoencephalitis (where infectious agents triggered the inflammatory response). Additional scientific evidence suggests a potential role of inflammatory mechanisms in other neurological conditions such as Alzheimer's disease, Parkinson's disease, Huntington' disease, amyotrophic lateral sclerosis, stroke and traumatic brain injuries. In one embodiment, the compounds of the present invention are useful in treating neuroinflammation. In another embodiment, the compounds of the present invention are useful in treating inflammation in neurological conditions, including Alzheimer's disease, Parkinson's disease, Huntington's disease, amyotrophic lateral sclerosis, stroke, and traumatic brain injuries.

In certain embodiments, the compound is administered to the subject chronically. In certain embodiments, the compound is administered to the subject orally, subcutaneously, intramuscularly, or intravenously.

Neuroendocrine Disorders and Dysfunction

Provided herein are methods that can be used for treating neuroendocrine disorders and dysfunction. As used herein, "neuroendocrine disorder" or "neuroendocrine dysfunction" refers to a variety of conditions caused by imbalances in the body's hormone production directly related to the brain. Neuroendocrine disorders involve interactions between the nervous system and the endocrine system. Because the hypothalamus and the pituitary gland are two areas of the brain that regulate the production of hormones, damage to the hypothalamus or pituitary gland, e.g., by traumatic brain injury, may impact the production of hormones and other neuroendocrine functions of the brain. In some embodiments, the neuroendocrine disorder or dysfunction is associated with a women's health disorder or condition (e.g., a women's health disorder or condition described herein). In some embodiments, the neuroendocrine disorder or dysfunction is associated with a women's health disorder or condition is polycystic ovary syndrome.

Symptoms of neuroendocrine disorder include, but are not limited to, behavioral, emotional, and sleep-related symptoms, symptoms related to reproductive function, and somatic symptoms; including but not limited to fatigue, poor memory, anxiety, depression, weight gain or loss, emotional lability, lack of concentration, attention difficulties, loss of lipido, infertility, amenorrhea, loss of muscle mass, increased belly body fat, low blood pressure, reduced heart rate, hair loss, anemia, constipation, cold intolerance, and dry skin.

Neurodegenerative Diseases and Disorders

The methods described herein can be used for treating neurodegenerative diseases and disorders. The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cycloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Mood Disorders

Also provided herein are methods for treating a mood disorder, for example clinical depression, postnatal depression or postpartum depression, perinatal depression, atypical depression, melancholic depression, psychotic major depression, cataonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with a disease or disorder described herein (e.g., neuroendocrine diseases and disorders, neurodegenerative diseases and disorders (e.g., epilepsy), movement disorders, tremor (e.g., Parkinson's Disease), women's health disorders or conditions).

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Peripartum depression refers to depression in pregnancy. Symptoms include irritability, crying, feeling restless, trouble sleeping, extreme exhaustion (emotional and/or physical), changes in appetite, difficulty focusing, increased anxiety and/or worry, disconnected feeling from baby and/or fetus, and losing interest in formerly pleasurable activities.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self-harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or physchological counseling (psychotherapy) do not ease depression symptoms for individuals with treatment-resistant depression. In some cases, individuals with treatment-resistant depression improve symptoms, but come back.

Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Post-surgical depression refers to feelings of depression that follow a surgical procedure (e.g., as a result of having to confront one's mortality). For example, individuals may feel sadness or empty mood persistently, a loss of pleasure or interest in hobbies and activities normally enjoyed, or a persistent felling of worthlessness or hopelessness.

Mood disorder associated with conditions or disorders of women's health refers to mood disorders (e.g., depression) associated with (e.g., resulting from) a condition or disorder of women's health (e.g., as described herein).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

In some embodiments, the method comprises monitoring a subject with a known depression scale, e.g., the Hamilton Depression (HAM-D) scale, the Clinical Global Impression-Improvement Scale (CGI), and the Montgomery-Asberg Depression Rating Scale (MADRS). In some embodiments, a therapeutic effect can be determined by reduction in Hamilton Depression (HAM-D) total score exhibited by the subject. Reduction in the HAM-D total score can happen within 4, 3, 2, or 1 days; or 96, 84, 72, 60, 48, 24, 20, 16, 12, 10, 8 hours or less. The therapeutic effect can be assessed across a specified treatment period. For example, the therapeutic effect can be determined by a decrease from baseline in HAM-D total score after administering a compound described herein, e.g., a compound of Formula (I) (e.g., 12, 24, or 48 hours after administration; or 24, 48, 72, or 96 hours or more; or 1 day, 2 days, 14 days, 21 days, or 28 days; or 1 week, 2 weeks, 3 weeks, or 4 weeks; or 1 month, 2 months, 6 months, or 10 months; or 1 year, 2 years, or for life).

In some embodiments, the subject has a mild depressive disorder, e.g., mild major depressive disorder. In some embodiments, the subject has a moderate depressive disorder, e.g., moderate major depressive disorder. In some embodiments, the subject has a severe depressive disorder, e.g., severe major depressive disorder. In some embodiments, the subject has a very severe depressive disorder, e.g., very severe major depressive disorder. In some embodiments, the baseline HAM-D total score of the subject (i.e., prior to treatment with a compound described herein, e.g., a compound of Formula (I)) is at least 24. In some embodiments, the baseline HAM-D total score of the subject is at least 18. In some embodiments, the baseline HAM-D total score of the subject is between and including 14 and 18. In some embodiments, the baseline HAM-D total score of the subject is between and including 19 and 22. In some embodiments, the HAM-D total score of the subject before treatment with a compound described herein, e.g., a compound of Formula (I), is greater than or equal to 23. In some embodiments, the baseline score is at least 10, 15, or 20. In some embodiments, the HAM-D total score of the subject after treatment with a compound described herein, e.g., a compound of Formula (I), is about 0 to 10 (e.g., less than 10; 0 to 10, 0 to 6, 0 to 4, 0 to 3, 0 to 2, or 1.8). In some embodiments, the HAM-D total score after treatment with a compound described herein, e.g., a compound of Formula (I), is less than 10, 7, 5, or 3. In some embodiments, the decrease in HAM-D total score is from a baseline score of about 20 to 30 (e.g., 22 to 28, 23 to 27, 24 to 27, 25 to 27, 26 to 27) to a HAM-D total score at about 0 to 10 (e.g., less than 10; 0 to 10, 0 to 6, 0 to 4, 0 to 3, 0 to 2, or 1.8) after treatment with a compound described herein, e.g., a compound of Formula (I). In some embodiments, the decrease in the baseline HAM-D total score to HAM-D total score after treatment with a compound described herein, e.g., a compound of Formula (I), is at least 1, 2, 3, 4, 5, 7, 10, 25, 40, 50, or 100 fold). In some embodiments, the percentage decrease in the baseline HAM-D total score to HAM-D total score after treatment with a compound described herein, e.g., a compound of Formula (I), is at least 50% (e.g., 60%, 70%, 80%, or 90%). In some embodiments, the therapeutic effect is measured as a decrease in the HAM-D total score after treatment with a compound described herein, e.g., a compound of Formula (I), relative to the baseline HAM-D total score (e.g., 12, 24, 48 hours after administration; or 24, 48, 72, 96 hours or more; or 1 day, 2 days, 14 days, or more) is at least 10, 15, or 20 points.

In some embodiments, the method of treating a depressive disorder, e.g., major depressive disorder provides a therapeutic effect (e.g., as measured by reduction in Hamilton Depression Score (HAM-D)) within 14, 10, 4, 3, 2, or 1 days, or 24, 20, 16, 12, 10, or 8 hours or less. In some embodiments, the method of treating the depressive disorder, e.g., major depressive disorder, provides a therapeutic effect (e.g., as determined by a statistically significant reduction in HAM-D total score) within the first or second day of the treatment with a compound described herein, e.g., a compound of Formula (I). In some embodiments, the method of treating the depressive disorder, e.g., major depressive disorder, provides a therapeutic effect (e.g., as determined by a statistically significant reduction in HAM-D total score) within less than or equal to 14 days since the beginning of the treatment with a compound described herein, e.g., a compound of Formula (I). In some embodiments, the method of treating the depressive disorder, e.g., major depressive disorder, provides a therapeutic effect (e.g., as determined by a statistically significant reduction in HAM-D total score) within less than or equal to 21 days since the beginning of the treatment with a compound described herein, e.g., a compound of Formula (I). In some embodiments, the method of treating the depressive disorder, e.g., major depressive disorder, provides a therapeutic effect (e.g., as determined by a statistically significant reduction in HAM-D total score) within less than or equal to 28 days since the beginning of the treatment with a compound described herein, e.g., a compound of Formula (I). In some embodiments, the therapeutic effect is a decrease from baseline in HAM-D total score after treatment with a compound described herein, e.g., a compound of Formula (I) (e.g., treatment with a compound described herein, e.g., a compound of Formula (I), once a day for 14 days). In some embodiments, the HAM-D total score of the subject before treatment with a compound described herein, e.g., a compound of Formula (I), is at least 24. In some embodiments, the HAM-D total score of the subject before treatment with a compound described herein, e.g., a compound of Formula (I), is at least 18. In some embodiments, the HAM-D total score of the subject before treatment with a compound described herein, e.g., a compound of Formula (I), is between and including 14 and 18. In some embodiments, the decrease in HAM-D total score after treating the subject with a compound described herein, e.g., a compound of Formula (I), relative to the baseline HAM-D total score is at least 10. In some embodiments, the decrease in HAM-D total score after treating the subject with a compound described herein, e.g., a compound of Formula (I), relative to the baseline HAM-D total score is at least 15 (e.g., at least 17). In some embodiments, the HAM-D total score associated with treating the subject with a compound described herein, e.g., a compound of Formula (I), is no more than a number ranging from 6 to 8. In some embodiments, the HAM-D total score associated with treating the subject with a compound described herein, e.g., a compound of Formula (I), is no more than 7.

In some embodiments, the method provides therapeutic effect (e.g., as measured by reduction in Clinical Global Impression-Improvement Scale (CGI)) within 14, 10, 4, 3, 2, or 1 days, or 24, 20, 16, 12, 10, or 8 hours or less. In some embodiments, the CNS-disorder is a depressive disorder, e.g., major depressive disorder. In some embodiments, the method of treating the depressive disorder, e.g., major depressive disorder provides a therapeutic effect within the second day of the treatment period. In some embodiments, the therapeutic effect is a decrease from baseline in CGI score at the end of a treatment period (e.g., 14 days after administration).

In some embodiments, the method provides therapeutic effect (e.g., as measured by reduction in Montgomery-Asberg Depression Rating Scale (MADRS)) within 14, 10, 4, 3, 2, or 1 days, or 24, 20, 16, 12, 10, or 8 hours or less. In some embodiments, the CNS-disorder is a depressive disorder, e.g., major depressive disorder. In some embodiments, the method of treating the depressive disorder, e.g., major depressive disorder provides a therapeutic effect within the second day of the treatment period. In some embodiments, the therapeutic effect is a decrease from baseline in MADRS score at the end of a treatment period (e.g., 14 days after administration).

A therapeutic effect for major depressive disorder can be determined by a reduction in Montgomery-Asberg Depression Rating Scale (MADRS) score exhibited by the subject. For example, the MADRS score can be reduced within 4, 3, 2, or 1 days; or 96, 84, 72, 60, 48, 24, 20, 16, 12, 10, 8 hours or less. The Montgomery-Asberg Depression Rating Scale (MADRS) is a ten-item diagnostic questionnaire (regarding apparent sadness, reported sadness, inner tension, reduced sleep, reduced appetite, concentration difficulties, lassitude, inability to feel, pessimistic thoughts, and suicidal thoughts) which psychiatrists use to measure the severity of depressive episodes in patients with mood disorders.

In some embodiments, the method provides therapeutic effect (e.g., as measured by reduction in Edinburgh Postnatal Depression Scale (EPDS)) within 4, 3, 2, 1 days; 24, 20, 16, 12, 10, 8 hours or less. In some embodiments, the therapeutic effect is an improvement measured by the EPDS.

In some embodiments, the method provides therapeutic effect (e.g., as measured by reduction in Generalized Anxiety Disorder 7-Item Scale (GAD-7)) within 4, 3, 2, 1 days; 24, 20, 16, 12, 10, 8 hours or less.

Anxiety Disorders

Provided herein are methods for treating anxiety disorders (e.g., generalized anxiety disorder, panic disorder, obsessive compulsive disorder, phobia, post-traumatic stress disorder). Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Women's Health Disorders

Provided herein are methods for treating conditions or disorders related to women's health. Conditions or disorders related to women's health include, but are not limited to, gynecological health and disorders (e.g., premenstrual syndrome (PMS), premenstrual dysphoric disorder (PMDD)), pregnancy issues (e.g., miscarriage, abortion), infertility and related disorders (e.g., polycystic ovary syndrome (PCOS)), other disorders and conditions, and issues related to women's overall health and wellness (e.g., menopause).

Gynecological health and disorders affecting women include menstruation and menstrual irregularities; urinary tract health, including urinary incontinence and pelvic floor disorders; and such disorders as bacterial vaginosis, vaginitis, uterine fibroids, and vulvodynia.

Premenstrual syndrome (PMS) refers to physical and emotional symptoms that occur in the one to two weeks before a women's period. Symptoms vary but can include bleeding, mood swings, tender breasts, food cravings, fatigue, irritability, acne, and depression.

Premenstrual dysphoric disorder (PMDD) is a severe form of PMS. The symptoms of PMDD are similar to PMS but more severe and may interfere with work, social activity, and relationships. PMDD symptoms include mood swings, depressed mood or feelings of hopelessness, marked anger, increased interpersonal conflicts, tension and anxiety, irritability, decreased interest in usual activities, difficulty concentrating, fatigue, change in appetite, feeling out of control or overwhelmed, sleep problems, physical problems (e.g., bloating, breast tenderness, swelling, headaches, joint or muscle pain).

Pregnancy issues include preconception care and prenatal care, pregnancy loss (miscarriage and stillbirth), preterm labor and premature birth, sudden infant death syndrome (SIDS), breastfeeding, and birth defects.

Miscarriage refers to a pregnancy that ends on its own, within the first 20 weeks of gestation.

Abortion refers to the deliberate termination of a pregnancy, which can be performed during the first 28 weeks of pregnancy.

Infertility and related disorders include uterine fibroids, polycystic ovary syndrome, endometriosis, and primary ovarian insufficiency.

Polycystic ovary syndrome (PCOS) refers to an endocrine system disorder among women of reproductive age. PCOS is a set of symptoms resulting from an elevated male hormone in women. Most women with PCOS grow many small cysts on their ovaries. Symptoms of PCOS include irregular or no menstrual periods, heavy periods, excess body and facial hair, acne, pelvic pain, difficulty getting pregnant, and patches of thick, darker, velvety skin. PCOS may be associated with conditions including type 2 diabetes, obesity, obstructive sleep apnea, heart disease, mood disorders, and endometrial cancer.

Other disorders and conditions that affect only women include Turner syndrome, Rett syndrome, and ovarian and cervical cancers.

Issues related to women's overall health and wellness include violence against women, women with disabilities and their unique challenges, osteoporosis and bone health, and menopause.

Menopause refers to the 12 months after a woman's last menstrual period and marks the end of menstrual cycles. Menopause typically occurs in a woman's 40s or 50s. Physical symptoms such as hot flashes and emotional symptoms of menopause may disrupt sleep, lower energy, or trigger anxiety or feelings of sadness or loss. Menopause includes natural menopause and surgical menopause, which is a type of induced menopause due to an event such as surgery (e.g., hysterectomy, oophorectomy; cancer). It is induced when the ovaries are gravely damaged by, e.g., radiation, chemotherapy, or other medications.

Epilepsy

The compound of Formula (I), or pharmaceutically acceptable salt, or a pharmaceutically acceptable composition thereof, can be used in a method described herein, for example in the treatment of a disorder described herein such as epilepsy, status epilepticus, or seizure.

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Epileptogenesis

The compounds and methods described herein can be used to treat or prevent epileptogenesis. Epileptogenesis is a gradual process by which a normal brain develops epilepsy (a chronic condition in which seizures occur). Epileptogenesis results from neuronal damage precipitated by the initial insult (e.g., status epilepticus).

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

The compound of Formula (I) or pharmaceutically acceptable salt, or a pharmaceutically acceptable composition thereof, can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well-known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures. In some embodiments, the seizure is a generalized seizure associated with Dravet Syndrome, Lennox-Gastaut Syndrome, Tuberous Sclerosis Complex, Rett Syndrome or PCDH19 Female Pediatric Epilepsy.

Movement Disorders

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

Tremor

The methods described herein can be used to treat tremor, for example the compound of Formula (I) can be used to treat cerebellar tremor or intention tremor, dystonic tremor, essential tremor, orthostatic tremor, parkinsonian tremor, physiological tremor, psychogenic tremor, or rubral tremor. Tremor includes hereditary, degenerative, and idiopathic disorders such as Wilson's disease, Parkinson's disease, and essential tremor, respectively; metabolic diseases (e.g., thyroid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor.

Tremor is an involuntary, at times rhythmic, muscle contraction and relaxation that can involve oscillations or twitching of one or more body parts (e.g., hands, arms, eyes, face, head, vocal folds, trunk, legs).

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occurs in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawal, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's Disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's Disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face. Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myloclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part. Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

Anesthesia/Sedation

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

Also described herein are methods of ameliorating one or more symptoms of a respiratory condition in a subject, comprising administering to the subject an effective amount of a compound or pharmaceutical composition described herein (e.g., a compound of Formula I, or a pharmaceutical salt thereof, or a composition comprising a compound of Formula I, or a pharmaceutically acceptable salt thereof).

In one aspect, provided herein is a method of treating a subject wherein the subject exhibits one or more symptoms of a respiratory condition and/or has been diagnosed with a respiratory condition, comprising administering to said subject an effective amount of a compound or pharmaceutical composition described herein (e.g., a compound of Formula I, or a pharmaceutical salt thereof, or a composition comprising a compound of Formula I, or a pharmaceutically acceptable salt thereof).

In some embodiments, the present disclosure contemplates a method of treating a subject comprising administering to said subject a compound or pharmaceutical composition described herein (e.g., a compound of Formula I, or a pharmaceutical salt thereof, or a composition comprising a compound of Formula I, or a pharmaceutically acceptable salt thereof), wherein the subject has a respiratory condition.

In some embodiments, administration of a compound or pharmaceutical composition described herein (e.g., a compound of Formula I, or a pharmaceutical salt thereof, or a composition comprising a compound of Formula I, or a pharmaceutically acceptable salt thereof) to a subject exhibiting symptoms of a respiratory condition, may result in the reduction of the severity of one or more symptoms of a respiratory condition or retard or slow the progression of one or more symptoms of a respiratory condition.

In some embodiments, a subject with a respiratory condition has been or is being treated with mechanical ventilation or oxygen. In some embodiments, a subject with a respiratory condition has been or is being treated with mechanical ventilation.

In some embodiments, a compound or pharmaceutical composition described herein (e.g., a compound of Formula I, or a pharmaceutical salt thereof, or a composition comprising a compound of Formula I, or a pharmaceutically acceptable salt thereof) is administered to a subject that is being or has been treated with mechanical ventilation. In some embodiments, administration of a compound or pharmaceutical composition described herein (e.g., a compound of Formula I, or a pharmaceutical salt thereof, or a composition comprising a compound of Formula I, or a pharmaceutically acceptable salt thereof) continues throughout a subject's treatment with mechanical ventilation. In some embodiments, administration of a compound or pharmaceutical composition described herein (e.g., a compound of Formula I, or a pharmaceutical salt thereof, or a composition comprising a compound of Formula I, or a pharmaceutically acceptable salt thereof) continues after a subject has ended treatment with mechanical ventilation.

In some embodiments, a compound or pharmaceutical composition described herein (e.g., a compound of Formula I, or a pharmaceutical salt thereof, or a composition comprising a compound of Formula I, or a pharmaceutically acceptable salt thereof) is administered to a subject who is receiving or has received treatment with a sedative. In some embodiments, a sedative is propofol or a benzodiazepine.

In some embodiments, the present disclosure includes administering to a subject in need thereof a compound or pharmaceutical composition described herein (e.g., a compound of Formula I, or a pharmaceutical salt thereof, or a composition comprising a compound of Formula I, or a pharmaceutically acceptable salt thereof) in an amount sufficient to increase oxygen saturation in blood. In some embodiments, oxygen saturation in blood is measured using pulse oximetry.

In some embodiments, the present disclosure contemplates a method of treating a cytokine storm in a patient. In some embodiments a method of treating a cytokine storm comprising the step of administering to the patient a compound or pharmaceutical composition described herein (e.g., a compound of Formula I, or a pharmaceutical salt thereof, or a composition comprising a compound of Formula I, or a pharmaceutically acceptable salt thereof). In some embodiments, a symptom of a cytokine storm is lung inflammation. In some embodiments, a patient undergoing a cytokine storm has acute respiratory distress syndrome (ARDS).

Respiratory Condition

In some embodiments, a subject with a respiratory condition suffers from respiratory distress. In some embodiments, respiratory distress includes acute respiratory distress.

In some embodiments, a subject with a respiratory condition may exhibit one or more symptoms selected from the group consisting of airway hyper-responsiveness, inflammation of lung tissue, lung hypersensitivity, and inflammation-related pulmonary pain.

In some embodiments a subject with a respiratory condition may exhibit inflammation of lung tissue. In some embodiments, inflammation of lung tissue is bronchitis or bronchiectasis. In some embodiments, inflammation of lung tissue is pneumonia. In some embodiments, pneumonia is ventilator-associated pneumonia or hospital-acquired pneumonia. In some embodiments, pneumonia is ventilator-associated pneumonia.

In some embodiments, administration of the compound or pharmaceutical composition described herein to a subject exhibiting symptoms of a respiratory condition, results in reduction of the severity of respiratory distress in a subject with a respiratory condition or retard or slow the progression of respiratory distress in a subject with a respiratory condition.

In some embodiments, administration of a compound or pharmaceutical composition described herein (e.g., a compound of Formula I, or a pharmaceutical salt thereof, or a composition comprising a compound of Formula I, or a pharmaceutically acceptable salt thereof) to a subject exhibiting symptoms of a respiratory condition, results in reduction of the severity of airway hyper-responsiveness in a subject with a disease associated with a coronavirus or retard or slow the progression of airway hyper-responsiveness in a subject with a respiratory condition.

In some embodiments, administration of a compound or pharmaceutical composition described herein (e.g., a compound of Formula I, or a pharmaceutical salt thereof, or a composition comprising a compound of Formula I, or a pharmaceutically acceptable salt thereof) to a subject exhibiting symptoms of a respiratory condition, results in reduction of the severity of inflammation of lung tissue in a subject with a respiratory condition or retard or slow the progression of inflammation of lung tissue in a subject with a respiratory condition. In some embodiments, administration of a compound or pharmaceutical composition described herein (e.g., a compound of Formula I, or a pharmaceutical salt thereof, or a composition comprising a compound of Formula I, or a pharmaceutically acceptable salt thereof) to a subject exhibiting symptoms of a respiratory condition, results in reduction of the severity of pneumonia in a subject with a respiratory condition or retard or slow the progression of pneumonia in a subject with a respiratory condition.

In some embodiments, administration of a compound or pharmaceutical composition described herein (e.g., a compound of Formula I, or a pharmaceutical salt thereof, or a composition comprising a compound of Formula I, or a pharmaceutically acceptable salt thereof) to a subject exhibiting symptoms of a respiratory condition, results in reduction of the severity of lung hypersensitivity in a subject with a respiratory condition or retard or slow the progression of lung hypersensitivity in a subject with a respiratory condition.

In some embodiments, administration of a compound or pharmaceutical composition described herein (e.g., a compound of Formula I, or a pharmaceutical salt thereof, or a composition comprising a compound of Formula I, or a pharmaceutically acceptable salt thereof) to a subject exhibiting symptoms of a respiratory condition, results in reduction of the severity of inflammation-related pulmonary pain in a subject with a respiratory condition or retard or slow the progression of inflammation-related pulmonary pain in a subject with a respiratory condition.

In some embodiments, a subject with a respiratory condition is undergoing or has undergone treatment for an infection, fibrosis, a fibrotic episode, chronic obstructive pulmonary disease, Sarcoidosis (or pulmonary sarcoidosis) or asthma/asthma-related inflammation.

In some embodiments, a subject exhibits symptoms of and/or has been diagnosed with asthma. In some embodiments, a subject is or has undergone an asthmatic attack.

In some embodiments, a subject is undergoing or has undergone treatment for fibrosis or a fibrotic episode. In some embodiments, the fibrosis is cystic fibrosis.

In some embodiments, a respiratory condition is the result of and/or related to a disease or condition selected from the group consisting of cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, pulmonary sarcoidosis, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington, spinocerebellar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease.

Infections

The present disclosure contemplates, among other things, treatment of a subject who has an infection. The present disclosure contemplates, among other things, treatment of a subject who has a disease associated with an infection. In some embodiments, an infection is a viral infection or a bacterial infection. In some embodiments, an infection is a viral infection. In some embodiments, an infection is a bacterial infection.

In some embodiments, a viral infection is an infection of a virus selected from the group consisting of a coronavirus, an influenza virus, human rhinovirus, a human parainfluenza virus, human metapneumovirus and a hantavirus. In some embodiments, a virus is a coronavirus. In some embodiments, a coronavirus is selected from the group consisting of SARS-CoV, SARS-CoV-2, and MERS-CoV.

The present disclosure contemplates, among other things, treatment of a subject who has a disease associated with coronavirus. In some embodiments, a disease associated with a coronavirus is selected from the group consisting of coronavirus disease 2019 (COVID-19), severe acute respiratory syndrome (SARS) and Middle East respiratory syndrome (MERS). In some embodiments, a disease associated with a coronavirus is selected from the group consisting of COVID-19. In some embodiments, a coronavirus is selected from a group consisting of SARS-CoV-1, SARS-CoV-2, and 2012-nCoV. In some embodiments, a coronavirus is SARS-CoV-2.

In some embodiments, a bacterial infection is an infection of a bacteria selected from the group consisting of *Streptococcus pneumoniae, Chlamydia pneumoniae, Staphylococcus aureus, Pseudomonas aeruginosa*, and *Haemophilus influenzae*. In some embodiments, *Staphylococcus aureus* is methicillin-resistant *Staphylococcus aureus*.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) trituration, column chromatography, HPLC, or supercritical fluid chromatography (SFC). The following schemes are presented with details as to the preparation of representative oxysterols that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

$^1$H-NMR reported herein (e.g., for the region between δ (ppm) of about 0.5 to about 4 ppm) will be understood to be an exemplary interpretation of the NMR spectrum (e.g., exemplary peak integratations) of a compound.

Abbreviations: PE: petroleum ether; EtOAc: ethyl acetate; THF: tetrahydrofuran; PCC: pyridinium chlorochromate; TLC: thin layer chromatography; PCC: pyridinium chlorochromate; t-BuOK: potassium tert-butoxide; 9-BBN: 9-borabicyclo[3.3.1]nonane; Pd(t-Bu$_3$P)$_2$: bis(tri-tert-butylphosphine)palladium(0); AcCl: acetyl chloride; i-PrMgCl: Isopropylmagnesium chloride; TBSCl: tert-Butyl (chloro)dimethylsilane; (i-PrO)$_4$Ti: titanium tetraisopropoxide; BHT: 2,6-di-t-butyl-4-methylphenoxide; Me: methyl; i-Pr: iso-propyl; t-Bu: tert-butyl; Ph: phenyl; Et: ethyl; Bz: benzoyl; BzCl: benzoyl chloride; CsF: cesium fluoride; DCC: dicyclohexylcarbodiimide; DCM: dichloromethane; DMAP: 4-dimethylaminopyridine; DMP: Dess-Martin periodinane; EtMgBr: ethylmagnesium bromide; EtOAc: ethyl acetate; TEA: triethylamine; AlaOH: alanine; Boc: t-butoxycarbonyl. Py: pyridine; TBAF: tetra-n-butylammonium fluoride; THF: tetrahydrofuran; TBS: t-butyldimethylsilyl; TMS: trimethylsilyl; TMSCF$_3$: (Trifluoromethyl)trimethylsilane; Ts: p-toluenesulfonyl; Bu: butyl; Ti(OiPr)$_4$: tetraisopropoxytitanium; LAH: Lithium Aluminium Hydride; LDA: lithium diisopropylamide; LiOH.H$_2$O: lithium hydroxide hydrates; MAD: methyl aluminum bis(2, 6-di-t-butyl-4-methylphenoxide); MeCN: acetonitrile; NBS: N-bromosuccinimide; Na$_2$SO$_4$: sodium sulfate; Na$_2$S$_2$O$_3$: sodium thiosulfate; MeCN: acetonitrile; MeOH: methanol; Boc: t-butoxycarbonyl; MTBE: methyl tert-butyl ether; K-selectride: Potassium tri(s-butyl)borohydride; 9-BBNdimer: 9-borabicyclo(3.3.1)nonane(dimer); DIPEA: diisopropylethylamine; DMF: dimethylformamide; FA: formic acid; SM: starting material.

Example 1 & 2: Synthesis of 1-((R)-2-hydroxy-2-((3R,5R,8R,9R,10S,13S,14S,17S)-3-hydroxy-3,13-dimethylhexadecahydro-1H-cyclopenta[a]phenanthren-17-yl)propyl)-1H-pyrazole-4-carbonitrile (1) & 1-((S)-2-hydroxy-2-((3R,5R,8R,9R,10S,13S,14S,17S)-3-hydroxy-3,13-dimethylhexadecahydro-1H-cyclopenta[a]phenanthren-17-yl)propyl)-1H-pyrazole-4-carbonitrile (2)

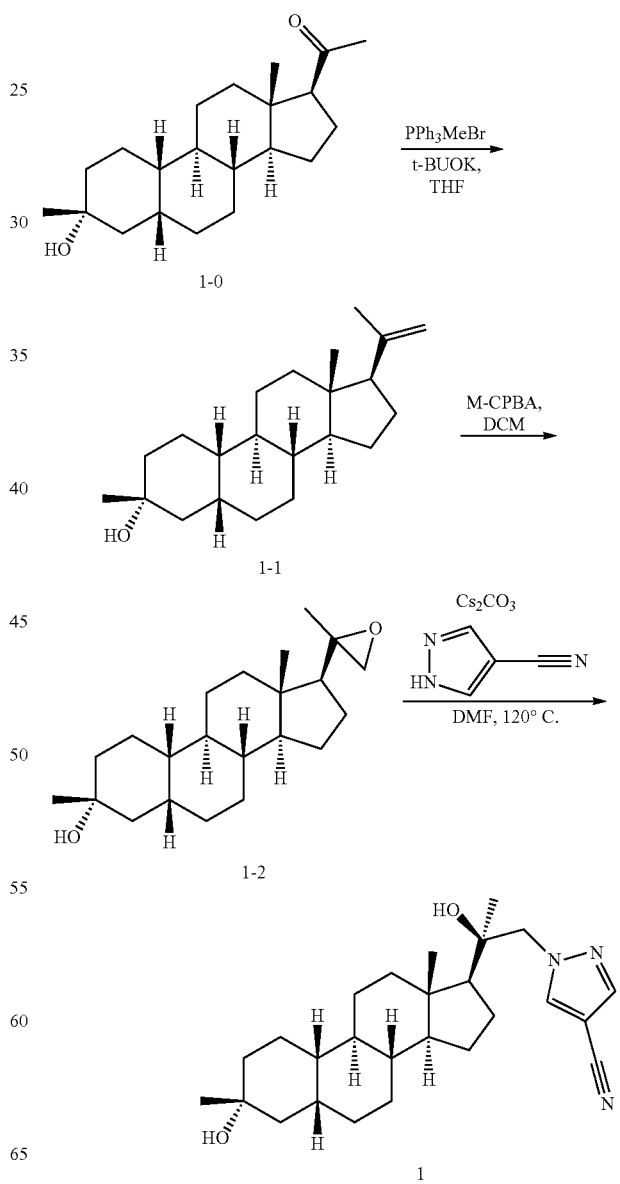

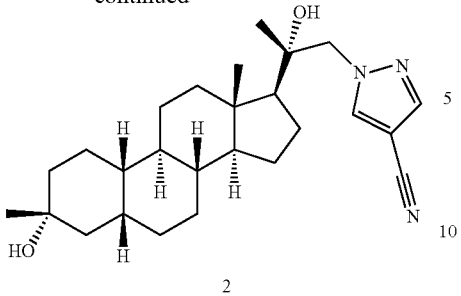

2

Synthesis of 1-1

To a suspension of Ph₃PMeBr (10 g, 28.2 mmol) in anhydrous THF (40 mL) was added t-BuOK (3.16 g, 28.2 mmol) at 25° C. under N₂. After stirring at 50° C. for 30 min, a solution of 1-0 (3 g, 9.4 mmol) in anhydrous THF (10 mL) was added dropwise. After stirring at 60° C. for 1 h, the mixture was poured into 10% NH₄Cl (50 mL) and stirred for 10 min. The aqueous phase was extracted with EtOAc (3×50 mL). The combine organic solution was washed with saturated brine (2×50 mL), filtered and concentrated. The residue was dissolved in MeOH (50 mL) and water (50 mL). The resulting compound was collected by filtration and dried to give desired 1-1 (2.97 g, 100%). ¹H NMR (400 MHz, CDCl₃) δ$_H$ 4.84 (s, 1H), 4.70 (s, 1H), 2.08-1.99 (m, 1H), 1.90-1.78 (m, 4H), 1.75 (s, 3H), 1.74-1.56 (m, 5H), 1.49-1.28 (m, 8H), 1.26 (s, 3H), 1.23-1.13 (m, 3H), 1.11-0.97 (m, 3H), 0.57 (s, 3H)

Synthesis of 1-2

To a solution of 1-1 (500 mg, 1.57 mmol) in DCM (10 mL) was added mCPBA (541 mg, 3.14 mmol) at 25° C. After stirring at 40° C. for 1 h, the mixture was quenched with saturated NaHCO₃ aqueous (100 mL) at 15° C. The DCM phase was separated and washed with saturated NaHCO₃/Na₂S₂O₃ aqueous (1:1, 2×100 mL), brine (100 mL), dried over anhydrous Na₂SO₄, filtered and concentrated under vacuum to give a residue, which was purified by flash column (10~20% of EtOAc in PE) to give 1-2 (685 mg).

Synthesis of 1 & 2

To a solution of 1-2 (685 mg, 2.05 mmol) in DMF (10 mL) was added 1H-pyrazole-4-carbonitrile (285 mg, 3.07 mmol) and Cs₂CO₃ (3.32 g, 10.2 mmol) at 20° C. After stirring at 120° C. for 2 h, the mixture was diluted with water (100 mL) and extracted with EtOAc (2×50 mL). The combined organic solution was separated, concentrated and purified by flash column (30~65% EtOAc in PE) to give a mixture of epimers (600 mg, 69%). The epimers were separated by HPLC (Column: XtimateC18 150*25 mm*5 μm; Condition: water (0.225% FA)-ACN; Begin B: 74%; End B: 74%.) to afford 1 (133 mg) and 2 (259.2 mg).

1: ¹H NMR (400 MHz, CDCl₃) δ7.93 (s, 1H), 7.82 (s, 1H), 4.35 (d, J=14.0 Hz, 1H), 4.08 (d, J=13.6 Hz, 1H), 2.51 (s, 1H), 2.05-1.98 (m, 1H), 1.83-1.71 (m, 5H), 1.70-1.62 (m, 3H), 1.51-1.41 (m, 3H), 1.40 (br s, 2H), 1.37-1.27 (m, 3H), 1.26 (s, 3H), 1.23-1.20 (m, 1H), 1.19-1.10 (m, 2H), 1.10-1.02 (m, 4H), 0.97 (s, 3H), 0.92 (s, 3H); LC-ELSD/MS purity 99%, 100% de based on H-NMR; MS ESI calcd. for C₂₆H₃₆N₃ [M−2H₂O+H]⁺ 390.3, found 390.3.

2: ¹H NMR (400 MHz, CDCl₃) δ7.89 (s, 1H), 7.80 (s, 1H), 4.22-4.13 (m, 1H), 4.06-3.94 (m, 1H), 2.31 (br s, 1H), 2.10-2.02 (m, 1H), 1.96-1.82 (m, 2H), 1.80 (br d, J=6.8 Hz, 2H), 1.70-1.61 (m, 4H), 1.40 (br s, 8H), 1.26 (s, 3H), 1.25-1.09 (m, 5H), 1.09 (s, 3H), 1.07-1.00 (m, 2H), 0.87 (s, 3H); LC-ELSD/MS purity 99%, 100% de based on H-NMR; MS ESI calcd. for C₂₆H₃₆N₃ [M−2H₂O+H]⁺ 390.3, found 390.3.

Examples 3 & 4: Synthesis of 1-((S)-2-((3R,5R,8S, 9S,10S,13S,14S,17S)-10-ethyl-3-hydroxy-3,13-dimethylhexadecahydro-1H-cyclopenta[a]phenanthren-17-yl)-2-hydroxypropyl)-1H-pyrazole-4-carbonitrile (3) & 1-((R)-2-((3R,5R,8S,9S,10S,13S,14S,17S)-10-ethyl-3-hydroxy-3,13-dimethylhexadecahydro-1H-cyclopenta[a]phenanthren-7-yl)-2-hydroxypropyl)-1H-pyrazole-4-carbonitrile (4)

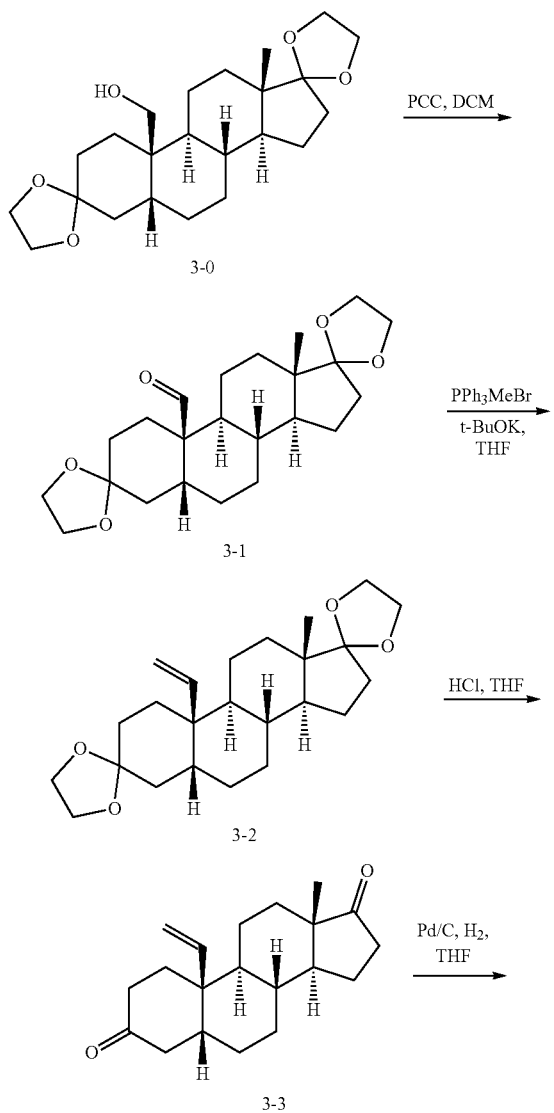

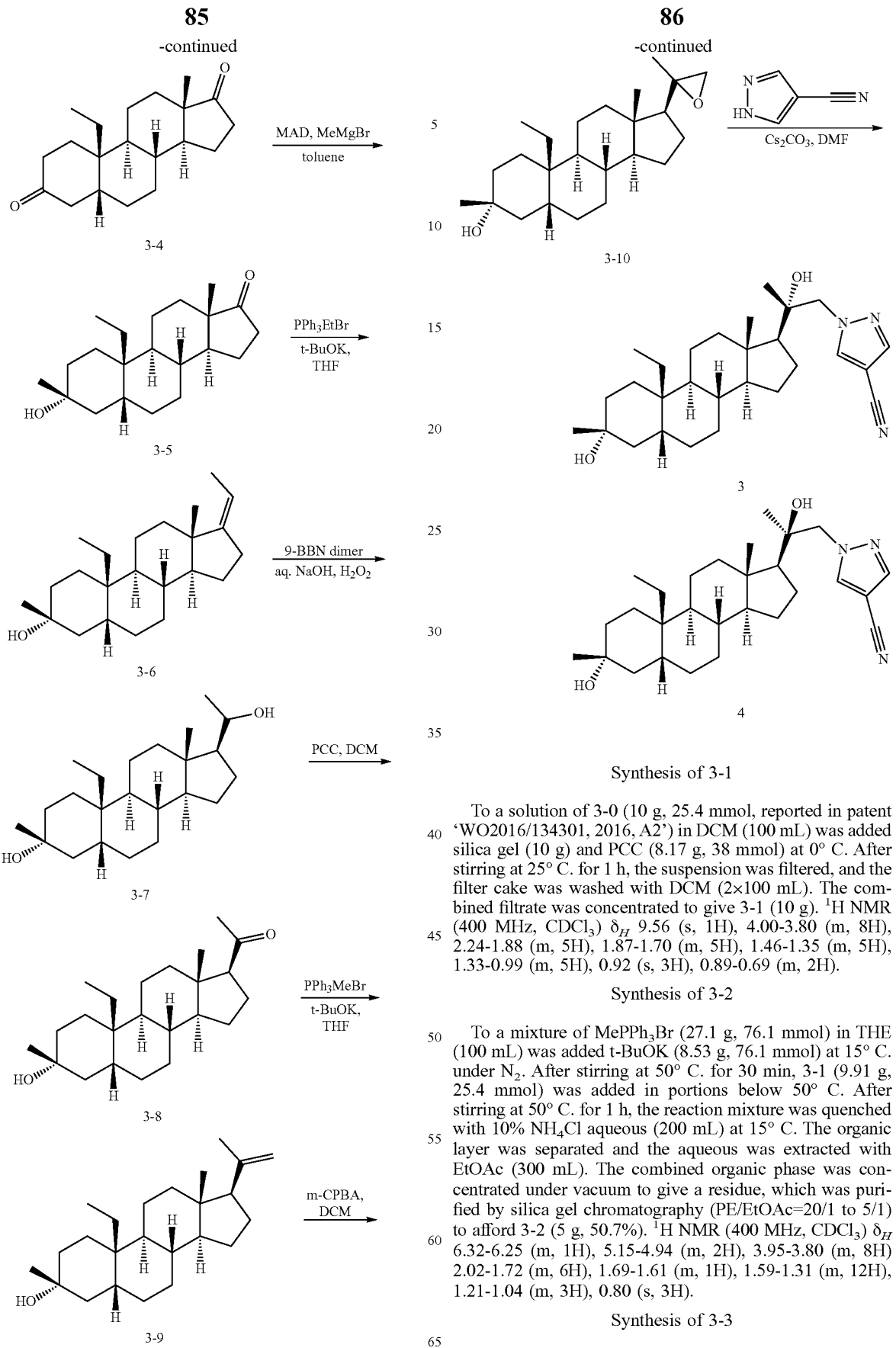

Synthesis of 3-1

To a solution of 3-0 (10 g, 25.4 mmol, reported in patent 'WO2016/134301, 2016, A2') in DCM (100 mL) was added silica gel (10 g) and PCC (8.17 g, 38 mmol) at 0° C. After stirring at 25° C. for 1 h, the suspension was filtered, and the filter cake was washed with DCM (2×100 mL). The combined filtrate was concentrated to give 3-1 (10 g). $^1$H NMR (400 MHz, CDCl$_3$) $\delta_H$ 9.56 (s, 1H), 4.00-3.80 (m, 8H), 2.24-1.88 (m, 5H), 1.87-1.70 (m, 5H), 1.46-1.35 (m, 5H), 1.33-0.99 (m, 5H), 0.92 (s, 3H), 0.89-0.69 (m, 2H).

Synthesis of 3-2

To a mixture of MePPh$_3$Br (27.1 g, 76.1 mmol) in THF (100 mL) was added t-BuOK (8.53 g, 76.1 mmol) at 15° C. under N$_2$. After stirring at 50° C. for 30 min, 3-1 (9.91 g, 25.4 mmol) was added in portions below 50° C. After stirring at 50° C. for 1 h, the reaction mixture was quenched with 10% NH$_4$Cl aqueous (200 mL) at 15° C. The organic layer was separated and the aqueous was extracted with EtOAc (300 mL). The combined organic phase was concentrated under vacuum to give a residue, which was purified by silica gel chromatography (PE/EtOAc=20/1 to 5/1) to afford 3-2 (5 g, 50.7%). $^1$H NMR (400 MHz, CDCl$_3$) $\delta_H$ 6.32-6.25 (m, 1H), 5.15-4.94 (m, 2H), 3.95-3.80 (m, 8H) 2.02-1.72 (m, 6H), 1.69-1.61 (m, 1H), 1.59-1.31 (m, 12H), 1.21-1.04 (m, 3H), 0.80 (s, 3H).

Synthesis of 3-3

To a solution of 3-2 (15 g, 12.8 mmol) in THF (30 mL) were added aq. HCl (38.6 mL, 2M, 77.2 mmol) and at 25°

C. under N$_2$. After stirring at 25° C. for 5 h, the mixture was quenched with saturated NaHCO$_3$(100 mL). The organic layer was separated, and the aqueous layer was extracted with EtOAc (2×100 mL). The combined organic layer was washed with brine (30 mL), dried over anhydrous Na$_2$SO$_4$, filtered and concentrated to give 3-3 (9.3 g, 80.8%). $^1$H NMR (400 MHz, CDCl$_3$) δ$_H$ 6.35-6.25 (m, 1H), 5.19 (d, J=11.2 Hz, 1H), 5.09 (d, J=18.0 Hz, 1H), 2.79-2.64 (m, 1H), 2.54-2.13 (m, 5H), 2.13-2.05 (m, 3H), 2.02-1.79 (m, 3H), 1.69-1.50 (m, 6H), 1.37-1.23 (m, 4H), 0.87 (s, 3H).

Synthesis of 3-4

To a solution of 3-3 (11 g, 36.6 mmol) in TH (200 mL) was added Pd/C (wet, 50%, 2 g) under N$_2$. The suspension was degassed under vacuum and purged with H$_2$ for three times. After stirring under H$_2$ (30 psi) at 25° C. for 16 h, the reaction mixture was filtered through a pad of Celite and washed with THE (2×100 mL). The residue was triturated from PE (300 mL) to give 3-4 (12 g). $^1$H NMR (400 MHz, CDCl$_3$) δ$_H$ 2.67 (t, J=13.60 Hz, 1H), 2.52-2.06 (m, 5H), 2.00-1.91 (m, 1H), 1.89-1.48 (m, 12H), 1.39-1.19 (m, 5H), 0.87 (s, 3H), 0.80 (t, J=7.53 Hz, 3H).

Synthesis of 3-5

To a solution of BHT (26 g, 118 mmol) in toluene (60 mL) under nitrogen at 0° C. was added AlMe$_3$ (2 M in toluene, 29.7 mL, 59.4 mmol) dropwise. After stirring at 15° C. for 1 h, a solution of 3-4 (6.0 g, 19.8 mmol) in DCM (10 mL) was added dropwise at −70° C. After stirring at −70° C. for 1 h under N$_2$, MeMgBr (19.8 mL, 59.4 mmol, 3M in ethyl ether) was added dropwise at −70° C. After stirring at −70° C. for 4 h, the reaction mixture was poured into saturated 20% citric acid (300 mL) below 10° C. The reaction mixture was extracted with EtOAc (2×100 mL). The combined organic layer was dried over Na$_2$SO$_4$, filtered and concentrated in vacuum. The residue was purified by a silica gel column (PE/EtOAc=0-20%) to give 3-5 (5.6 g, 88.8%). $^1$H NMR (400 MHz, CDCl$_3$) δ$_H$ 2.50-2.37 (m, 1H), 2.13-2.04 (m, 1H), 2.04-1.81 (m, 3H), 1.81-1.62 (m, 5H), 1.62-1.47 (m, 5H), 1.46-1.28 (m, 6H), 1.25 (s, 3H), 1.24-1.11 (m, 4H), 0.84 (s, 3H), 0.80 (t, J=7.60 Hz, 3H).

Synthesis of 3-6

To a mixture of EtPPh$_3$Br (9.72 g, 26.2 mmol) in THE (50 mL) was added t-BuOK (2.93 g, 26.2 mmol) at 15° C. under N$_2$. After stirring at 50° C. for 30 min, 3-5 (5.6 g, 17.5 mmol) was added in portions below 40° C. After stirring at 40° C. for 1 h, the reaction mixture was quenched with 10% NH$_4$Cl aqueous (200 mL) at 15° C. The organic layer was collected and the aqueous layer was extracted with EtOAc (300 mL). The combined organic phase was concentrated under vacuum to give a residue, which was purified by silica gel chromatography (PE/EtOAc=20/1 to 5/1) to afford 3-6 (4.9 g, 84.7%). $^1$H NMR (400 MHz, CDCl$_3$) δ$_H$ 5.15-5.05 (m, 1H), 2.41-2.09 (m, 3H), 2.03-1.89 (m, 1H), 1.85-1.71 (m, 1H), 1.70-1.59 (m, 6H), 1.59-1.37 (m, 9H), 1.37-1.27 (m, 3H), 1.25 (s, 3H), 1.22-1.04 (m, 5H), 0.85 (s, 3H), 0.79 (t, J=7.6 Hz, 3H).

Synthesis of 3-7

To a solution of 3-6 (4.9 g, 14.8 mmol) in THE (50 mL) was added 9-BBN dimer (10.8 g, 44.4 mmol) at 15° C. After stirring at 40° C. for 1 h, ethanol (6.8 g, 148 mmol) was added at 15° C. followed by NaOH aqueous (29.5 mL, 5M, 148 mmol) and then H$_2$O$_2$ (14.7 mL, 10 M, 148 mmol) dropwise at −10° C. After stirring at 80° C. for 1 h, the reaction mixture was added sat. Na$_2$S$_2$O$_3$ (50 mL). After stirring for 30 min, the mixture was extracted with EtOAc (2×100 mL). The combined organic phase was washed with saturated brine (2×100 mL), dried over anhydrous Na$_2$SO$_4$, and concentrated under vacuum to give 3-7 (11 g). $^1$H NMR (400 MHz, CDCl$_3$) δ$_H$ 3.77-3.62 (m, 1H), 2.03-1.91 (m, 3H), 1.83-1.71 (m, 5H), 1.57-1.45 (m, 12H), 1.24 (s, 3H), 1.21 (d, J=6.40 Hz, 3H), 1.18-0.94 (m, 7H), 0.81-0.76 (m, 3H), 0.64 (s, 3H).

Synthesis of 3-8

To a solution of 3-7 (5.15 g, 14.8 mmol) in DCM (100 mL) was added silica gel (10 g) and PCC (6.36 g, 29.6 mmol) at 0° C. After stirring at 15° C. for 3 h, the suspension was filtered, and the filter cake was washed with DCM (2×100 mL). The combined filtrate was concentrated under vacuum to give a residue, which was purified by flash column (PE/EtOAc=20/1 to 4/1) to afford 3-8 (2.8 g, 54.6%). $^1$H NMR (400 MHz, CDCl$_3$) δ$_H$ 2.60-2.45 (m, 1H) 2.28-2.12 (m, 1H), 2.11 (s, 3H), 2.03-1.91 (m, 2H), 1.82-1.59 (m, 6H), 1.54-1.28 (m, 10H), 1.25 (s, 3H), 1.24-1.03 (m, 6H), 0.79 (t, J=7.60 Hz, 3H), 0.59 (s, 3H).

Synthesis of 3-9

To a mixture of MePPh$_3$Br (4.5 g, 12.6 mmol) in THE (20 mL) was added t-BuOK (1.41 g, 12.6 mmol) at 15° C. under N$_2$. After stirring at 50° C. for 30 min, 3-8 (2.2 g, 6.34 mmol) was added in portions below 50° C. After stirring at 50° C. for 1 h, the reaction mixture was quenched with 10% NH$_4$Cl aqueous (100 mL) at 15° C. The organic layer was collected, and the aqueous layer was extracted with EtOAc (100 mL). The combined organic phase was concentrated under vacuum to give a residue, which was purified by silica gel chromatography (PE/EtOAc=20/1 to 5/1) to afford 3-9 (1.6 g, 73.3%). $^1$H NMR (400 MHz, CDCl$_3$) SH 4.84 (s, 1H), 4.69 (s, 1H), 2.04-1.90 (m, 2H), 1.87-1.76 (m, 2H), 1.75 (s, 3H), 1.73-1.57 (m, 5H), 1.53-1.26 (m, 9H), 1.25 (s, 3H), 1.23-0.82 (m, 8H), 0.79 (t, J=7.60 Hz, 3H), 0.54 (s, 3H).

Synthesis of 3-10

To a solution of 3-9 (600 mg, 1.74 mmol) and NaHCO$_3$ (146 mg, 1.74 mmol) in DCM (30 mL) was added mCPBA (352 mg, 1.74 mmol) at 20° C. After stirring at 20° C. for 2 h, the mixture was quenched by saturated NaHCO$_3$ aqueous (50 mL) at 20° C. The DCM phase was separated and washed with saturated NaHCO$_3$/Na$_2$S$_2$O$_3$ aqueous (1:1, 2×100 mL), brine (100 mL), dried over Na$_2$SO$_4$, filtered and concentrated under vacuum to give 3-10 (600 mg). $^1$H NMR (400 MHz, CDCl$_3$) δ$_H$ 2.88-2.30 (m, 2H), 2.08-1.60 (m, 9H), 1.54-1.37 (m, 8H), 1.36-1.32 (m, 3H), 1.31-1.27 (m, 1H), 1.25 (s, 3H), 1.23-0.97 (m, 8H), 0.83-0.74 (m, 4H), 0.66 (s, 2H).

Synthesis of 3 & 4

To a solution of 3-10 (600 mg, 1.66 mmol) in DMF (20 mL) was added Cs$_2$CO$_3$ (1.08 g, 3.32 mmol) and 1H-pyrazole-4-carbonitrile (230 mg, 2.48 mmol). After stirring at 120° C. for 16 h, the mixture was added into saturated NH$_4$Cl (100 mL). The organic layer was collected and the aqueous layer was extracted with EtOAc (3×100 mL). The combined organic layer was washed with LiCl (100 mL, 5% in water), saturated brine (2×100 mL), dried over anhydrous Na$_2$SO$_4$, filtered and concentrated to give a mixture of 3 & 4 (800 mg).

The epimers (500 mg, 1.1 mmol) were separated by SFC (Column: DAICEL CHIRALPAK AS (250 mm*30 mm, 10 um)), Condition: 0.1% NH$_3$H$_2$O EtOH, Begin B: 30%, End B: 30%, FlowRate (ml/min): 80) to afford 3 (200 mg, 40%) and 4 (150 mg, 30%).

3: $^1$H NMR (400 MHz, CDCl$_3$) $\delta_H$ 7.92 (s, 1H), 7.82 (s, 1H), 4.34 (d, J=13.60 Hz, 1H), 4.07 (d, J=13.60 Hz, 1H), 2.52 (s, 1H), 2.08-1.88 (m, 2H), 1.83-1.59 (m, 6H), 1.55-1.45 (m, 3H), 1.44-1.27 (m, 8H), 1.25 (s, 3H), 1.23-1.02 (m, 7H), 0.97 (s, 3H), 0.89 (s, 3H), 0.79 (t, J=7.60 Hz, 3H). LC-ELSD/MS: purity >99%; analytic SFC: 100% de; MS ESI calcd. for C$_{28}$H$_{40}$N$_3$ [M−2H$_2$O+H]$^+$ 418.3, found 418.3.

4: $^1$H NMR (400 MHz, CDCl$_3$) $\delta_H$ 7.89 (s, 1H), 7.80 (s, 1H), 4.15 (d, J=14.0 Hz, 1H), 4.00 (d, J=14.0 Hz, 1H), 2.31 (s, 1H), 2.10-1.84 (m, 3H), 1.83-1.60 (m, 5H), 1.55-1.47 (m, 3H), 1.46-1.26 (m, 8H), 1.25 (s, 3H), 1.24-1.09 (m, 7H), 1.08 (s, 3H), 0.85 (s, 3H), 0.79 (t, J=7.60 Hz, 3H). LC-ELSD/MS: purity >99%; analytic SFC: 99.18% de; MS ESI calcd. for C$_{28}$H$_{40}$N$_3$ [M−2H$_2$O+H]$^+$ 418.3, found 418.3.

Example 5: Synthesis of 1-((S)-2-((3R,5R,8S,9S,10S,13S,14S,17S)-10-ethyl-3-hydroxy-3,13-dimethylhexadecahydro-1H-cyclopenta[a]phenanthren-17-yl)-2-methoxypropyl)-1H-pyrazole-4-carbonitrile

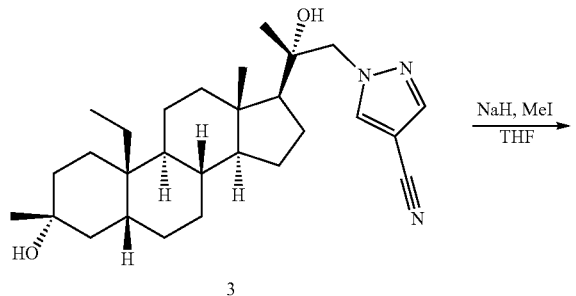

3

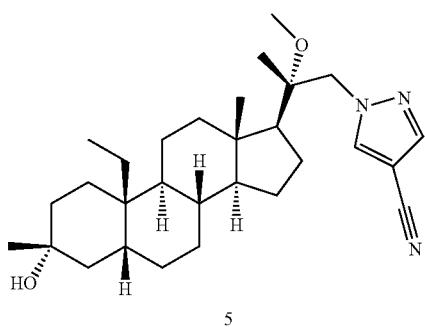

5

To a solution of 3 (200 mg, 0.4408 mmol) in THF (5 mL) was added NaH (52.6 mg, 1.32 mmol, 60% in oil) at 0° C. After stirring for 20 min, MeI (93.8 mg, 0.6612 mmol) was added. After stirring at 25° C. for 16 h, the reaction mixture was diluted with H$_2$O (50 mL) and extracted with EtOAc (3×20 mL). The combined organic phase was washed with saturated brine (50 mL), dried over anhydrous Na$_2$SO$_4$, filtered and concentrated. The residue was purified by flash column (0-50% of EtOAc in PE) to give product 5 (68.8 mg, 33.3%). $^1$H NMR (400 MHz, CDCl$_3$) $\delta_H$ 7.91 (s, 1H), 7.75 (s, 1H), 4.30-4.15 (m, 2H), 3.18 (s, 3H), 2.00-1.88 (m, 2H), 1.81-1.71 (m, 2H), 1.66-1.60 (m, 3H), 1.54-1.47 (m, 3H), 1.47-1.26 (m, 8H), 1.24 (s, 3H), 1.23-1.07 (m, 7H), 1.06 (s, 3H), 1.05-1.00 (m, 1H), 0.86-0.75 (m, 6H). LC-ELSD/MS: purity >99%; analytic SFC: 100% de; MS ESI calcd. for C$_{28}$H$_{43}$N$_3$ [M−2H$_2$O-CH$_3$+2H]$^+$ 418.3, found 418.3.

Example 6: Synthesis of 1-((R)-2-((3R,5R,8S,9S,10S,13S,14S,17S)-10-ethyl-3-hydroxy-3,13-dimethylhexadecahydro-1H-cyclopenta[a]phenanthren-17-yl)-2-methoxypropyl)-1H-pyrazole-4-carbonitrile

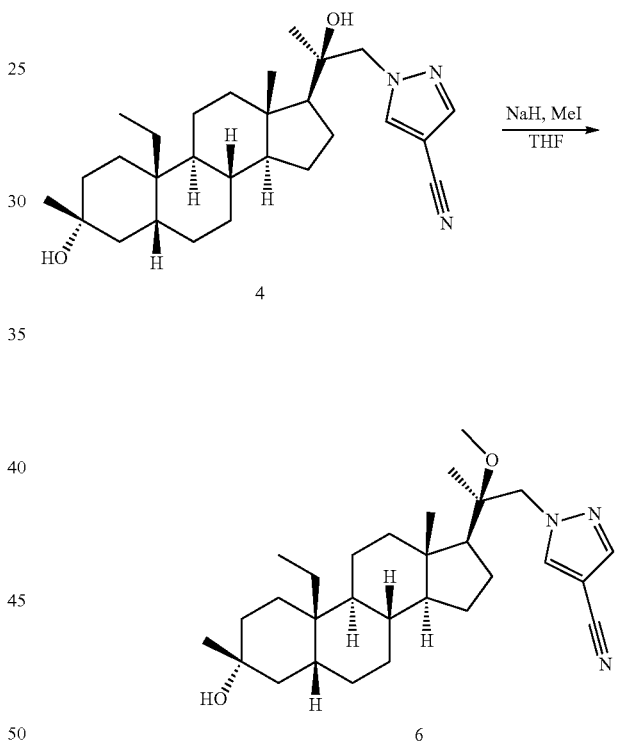

To a solution of 4 (150 mg, 0.3306 mmol) in THF (5 mL) was added NaH (39.6 mg, 0.9918 mmol, 60% in oil) at 0° C. After stirring for 20 min, MeI (70.3 mg, 0.4959 mmol) was added. After stirring at 25° C. for 16 h, the reaction mixture was diluted with H$_2$O (50 mL) and extracted with EtOAc (3×20 mL). The combined organic phase was washed with saturated brine (50 mL), dried over anhydrous Na$_2$SO$_4$, filtered and concentrated. The residue was purified by flash column (0-50% of EtOAc in PE) to give product 6 (23.4 mg). $^1$H NMR (400 MHz, CDCl$_3$) $\delta_H$ 7.90 (s, 1H), 7.75 (s, 1H), 4.23 (s, 2H), 3.14 (s, 3H), 2.12-1.91 (m, 2H), 1.80-1.61 (m, 7H), 1.53-1.27 (m, 10H), 1.25 (s, 3H), 1.22-1.06 (m, 7H), 1.01 (s, 3H), 0.82-0.77 (m, 6H). LC-ELSD/MS: purity >99%; analytic SFC: 99.62% de; MS ESI calcd. for C$_{28}$H$_{43}$N$_3$ [M−2H$_2$O-CH$_3$+2H]$^+$ 418.3, found 418.3.

Examples 7 & 8: Synthesis of 1-((S)-2-hydroxy-2-((3R,5R,8R,9R,10S,13S,14S,17S)-3-hydroxy-13-methyl-3-propylhexadecahydro-1H-cyclopenta[a]phenanthren-17-yl)propyl)-1H-pyrazole-4-carbonitrile (7) & 1-((R)-2-hydroxy-2-((3R,5R,8R,9R,10S,13S,14S,17S)-3-hydroxy-13-methyl-3-propylhexadecahydro-1H-cyclopenta[a]phenanthren-17-yl)propyl)-1H-pyrazole-4-carbonitrile (8)

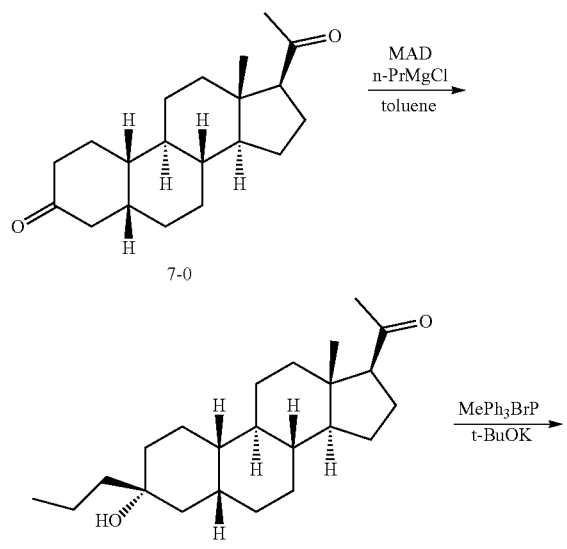

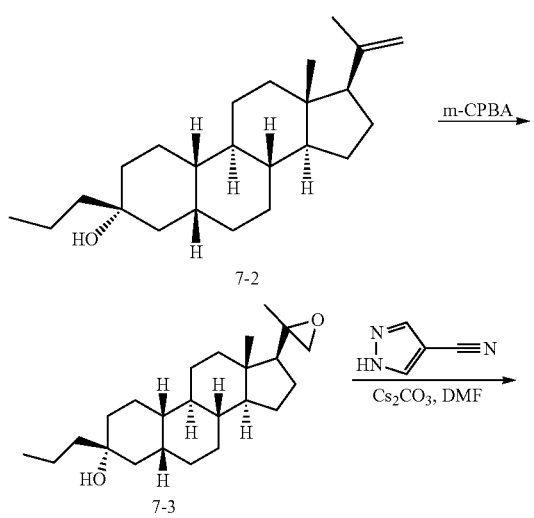

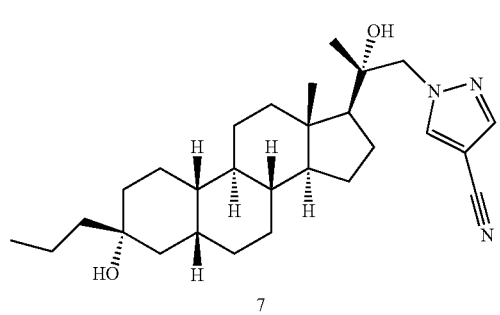

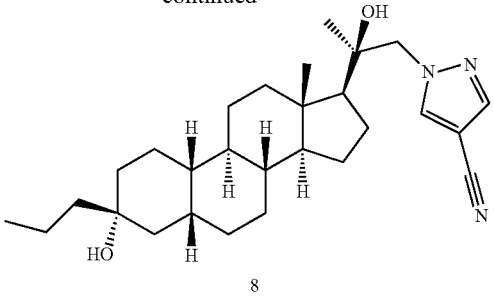

8

Synthesis of 7-1

To a solution of 2,6-di-tert-butyl-4-methylphenol (13.1 g, 59.6 mmol) in toluene (20 mL) was added AlMe₃ (14.9 mL, 29.8 mmol, 2 M in toluene) dropwise at 0° C. After stirring at 25° C. for 30 min, a solution of 7-0 (3 g, 9.91 mmol) in anhydrous toluene (40 mL) was added dropwise at −70° C. After stirring at −70° C. for 1 h under N₂, n-PrMgCl (14.8 mL, 29.7 mmol, 2 M in diethyl ether) was added dropwise at −70° C. After stirring at −70° C. for another 2 h, the reaction mixture was poured into saturated aqueous citric acid (100 mL) below 10° C. and extracted with EtOAc (2×100 mL). The combined organic layer was dried over Na₂SO₄, filtered and concentrated in vacuum. The residue was purified by flash column (0-10% of EtOAc in PE) to give 7-1 (1.7 g, 49%). ¹H NMR (400 MHz, CDCl₃) $\delta_H$ 2.53 (t, J=8 Hz, 1H), 2.16-2.11 (m, 4H), 2.04-1.98 (m, 1H), 1.83-1.52 (m, 3H), 1.50-1.30 (m, 5H), 1.27-1.02 (m, 10H), 0.97-0.77 (m, 11H), 0.61 (s, 3H).

Synthesis of 7-2

To a suspension of Ph₃PMeBr (3.50 g, 9.80 mmol) in THF (20 mL) was added t-BuOK (1.09 g, 9.80 mmol). After stirring for 30 min at 16° C. under N₂, 7-1 (1.7 g, 4.90 mmol) was added. After stirring at 35° C. for 16 h, the reaction mixture was poured into water (300 mL) and extracted with EtOAc (3×100 mL). The combined organic phase was washed with brine (150 mL), dried over anhydrous Na₂SO₄ and concentrated. The residue was purified by flash column (0~5% of EtOAc in PE) to give 7-2 (1.3 g). ¹H NMR (400 MHz, CDCl₃) $\delta_H$ 4.84 (s, 1H), 4.70 (s, 1H), 2.06-2.01 (m, 1H), 1.85-1.58 (m, 9H), 1.56-1.25 (m, 12H), 1.19-0.96 (m, 7H), 0.95-0.91 (m, 3H), 0.9-0.83 (m, 3H), 0.57 (s, 3H).

Synthesis of 7-3

To a solution of 7-2 (1 g, 2.90 mmol) in DCM (10 mL) was added m-CPBA (1.17 g, 85%, 5.80 mmol) at 15° C. After stirring at 15° C. for 1 h, the mixture was quenched by saturated NaHCO₃ aqueous (200 mL). The organic phase was separated and washed with saturated NaHCO₃/Na₂S₂O₃ aqueous (1:1, 3×100 mL), brine (100 mL), dried over Na₂SO₄, filtered and concentrated under vacuum to give 7-3 (1 g). ¹H NMR (400 MHz, CDCl₃) $\delta_H$ 2.89 (d, J=4 Hz, 0.7H), 2.56-2.49 (m, 1H), 2.32 (d, J=4 Hz, 0.3H), 2.04-1.51 (m, 10H), 1.48-1.23 (m, 15H), 1.21-0.99 (m, 6H), 0.95-0.91 (m, 3H), 0.81-0.76 (m, 1H), 0.68 (s, 3H).

Synthesis of 7 & 8

To a solution of 7-3 (680 mg, 1.88 mmol) in DMF (10 mL) was added 1H-pyrazole-4-carbonitrile (349 mg, 3.76 mmol) and Cs₂CO₃ (3.06 g, 9.40 mmol). After stirring at 125° C. for 12 h, the reaction mixture was diluted with water (100 mL) and extracted with EtOAc (2×100 mL). The combined organic layer was separated, concentrated and purified by flash column (0-20% EtOAc in PE) to give a mixture of epimers. The epimers were separated by SFC (Column: DAICEL CHIRALPAK AS (250 mm*50 mm, 10 um); Condition: 0.1% NH₃.H₂O EtOH; Begin B: 30; End B: 30; Flow Rate (mL/min): 200) to give 7 (250 mg) and 8 (104 mg).

7: ¹H NMR (400 MHz, CDCl₃) δ$_H$ 7.93 (s, 1H), 7.81 (s, 1H), 4.36-4.33 (m, 1H), 4.09-4.06 (m, 1H), 2.52 (s, 1H), 2.02-1.99 (m, 1H), 1.80-1.60 (m, 8H), 1.56-1.41 (m, 5H), 1.40-1.03 (m, 15H), 0.97-0.91 (m, 9H). LC-ELSD/MS purity 99%, MS ESI calcd. for C₂H₄₀N₃ [M−2H₂O+H]⁺ 418.3, found 418.3. SFC 99.9% de 8: ¹H NMR (400 MHz, CDCl₃) δ$_H$ 7.89 (s, 1H), 7.80 (s, 1H), 4.17-4.14 (m, 1H), 4.03-3.99 (m, 1H), 2.31 (s, 1H), 2.08-2.03 (m, 1H), 1.95-1.50 (m, 10H), 1.47-1.18 (m, 13H), 1.16-1.00 (m, 8H), 0.95-0.87 (m, 6H). LC-ELSD/MS purity 99%, MS ESI calcd. for C₂H₄₀N₃ [M−2H₂O+H]⁺ 418.3, found 418.3. SFC 98.22% de Examples 9 & 10: Synthesis of 1-((S)-2-hydroxy-2-((3R,5S,8R,9R,10S,13S,14S,17S)-3-hydroxy-13-methyl-3-propylhexadecahydro-1H-cyclopenta[a]phenanthren-17-yl)propyl)-1H-pyrazole-4-carbonitrile (9) & 1-((R)-2-hydroxy-2-((3R,5S,8R,9R,10S,13S,14S,17S)-3-hydroxy-13-methyl-3-propylhexadecahydro-1H-cyclopenta[a]phenanthren-17-yl)propyl)-1H-pyrazole-4-carbonitrile (10)

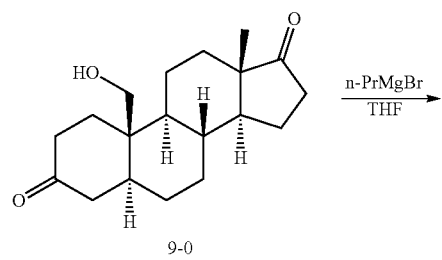
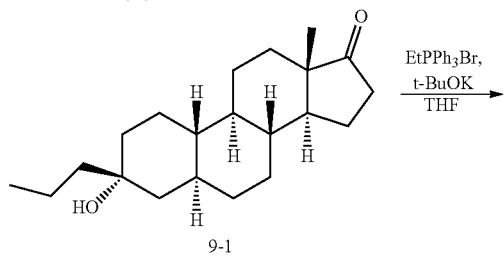
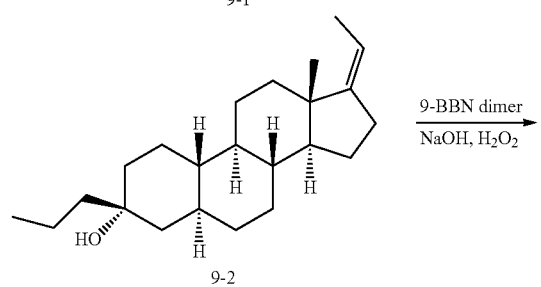
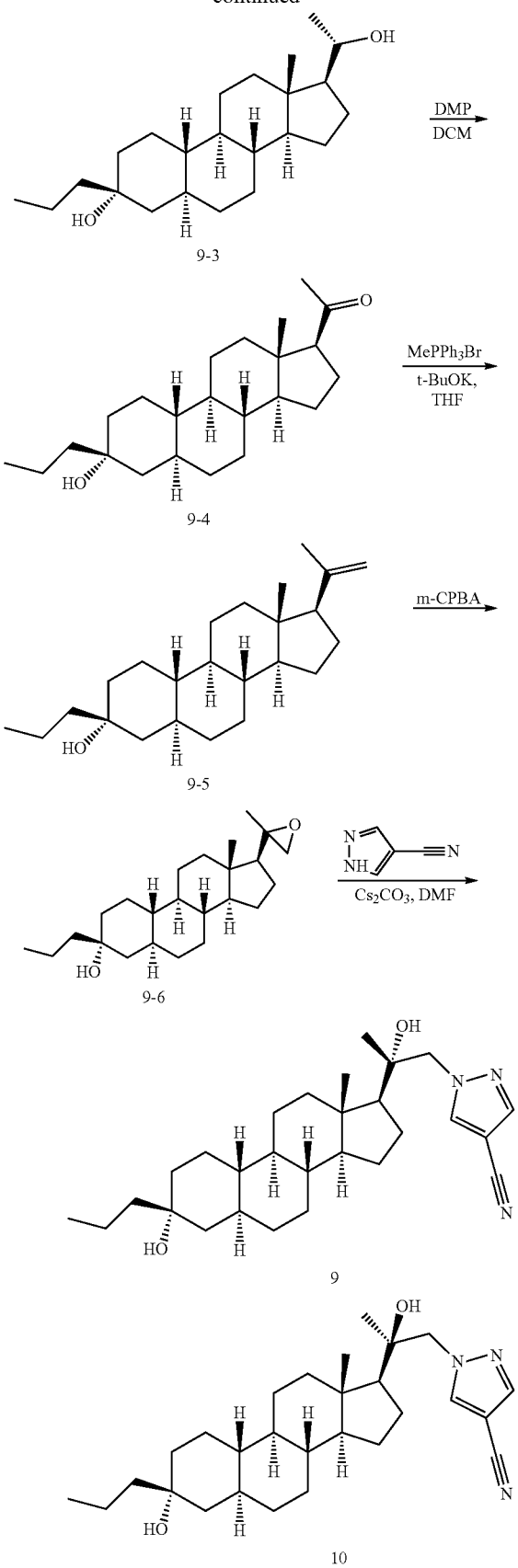

Synthesis of 9-1

To the solution of 9-0 (15 g, 54.6 mmol) in TH (200 mL) was added n-PrMgCl (81.5 mL, 163 mmol, 2M in THF) dropwise at −60° C. After stirring at −60° C. for 2 h, the reaction mixture was poured into saturated aqueous NH$_4$Cl (100 mL) at 0° C. and extracted with EtOAc (2×200 mL). The combined organic layer was dried over Na$_2$SO$_4$, filtered and concentrated. The residue was triturated from MeCN (50 mL) at 80° C. to give 9-1 (7 g, 40.4%). $^1$H NMR (400 MHz, CDCl$_3$) δ$_H$ 2.44 (dd, J=8.4, 19.2 Hz, 1H), 2.14-2.00 (m, 1H), 1.99-1.84 (m, 2H), 1.83-1.71 (m, 3H), 1.70-1.44 (m, 5H), 1.43-1.12 (m, 10H), 1.11-0.99 (m, 4H), 0.97-0.90 (m, 3H), 0.88 (s, 3H), 0.81-0.66 (m, 2H).

Synthesis of 9-2

To a mixture of EtPPh$_3$Br (24.3 g, 65.6 mmol) in THE (80 mL) was added t-BuOK (7.36 g, 65.6 mmol) at 15° C. under N$_2$. After stirring at 15° C. for 30 min, 9-1 (7 g, 21.9 mmol) in THE (20 mL) was added. After stirring at 40° C. for 1 h, the mixture was poured into NH$_4$Cl (50 mL) and the aqueous phase was extracted with EtOAc (2×100 mL). The combined organic phase was washed with brine (100 mL), dried over anhydrous Na$_2$SO$_4$, filtered and concentrated. The residue was heated at 70° C. in MeOH (50 mL) for 30 minutes, cooled to room temperature, poured into water (50 mL) and the resulting residue was filtered to give 9-2 (11 g).

$^1$H NMR (400 MHz, CDCl$_3$) δ$_H$ 5.24-4.98 (m, 1H), 2.45-2.30 (m, 1H), 2.28-2.11 (m, 2H), 1.88-1.74 (m, 2H), 1.73-1.57 (m, 7H), 1.55-1.48 (m, 2H), 1.44-1.25 (m, 6H), 1.24-0.96 (m, 9H), 0.95-0.90 (m, 3H), 0.88 (s, 3H), 0.78-0.62 (m, 2H).

Synthesis of 9-3

To a solution of 9-2 (6 g, 18.1 mmol) in anhydrous THE (60 mL) was added 9-BBN dimer (13.2 g, 54.3 mmol) at 15° C. under N$_2$. After stirring at 60° C. for 2 h, the mixture was cooled and quenched by EtOH (15 mL). NaOH (15 mL, 5M, 75.5 mmol) was added very slowly. After the addition, H$_2$O$_2$ (22.6 mL, 226 mmol, 10 M) was added slowly below 30° C. After stirring at 60° C. for 2 h, the mixture was cooled, poured into water (50 mL) and extracted with EtOAc (2×50 mL). The combined organic layer was dried over Na$_2$SO$_4$, filtered and concentrated in vacuum. The residue was purified by column chromatography (20-25% of EtOAc in PE) to give 9-3 (6.1 g, 52.8%). $^1$H NMR (400 MHz, CDCl$_3$) δ$_H$ 3.86-3.57 (m, 1H), 1.98-1.81 (m, 2H), 1.81-1.70 (m, 2H), 1.70-1.60 (m, 3H), 1.57-1.48 (m, 3H), 1.42-1.25 (m, 7H), 1.23 (d, J=6.0 Hz, 3H), 1.17-0.96 (m, 9H), 0.95-0.89 (m, 3H), 0.67 (s, 5H).

Synthesis of 9-4

To a solution of 9-3 (6.1 g, 17.5 mmol) in DCM (50 mL) was added PCC (11.2 g, 52.5 mmol) and silica gel (15 g) at 25° C. After stirring at 25° C. for 1 h, the reaction mixture was filtered and the residue was washed with anhydrous DCM (2×20 mL). The combined filtrate was concentrated in vacuum and then purified by column (15-20% of EtOAc in PE) to give 9-4 (3 g, 49.5%). $^1$H NMR (400 MHz, CDCl$_3$) δ$_H$ 2.55 (t, J=8.8 Hz, 1H), 2.12 (s, 4H), 2.00 (td, J=3.2, 12.0 Hz, 1H), 1.89-1.73 (m, 2H), 1.59 (br d, J=2.8 Hz, 1H), 1.55-1.50 (m, 1H), 1.49-1.16 (m, 10H), 1.15-0.97 (m, 6H), 0.96-0.90 (m, 3H), 0.81-0.65 (m, 2H), 0.62 (s, 3H).

Synthesis of 9-5

To a mixture of MePPh$_3$Br (9.25 g, 25.9 mmol) in THE (40 mL) was added t-BuOK (2.9 g, 25.9 mmol) at 15° C. under N$_2$. After stirring at 15° C. for 30 min, 9-4 (3 g, 8.65 mmol) in THE (10 mL) was added. After stirring at 40° C. for 2 h, the mixture was poured into NH$_4$Cl.aq (150 mL) and the aqueous phase was extracted with EtOAc (2×200 mL). The combined organic phase was washed with brine (20 mL), dried over anhydrous Na$_2$SO$_4$, filtered and concentrated. The residue was heated in MeOH (500 mL) at 70° C. for 30 minutes, cooled to room temperature, added water (300 mL), filtered and dried to give 9-5 (3 g, 100%). $^1$H NMR (400 MHz, CDCl$_3$) δ$_H$ 4.85 (s, 1H), 4.71 (s, 1H), 2.11-1.98 (m, 1H), 1.76 (s, 7H), 1.71-1.64 (m, 3H), 1.64-1.53 (m, 3H), 1.39 (d, J=3.6 Hz, 4H), 1.14 (br s, 12H), 0.95-0.88 (m, 3H), 0.77-0.62 (m, 2H), 0.58 (s, 3H).

Synthesis of 9-6

To a solution of 9-5 (1 g, 2.90 mmol) in DCM (10 mL) was added m-CPBA (750 mg, 4.35 mmol) at 20° C. After stirring at 20° C. for 2 h, the mixture was poured into saturated NaHCO$_3$ aqueous (20 mL) and extracted with EtOAc (2×50 mL). The combined organic solution was washed with saturated NaHCO$_3$/Na$_2$S$_2$O$_3$ aqueous (1:1, 2×20 mL), brine (20 mL), dried over Na$_2$SO$_4$, filtered and concentrated to give 9-6 (1.5 g). $^1$H NMR (400 MHz, CDCl$_3$) δ$_H$ 2.89 (d, J=4.4 Hz, 1H), 2.58-2.54 (m, 1H), 2.04-1.86 (m, 2H), 1.81-1.72 (m, 3H), 1.66-1.50 (m, 8H), 1.39-1.37 (m, 6H), 1.35 (s, 3H), 1.31-1.16 (m, 5H), 1.15-1.05 (m, 7H), 1.04-0.94 (m, 5H), 0.93-0.89 (m, 5H), 0.68 (s, 3H).

Synthesis of 9 & 10

To a solution of 9-6 (750 mg, 2.07 mmol) in DMF (10 mL) was added 1H-pyrazole-4-carbonitrile (481 mg, 5.17 mmol) and Cs$_2$CO$_3$ (3.35 g, 10.3 mmol). After stirring at 130° C. for 16 h, the reaction mixture was diluted with water (20 mL) and extracted with EtOAc (2×30 mL). The combined organic phase was washed with brine (20 mL), dried over anhydrous Na$_2$SO$_4$, filtered and concentrated. The residue was purified by flash column (0~20% EtOAc in PE) to give a mixture of epimers (600 mg, 63.8%) which were separated SFC (Column: DAICEL CHIRALPAK AS 250 mm×30 mm, 10 um; Condition: 0.1% NH$_3$H$_2$O EtOH; Gradient: from 25% to 25% of B; Flow rate: 70 mL/min; Column temperature: 40° C.) to afford 9 (230 mg) and 10 (86.9 mg). 9 (230 mg) was triturated from MeCN (5 mL) at 20° C. to give 9 (193.3 mg).

9: $^1$H NMR (400 MHz, CDCl$_3$) δ$_H$ 7.92 (s, 1H), 7.81 (s, 1H), 4.36 (d, J=14.0 Hz, 1H), 4.08 (d, J=14.0 Hz, 1H), 2.49 (s, 1H), 2.04-1.96 (m, 1H), 1.78-1.57 (m, 8H), 1.54-1.49 (m, 1H), 1.45-1.41 (m, 1H), 1.38 (br d, J=3.2 Hz, 4H), 1.34-1.12 (m, 5H), 1.12-1.02 (m, 5H), 1.01-0.94 (m, 5H), 0.92 (s, 6H), 0.71-0.62 (m, 2H). LC-ELSD/MS purity 99%, MS ESI calcd. for C$_{28}$H$_{40}$N$_3$ [M−2H$_2$O+H]$^+$ 418.3 found 418.3. SFC 99% de.

10: $^1$H NMR (400 MHz, CDCl$_3$) δ$_H$ 7.89 (s, 1H), 7.80 (s, 1H), 4.19-4.12 (m, 1H), 4.04-3.98 (m, 1H), 2.27 (s, 1H), 2.07-2.01 (m, 1H), 1.91 (q, J=10.4 Hz, 1H), 1.75 (br d, J=13.2 Hz, 2H), 1.70-1.57 (m, 5H), 1.52-1.45 (m, 2H), 1.38 (br d, J=3.2 Hz, 4H), 1.35-1.12 (m, 6H), 1.11-1.08 (m, 5H), 1.05-0.90 (m, 7H), 0.88 (s, 3H), 0.72-0.63 (m, 2H). LC-

ELSD/MS purity 99%, MS ESI calcd. for C₂H₄₀N₃ [M−2H₂O+H]⁺ 418.3 found 418.3. SFC 99% de.

Examples 11 & 12: Synthesis of 1-((S)-2-((3R,5R, 8R,9R,10S,13S,14S,17S)-3-ethyl-3-hydroxy-13-methylhexadecahydro-1H-cyclopenta[a]phenanthren-17-yl)-2-hydroxypropyl)-1H-pyrazole-4-carbonitrile (11) & 1-((R)-2-((3R,5R,8R,9R,10S,13S,14S,17S)-3-ethyl-3-hydroxy-13-methylhexadecahydro-1H-cyclopenta[a]phenanthren-17-yl)-2-hydroxypropyl)-1H-pyrazole-4-carbonitrile (12)

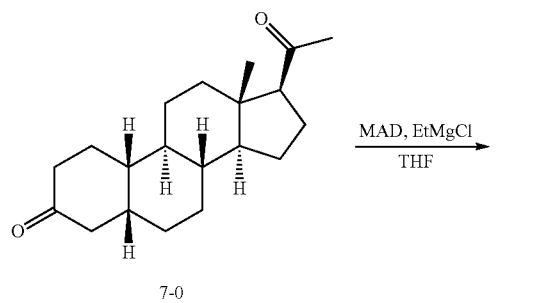

7-0

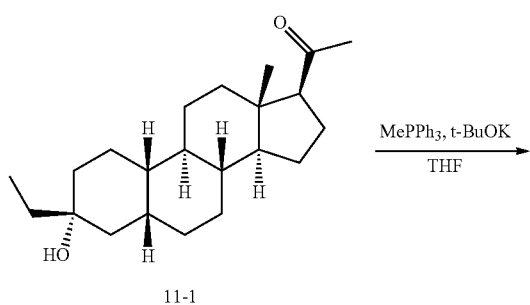

11-1

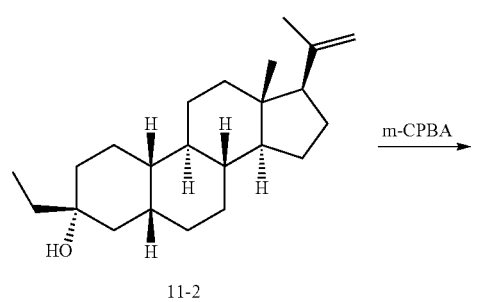

11-2

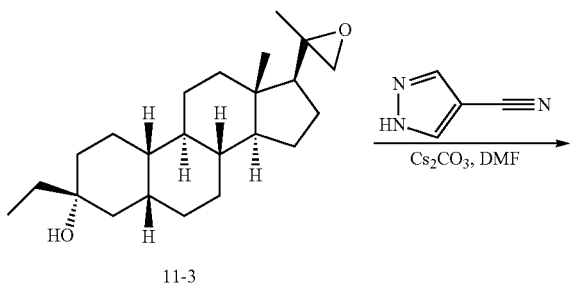

11-3

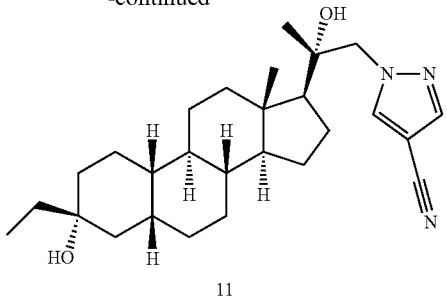

11

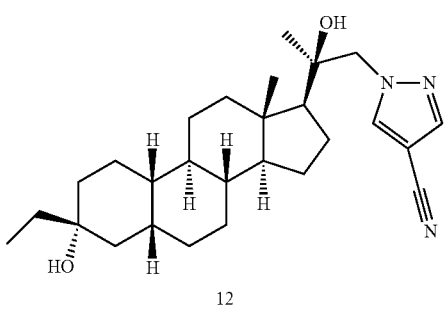

12

Synthesis of 11-1

To a solution of BHT (12 g, 54.4 mmol) in toluene (120 mL) under nitrogen at 0° C. was added trimethylaluminum (2 M in toluene, 14 mL, 28 mmol) dropwise. After stirring at 25° C. for 1 h, to the MAD solution was added a solution of 7-0 (6 g, 19.8 mmol) in DCM (60 mL) dropwise at −70° C. After stirring at −70° C. for 1 h under N₂, EtMgBr (20 mL, 60 mmol, 3M in ethyl ether) was added dropwise at −70° C. After stirring at −70° C. for 1 h, the reaction mixture was poured into saturated aqueous citric acid (600 mL) below 10° C. and extracted with DCM (2×800 mL). The combined organic layer was dried over Na₂SO₄, filtered and concentrated. The residue was triturated by PE to give 11-1 (3.83 g, 58%). ¹H NMR (400 MHz, CDCl₃) δ$_H$ 2.56-2.50 (m, 1H), 2.24-2.10 (m, 4H), 2.07-1.99 (m, 1H), 1.89-1.51 (m, 9H), 1.50-1.20 (m, 12H), 1.19-1.00 (m, 3H), 0.98-0.80 (m, 3H), 0.61 (s, 3H).

Synthesis of 11-2

To a suspension of MePh₃PBr (6.4 g, 18.0 mmol) in THF (50 mL) was added t-BuOK (2.01 g, 18.0 mmol). After stirring at 40° C. for 10 min, the mixture was slowly added dropwise to a solution of 11-1 (3 g, 9.02 mmol) in THF (30 mL). After stirring at 20° C. for 18 h, the mixture was quenched with sat. NH₄Cl (100 mL) and extracted with EtOAc (3×100 mL). The combined organic phase was washed with sat. NH₄Cl (100 mL), dried over Na₂SO₄, filtered, and concentrated. The residue was purified by combi-flash (0-25% of EtOAc in PE) to give 11-2 (2.445 g, 82%). ¹H NMR (400 MHz, CDCl₃) δ$_H$ 4.84 (s, 1H), 4.69 (s, 1H), 2.02-1.53 (m, 13H), 1.50-1.33 (m, 4H), 1.32-1.11 (m, 11H), 1.10-0.99 (m, 2H), 0.85-0.80 (m, 3H), 0.56 (s, 3H).

Synthesis of 11-3

To a solution of 11-2 (1.8 g, 5.44 mmol) in DCM (20 mL) was added m-CPBA (2.18 g, 85%, 10.8 mmol). After stirring at 15° C. for 1 h, the mixture was quenched by NaHCO₃(50 mL, sat. aq.) and Na$_2$S$_2$O$_3$ (20 mL, sat. aq.). The organic layer was separated, dried over Na$_2$SO$_4$, filtered and concentrated in vacuum to give 11-3 (1.7 g), which was used as is.

Synthesis of 11 & 12

To a solution of 11-3 (850 mg, 2.45 mmol) in DMF (10 mL) was added 1H-pyrazole-4-carbonitrile (341 mg, 3.67 mmol) and Cs$_2$CO$_3$ (3.97 g, 12.2 mmol) at 20° C. After stirring at 120° C. for 2 h, the reaction mixture was diluted with water (100 mL) and extracted with EtOAc (2×50 mL). The combined organic layer was separated, concentrated and purified by flash column (30~65% EtOAc in PE) to give a mixture of epimers. The epimers were separated by SFC (Column DAICEL CHIRALPAK AS (250 mm*30 mm, 10 um) Condition 0.1% NH$_3$H$_2$O EtOH Begin B 25% End B 25% Gradient Time(min) 100% B Hold Time(min) Flow-Rate (ml/min) 70) to give 11 (395.8 mg, 49.6%) and 12 (155.4 mg, 19.4%).

11: $^1$H NMR (400 MHz, CDCl$_3$) $\delta_H$ 7.93 (s, 1H), 7.82 (s, 1H), 4.45-3.99 (m, 2H), 2.50 (br s, 1H), 2.08-1.94 (m, 1H), 1.84-1.57 (m, 10H), 1.47-1.02 (m, 16H), 0.97 (s, 3H), 0.92 (s, 3H), 0.88 (t, J=7.5 Hz, 3H). LC-ELSD/MS purity 99%, MS ESI calcd. for C$_{27}$H$_{38}$N$_3$ [M−2H$_2$O+H]$^+$ 404.3, found 404.3. SFC 100% de 12: $^1$H NMR (400 MHz, CDCl$_3$) $\delta_H$ 7.90 (br s, 1H), 7.81 (s, 1H), 4.24-3.90 (m, 2H), 2.29 (br s, 1H), 2.06 (br d, J=12.3 Hz, 1H), 1.96-1.86 (m, 1H), 1.84-1.56 (m, 9H), 1.53-1.19 (m, 12H), 1.19-1.09 (m, 7H), 0.92-0.85 (m, 6H). LC-ELSD/MS purity 99%, MS ESI calcd. for C$_{27}$H$_{38}$N$_3$ [M−2H$_2$O+H]$^+$ 404.3, found 404.3. SFC 99% de.

Examples 13 & 14: Synthesis of 1-((S)-2-((3R,5S, 8R,9R,10S,13S,14S,17S)-3-ethyl-3-hydroxy-13-methylhexadecahydro-1H-cyclopenta[a]phenanthren-17-yl)-2-hydroxypropyl)-1H-pyrazole-4-carbonitrile (13) & 1-((R)-2-((3R,5S,8R,9R,10S, 13S,14S,17S)-3-ethyl-3-hydroxy-13-methylhexadecahydro-1H-cyclopenta[a]phenanthren-17-yl)-2-hydroxypropyl)-1H-pyrazole-4-carbonitrile (14)

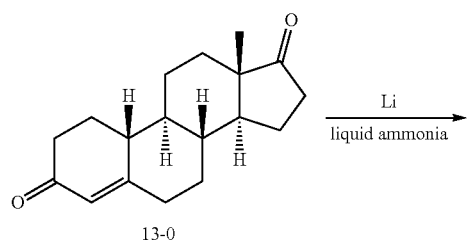

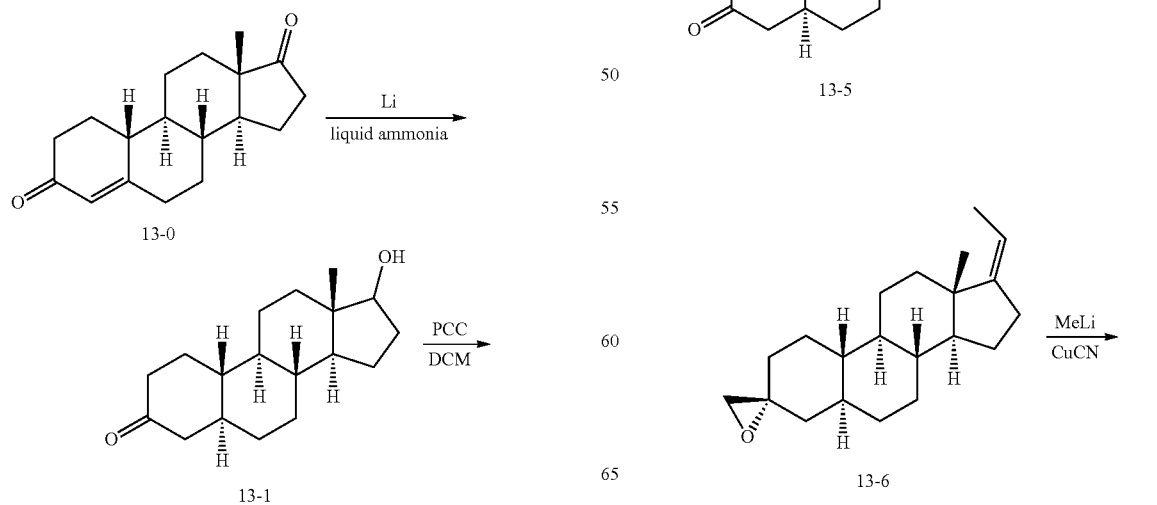

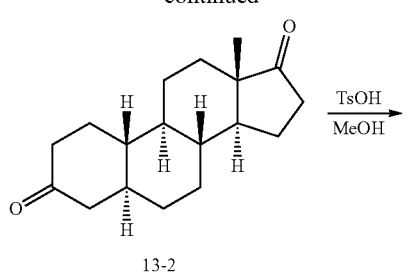

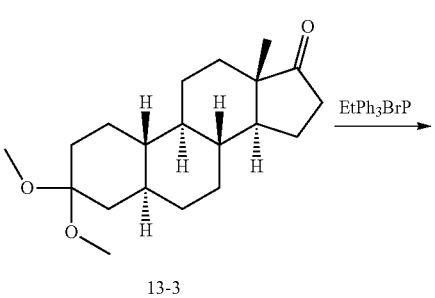

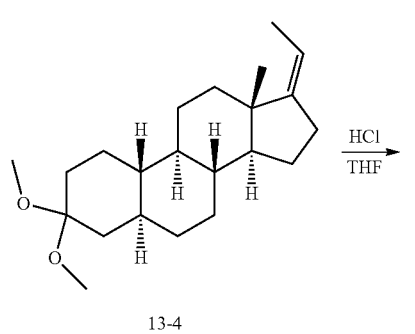

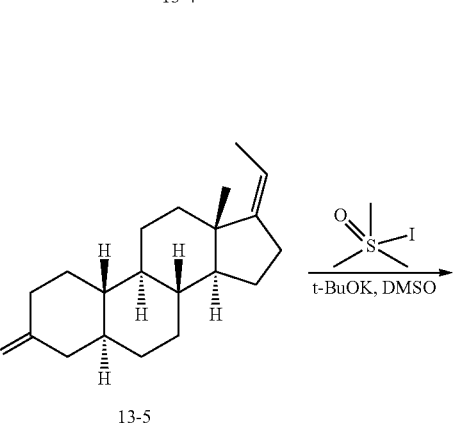

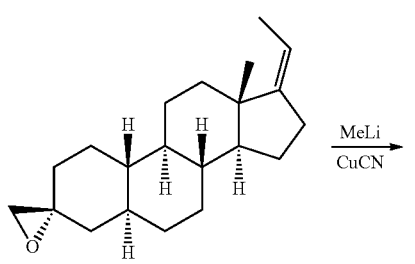

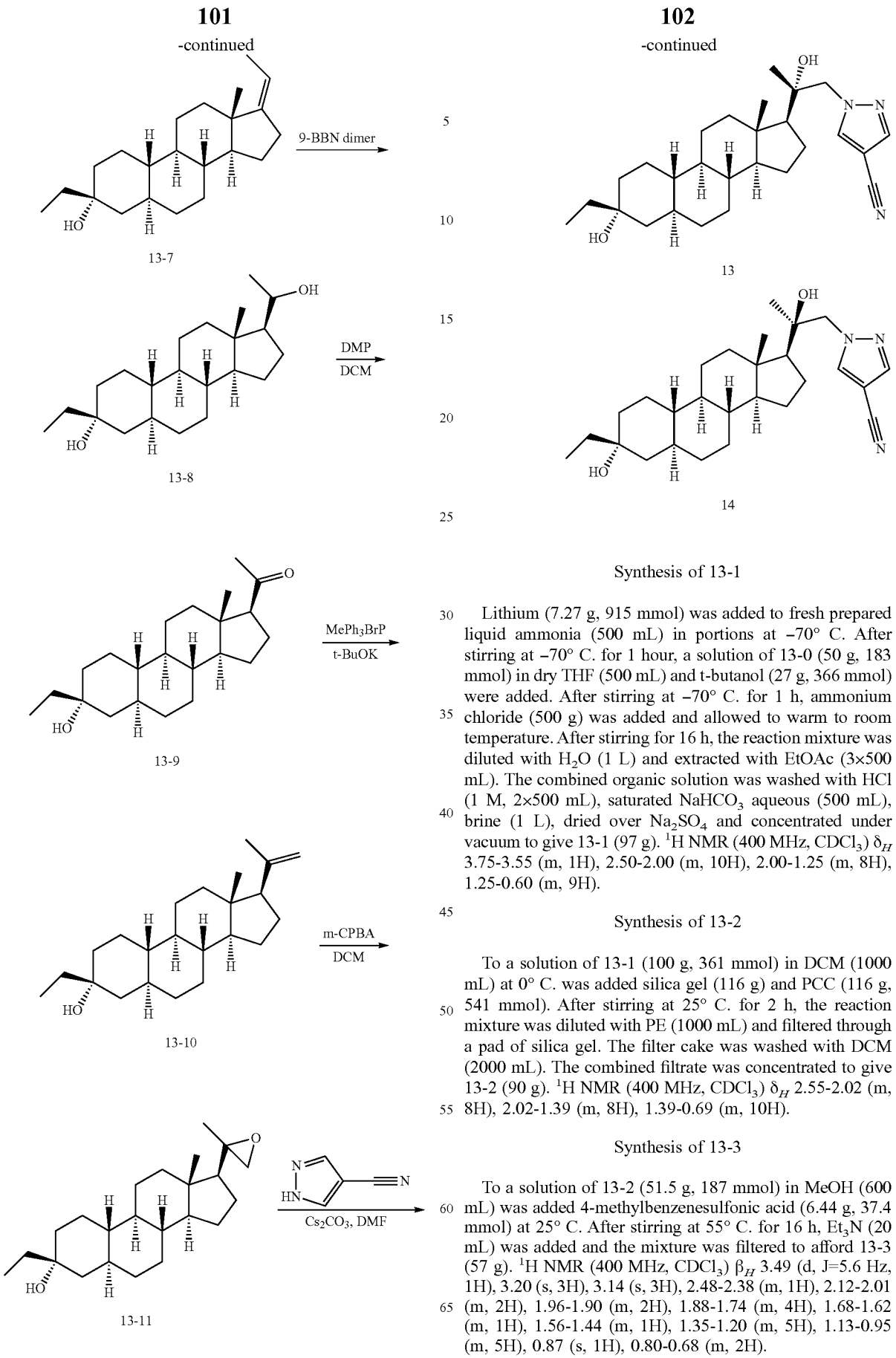

Synthesis of 13-1

Lithium (7.27 g, 915 mmol) was added to fresh prepared liquid ammonia (500 mL) in portions at −70° C. After stirring at −70° C. for 1 hour, a solution of 13-0 (50 g, 183 mmol) in dry THF (500 mL) and t-butanol (27 g, 366 mmol) were added. After stirring at −70° C. for 1 h, ammonium chloride (500 g) was added and allowed to warm to room temperature. After stirring for 16 h, the reaction mixture was diluted with $H_2O$ (1 L) and extracted with EtOAc (3×500 mL). The combined organic solution was washed with HCl (1 M, 2×500 mL), saturated $NaHCO_3$ aqueous (500 mL), brine (1 L), dried over $Na_2SO_4$ and concentrated under vacuum to give 13-1 (97 g). $^1H$ NMR (400 MHz, $CDCl_3$) $\delta_H$ 3.75-3.55 (m, 1H), 2.50-2.00 (m, 10H), 2.00-1.25 (m, 8H), 1.25-0.60 (m, 9H).

Synthesis of 13-2

To a solution of 13-1 (100 g, 361 mmol) in DCM (1000 mL) at 0° C. was added silica gel (116 g) and PCC (116 g, 541 mmol). After stirring at 25° C. for 2 h, the reaction mixture was diluted with PE (1000 mL) and filtered through a pad of silica gel. The filter cake was washed with DCM (2000 mL). The combined filtrate was concentrated to give 13-2 (90 g). $^1H$ NMR (400 MHz, $CDCl_3$) $\delta_H$ 2.55-2.02 (m, 8H), 2.02-1.39 (m, 8H), 1.39-0.69 (m, 10H).

Synthesis of 13-3

To a solution of 13-2 (51.5 g, 187 mmol) in MeOH (600 mL) was added 4-methylbenzenesulfonic acid (6.44 g, 37.4 mmol) at 25° C. After stirring at 55° C. for 16 h, $Et_3N$ (20 mL) was added and the mixture was filtered to afford 13-3 (57 g). $^1H$ NMR (400 MHz, $CDCl_3$) $\beta_H$ 3.49 (d, J=5.6 Hz, 1H), 3.20 (s, 3H), 3.14 (s, 3H), 2.48-2.38 (m, 1H), 2.12-2.01 (m, 2H), 1.96-1.90 (m, 2H), 1.88-1.74 (m, 4H), 1.68-1.62 (m, 1H), 1.56-1.44 (m, 1H), 1.35-1.20 (m, 5H), 1.13-0.95 (m, 5H), 0.87 (s, 1H), 0.80-0.68 (m, 2H).

Synthesis of 13-4

To a mixture of EtPPh$_3$Br (98.7 g, 266 mmol) in THF (250 mL) was added t-BuOK (29.8 g, 266 mmol) at 15° C. under N$_2$. After stirring at 15° C. for 30 min, 13-3 (28.5 g, 88.9 mmol) in THF (50 mL) was added. After stirring at 40° C. for 2 h, the mixture was poured into NH$_4$Cl.aq (150 mL) and extracted with EtOAc (2×200 mL). The combined organic phase was washed with brine (20 mL), dried over anhydrous Na$_2$SO$_4$, filtered and concentrated. The residue was heated in MeOH (500 mL) at 70° C. for 30 min, cooled to room temperature, diluted with water (300 mL), filtered and concentrated to give 13-4 (25.5 g). $^1$H NMR (400 MHz, CDCl$_3$) $\delta_H$ 5.15-5.07 (m, 1H), 3.20 (s, 3H), 3.14 (s, 3H), 2.41-2.31 (m, 1H), 2.27-2.12 (m, 2H), 2.10-2.02 (m, 1H), 1.91 (td, J=3.2, 13.2 Hz, 1H), 1.85-1.76 (m, 2H), 1.71-1.58 (m, 6H), 1.57-1.48 (m, 3H), 1.30-1.13 (m, 6H), 1.11-0.93 (m, 5H), 0.87 (s, 3H), 0.75-0.67 (m, 2H).

Synthesis of 13-5

To a solution of 13-4 (51 g, 153 mmol) in THF (500 mL) was added 1 M HCl (153 mL, 153 mmol). After stirring stirred at 15° C. for 2 h, the mixture was poured into NaHCO$_3$.aq (400 mL), and extracted with EtOAc (2×300 mL). The combined organic phase was washed with brine (200 mL), dried over anhydrous Na$_2$SO$_4$, filtered and concentrated to give 13-5 (42 g, 95.8%). $^1$H NMR (400 MHz, CDCl$_3$) $\delta_H$ 5.16-5.08 (m, 1H), 2.42-2.17 (m, 7H), 2.09 (t, J=13.2 Hz, 1H), 1.88-1.79 (m, 2H), 1.76-1.63 (m, 6H), 1.59 (s, 1H), 1.56-1.40 (m, 2H), 1.28-1.16 (m, 8H), 1.04-0.94 (m, 1H), 0.90 (s, 1H), 0.78-0.69 (m, 1H).

Synthesis of 13-6

To a stirred solution of Me$_3$SIO (47.9 g, 218 mmol) in DMSO (300 mL) and THF (300 mL) was added NaH (5.23 g, 218 mmol) at 0° C. After stirring for 1 h under N$_2$, 13-5 (42 g, 146 mmol) in THF (200 mL) was added. After stirring at 25° C. for 3 h, the reaction mixture was poured into water (1000 mL). After stirring at 25° C. for 3 h, the mixture was filtered to give 13-6 (48 g). $^1$H NMR (400 MHz, CDCl$_3$) $\delta_H$ 5.15-5.07 (m, 1H), 2.64-2.61 (m, 5H), 2.41-2.30 (m, 1H), 2.27-2.11 (m, 2H), 2.00-1.92 (m, 1H), 1.91-1.80 (m, 2H), 1.67-1.60 (m, 5H), 1.56-1.50 (m, 1H), 1.45-1.35 (m, 1H), 1.30-1.10 (m, 8H), 1.07-0.95 (m, 2H), 0.89 (s, 3H), 0.84-0.72 (m, 2H).

Synthesis of 13-7

To a suspension of CuCN (3.92 g, 43.8 mmol) in THF (40 mL) at −70° C. was added MeLi (54.7 mL, 87.6 mmol, 1.6M). After stirring at −70° C. for 1 h, 13-6 (4.4 g, 14.6 mmol) in THF (10 mL) was added at −70° C. After slowly warming to rt and stirring for 2 h, the reaction was slowly poured into 10% NH$_4$Cl (20 mL) and extracted with EtOAc (2×50 mL). The combined organic phase was washed with brine (20 mL), dried over anhydrous Na$_2$SO$_4$, filtered and concentrated to give 13-7 (4.4 g). $^1$H NMR (400 MHz, CDCl$_3$) $\delta_H$ 5.14-5.08 (m, 1H), 2.39-2.10 (m, 3H), 1.85-1.39 (m, 10H), 1.39-0.94 (m, 13H), 0.94-0.60 (m, 9H).

Synthesis of 13-8

To a solution of 13-7 (4.4 g, 13.3 mmol) in anhydrous THF (50 mL) was added 9-BBN dimer (8.03 g, 33.2 mmol) at 25° C. under N$_2$. After stirring at 60° C. for 16 h, the mixture was cooled, and diluted by EtOH (20 mL) at 0° C. NaOH (2.66 g, 13.3 mL, 5M, 66.5 mmol) was added very slowly followed by H$_2$O$_2$ (13.3 mL, 133 mmol, 10 M in water) very slowly until the inner temperature no longer rises and the inner temperature was maintained below 30° C. After stirring at 60° C. for 2 h, the mixture was cooled, diluted with Na$_2$S$_2$O$_3$ (100 mL, sat. aq.) and extracted with EtOAc (3×100 mL). The combined organic layer was dried over Na$_2$SO$_4$, filtered and concentrated in vacuum. The residue was purified by column (5%-30% of EtOAc in PE) to give 13-8 (10 g). $^1$H NMR (400 MHz, CDCl$_3$) $\delta_H$ 3.74-3.66 (m, 1H), 1.96-1.39 (m, 13H), 1.39-1.00 (m, 14H), 1.00-0.85 (m, 5H), 0.75-0.57 (m, 5H).

Synthesis of 13-9

To a solution of 13-8 (1.3 g, 3.88 mmol) in DCM (20 mL) was added DMP (3.29 g, 7.76 mmol). After stirring at 25° C. for 1 h, the mixture was quenched with NaHCO$_3$(50 mL) and extracted with EtOAc (3×30 mL). The combined organic layer was washed with Na$_2$S$_2$O$_3$ (3×30 mL, sat.), brine (50 mL), dried over Na$_2$SO$_4$, filtered and concentrated in vacuum. The residue was purified by column (5%-30% of EtOAc in PE) to give to give 13-9 (1.16 g, 90%). $^1$H NMR (400 MHz, CDCl$_3$) $\delta_H$ 2.53 (t, J=8.8 Hz, 1H), 2.21-1.53 (m, 9H), 1.53-1.10 (m, 10H), 1.10-0.63 (m, 13H), 0.61 (s, 3H).

Synthesis of 13-10

To a mixture of MePPh$_3$Br (2.48 g, 6.96 mmol) in THF (40 mL) was added t-BuOK (779 mg, 6.96 mmol) at 25° C. under N$_2$. After stirring at 50° C. for 30 mins. 13-9 (1.16 g, 3.48 mmol) in THF (10 mL) was added at 25° C. After stirring at 50° C. for 18 h, the reaction mixture was quenched with water (40 mL) at 25° C. and extracted with EtOAc (2×50 mL). The combined organic phase was washed with water (3×10 mL), brine (30 mL), dried over anhydrous Na$_2$SO$_4$, filtered and concentrated in vacuum. The residue was purified by column (2% of EtOAc in PE) to give 13-10 (620 mg, 54%). $^1$H NMR (400 MHz, CDCl$_3$) $\delta_H$ 4.84 (s, 1H), 4.70 (s, 1H), 2.08-1.57 (m, 10H), 1.57-1.06 (m, 13H), 1.06-0.52 (m, 13H).

Synthesis of 13-11

To a solution of 13-10 (620 mg, 1.87 mmol) in DCM (10 mL) was added m-CPBA (601 mg, 2.8 mmol, 80%) at 15° C. After stirring at 15° C. for 1 h, the mixture was quenched with sat.NaHCO$_3$ and Na$_2$S$_2$O$_3$ (40 mL, v:v=1:1) and extracted with DCM (2×20 mL). The combined organic phase was washed with sat. NaHCO$_3$ and Na$_2$S$_2$O$_3$ (50 mL, v:v=1:1), dried over Na$_2$SO$_4$, filtered and concentrated to give 13-11 (820 mg). $^1$H NMR (400 MHz, CDCl$_3$) $\delta_H$ 2.89 (d, J=4.8 Hz, 0.6H), 2.55-2.48 (m, 1H), 2.32 (d, J=5.2 Hz, 0.4H), 2.02-1.45 (m, 10H), 1.45-1.11 (m, 11H), 1.11-0.74 (m, 10H), 0.74-0.58 (m, 5H).

Synthesis of 13 & 14

To a solution of 13-11 (800 mg, 2.3 mmol) in DMF (10 mL) were added Cs$_2$CO$_3$ (2.24 g, 6.89 mmol) and 1H-pyrazole-4-carbonitrile (535 mg, 5.75 mmol). After stirring at 120° C. for 48 h, the reaction mixture was added into saturated NH$_4$Cl (50 mL) and extracted with EtOAc (3×50 mL). The combined organic layer was washed with LiCl (100 mL, 5% in water), saturated brine (2×100 mL), dried over anhydrous Na$_2$SO$_4$, filtered and concentrated. The residue was purified by column (0~10% of EtOAc in PE) to afford a mixture of epimers (800 mg). The epimers were separated by SFC (Column: DAICEL CHIRALCEL OJ-H (250 mm*30 mm, 5 um), Condition: 0.1% NH₃H₂O EtOH, Begin B: 25%, End B: 25%) to give 13 (264 mg) and 14 (122 mg).

13: ¹H NMR (400 MHz, CDCl₃) δ_H 7.92 (s, 1H), 7.81 (s, 1H), 4.37-4.33 (m, 1H), 4.10-4.06 (m, 1H), 2.48 (s, 1H), 2.02-1.96 (m, 1H), 1.79-1.37 (m, 12H), 1.37-0.94 (m, 15H), 0.94-0.87 (m, 6H), 0.75-0.61 (m, 2H). LC-ELSD/MS purity 99%, MS ESI calcd. for C₂₇H₃₈N₃ [M−2H₂O+H]⁺ 404 found 404. SFC 99.522% de.

14: ¹H NMR (400 MHz, CDCl₃) δ_H 7.88 (s, 1H), 7.79 (s, 1H), 4.17-4.13 (m, 1H), 4.02-3.99 (m, 1H), 2.27 (s, 1H), 2.07-1.53 (m, 1H), 1.53-1.12 (m, 12H), 1.12-0.94 (m, 15H), 0.94-0.84 (m, 6H), 0.73-0.61 (m, 2H). LC-ELSD/MS purity 99%, MS ESI calcd. for C₂₇H₃₈N₃ [M−2H₂O+H]⁺ 404 found 404. SFC 100% de.

Examples 15 & 16: Synthesis of 1-((S)-2-hydroxy-2-((3R,5R,8R,9R,10S,13S,14S,17S)-3-hydroxy-3-(hydroxymethyl)-13-methylhexadecahydro-1H-cyclopenta[a]phenanthren-17-yl)propyl)-1H-pyrazole-4-carbonitrile (15) & 1-((R)-2-((3R,5R,8R,9R,10S,13S,14S,17S)-3-(ethoxymethyl)-3-hydroxy-13-methylhexadecahydro-1H-cyclopenta[a]phenanthren-7-yl)-2-hydroxypropyl)-1H-pyrazole-4-carbonitrile (16)

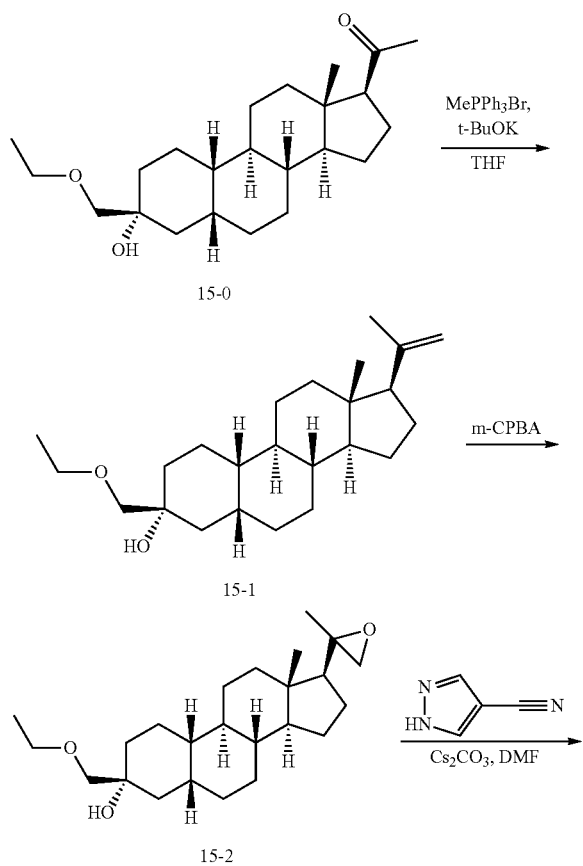

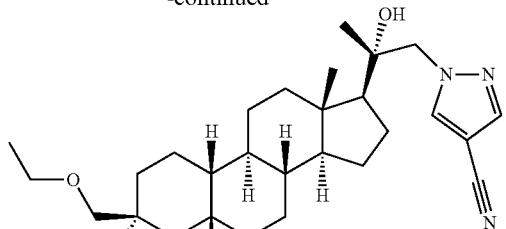

15

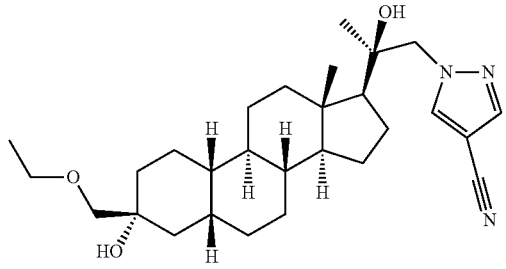

16

Synthesis of 15-1

To a solution of MePPh₃Br (2.94 g, 8.25 mmol) in THF (20 mL) was added t-BuOK (925 mg, 8.25 mmol) under N₂ at 25° C. After stirring for 1 h, 15-0 (1 g, 2.75 mmol, WO 2018013613) in THF (10 mL) was added. After stirring at 40° C. for 3 h, the reaction mixture was poured into NH₄Cl.aq (50 mL) and extracted with EtOAc (2×80 mL). The combined organic phase was washed with saturated brine (50 mL), dried over anhydrous Na₂SO₄, filtered and concentrated. The residue was purified by flash column (0-6% of EtOAc in PE) to give 15-1 (750 mg, 76%). ¹H NMR (400 MHz, CDCl₃) δ_H 4.84 (s, 1H), 4.70 (s, 1H), 3.57-3.49 (m, 2H), 3.47-3.38 (m, 2H), 2.70 (s, 1H), 2.07-2.00 (m, 1H), 1.75 (s, 7H), 1.72-1.59 (m, 5H), 1.49-1.33 (m, 6H), 1.28-0.97 (m, 11H), 0.56 (s, 3H).

Synthesis of 15-2

To a solution of 15-1 (880 mg, 2.44 mmol) in DCM (20 mL) was added m-CPBA (990 mg, 85%, 4.88 mmol) at 15° C. After the reaction mixture was stirred at 15° C. for 1 h, the reaction mixture was quenched by saturated NaHCO₃ aqueous (200 mL). The organic phase was separated and washed with saturated NaHCO₃/Na₂S₂O₃ aqueous (1:1, 3×100 mL), brine (100 mL), dried over Na₂SO₄, filtered and concentrated under vacuum to give 15-2 (900 mg). ¹H NMR (400 MHz, CDCl₃) δ_H 3.54 (q, J=8 Hz, 2H), 3.43 (q, J=8 Hz, 2H), 2.88 (d, J=4 Hz, 0.6H), 2.55 (d, J=4 Hz, 0.7H), 2.49 (d, J=4 Hz, 0.3H), 2.31 (d, J=4 Hz, 0.4H), 2.03-1.57 (m, 10H), 1.48-1.32 (m, 9H), 1.28-0.93 (m, 12H), 0.79 (s, 1H), 0.67 (s, 2H).

Synthesis of 15 & 16

To a solution of 15-2 (600 mg, 1.59 mmol) in DMF (5 mL) were added 1H-pyrazole-4-carbonitrile (369 mg, 3.97 mmol) and Cs₂CO₃ (2.59 g, 7.95 mmol). After stirring at 125° C. for 12 h, the reaction mixture was diluted with water (100 mL) and extracted with EtOAc (3×60 mL). The combined organic layer was washed with LiCl (3×150 mL, 5%, aq.) and then concentrated. The residue was purified by flash column (0~20% of EtOAc in PE) to give a mixture of epimers (600 mg). The epimers were separated by SFC (Column: DAICEL CHIRALPAK AS (250 mm*50 mm, 10 um); Condition: 0.1% NH$_3$H$_2$O EtOH; Begin B: 60%; End B: 60%; Flow Rate (ml/min): 80) to give 15 (353.8 mg, 59%) and 16 (138.3 mg, 23%).

15: $^1$H NMR (400 MHz, CDCl$_3$) δ$_H$ 7.92 (s, 1H), 7.82 (s, 1H), 4.37-4.34 (m, 1H), 4.10-4.07 (m, 1H), 3.54 (q, J=8 Hz, 2H), 3.41 (q, J=8 Hz, 2H), 2.70 (s, 1H), 2.51 (s, 1H), 2.02-1.99 (m, 1H), 1.83-1.55 (m, 8H), 1.50-1.19 (m, 13H), 1.15-1.02 (m, 5H), 0.96-0.91 (m, 6H). LC-ELSD/MS purity 99%, MS ESI calcd. for C$_{28}$H$_{42}$N$_3$O$_2$[M+H-H$_2$O]$^+$ 452, found 452. SFC 100% de.

16: $^1$H NMR (400 MHz, CDCl$_3$) δ$_H$ 7.89 (s, 1H), 7.80 (s, 1H), 4.18-4.15 (m, 1H), 4.03-3.99 (m, 1H), 3.54 (q, J=8 Hz, 2H), 3.41 (q, J=8 Hz, 2H), 2.71 (s, 1H), 2.33 (s, 1H), 2.07-2.04 (m, 1H), 1.95-1.56 (m, 9H), 1.50-1.19 (m, 13H), 1.16-1.00 (m, 8H), 0.87 (s, 3H). LC-ELSD/MS purity 99%, MS ESI calcd. for C$_2$H$_{42}$N$_3$O$_2$ [M+H-H$_2$O]$^+$ 452, found 452. SFC 99.94% de.

Examples 17 & 18: Synthesis of 1-((S)-2-hydroxy-2-((3R,5S,8R,9S,10S,13S,14S,17S)-3-hydroxy-10,13-dimethyl-3-propylhexadecahydro-1H-cyclopenta[a]phenanthren-17-yl)propyl)-1H-pyrazole-4-carbonitrile (17) & 1-((R)-2-hydroxy-2-((3R,5S,8R,9S,10S,13S,14S,17S)-3-hydroxy-10,13-dimethyl-3-propylhexadecahydro-1H-cyclopenta[a]phenanthren-17-yl)propyl)-1H-pyrazole-4-carbonitrile (18)

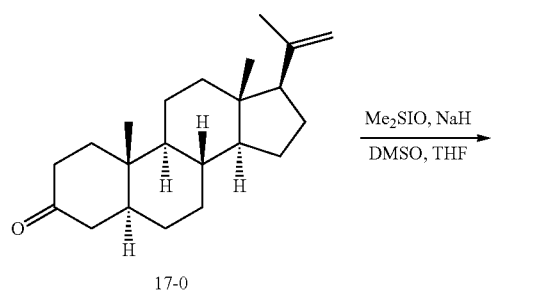

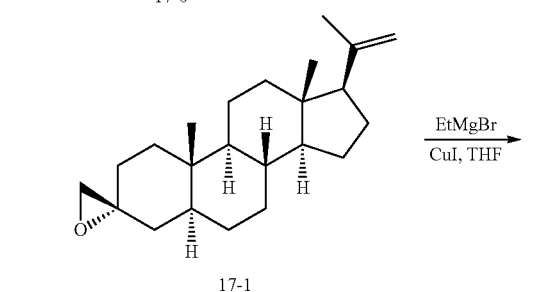

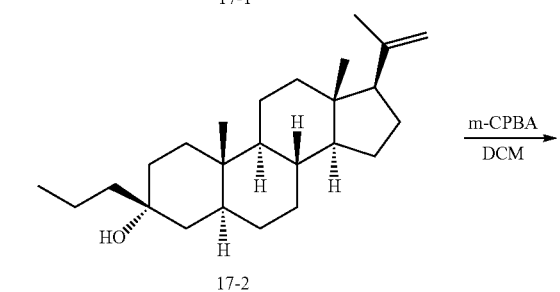

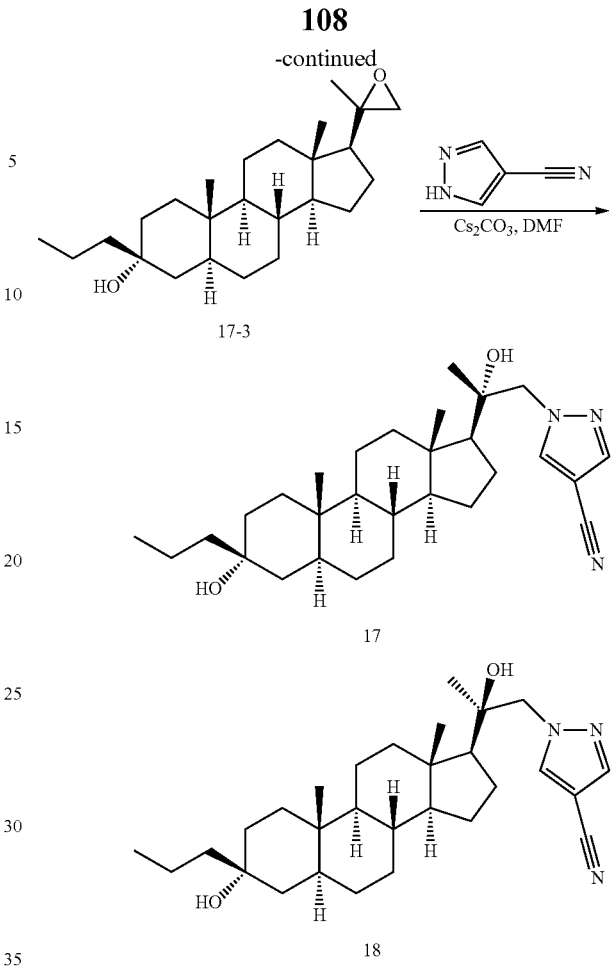

Synthesis of 17-1

To a stirred solution of Me$_3$SIO (3.12 g, 14.2 mmol) in DMSO (30 mL) and THF (30 mL) was added NaH (340 mg, 14.2 mmol) at 0° C. After stirring for 1 h, the reaction mixture was added 17-0 (Pregn-20-en-3-one, 20-methyl-, (5α)-, described in WO2018/75699) (3 g, 9.53 mmol) in DMSO (30 mL). After stirring at 25° C. for 3 h, the reaction mixture was poured into water (200 mL). After stirring at 25° C. for 3 h, the reaction mixture was filtered to give 17-1 (3.3 g). $^1$H NMR (400 MHz, CDCl$_3$) δ$_H$ 4.84 (s, 1H), 4.70 (s, 1H), 2.64-2.59 (m, 2H), 2.06-1.98 (m, 2H), 1.88-1.79 (m, 2H), 1.75 (s, 3H), 1.71-1.65 (m, 3H), 1.60-1.52 (m, 3H), 1.35-1.12 (m, 8H), 1.00-0.76 (m, 8H), 0.57 (s, 3H).

Synthesis of 17-2

To a solution of 17-1 (2.7 g, 8.21 mmol) in THF (20 mL) with CuI (234 mg, 1.23 mmol) at 0° C. was added EtMgBr (8.20 mL, 3 M, 24.6 mmol). After stirring at 0° C. for 1 h, the reaction was diluted with water (50 mL) and extracted with EtOAc (2×50 mL). The combined organic phase was washed with brine (100 mL), dried over anhydrous Na$_2$SO$_4$, filtered and concentrated. The residue was purified by column (0~3% of EtOAc in PE) to give 17-2 (1.8 g, 61%). $^1$H NMR (400 MHz, CDCl$_3$) δ$_H$ 4.83 (s, 1H), 4.69 (s, 1H), 2.01 (t, J=9.2 Hz, 1H), 1.83-1.40 (m, 13H), 1.40-1.02 (m, 15H), 1.02-0.70 (m, 8H), 0.55 (s, 3H).

Synthesis of 17-3

To a solution of 17-2 (1.7 g, 4.74 mmol) in DCM (10 mL) was added m-CPBA (2.03 g, 9.48 mmol, 80%) at 15° C. After stirring at 15° C. for 1 h, the mixture was quenched with sat.NaHCO$_3$ and Na$_2$S$_2$O$_3$ (40 mL, v:v=1:1) and extracted with DCM (2×20 mL). The combined organic phase was washed with sat. NaHCO$_3$ and Na$_2$S$_2$O$_3$ (50 mL, v:v=1:1), dried over Na$_2$SO$_4$, filtered and concentrated to give 17-3 (2.35 g). $^1$H NMR (400 MHz, CDCl$_3$) $\delta_H$ 2.88 (d, J=4.4 Hz, 0.7H), 2.55-2.48 (m, 1H), 2.30 (d, J=4.8 Hz, 0.3H), 2.04-1.55 (m, 10H), 1.55-1.37 (m, 10H), 1.37-1.23 (m, 10H), 1.23-0.66 (m, 10H),

Synthesis of 17 & 18

To a solution of 17-3 (600 mg, 1.6 mmol) in DMF (5 mL) were added Cs$_2$CO$_3$ (1.56 g, 4.8 mmol) and 1H-pyrazole-4-carbonitrile (372 mg, 4 mmol). After stirring at 120° C. for 48 h, the reaction mixture was added into saturated NH$_4$Cl (50 mL) and extracted with EtOAc (3×50 mL). The combined organic layer was washed with LiCl (100 mL, 5% in water), brine (2×100 mL), dried over anhydrous Na$_2$SO$_4$, filtered and concentrated. The residue was purified by column (5~20% of EtOAc in PE) to afford a mixture of epimers (750 mg). The epimers were separated by SFC (Column: DAICEL CHIRALCEL OJ-H (250 mm*30 mm, 5 um), Condition: 0.1% NH$_3$H$_2$O EtOH, Begin B: 30%, End B: 30%) to give 17 (272 mg) and 18 (123 mg).

17: $^1$H NMR (400 MHz, CDCl$_3$) $\delta_H$ 7.92 (s, 1H), 7.80 (s, 1H), 4.36-4.33 (m, 1H), 4.09-4.06 (m, 1H), 2.49 (s, 1H), 2.01-1.98 (m, 1H), 1.77-1.42 (m, 11H), 1.42-1.08 (m, 13H), 1.08-0.80 (m, 11H), 0.77-0.70 (m, 4H). LC-ELSD/MS purity 99%, MS ESI calcd. for C$_{29}$H$_{42}$N$_3$ [M−2H$_2$O+H]$^+$ 432 found 432. SFC 99.06% de.

18: $^1$H NMR (400 MHz, CDCl$_3$) $\delta_H$ 7.88 (s, 1H), 7.79 (s, 1H), 4.17-4.13 (m, 1H), 4.02-3.98 (m, 1H), 2.28 (s, 1H), 2.06-1.86 (m, 2H), 1.71-1.42 (m, 10H), 1.42-1.11 (m, 13H), 1.11-0.60 (m, 11H), 0.77-0.70 (m, 4H). LC-ELSD/MS purity 99%, MS ESI calcd. for C$_{29}$H$_{42}$N$_3$ [M−2H$_2$O+H]$^+$ 432 found 432. SFC 100% de.

Examples 19 & 20: Synthesis of 1-((S)-2-hydroxy-2-((3R,5S,8R,9R,10S,13S,14S,17S)-3-hydroxy-3-(methoxymethyl)-13-methylhexadecahydro-1H-cyclopenta[a]phenanthren-17-yl)propyl)-1H-pyrazole-4-carbonitrile (19) & 1-((R)-2-hydroxy-2-((3R,5S,8R,9R,10S,13S,14S,17S)-3-hydroxy-3-(methoxymethyl)-13-methylhexadecahydro-1H-cyclopenta[a]phenanthren-17-yl)propyl)-1H-pyrazole-4-carbonitrile (20)

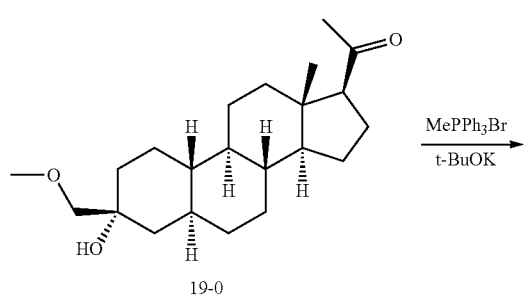

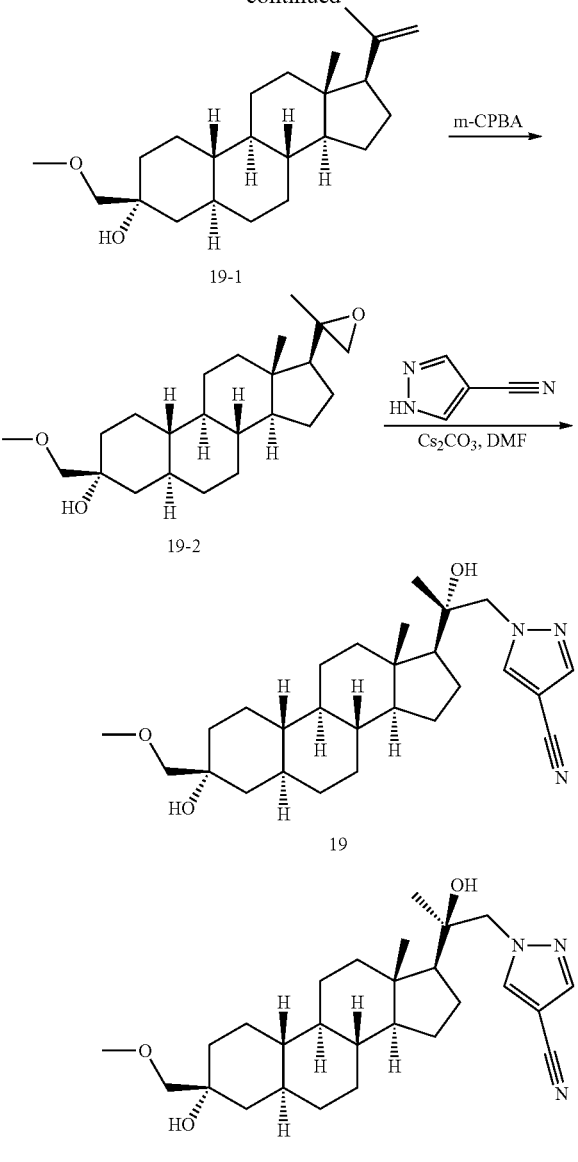

Synthesis of 19-1

To a mixture of MePPh$_3$Br (4.28 g, 12.0 mmol) in THF (15 mL) was added t-BuOK (1.34 g, 12.0 mmol) at 25° C. under N$_2$. After stirring at 50° C. for 30 min, 19-0 (1.4 g, 4.01 mmol) in THF (5 mL) was added. After stirring at 60° C. for 3 h, the reaction mixture was cooled, poured to ice water, and with EtOAc (100 mL×2). The combined organic layer was dried over anhydrous sodium sulfate, filtered and concentrated. The residue was purified by flash column (0~30% of EtOAc in PE) to give 19-1 (1.1 g). $^1$H NMR (400 MHz, CDCl$_3$) $\delta_H$ 4.94-4.61 (m, 2H), 3.45-3.32 (m, 3H), 3.25-3.12 (m, 2H), 2.11-1.97 (m, 2H), 1.87-1.53 (m, 10H), 1.49-0.82 (m, 14H), 0.79-0.65 (m, 2H), 0.57 (s, 3H).

Synthesis of 19-2

To a solution of 19-1 (600 mg, 1.73 mmol) in DCM (20 mL) was added m-CPBA (556 mg, 2.59 mmol, 80%) at 15°

C. After stirring at 15° C. for 1 h, the reaction mixture was quenched with sat. NaHCO₃ and Na₂S₂O₃ (40 mL, v:v=1:1) and extracted with DCM (2×20 mL). The combined organic phase was washed with sat. NaHCO₃ and Na₂S₂O₃ (50 mL, v:v=1:1), dried over Na₂SO₄, filtered and concentrated to give 19-2 (650 mg). ¹H NMR (400 MHz, CDCl₃) $\delta_H$ 3.38 (s, 3H), 3.24-3.14 (m, 2H), 2.88 (d, J=4.4 Hz, 1H), 2.55 (d, J=4.4 Hz, 1H), 2.49 (d, J=4.8 Hz, 1H), 2.31 (d, J=4.8 Hz, 1H), 2.09-1.52 (m, 10H), 1.47-0.87 (m, 14H), 0.80 (s, 1H), 0.74-0.64 (m, 4H).

Synthesis of 19 & 20

To a solution of 19-2 (650 mg, 1.79 mmol) in DMF (10 mL) were added Cs₂CO₃ (1.75 g, 5.37 mmol) and 1H-pyrazole-4-carbonitrile (416 mg, 4.47 mmol). After stirring at 130° C. for 12 h, the reaction mixture was added into saturated NH₄Cl (50 mL) and extracted with EtOAc (3×50 mL). The combined organic layer was washed with LiCl (100 mL, 5% in water), brine (2×100 mL), dried over anhydrous Na₂SO₄, filtered and concentrated. The residue was purified by column (0~50% of EtOAc in PE) to afford a mixture of epimers (750 mg). The epimers were separated by SFC (Column: DAICEL CHIRALCEL OJ-H (250 mm*30 mm, 5 um); Condition: 0.1% NH₃H₂O EtOH) to afford 20 (116.0 mg, 15.5%) and 19 (280.6 mg, 37.4%).

19: ¹H NMR (400 MHz, CDCl₃) $\delta_H$ 7.92 (s, 1H), 7.81 (s, 1H), 4.36 (d, J=13.6 Hz, 1H), 4.08 (d, J=13.6 Hz, 1H), 3.38 (s, 3H), 3.18 (s, 2H), 2.48 (s, 1H), 2.13-1.92 (m, 2H), 1.81-1.56 (m, 9H), 1.43 (br t, J=9.6 Hz, 2H), 1.29-0.98 (m, 9H), 0.96 (s, 4H), 0.92 (s, 3H), 0.69 (br s, 2H). LC-ELSD/MS purity 99%, MS ESI calcd for C₂₆H₃₅N₃ [M−MeOH−2H₂O+H]⁺ 388.2, found 388.2. SFC 96.66% de 20: ¹H NMR (400 MHz, CDCl₃) $\delta_H$ 7.89 (s, 1H), 7.82-7.75 (m, 1H), 4.22-4.09 (m, 1H), 4.06-3.93 (m, 1H), 3.48-3.31 (m, 3H), 3.27-3.11 (m, 2H), 2.35-2.22 (m, 1H), 2.12-1.99 (m, 2H), 1.97-1.83 (m, 1H), 1.81-1.60 (m, 8H), 1.53-1.32 (m, 2H), 1.29-1.14 (m, 4H), 1.09 (s, 5H), 1.05-0.92 (m, 4H), 0.87 (s, 3H), 0.69 (br t, J=7.2 Hz, 2H). LC-ELSD/MS purity 99%, MS ESI calcd for C₂₆H₃₅N₃ [M−MeOH−2H₂O+H]⁺ 388.2, found 388.2. SFC 100% de Example 21: Synthesis of 1-(2,2-difluoro-2-((3R,5R,8R,9R,10S,13S,14S,17S)-3-hydroxy-3,13-dimethylhexadecahydro-1H-cyclopenta[a]phenanthren-17-yl)ethyl)-1H-pyrazole-4-carbonitrile

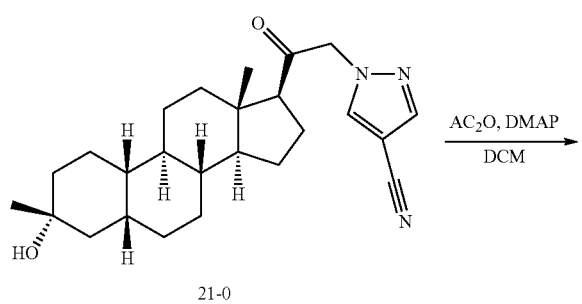

21-0

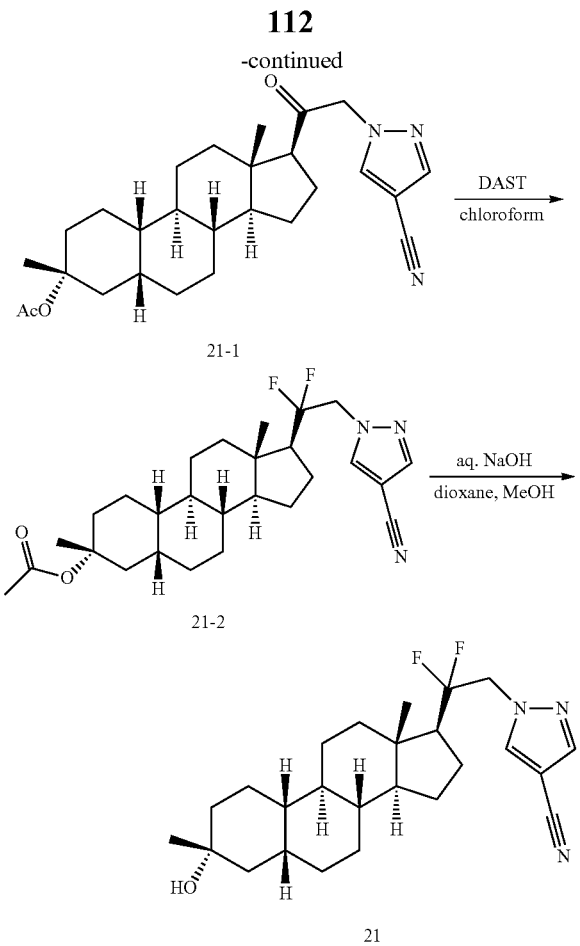

Synthesis of 21-1

To a solution of 21-0 (1 g, 2.44 mmol) in DCM (10 mL) was added DMAP (298 mg, 2.44 mmol) and acetyl acetate (622 mg, 6.10 mmol). After stirring at 25° C. for 16 h, the reaction mixture was poured into ice-water (50 mL), stirred for 10 min, and extracted with DCM (2×30 mL). The combined organic phase was washed with saturated brine (2×50 mL), dried over anhydrous Na₂SO₄, filtered and concentrated. The residue was purified by flash column (0-20% of EtOAc in PE) to give 21-1 (650 mg, 59%). ¹H NMR (400 MHz, CDCl₃) $\delta_H$ 7.86 (s, 1H), 7.81 (s, 1H), 5.05-4.87 (m, 2H), 2.64-2.57 (m, 1H), 2.34-2.06 (m, 2H), 1.99 (s, 3H), 1.87-1.58 (m, 10H), 1.54 (s, 3H), 1.51-1.30 (m, 7H), 1.15-0.82 (m, 4H), 0.67 (s, 3H).

Synthesis of 21-2

To a solution of 21-1 (300 mg, 0.66 mmol) in chloroform (5 mL) was added dropwise DAST (0.79 ml, 5.97 mmol) at 0° C. under N₂. After stirring at 60° C. for 12 h, the reaction mixture was quenched with sat. NaHCO₃(50 mL) and extracted with EtOAc (2×30 mL). The combined organic phase was washed with sat. NaHCO₃(50 mL), dried over Na₂SO₄, filtered, concentrated. The residue was purified by combi-flash (0-30% of EtOAc in PE) to give 21-2 (65 mg, 20%). ¹H NMR (400 MHz, CDCl₃) $\delta_H$ 7.92 (s, 1H), 7.82 (s, 1H), 4.59-4.30 (m, 2H), 1.97 (s, 3H), 1.85-1.58 (m, 12H), 1.53 (s, 3H), 1.49-1.28 (m, 7H), 1.14-1.03 (m, 5H), 0.88-0.86 (m, 3H)

Synthesis of 21

To a solution of 21-2 (35 mg, 0.074 mmol) in dioxane (0.5 mL) was added MeOH (1 mL) and NaOH (2.94 ml, 5 M, 14.7 mmol) at 15° C. After stirring at 35° C. for 16 h, the reaction mixture was poured into water (20 mL), stirred for 10 min, and extracted with EtOAc (3×40 mL). The combined organic phase was washed with saturated brine (2×50 mL), dried over anhydrous $Na_2SO_4$, filtered and concentrated. The residue was purified by flash column (0-40% of EtOAc in PE) and purified by SFC (Method: Column: DAICEL CHIRALPAK AD (250 mm*50 mm, 10 um); Condition: 0.1% $NH_3H_2O$ EtOH; Begin B: 60%; End B: 60%) to afford 21 (14.4 mg, 41%). $^1$H NMR (400 MHz, $CDCl_3$) $\delta_H$ 7.92 (s, 1H), 7.82 (s, 1H), 4.55-4.34 (m, 2H), 2.02-1.96 (m, 1H), 1.86-1.60 (m, 10H), 1.49-1.27 (m, 9H), 1.25 (s, 3H), 1.13-1.05 (m, 5H), 0.87 (d, J=3.2 Hz, 3H). LC-ELSD/MS: purity >99%; MS ESI calcd. for $C_{25}H_{35}F_2N_3O$ $[M-H_2O+H]^+$ 414.2, found 414.2.

Example 22 & 23: Synthesis of 1-((S)-2-hydroxy-2-((3R,5R,8R,9R,10S,13S,14S,17S)-3-hydroxy-13-methyl-3-propylhexadecahydro-1H-cyclopenta[a]phenanthren-17-yl)propyl)-1H-pyrazole-3-carbonitrile (22) & 1-((R)-2-hydroxy-2-((3R,5R,8R,9R,10S,13S,14S,17S)-3-hydroxy-13-methyl-3-propylhexadecahydro-1H-cyclopenta[a]phenanthren-17-yl)propyl)-1H-pyrazole-3-carbonitrile (23)

To a solution of 7-3 (300 mg, 0.831 mmol) in DMF (5 mL) were added 1H-pyrazole-3-carbonitrile (154 mg, 1.66 mmol) and $Cs_2CO_3$ (1.35 g, 4.15 mmol). After stirring at 125° C. for 12 h, the mixture was diluted with water (100 mL) and extracted with EtOAc (3×50 mL). The combined organic layer was concentrated and purified by flash column (0-25% of EtOAc in PE) to give mixture of epimers (200 mg, 53%). The epimers were separated by SFC (Column: DAICEL CHIRALPAK AD (250 mm*30 mm, 10 um; Condition: 0.1% $NH_3H_2O$ IPA; Begin: B 55%; End B: 55%; FlowRate (ml/min): 80) to give 22 (80.5 mg) and 23 (47.2 mg). The regiochemistry of pyrazole was assigned by HMBC (H22 correlated with C5 in pyrazole ring).

22: $^1$H NMR (400 MHz, $CDCl_3$) $\delta_H$ 7.58 (d, J=4 Hz, 1H), 6.68 (d, J=4 Hz, 1H), 4.38-4.35 (m, 1H), 4.13-4.09 (m, 1H), 2.35 (s, 1H), 2.02-1.99 (m, 1H), 1.81-1.60 (m, 10H), 1.55-1.31 (m, 7H), 1.28-1.03 (m, 11H), 0.96-0.91 (m, 9H). LC-ELSD/MS: purity 99%, MS ESI calcd. for $C_{28}H_{40}N_3$ $[M-2H_2O+H]^+$ 418.3, found 418.3. SFC 100% de.

23: $^1$H NMR (400 MHz, $CDCl_3$) $\delta_H$ 7.53 (d, J=4 Hz, 1H), 6.67 (d, J=4 Hz, 1H), 4.19-4.16 (m, 1H), 4.05-4.02 (m, 1H), 2.21 (s, 1H), 2.07-2.04 (m, 1H), 1.94-1.58 (m, 10H), 1.55-1.25 (m, 11H), 1.22-1.02 (m, 10H), 0.95-0.87 (m, 6H). LC-ELSD/MS: purity 99%, MS ESI calcd. for $C_{28}H_{40}N_3$ $[M-2H_2O+H]^+$ 418.3, found 418.3. SFC 100% de.

Example 24 & 25: Synthesis of 1-((S)-2-((3R,5R,8R,9S,10S,13S,14S,17S)-3-(ethoxymethyl)-3-hydroxy-10,13-dimethylhexadecahydro-1H-cyclopenta[a]phenanthren-17-yl)-2-hydroxypropyl)-1H-pyrazole-4-carbonitrile (24) & 1-((R)-2-((3R,5R,8R,9S,10S,13S,14S,17S)-3-(ethoxymethyl)-3-hydroxy-10,13-dimethylhexadecahydro-1H-cyclopenta[a]phenanthren-17-yl)-2-hydroxypropyl)-1H-pyrazole-4-carbonitrile(25)

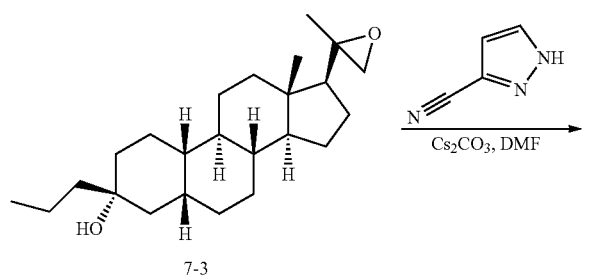

7-3

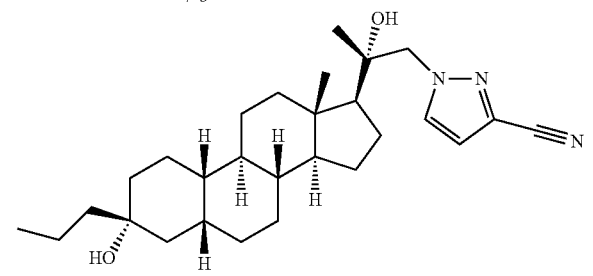

22

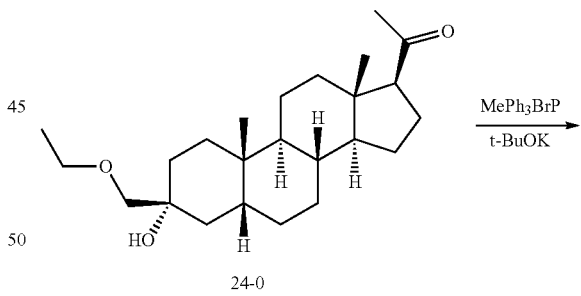

24-0

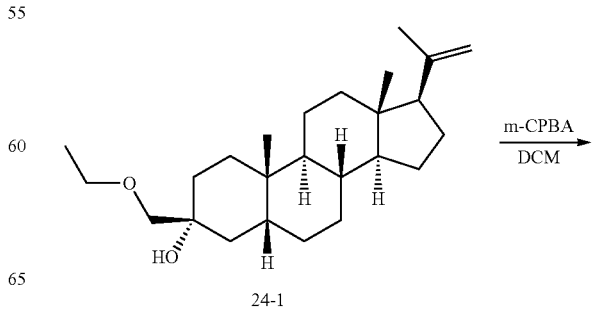

23

24-1

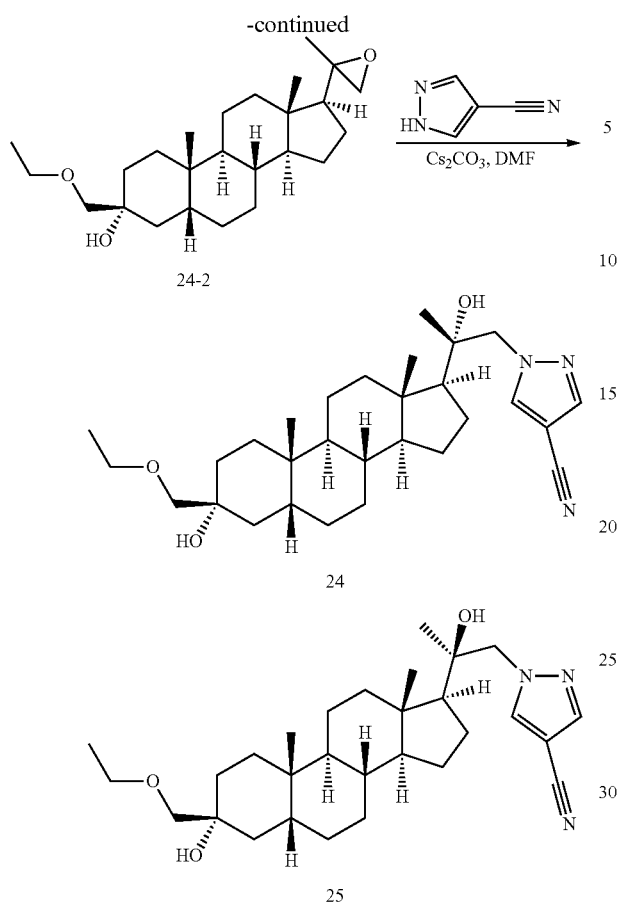

Synthesis of 24-1

To a mixture of MePPh₃Br (5.67 g, 15.9 mmol) in THF (70 mL) was added t-BuOK (1.78 mg, 15.9 mmol) at 25° C. under N₂. After stirring at 55° C. for 30 min, 24-0 (2.0 g, 5.31 mmol) in THF (30 mL) was added in portions blow 55° C. After stirring at 55° C. for 2 h, the reaction mixture was poured into water (300 mL) at 25° C. and extracted with EtOAc (2×300 mL). The combined organic layer was washed with water (300 mL), brine (200 mL), dried over Na₂SO₄, filtered and concentrated in vacuum. The residue was purified by silica gel chromatography (0-5% EtOAc in PE) to give 24-1 (900 mg). ¹H NMR (400 MHz, CDCl₃) δ$_H$ 4.84 (s, 1H), 4.69 (s, 1H), 3.55-3.51 (q, J=6.9 Hz, 2H), 3.47-3.33 (m, 2H), 2.73-2.65 (m, 1H), 2.06-1.97 (m, 2H), 1.96-1.81 (m, 3H), 1.77-1.72 (m, 4H), 1.58-1.54 (m, 2H), 1.45-1.38 (m, 4H), 1.25-1.18 (m, 8H), 0.90-0.82 (m, 9H), 0.54 (s, 3H).

Synthesis of 24-2

To a solution of 24-1 (900 mg, 2.40 mmol) in DCM (20 mL) was added m-CPBA (974 mg, 85%, 4.80 mmol) at 15° C. After stirring at 15° C. for 1 h, the mixture was quenched with saturated NaHCO₃ aqueous (200 mL). The organic phase was separated and washed with saturated NaHCO₃/Na₂S₂O₃ aqueous (1:1, 3×100 mL), brine (100 mL), dried over Na₂SO₄, filtered and concentrated under vacuum to give 24-2 (1.0 g). ¹H NMR (400 MHz, CDCl₃) δ$_H$ 3.55-3.51 (q, J=6.9 Hz, 2H), 3.47-3.35 (m, 2H), 1.98-1.77 (m, 4H), 1.76-1.66 (m, 2H), 1.64-1.44 (m, 6H), 1.43-1.31 (m, 7H), 1.27-1.17 (m, 7H), 1.16-0.99 (m, 4H), 0.95-0.90 (m, 3H), 0.81-0.74 (m, 1H), 0.71-0.61 (m, 2H).

Synthesis of 24 & 25

To a solution of 24-2 (1.0 g, 2.56 mmol) in DMF (15 mL) were added 1H-pyrazole-4-carbonitrile (595 mg, 6.40 mmol) and Cs₂CO₃ (4.17 g, 12.8 mmol). After stirring at 125° C. for 12 h, the reaction mixture was diluted with water (100 mL) and extracted with EtOAc (3×60 mL). The combined organic layer was washed with saturated LiCl (3×150 mL) and then concentrated. The residue was purified by flash column (0~20% of EtOAc in PE) to give a mixture of epimers (700 mg). The epimers were separated by SFC (Column: Chiralpak AD-3 50×4.6 mm I.D., 3 um Mobile phase: A: CO₂ B:ethanol (0.05% DEA) Gradient: from 5% to 40% of B in 2 min and hold 40% for 1.2 min, then 5% of B for 0.8 min Flow rate: 4 mL/min Column temp.: 35° C. ABPR: 1500 psi) afford 24 (284.9 mg, 40.8%) and 25 (88.4 mg, 12.7%).

24: ¹H NMR (400 MHz, CDCl₃) δ$_H$ 7.92 (s, 1H), 7.82 (s, 1H), 4.36-4.32 (d, J=13.8 Hz, 1H), 4.09-4.05 (d, J=13.8 Hz, 1H), 3.53-3.50 (q, J=6.9 Hz, 2H), 3.47-3.36 (m, 2H), 2.72 (s, 1H), 2.54 (s, 1H), 2.01-1.99 (d, J=10.8 Hz, 1H), 1.96-1.79 (m, 2H), 1.77-1.64 (m, 4H), 1.62-1.46 (m, 5H), 1.45-1.35 (m, 6H), 1.26-1.18 (m, 6H), 1.13-1.08 (m, 1H), 0.96-0.93 (d, J=10.8 Hz, 7H), 0.89 (s, 3H). LC-ELSD/MS purity 99%, MS ESI calcd. for C₂₇H₃₆N₃ [M−EtOH−2H₂O+H]⁺ 402.3 found 402.3. SFC 100% de.

25: ¹H NMR (400 MHz, CDCl₃) δ$_H$ 7.89 (s, 1H), 7.81 (s, 1H), 4.17-4.14 (d, J=13.8 Hz, 1H), 4.02-3.99 (d, J=13.8 Hz, 1H), 3.55-3.50 (q, J=7.0 Hz, 2H), 3.46-3.35 (m, 2H), 2.72 (s, 1H), 2.34 (s, 1H), 2.06 (d, 1H), 1.97-1.79 (m, 3H), 1.73-1.64 (m, 3H), 1.62-1.53 (m, 3H), 1.53-1.34 (m, 8H), 1.27-1.18 (m, 6H), 1.17-1.10 (m, 2H), 1.07 (s, 3H), 0.93 (s, 3H), 0.85 (s, 3H). LC-ELSD/MS purity 99%, MS ESI calcd. for C₂₇H₃₆N₃ [M−EtOH−2H₂O+H]⁺ 402.3 found 402.3. SFC 100% de.

Example 26 & 27: Synthesis of 1-((S)-2-hydroxy-2-((3R,5R,8R,9S,10S,13S,14S,17S)-3-hydroxy-10,13-dimethyl-3-propylhexadecahydro-1H-cyclopenta[a]phenanthren-17-yl)propyl)-1H-pyrazole-4-carbonitrile (26) & 1-((R)-2-hydroxy-2-((3R,5R,8R,9S,10S,13S,14S,17S)-3-hydroxy-10,13-dimethyl-3-propylhexadecahydro-1H-cyclopenta[a]phenanthren-17-yl)propyl)-1H-pyrazole-4-carbonitrile(27)

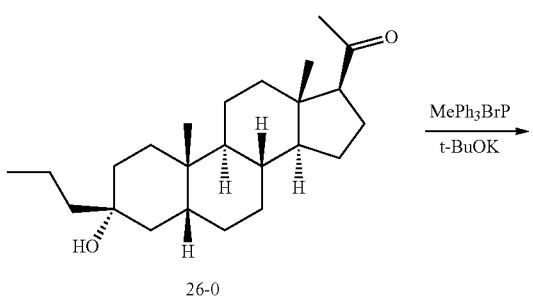

26-0

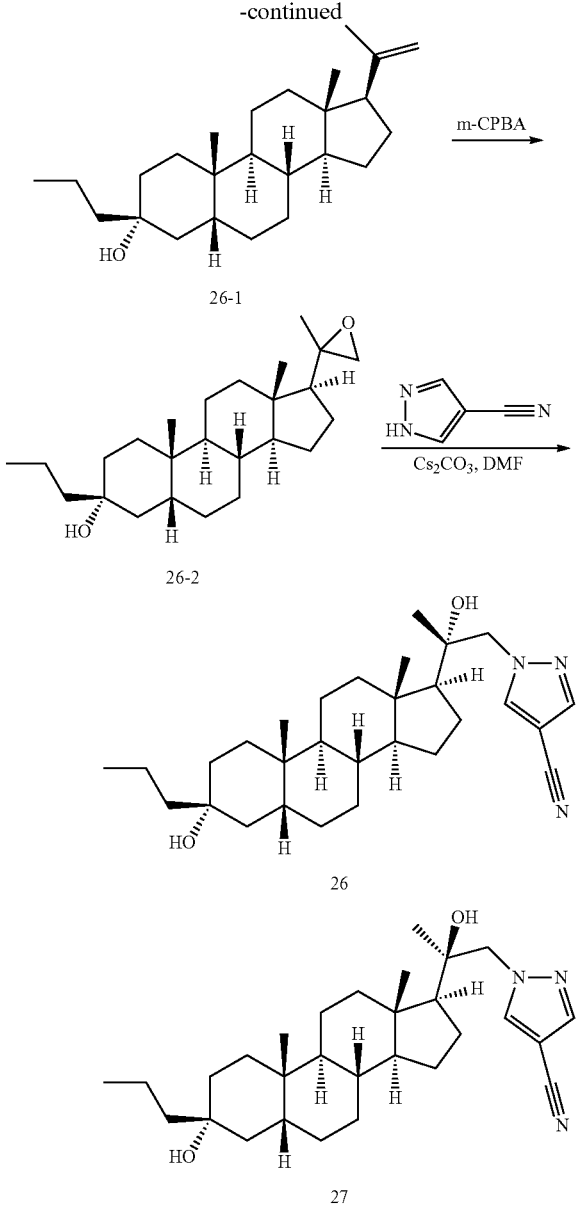

Synthesis of 26-2

To a solution of 26-1 (880 mg, 2.45 mmol) in DCM (20 mL) was added m-CPBA (994 mg, 85%, 4.90 mmol) at 15° C. After stirring at 15° C. for 1 h, the mixture was quenched by saturated NaHCO$_3$ aqueous (200 mL). The organic phase was separated and washed with saturated NaHCO$_3$/Na$_2$S$_2$O$_3$ aqueous (1:1, 3×100 mL), brine (100 mL), dried over Na$_2$SO$_4$, filtered and concentrated under vacuum to give 26-2 (900 mg). $^1$H NMR (400 MHz, CDCl$_3$) δ$_H$ 2.89-2.86 (d, J=4.3 Hz, 1H), 2.57-2.53 (d, J=4.3 Hz, 1H), 2.51-2.29 (m, 1H), 1.95-1.80 (m, 5H), 1.73-1.64 (m, 2H), 1.63-1.54 (m, 4H), 1.39-1.32 (m, 9H), 1.27-1.20 (m, 5H), 0.97-0.88 (m, 10H), 0.77 (s, 1H), 0.65 (s, 3H).

Synthesis of 26 & 27

To a solution of 26-2 (900 mg, 2.40 mmol) in DMF (5 mL) were added 1H-pyrazole-4-carbonitrile (557 mg, 5.99 mmol) and Cs$_2$CO$_3$ (3.87 g, 11.9 mmol). After stirring at 125° C. for 12 h, the reaction mixture was diluted with water (100 mL) and extracted with EtOAc (3×60 mL). The combined organic layer was washed with saturated LiCl (3×150 mL) and then concentrated. The residue was purified by flash column (0-20% of EtOAc in PE) to give a mixture of epimers (740 mg, 66.0%). The epimers were separated by SFC (Column: Chiralpak AD-3 50×4.6 mm I.D., 3 um Mobile phase: A: CO$_2$ B: ethanol (0.05% DEA) Gradient: from 5% to 40% of B in 2 min and hold 40% for 1.2 min, then 5% of B for 0.8 min Flow rate: 4 mL/min Column temp.: 35° C. ABPR: 1500 psi) afford 26 (318.7 mg) and 27 (154.0 mg).

26: $^1$H NMR (400 MHz, CDCl$_3$) δ$_H$ 7.92 (s, 1H), 7.82 (s, 1H), 4.35-4.32 (d, J=13.6 Hz, 1H), 4.09-4.05 (d, J=13.8 Hz, 1H), 2.52 (s, 1H), 2.05-1.98 (m, 1H), 1.91-1.82 (m, 2H), 1.78-1.63 (m, 4H), 1.57-1.49 (m, 5H), 1.48-1.32 (m, 10H), 1.30-1.19 (m, 5H), 1.16-1.02 (m, 4H), 0.97 (s, 3H), 0.95-0.92 (m, 5H), 0.89 (s, 3H). LC-ELSD/MS purity 99%, MS ESI calcd. for C$_{29}$H$_{41}$N$_3$ [M−2H$_2$O+H]$^+$ 432.3 found 432.3. SFC 100% de.

27: $^1$H NMR (400 MHz, CDCl$_3$) δ$_H$ 7.89 (s, 1H), 7.80 (s, 1H), 4.21-4.11 (m, 1H), 4.02-3.98 (d, J=13.8 Hz, 1H), 2.30 (s, 1H), 2.06 (s, 1H), 1.97-1.78 (m, 3H), 1.73-1.63 (m, 3H), 1.55 (s, 3H), 1.52-1.33 (m, 12H), 1.32-1.18 (m, 6H), 1.08 (s, 3H), 0.97-0.91 (m, 6H), 0.85 (s, 3H). LC-ELSD/MS purity 99%, MS ESI calcd. for C$_{29}$H$_{41}$N$_3$ [M−2H$_2$O+H]$^+$ 432.3 found 432.3.

Example 28: Synthesis of 1-((3-((3R,5R,8R,9R,10S,13S,14S,17S)-3-hydroxy-3,13-dimethylhexadecahydro-1H-cyclopenta[a]phenanthren-17-yl)oxetan-3-yl)methyl)-1H-pyrazole-4-carbonitrile

Synthesis of 26-1

To a mixture of MePPh$_3$Br (2.96 g, 8.30 mmol) in THF (30 mL) was added t-BuOK (931 mg, 236 mmol) at 25° C. under N$_2$. After stirring at 50° C. for 30 min, 26-0 (1.0 g, 2.77 mmol) in THF (20 mL) was added in portions blow 50° C. After stirring at 50° C. for 2 h, the reaction mixture was poured into water (300 mL) at 25° C. and extracted with EtOAc (2×300 mL). The combined organic layer was washed with water (300 mL), brine (200 mL), dried over Na$_2$SO$_4$, filtered and concentrated in vacuum. The residue was purified by silica gel chromatography (0-5% EtOAc in PE) to give 26-1 (880 mg, 88.6%). $^1$H NMR (400 MHz, CDCl$_3$) δ$_H$ 4.84 (s, 1H), 4.69 (s, 1H), 2.06-1.98 (m, 1H), 1.93-1.79 (m, 3H), 1.75 (s, 3H), 1.73-1.64 (m, 3H), 1.60-1.49 (m, 3H), 1.48-1.33 (m, 8H), 1.32-1.17 (m, 6H), 1.17-0.99 (m, 4H), 0.97-0.90 (m, 6H), 0.54 (s, 3H).

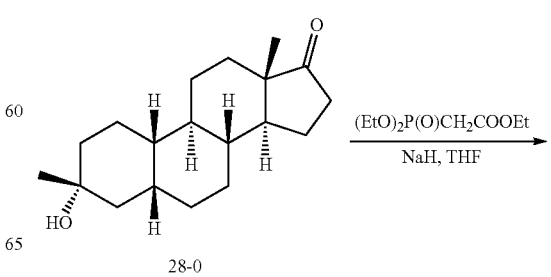

28-0

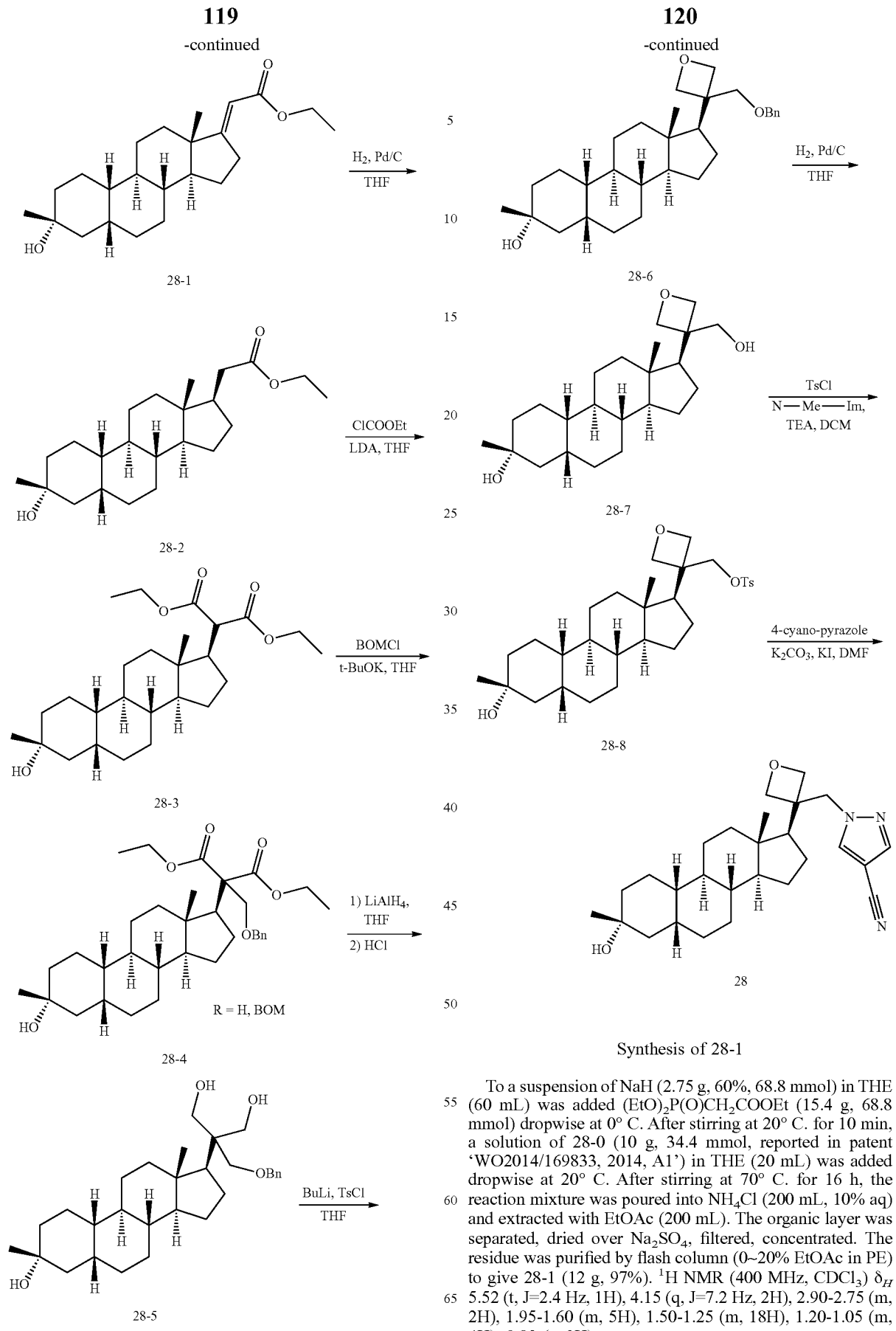

Synthesis of 28-1

To a suspension of NaH (2.75 g, 60%, 68.8 mmol) in THF (60 mL) was added (EtO)$_2$P(O)CH$_2$COOEt (15.4 g, 68.8 mmol) dropwise at 0° C. After stirring at 20° C. for 10 min, a solution of 28-0 (10 g, 34.4 mmol, reported in patent 'WO2014/169833, 2014, A1') in THF (20 mL) was added dropwise at 20° C. After stirring at 70° C. for 16 h, the reaction mixture was poured into NH$_4$Cl (200 mL, 10% aq) and extracted with EtOAc (200 mL). The organic layer was separated, dried over Na$_2$SO$_4$, filtered, concentrated. The residue was purified by flash column (0~20% EtOAc in PE) to give 28-1 (12 g, 97%). $^1$H NMR (400 MHz, CDCl$_3$) $\delta_H$ 5.52 (t, J=2.4 Hz, 1H), 4.15 (q, J=7.2 Hz, 2H), 2.90-2.75 (m, 2H), 1.95-1.60 (m, 5H), 1.50-1.25 (m, 18H), 1.20-1.05 (m, 4H), 0.82 (s, 3H).

Synthesis of 28-2

To a solution of 28-1 (12 g, 33.2 mmol) in THF (150 mL) was added Pd/C (2 g, dry, 10%) under $N_2$. After stirring under $H_2$ (40 psi) at 40° C. for 24 h, the reaction mixture was filtered through a pad of celite which was then washed with THF (3×50 mL). The combined filtrate was concentrated to give 28-2 (11.7 g, 97.5%). $^1$H NMR (400 MHz, $CDCl_3$) $\delta_H$ 4.11 (q, J=6.8 Hz, 2H), 2.35 (dd, J=5.2, 14.4 Hz, 1H), 2.10 (dd, J=10.0, 14.8 Hz, 1H), 2.00-1.75 (m, 6H), 1.70-1.50 (m, 3H), 1.50-1.35 (m, 6H), 1.35-1.25 (m, 10H), 1.20-0.95 (m, 6H), 0.59 (s, 3H).

Synthesis of 28-3

To a solution of i-$Pr_2NH$ (1.66 g, 16.5 mmol) in THF (30 mL) was added BuLi (6.6 mL, 2.5 M in hexane, 16.5 mmol) at −70° C. After warming to 0° C. over 15 min and then cooling to −70° C. a solution of 28-2 (2 g, 5.5 mmol) in TH (10 mL) was added. After stirring at −70° C. for 1 h, a solution of ClCOOEt (1.79 g, 16.5 mmol) in TH was added. After stirring at −70° C. for 1 h, the reaction mixture was quenched with $NH_4Cl$ (20 mL, 10%) and extracted with EtOAc (2×20 mL). The combined organic layer was dried over $Na_2SO_4$, filtered and concentrated in vacuum to give 28-3 (2.7 g). $^1$H NMR (400 MHz, $CDCl_3$) $\delta_H$ 4.25-4.05 (m, 4H), 3.29 (d, J=11.2 Hz, 1H), 2.25-2.15 (m, 1H), 2.00-1.75 (m, 4H), 1.70-1.35 (m, 12H), 1.35-1.20 (m, 10H), 1.20-0.95 (m, 7H), 0.70 (s, 3H).

Synthesis of 28-4

To a suspension of t-BuOK (4.85 g, 31.0 mmol) in THF (20 mL) was added a solution of 28-3 (2.25 g, 5.17 mmol) in THF (20 mL) at 0° C. After stirring at 15° C. for 1 h, BOMCl (3.47 g, 31.0 mmol) was added at 0° C. After stirring at 0° C. for 1 h, the reaction mixture was poured into $NH_4Cl$ (100 mL, sat.) and extracted with EtOAc (100 mL). The organic layer was separated, dried over $Na_2SO_4$, filtered and concentrated to give 28-4 (8.5 g) which contain some diethyl 2-((3R,5R,8R,9R,10S,13S,14S,17S)-3-((benzyloxy)methoxy)-3,13-dimethylhexadecahydro-1H-cyclopenta[a]phenanthren-17-yl)-2-((benzyloxy)methyl)malonate.

Synthesis of 28-5

To a suspension of $LiAlH_4$ (1.96 g, 51.7 mmol) in THF (80 mL) was added a solution of 28-4 (5.17 mmol mixture) in THF (20 mL) dropwise at 0° C. After stirring at 0° C. for 1 h, the reaction mixture was quenched with water/THF (2 mL/100 mL) followed by NaOH (2 mL, 10%) and water (6 mL). The mixture was filtered and the residue was washed with THF (3×50 mL). The combined filtrate was concentrated to 100 mL and HCl (2 M, 10 mL) was added. After stirring at 50° C. for 1 h, the reaction mixture was diluted with $NaHCO_3$(50 mL, sat) and extracted with EtOAc (100 mL). The organic layer was separated, dried over $Na_2SO_4$, filtered, and concentrated. The residue was purified by flash column (30~80% EtOAc in PE) to give 28-5 (1 g, 41% above two steps). $^1$H NMR (400 MHz, $CDCl_3$) $\delta_H$ 7.45-7.30 (m, 5H), 4.50 (s, 2H), 3.95-3.55 (m, 6H), 2.80-2.70 (br, 1H), 2.70-2.60 (br, 1H), 1.95-1.70 (m, 4H), 1.70-1.50 (m, 5H), 1.50-1.20 (m, 13H), 1.15-0.90 (m, 6H), 0.73 (s, 3H).

Synthesis of 28-6

To a solution of 28-5 (1 g, 2.12 mmol) in THF (20 mL) was added BuLi (1.01 mL, 2.5 M in hexane, 2.54 mmol) at 0° C. After stirring at 0° C. for 10 min, a solution of TsCl (484 mg, 2.54 mmol) in THF (5 mL) was added. After stirring at 0° C. for 1 h, BuLi (1.01 mL, 2.5 M in hexane, 2.54 mmol) was added at 0° C. After stirring at 15° C. for 2 h, the reaction mixture was quenched with $NH_4Cl$ (20 mL, sat.) and extracted with EtOAc (2×30 mL). The combined organic layer was dried over $Na_2SO_4$, filtered, and concentrated under vacuum. The residue was purified by flash column (0~15% EtOAc in PE) to give 28-6 (650 mg, 68%). $^1$H NMR (400 MHz, $CDCl_3$) $\delta_H$ 7.45-7.30 (m, 5H), 4.83 (d, J=6.4 Hz, 1H), 4.60 (d, J=12.0 Hz, 1H), 4.55-4.50 (m, 2H), 4.44 (d, J=5.6 Hz, 1H), 4.23 (d, J=6.4 Hz, 1H), 3.89 (d, J=9.2 Hz, 1H), 3.66 (d, J=9.2 Hz, 1H), 2.20-2.10 (m, 1H), 2.00-1.60 (m, 8H), 1.50-1.30 (m, 7H), 1.30-0.95 (m, 12H), 0.52 (s, 3H).

Synthesis of 28-7

To a solution of 28-6 (650 mg, 1.43 mmol) in THF (20 mL) was added Pd/C (0.5 g, 10%, wet) under $N_2$. After stirring under $H_2$ (20 psi) at 20° C. for 20 h, the reaction mixture was filtered and the residue was washed with THF (20 mL). The combined filtrate was concentrated and purified by flash column (40~70% EtOAc in PE) to give 28-7 (380 mg, 73%). $^1$H NMR (400 MHz, $CDCl_3$) $\delta_H$ 4.85 (d, J=6.8 Hz, 1H), 4.54 (d, J=5.6 Hz, 1H), 4.46 (d, J=5.6 Hz, 1H), 4.24 (d, J=6.4 Hz, 1H), 4.08 (dd, J=4.0, 10.8 Hz, 1H), 3.82 (d, J=10.0 Hz, 1H), 2.20-2.10 (m, 1H), 2.00-1.65 (m, 10H), 1.55-1.00 (m, 18H), 0.53 (s, 3H). LC-ELSD/MS: purity>99%, MS ESI calcd. for $C_{23}H_{37}O_2$ $[M+H-H_2O]^+$ 345.3, found 345.3.

Synthesis of 28-8

To a solution of 28-7 (185 mg, 0.51 mmol) in DCM (5 mL) were added N-Me-Im (41.8 mg, 0.51 mmol), TEA (258 mg, 2.55 mmol) and TsCl (194 mg, 1.02 mmol). After stirring at 15° C. for 16 h, the reaction mixture was washed with water (5 mL), dried over $Na_2SO_4$, filtered, and concentrated. The residue was purified by flash column (0-25% EtOAc in PE/DCM (1:1)) to give 28-8 (200 mg, 76%). $^1$H NMR (400 MHz, $CDCl_3$) $\delta_H$ 7.83 (d, J=8.4 Hz, 2H), 7.37 (d, J=8.0 Hz, 2H), 4.82 (d, J=6.8 Hz, 1H), 4.50-4.40 (m, 2H), 4.22 (d, J=9.6 Hz, 1H), 4.18 (d, J=6.0 Hz, 1H), 4.11 (d, J=6.8 Hz, 1H), 2.46 (s, 3H), 2.10-2.00 (m, 1H), 1.95-1.55 (m, 8H), 1.50-0.90 (m, 19H), 0.47 (s, 3H).

Synthesis of 28

To a solution of 28-8 (200 mg, 0.39 mmol) in DMF (5 mL) were added 4-cyano-pyrazole (72 mg, 0.77 mmol), KI (64.2 mg, 0.38 mmol) and $K_2CO_3$ (108 mg, 0.77 mmol). After stirring at 80° C. for 16 h, the reaction mixture was poured into water (30 mL) and filtered. The residue was purified by flash column (20~50% EtOAc in PE), dissolved in MeCN (30 mL)/water (30 mL) and lyophilized to give 28 (135.7 mg, 79%). $^1$H NMR (400 MHz, $CDCl_3$) $\delta_H$ 7.88 (s, 1H), 7.83 (s, 1H), 4.96 (d, J=6.8 Hz, 1H), 4.70-4.60 (m, 2H), 4.53 (d, J=6.4 Hz, 1H), 4.47 (d, J=7.2 Hz, 1H), 4.35 (d, J=14.0 Hz, 1H), 2.10-2.00 (m, 1H), 2.00-1.65 (m, 8H), 1.55-0.95 (m, 19H), 0.69 (s, 3H). LC-ELSD/MS purity>99%, MS ESI calcd. for $C_{27}H_{40}N_3O_2$ $[M+H]^+$ 438.3, found 438.3.

Example 29 & 30: Synthesis of 1-((S)-2-hydroxy-2-((3R,5R,8R,9R,10S,13S,14S,17S)-3-hydroxy-3-(methoxymethyl)-13-methylhexadecahydro-1H-cyclopenta[a]phenanthren-17-yl)propyl)-1H-pyrazole-4-carbonitrile (29 & 1-((R)-2-hydroxy-2-((3R,5R,8R,9R,10S,13S,14S,17S)-3-hydroxy-3-(methoxymethyl)-13-methylhexadecahydro-1H-cyclopenta[a]phenanthren-17-yl)propyl)-1H-pyrazole-4-carbonitrile (30)

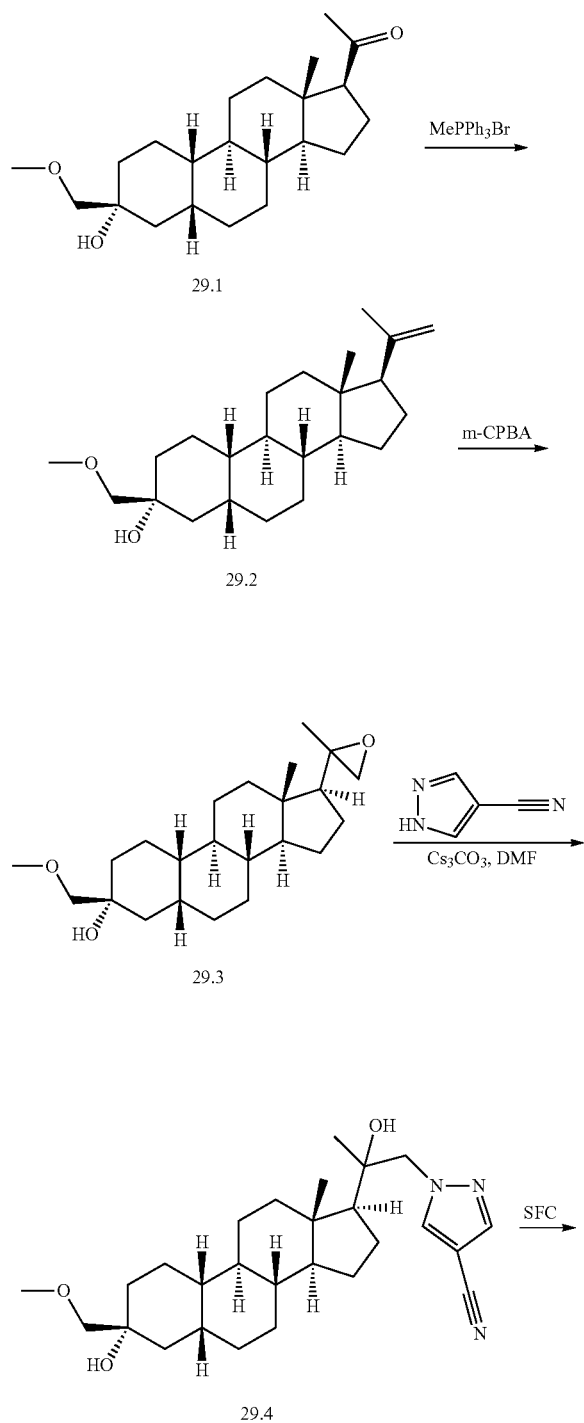

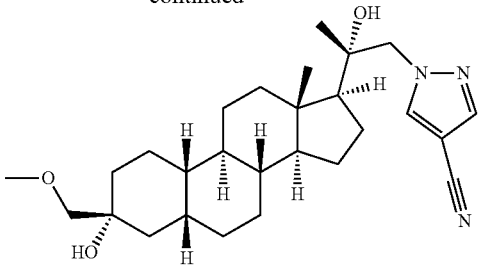

29

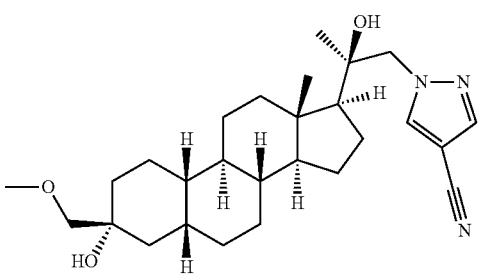

30

Synthesis of 29.2

To a solution of MePPh$_3$Br (12.2 g, 34.0 mmol) in THF (20 mL) was added t-BuOK (2.88 g, 25.8 mmol) at 15° C. After stirring for 1 h at 15° C., 29.1 (3 g, 8.60 mmol) in THF (20 mL) was added. After stirring at 45° C. for 3 h, the mixture was treated with saturated NH$_4$Cl (50 mL) and extracted with EtOAc (2×30 mL). The combined organic solution was washed with brine (100 mL), dried over anhydrous Na$_2$SO$_4$, filtered and concentrated. The residue was purified by flash column (0~40% of EtOAc in PE) to give 29.2 (4.5 g). $^1$H NMR (400 MHz, CDCl$_3$) δ 4.83 (s, 1H), 4.45 (s, 1H), 3.47-3.31 (m, 5H), 2.61 (s, 1H), 2.05-2.02 (m, 1H), 1.91-1.77 (m, 4H), 1.74 (s, 3H), 1.68-1.52 (m, 5H), 1.49-1.31 (m, 7H), 1.28-1.04 (m, 7H), 0.59-0.50 (m, 3H).

Synthesis of 29.3

To a solution of 29.2 (500 mg, 1.44 mmol) in DCM (20 mL) was added m-CPBA (461 mg, 2.15 mmol, 85%) at 15° C. After stirring for 1 h, the mixture was quenched with sat.NaHCO$_3$ and Na$_2$S$_2$O$_3$ (40 mL, v:v=1:1) and extracted with DCM (2×20 mL). The combined organic phase was washed with sat.NaHCO$_3$ and Na$_2$S$_2$O$_3$ (50 mL, v:v=1:1), dried over Na$_2$SO$_4$, filtered and concentrated to give 29.3 (520 mg). $^1$H NMR (400 MHz, CDCl$_3$) δ$_H$=3.46-3.32 (m, 8H), 2.88 (d, J=4.4 Hz, 1H), 2.55 (d, J=4.4 Hz, 1H), 2.51-2.47 (m, 1H), 2.31 (d, J=5.2 Hz, 1H), 2.04-1.98 (m, 1H), 1.95-1.53 (m, 8H), 1.50-1.29 (m, 8H), 1.28-0.98 (m, 5H), 0.82-0.78 (m, 1H), 0.68 (s, 3H).

Synthesis of 29.4

To solution of 29.3 (520 mg, 1.43 mmol) in DMF (10 mL) were added Cs$_2$CO$_3$ (1.39 g, 4.29 mmol) and 1H-pyrazole-4-carbonitrile (332 mg, 3.57 mmol) at 15° C. under N$_2$. After stirring at 130° C. for 12 h, the mixture was added into saturated NH$_4$Cl (50 mL) and extracted with EtOAc (3×50 mL). The combined organic layer was washed with LiCl (100 mL, 5% in water), brine (2×100 mL), dried over anhydrous $Na_2SO_4$, filtered and concentrated. The residue was purified by column (0~50% of EtOAc in PE) to afford 29.4 (650 mg). LC-ELSD/MS purity 99%, MS ESI calcd for $C_{26}H_{35}N_3$ $[M-2H_2O-CH_3OH+H]^+$ 388.3, found 388.3.

Separation of 29 & 30

29.4 was separated by SFC (Column: Chiralcel OD-3 50Å4.6 mm I.D., 3 um; Mobile phase: A: $CO_2$ B:ethanol (0.05% DEA); Gradient: from 5% to 40% of B in 2 min and hold 40% for 1.2 min, then 5% of B for 0.8 min; Flow rate: 4 mL/min) to afford 30 (73 mg, 18.2%) and 29 (189.9 mg, 47.3%).

29: $^1$H NMR (400 MHz, $CDCl_3$) $\delta_H$=7.92 (s, 1H), 7.82 (s, 1H), 4.36 (d, J=13.6 Hz, 1H), 4.08 (d, J=13.6 Hz, 1H), 3.46-3.33 (m, 5H), 2.59 (s, 1H), 2.52 (s, 1H), 2.01 (br d, J=12.0 Hz, 1H), 1.87-1.57 (m, 9H), 1.52-1.31 (m, 7H), 1.29-1.04 (m, 7H), 0.96 (s, 3H), 0.91 (s, 3H) LC-ELSD/MS purity 99%, MS ESI calcd for $C_{26}H_{35}N_3$ $[M-2H_2O-CH_3OH+H]^+$ 388.3, found 388.3.

30: $^1$H NMR (400 MHz, $CDCl_3$) $\delta_H$=7.89 (s, 1H), 7.80 (s, 1H), 4.17 (d, J=13.6 Hz, 1H), 4.01 (d, J=13.6 Hz, 1H), 3.48-3.32 (m, 5H), 2.60 (s, 1H), 2.32 (s, 1H), 2.06 (br d, J=13.6 Hz, 1H), 1.98-1.60 (m, 9H), 1.51-1.24 (m, 9H), 1.08 (s, 8H), 0.87 (s, 3H). LC-ELSD/MS purity 99%, MS ESI calcd for $C_{26}H_{35}N_3$ $[M-2H_2O-CH_3OH+H]^+$ 388.3, found 388.3.

Example 31: Synthesis of 1-(1-((S)-2-hydroxy-2-((3R,5R,8R,9R,10S,13S,14S,17S)-3-hydroxy-3,13-dimethylhexadecahydro-1H-cyclopenta[a]phenanthren-17-yl)propyl)-1H-pyrazol-4-yl)ethanone (31)

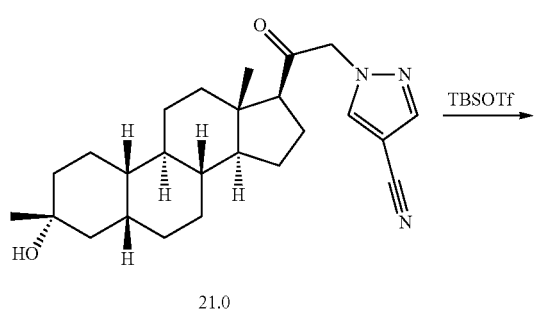

21.0

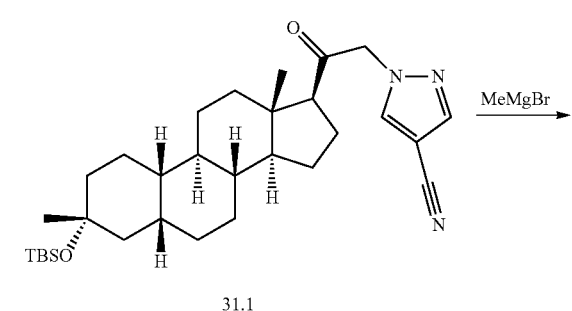

31.1

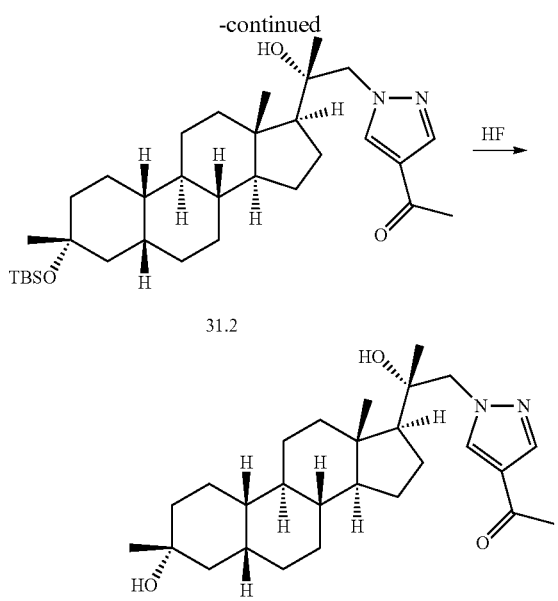

31.2

31

Synthesis of 31.1

To a solution of 21.0 (2 g, 4.88 mmol), 2,6-dimethylpyridine (1.30 g, 12.2 mmol) in DCM (20 mL) was added dropwise tert-butyldimethylsilyl trifluoromethanesulfonate (2.57 g, 9.76 mmol) at 0° C. After stirring at 15° C. for 5 hrs, the reaction mixture was quenched with water (60 mL) and extracted with DCM (2×50 mL). The combined organic phase washed with brine (50 mL), dried over $Na_2SO_4$, filtered and concentrated under vacuum. The residue was purified by flash column (10-20% of EtOAc in PE) to afford 31.1 (2.5 g, 98.0%). $^1$H NMR (400 MHz, $CDCl_3$) $\delta_H$ 7.87 (s, 1H), 7.82 (s, 1H), 5.10-4.97 (m, 1H), 4.96-4.84 (m, 1H), 2.72-2.60 (m, 1H), 2.28-2.17 (m, 1H), 2.09-2.02 (m, 1H), 1.87-1.67 (m, 7H), 1.46-1.40 (m, 4H), 1.29-1.26 (m, 3H), 1.24 (s, 4H), 1.16-1.07 (m, 3H), 0.88 (s, 11H), 0.68 (s, 3H), 0.09 (s, 6H).

Synthesis of 31.2

To a solution of 31.1 (200 mg, 0.381 mmol) in THF (5 mL) was added MeMgBr (1.27 mL, 3.81 mmol, 3.0 M) at −60° C. After stirring at 25° C. for 2 h, the mixture was added to $NH_4Cl$ (20 mL). and extracted with EtOAc (2×15 mL). The combined organic layers were washed with brine (15 mL), dried over anhydrous $Na_2SO_4$, filtered and concentrated. The residue was purified by flash column (0~20% of EtOAc in PE) to give 31.2 (120 mg, 56.6%). $^1$H NMR (400 MHz, $CDCl_3$) $\delta_H$ 7.94-7.93 (m, 1H), 7.92-7.90 (m, 1H), 4.41-4.30 (m, 1H), 4.08-4.00 (m, 1H), 2.68-2.62 (m, 1H), 2.45-2.44 (m, 3H), 2.28-2.17 (m, 1H), 2.11-2.02 (m, 2H), 1.81-1.74 (m, 8H), 1.44 (s, 3H), 1.24 (s, 6H), 1.15-1.06 (m, 6H), 1.01-0.93 (m, 4H), 0.88 (s, 9H), 0.70-0.68 (m, 3H), 0.09 (s, 6H), 0.10-0.09 (m, 1H).

Synthesis of 31

To a solution of 31.2 (120 mg, 0.215 mmol) in THF (2 mL) was added HF (21.4 mg, 1.07 mmol, 1.1 g/mL) in one portion at 25° C. under $N_2$. After stirring at 25° C. for 16 h, the mixture was added to NH₄Cl (10 mL) and extracted with EtOAc (2×15 mL). The combined organic layers were washed with brine (15 mL), dried over anhydrous Na₂SO₄, filtered and concentrated. The residue was purified by HPLC (Welch Xtimate C18 150×25 mm, 5 um; Condition: water (0.04% NH₃H₂O)-ACN; Gradient: from 50% to 80% of B in 8.5 min and hold 100% for 2 min; Flow rate: 30 mL/min; Injections: 6) to afford 31 (3.8 mg, 3.99%). ¹H NMR (400 MHz, CDCl₃) δ$_H$ 7.97-7.95 (m, 1H), 7.95-7.93 (m, 1H), 4.38-4.31 (m, 1H), 4.06-4.01 (m, 1H), 3.08-3.05 (m, 1H), 2.46 (s, 3H), 2.08-2.02 (m, 1H), 1.87-1.73 (m, 5H), 1.70-1.61 (m, 4H), 1.47-1.35 (m, 8H), 1.27 (s, 5H), 1.14-1.04 (m, 5H), 1.00 (s, 3H), 0.93 (s, 3H). LC-ELSD/MS purity 99%, MS ESI calcd. for $C_{27}H_{42}N_2O_3$ [M+H]⁺ 443.3 found 443.3.

Examples 32 & 33: Synthesis of 1-((R)-2-((3R,5R, 8R,9R,10S,13S,14S,17S)-3-hydroxy-3-(methoxymethyl)-13-methylhexadecahydro-1H-cyclopenta[a]phenanthren-17-yl)-2-methoxypropyl)-1H-pyrazole-4-carbonitrile (32) & 1-[(2S)-2-[(1S,3aS,3bR,5aR, 7R,9aS,9bR,11aS)-7-hydroxy-7-(methoxymethyl)-11α-methyl-hexadecahydro-1H-cyclopenta[a]phenanthren-1-yl]-2-methoxypropyl]-1H-pyrazole-4-carbonitrile (33)

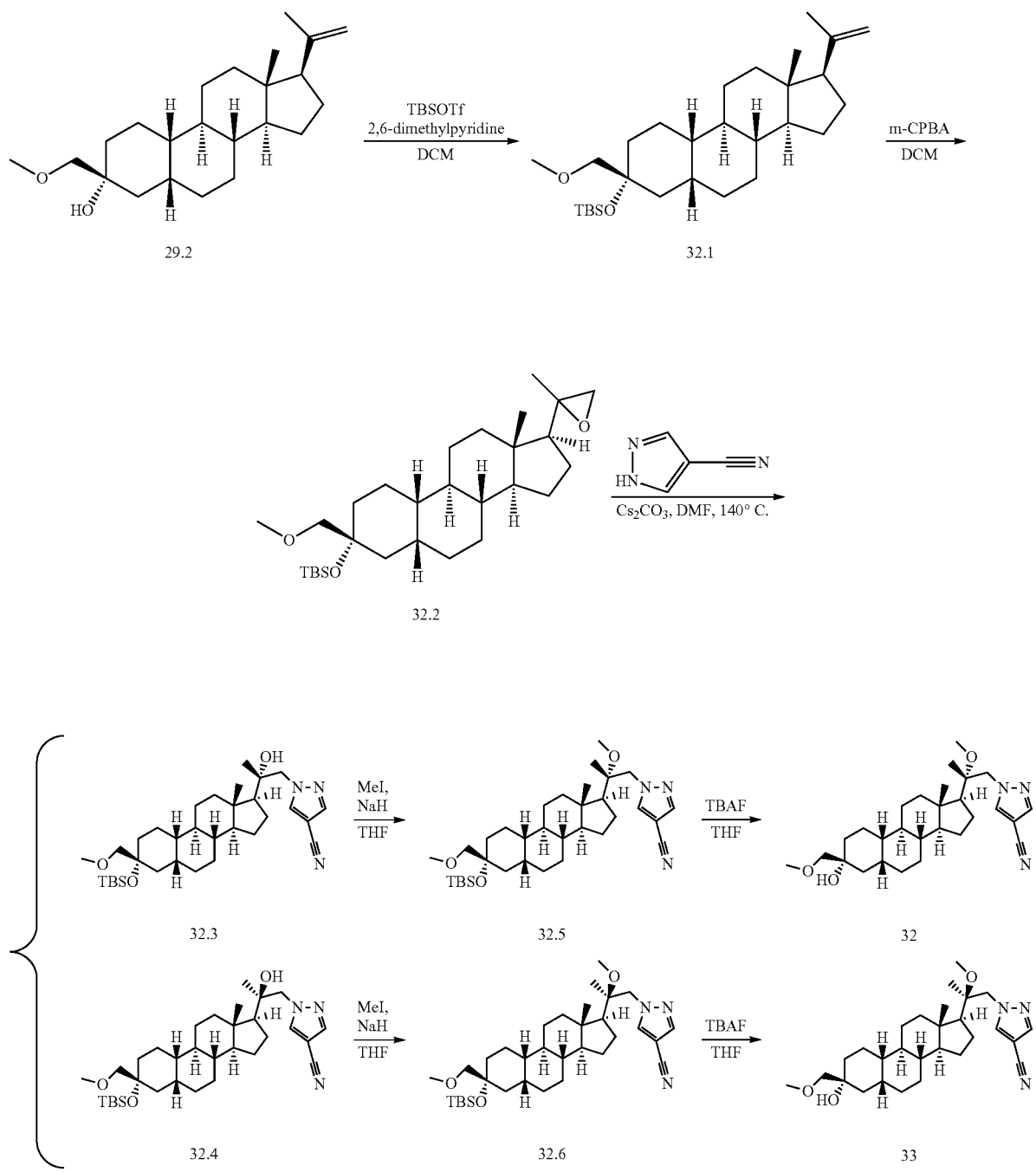

Synthesis of 32.1

To a solution of 29.2 (4 g, 11.5 mmol) and 2,6-dimethylpyridine (6.14 g, 57.4 mmol) in DCM (150 mL) was added TBSOTf (12.1 g, 46.0 mmol) at 0° C. After stirring at 25° C. for 16 h, the mixture was diluted with DCM (150 mL) and washed with water (300 mL). The organic phase was separated, dried over anhydrous $Na_2SO_4$, filtered and concentrated to give 32.1 (6 g), which was used directly for the next step. $^1$H NMR (400 MHz, $CDCl_3$) δ 4.85 (s, 1H), 4.70 (s, 1H), 3.42-3.29 (m, 5H), 2.11-2.05 (m, 1H), 1.89-1.79 (m, 5H), 1.72-1.56 (m, 8H), 1.49-0.99 (m, 16H), 0.95-0.88 (m, 6H), 0.57 (s, 3H), 0.08-0.05 (m, 6H).

Synthesis of 32.2

To a solution of 32.1 (3 g, 6.51 mmol) in DCM (150 mL) was added m-CPBA (1.96 g, 9.76 mmol, 85%). After stirring at 25° C. for 2 h, the reaction mixture was quenched with $NaHCO_3$ (150 mL, sat.) and extracted with DCM (2×80 mL). The combined organic phase was washed with brine (150 mL), dried over anhydrous $Na_2SO_4$, filtered and concentrated to give 32.2 (2.3 g).

Synthesis of 32.3 & 32.4

To a solution of 32.2 (2.3 g, 4.82 mmol) in DMF (50 mL) were added 1H-pyrazole-4-carbonitrile (1.34 g, 14.4 mmol) and $Cs_2CO_3$ (4.69 g, 14.4 mmol) at 25° C. After stirring at 140° C. for 8 h, the mixture was diluted with water (100 mL) and extracted with EtOAc (2×60 mL). The combined organic phase was washed with water (100 mL), brine (100 mL), dried over anhydrous $Na_2SO_4$, filtered and concentrated in vacuum. The residue was purified by flash column (0%-30% of EtOAc in PE) to give 32.4 (1.3 g, 47.4%) and 32.3 (680 mg, 24.8%).

32.3: $^1$H NMR (400 MHz, $CDCl_3$) δ 7.89 (s, 1H), 7.80 (s, 1H), 4.23-4.13 (m, 1H), 4.05-3.90 (m, 1H), 3.43-3.26 (m, 5H), 2.29 (s, 1H), 2.10-2.05 (m, 1H), 1.98-1.62 (m, 8H), 1.57-1.27 (m, 7H), 1.23-0.97 (m, 10H), 0.94-0.81 (m, 13H), 0.06 (s, 6H).

32.4: $^1$H NMR (400 MHz, $CDCl_3$) δ 7.93 (s, 1H), 7.82 (s, 1H), 4.36 (d, J=14.0 Hz, 1H), 4.10-4.05 (m, 1H), 3.41-3.29 (m, 5H), 2.50 (s, 1H), 1.83-1.59 (m, 9H), 1.53-1.27 (m, 7H), 1.24-1.01 (m, 8H), 1.00-0.90 (m, 6H), 0.85 (s, 9H), 0.06 (s, 6H).

Synthesis of 32.5

To a solution of 32.3 (680 mg, 1.19 mmol) in THF (20 mL) was added NaH (71.1 mg, 1.78 mmol, 60% in oil) at 25° C. under $N_2$. After stirring at 25° C. for 30 min, MeI (337 mg, 2.38 mmol) was added. After stirring at 25° C. for 16 h, the reaction mixture was poured into water (50 mL) and extracted with EtOAc (2×50 mL). The combined organic phase was washed with brine (2×50 mL), dried over anhydrous $Na_2SO_4$, filtered and concentrated. The residue was purified by flash column (0-20% of EtOAc in PE) to give 32.5 (600 mg).

Synthesis of 32

To a solution of 32.5 (1.3 g, 2.22 mmol) in THF (20 mL) was added TBAF (22.2 mL, 22.2 mmol, 1M in THF). After stirring at 80° C. for 16 h, the reaction mixture was quenched with $NH_4Cl$ (50 mL, sat.) and extracted with EtOAc (2×50 mL). The combined organic phase was washed with brine (2×50 mL), dried over anhydrous $Na_2SO_4$, filtered and concentrated. The residue was purified by flash column (0-50% of EtOAc in PE) to give 32 (301.8 mg, 28.9%). $^1$H NMR (400 MHz, $CDCl_3$) δ 7.91 (s, 1H), 7.75 (s, 1H), 4.33-4.12 (m, 2H), 3.45-3.32 (m, 5H), 3.18 (s, 3H), 2.57 (s, 1H), 1.98-1.91 (m, 1H), 1.85-1.59 (m, 9H), 1.50-1.22 (m, 8H), 1.18-1.00 (m, 9H), 0.85 (s, 3H). LCMS 30-90AB_2min_E, purity≥99%, MS ESI calcd. for $C_{27}H_{38}N_3O$ $[M+H-MeOH—H_2O]^+$ 420.3, found 420.2.

Synthesis of 32.6

To a solution of 32.4 (1.3 g, 2.28 mmol) in THF (20 mL) was added NaH (136 mg, 3.42 mmol, 60% in oil) at 25° C. under $N_2$. After stirring for 30 min, MeI (647 mg, 4.56 mmol) was added at 25° C. After stirring at 25° C. for 16 h, the reaction mixture was poured into water (50 mL) and extracted with EtOAc (2×50 mL). The combined organic phase was washed with brine (2×50 mL), dried over anhydrous $Na_2SO_4$, filtered and concentrated. The residue was purified by flash column (0-20% of EtOAc in PE) to give 32.6 (1.2 g).

Synthesis of 33

To a solution of 32.6 (600 mg, 1.02 mmol) in THF (10 mL) was added TBAF (5.10 mL, 5.10 mmol, 1M in THF). After stirring at 80° C. for 16 h, the reaction mixture was quenched with $NH_4Cl$ (50 mL, sat.) and extracted with EtOAc (2×50 mL). The combined organic phase was washed with brine (2×50 mL), dried over anhydrous $Na_2SO_4$, filtered and concentrated. The residue was purified by flash column (0-50% of EtOAc in PE) to give 33 (144.7 mg, 30%). $^1$H NMR (400 MHz, $CDCl_3$) δ 7.90 (s, 1H), 7.75 (s, 1H), 4.24 (s, 2H), 3.45-3.34 (m, 5H), 3.13 (s, 3H), 2.59 (s, 1H), 2.09-1.99 (m, 1H), 1.86-1.59 (m, 9H), 1.49-1.19 (m, 9H), 1.13-0.98 (m, 8H), 0.81 (s, 3H). LCMS purity≥99%, MS ESI calcd. for $C_{27}H_{38}N_3O$ $[M+H-MeOH—H_2O]^+$ 420.3, found 420.2.

Examples 34 & 35: Synthesis of 1-((S)-2-((2S,3S, 5R,8R,9R,10S,13S,14S,17S)-2-ethyl-3-hydroxy-3, 13-dimethylhexadecahydro-1H-cyclopenta[a] phenanthren-17-yl)-2-hydroxypropyl)-1H-pyrazole-4-carbonitrile (34) & 1-((R)-2-((2S,3S,5R,8R,9R, 10S,13S,14S,17S)-2-ethyl-3-hydroxy-3,13-dimethylhexadecahydro-1H-cyclopenta[a] phenanthren-17-yl)-2-hydroxypropyl)-1H-pyrazole-4-carbonitrile (35)

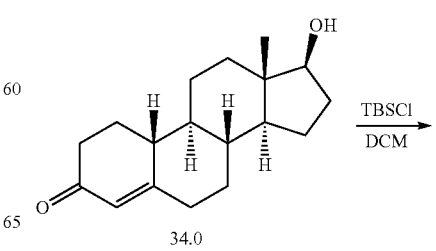

34.0

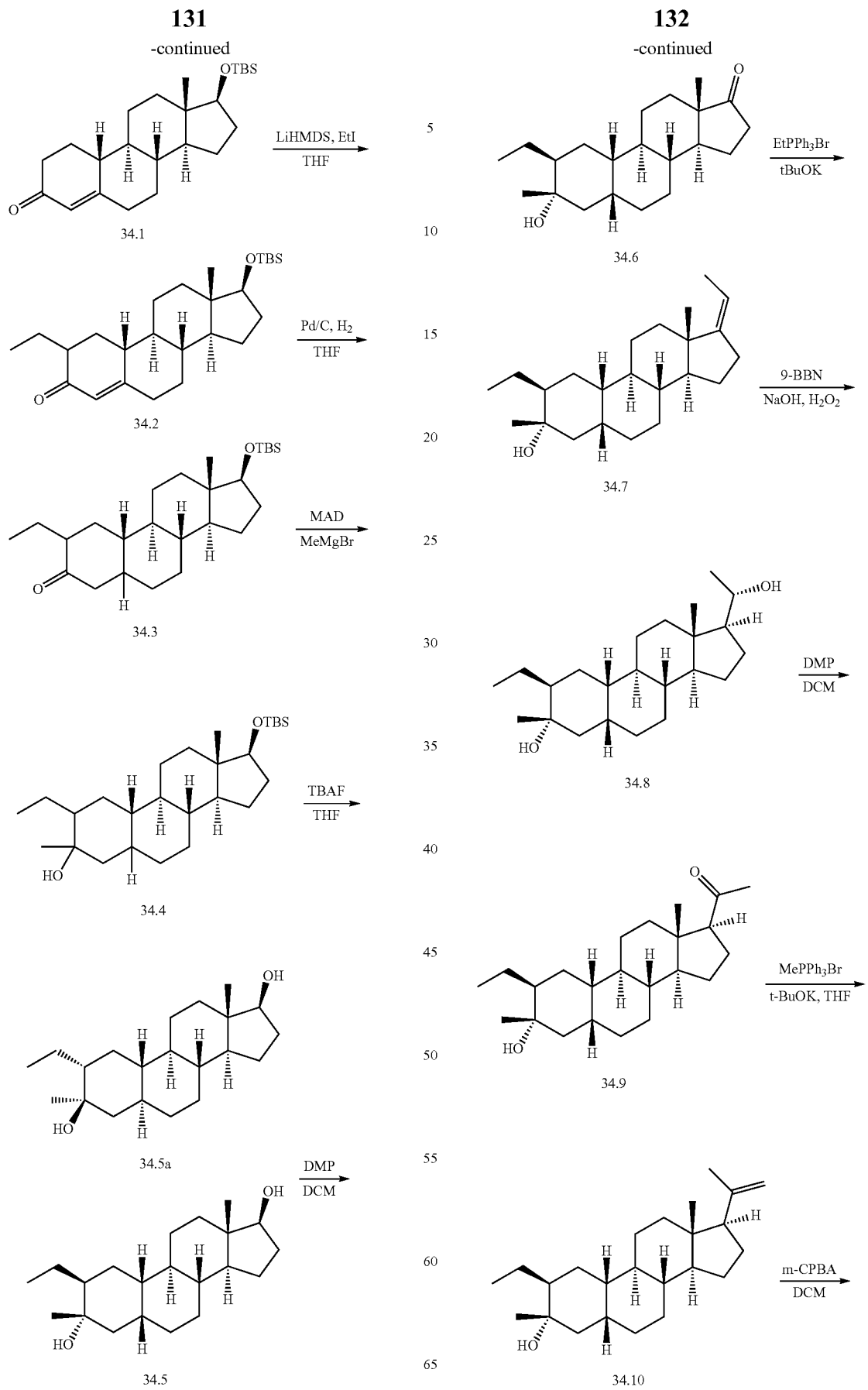

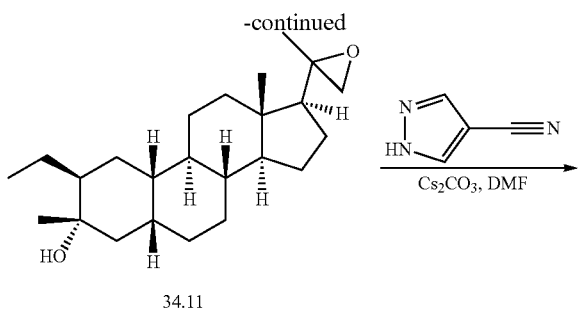

34.11

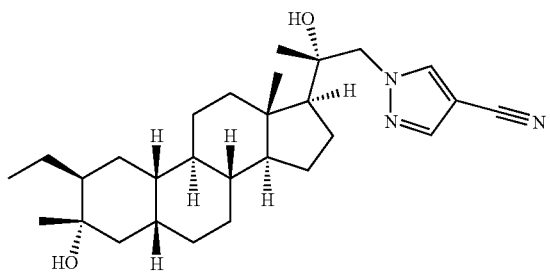

34

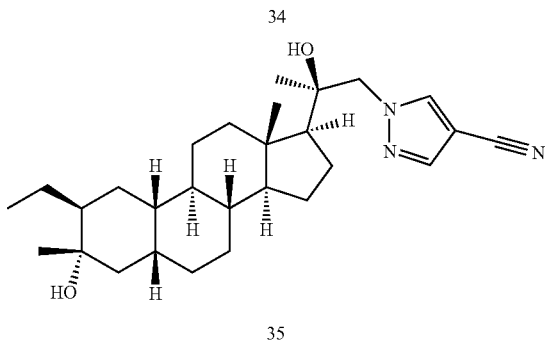

35

Synthesis of 34.1

To a solution of 34.0 (100 g, 364 mmol) in DCM (1000 mL) were added imidazole (49.5 g, 728 mmol) and TBSCl (109 g, 728 mmol) at 25° C. After stirring at 25° C. for 2 h, the mixture was poured into water (500 mL) and extracted with DCM (2×500 mL). The combined organic phase was washed with brine (500 mL), dried over anhydrous $Na_2SO_4$, filtered and concentrated. The residue was triturated from PE (200 mL) at 25° C. to give 34.1 (83 g). $^1$H NMR (400 MHz, $CDCl_3$) $\delta_H$ 5.82 (s, 1H), 3.56 (t, J=8.3 Hz, 1H), 2.50-2.36 (m, 2H), 2.32-2.19 (m, 3H), 2.14-2.04 (m, 1H), 1.94-1.74 (m, 3H), 1.59-1.21 (m, 6H), 1.07-0.90 (m, 4H), 0.88 (s, 9H), 0.84-0.78 (m, 1H), 0.76 (s, 3H), 0.00 (d, J=2.8 Hz, 6H).

Synthesis of 34.2

To a solution of 34.1 (50 g, 128 mmol) in TH (300 mL) was added LiHMDS (128 mL, 1 M in THF, 128 mmol) at −70° C. under $N_2$. After stirring at −70° C. for 30 min, HMPA (22.9 g, 22.4 mL, 128 mmol) was added under $N_2$. After stirring at −70° C. for 30 min, EtI (199 g, 102 mL, 128 mmol) was added under $N_2$. After stirring at 20° C. for 1 h, the mixture was cooled and concentrated with reduced pressure at 40° C. The residue was poured into $NH_4Cl$ (500 mL), stirred for 20 mins, and extracted with EtOAc (3×400 mL). The combined organic phase was washed with brine (2×200 mL), dried anhydrous $Na_2SO_4$, filtered and concentrated. The residue was purified by flash column (0~1% of EtOAc in PE) to give 34.2 (40 g). $^1$H NMR (400 MHz, $CDCl_3$) $\delta_H$ 5.79 (s, 1H), 5.72 (s, 1H), 3.57 (t, J=8.3 Hz, 1H), 2.48-2.39 (m, 1H), 2.34-2.06 (m, 4H), 1.96-1.61 (m, 3H), 1.26 (br d, J=1.8 Hz, 9H), 1.07-0.98 (m, 2H), 0.93 (br t, J=7.5 Hz, 4H), 0.88 (s, 10H), 0.76 (s, 3H), 0.01 (d, J=2.8 Hz, 6H).

Synthesis of 34.3

To a mixture of 34.2 (20 g, 47.9 mmol) in THE (200 mL) was added Pd/C (2 g, 10%). The mixture was degassed under vacuum and purged with $H_2$ three times. After stirring under $H_2$ (15 psi) at 25° C. for 24 h, the reaction mixture was filtered through a pad of Celite and washed with THE (3×500 mL). The filtrate was concentrated to give 34.3 (18 g). $^1$H NMR (400 MHz, $CDCl_3$) $\delta_H$ 3.61-3.52 (m, 1H), 2.67-2.55 (m, 1H), 2.34-2.05 (m, 4H), 1.94-1.62 (m, 4H), 1.58-0.92 (m, 14H), 0.92-0.85 (m, 13H), 0.73 (d, J=3.8 Hz, 3H), 0.00 (dd, J=3.0, 4.4 Hz, 6H).

Synthesis of 34.4

To a solution of BHT (60 g, 272 mmol) in toluene (200 mL) under $N_2$ at 0° C. was added trimethylaluminum (68 mL, 2 M in toluene, 136 mmol) dropwise slowly. After stirring at 0° C. for 1 h, the MAD solution was used directly without further purification. To the MAD (64.8 g in toluene, 135 mmol) solution was added a solution of 34.3 (19 g, 45.3 mmol) in DCM (200 mL) dropwise at −70° C. under $N_2$. After stirring at −70° C. for 1 h under $N_2$, MeMgBr (30.2 mL, 3M in ethyl ether, 90.6 mmol) was added dropwise at −70° C. After stirring for 2 h, the reaction mixture was poured slowly into aqueous citric acid (500 mL, sat.) at 10° C. and extracted with DCM (2×200 mL). The combined organic phase was washed with brine (300 mL), dried over anhydrous $Na_2SO_4$, filtered and concentrated. The residue was purified by flash column (0-5% of EtOAc in PE) to give 34.4 (11 g). $^1$H NMR (400 MHz, $CDCl_3$) $\delta_H$ 3.54 (t, J=8.3 Hz, 1H), 2.03-1.94 (m, 1H), 1.91-1.61 (m, 6H), 1.58-1.36 (m, 5H), 1.32-1.13 (m, 6H), 1.12-0.89 (m, 11H), 0.87 (s, 11H), 0.70 (d, J=2.3 Hz, 3H), 0.00 (t, J=2.6 Hz, 6H).

Synthesis of 34.5 & 34.5a

To a solution of 34.4 (11 g, 25.3 mmol) in TH (20 mL) was added TBAF.3$H_2$O (126 ml, 1M, 126 mmol) at 15° C. After stirring at 55° C. for 12 h, the mixture was poured into water (200 mL) and extracted with EtOAc (2×200 mL). The organic layer was washed with brine (2×20 mL), dried over anhydrous $Na_2SO_4$, filtered and concentrated. The residue was purified by column (10-15% of EtOAc in PE) to give 34.5a (3.8 g) and 34.5 (4.7 g).

34.5a: $^1$H NMR (400 MHz, $CDCl_3$) $\delta_H$ 3.63 (br t, J=8.3 Hz, 1H), 2.11-1.98 (m, 2H), 1.84-1.73 (m, 3H), 1.61-1.54 (m, 2H), 1.48-1.33 (m, 3H), 1.32-1.12 (m, 6H), 1.06 (s, 6H), 1.02-0.82 (m, 8H), 0.74 (s, 4H), 0.67-0.58 (m, 1H).

34.5: $^1$H NMR (400 MHz, $CDCl_3$) $\delta_H$ 3.64 (t, J=8.6 Hz, 1H), 2.12-1.92 (m, 3H), 1.85-1.54 (m, 4H), 1.52-1.36 (m, 6H), 1.32-1.16 (m, 5H), 1.09 (s, 4H), 1.06 (br s, 4H), 0.95-0.81 (m, 6H), 0.73 (s, 3H).

Synthesis of 34.6

To a mixture of 34.5 (4.7 g, 14.6 mmol) in DCM (50 mL) was added DMP (12.3 g, 29.2 mmol) at 25° C. After stirring at 25° C. for 1 h, the mixture was quenched with saturated $NaHCO_3$ and $Na_2S_2O_3$ (20 mL, v/v=1/1) and extracted with DCM (2×10 mL). The combined organic phase was washed with saturated NaHCO$_3$ and Na$_2$S$_2$O$_3$ (20 mL, v/v=1/1), dried over anhydrous Na$_2$SO$_4$, filtered and concentrated to give 34.6 (3 g). $^1$H NMR (400 MHz, CDCl$_3$) $\delta_H$ 2.43 (dd, J=8.3, 19.3 Hz, 1H), 2.14-1.59 (m, 9H), 1.57-1.40 (m, 5H), 1.38-1.12 (m, 8H), 1.10 (s, 3H), 1.08-1.02 (m, 1H), 0.95-0.88 (m, 1H), 0.90 (d, J=4.8 Hz, 3H), 0.86 (s, 3H).

Synthesis of 34.7

To a suspension of PPh$_3$EtBr (10.4 g, 28.2 mmol) in THF (90 mL) was added t-BuOK (3.16 g, 28.2 mmol). After stirring at 40° C. for 30 min, a solution of 34.6 (3 g, 9.41 mmol) in THF (10 mL) was added into the reaction at 40° C. After stirring at 40° C. for 12 h, the mixture was poured into NH$_4$Cl (100 mL, sat.) and extracted with EtOAc (2×100 mL). The combined organic phase was washed with brine (2×100 mL), dried over anhydrous Na$_2$SO$_4$, filtered and concentrated in vacuum. The residue was purified by flash column (0-5% of EtOAc in PE) to give 34.7 (5 g). $^1$H NMR (400 MHz, CDCl$_3$) $\delta_H$ 5.10 (tq, J=1.9, 7.2 Hz, 1H), 2.40-2.10 (m, 3H), 2.01-1.93 (m, 1H), 1.82 (br d, J=6.5 Hz, 2H), 1.65 (td, J=2.0, 7.1 Hz, 9H), 1.55-1.37 (m, 5H), 1.22-1.12 (m, 4H), 1.09 (s, 5H), 0.90 (d, J=5.5 Hz, 4H), 0.87 (s, 4H).

Synthesis of 34.8

To a solution of 34.7 (5 g, 15.1 mmol) in THF (100 mL) was added 9-BBN dimer (7.30 g, 30.2 mmol) under N$_2$. After stirring at 50° C. under N$_2$ for 2 h, the mixture was cooled to 0° C. and sequentially treated with EtOH (12.8 mL, 226 mmol), NaOH (45.2 mL, 5M, 226 mmol) and H$_2$O$_2$ (22.6 mL, 10 M, 226 mmol) dropwise at 15° C. After stirring at 50° C. for 2 h, the mixture was cooled, poured into H$_2$O (500 mL) and extracted with EtOAc (2×500 mL). The organic layer was checked by potassium iodide-starch test paper to confirm excess H$_2$O$_2$ was destroyed (did not changed to blue). The combined organic phase was washed with aqueous Na$_2$S$_2$O$_3$ (2×800 mL, sat.) and brine (800 mL), dried over anhydrous Na$_2$SO$_4$, filtered and concentrated. The residue was purified by flash column (0-15% of EtOAc in PE) to give 34.8 (1.8 g). $^1$H NMR (400 MHz, CDCl$_3$) $\delta_H$ 3.75-3.65 (m, 1H), 2.00-1.78 (m, 6H), 1.77-1.68 (m, 2H), 1.60-1.25 (m, 13H), 1.22 (d, J=6.3 Hz, 4H), 1.09 (s, 5H), 0.94-0.80 (m, 6H), 0.66 (s, 3H).

Synthesis of 34.9

To a mixture of 34.8 (1.7 g, 4.87 mmol) in DCM (50 mL) was added DMP (4.13 g, 9.74 mmol) at 25° C. After stirred at 25° C. for 1 h, the mixture was quenched with saturated NaHCO$_3$ and Na$_2$S$_2$O$_3$ (80 mL, v/v=1/1) and extracted with DCM (2×10 mL). The combined organic phase was washed with saturated NaHCO$_3$ and Na$_2$S$_2$O$_3$ (20 mL, v/v=1/1), dried over anhydrous Na$_2$SO$_4$, filtered and concentrated to give 34.9 (1.8 g). $^1$H NMR (400 MHz, CDCl$_3$) $\delta_H$ 2.59-2.47 (m, 2H), 2.28-2.15 (m, 1H), 2.11 (s, 3H), 2.05-1.92 (m, 3H), 1.85-1.80 (m, 2H), 1.76-1.66 (m, 1H), 1.50.1.38 (m, 5H), 1.35-1.16 (m, 6H), 1.10 (s, 3H), 1.08-1.01 (m, 2H), 1.08-1.01 (m, 2H), 0.90 (br d, J=4.8 Hz, 5H), 0.60 (s, 3H).

Synthesis of 34.10

To a mixture of MePPh$_3$Br (5.10 g, 14.3 mmol) in THF (45 mL) was added t-BuOK (1.60 g, 14.3 mmol) at 25° C. under N$_2$. After stirring at 25° C. for 30 mins, 34.9 (500 mg, 1.44 mmol) in THF (5 mL) was added at 25° C. After stirring at 60° C. for 3 h, the reaction mixture was cooled, poured into NH$_4$Cl (50 ml) and extracted with EtOAc (2×50 mL). The combined organic layer was dried over anhydrous Na$_2$SO$_4$, filtered and concentrated. The residue was purified by flash column (0~10% of EtOAc in PE) to give 34.10 (450 mg). $^1$H NMR (400 MHz, CDCl$_3$) $\delta_H$ 4.85 (s, 1H), 4.70 (s, 1H), 2.08-1.93 (m, 2H), 1.89-1.80 (m, 3H), 1.76 (s, 4H), 1.73-1.60 (m, 2H), 1.55 (s, 2H), 1.52-1.36 (m, 4H), 1.29 (br s, 3H), 1.10 (s, 4H), 1.08-0.98 (m, 3H), 0.90 (br d, J=5.0 Hz, 6H), 0.57 (s, 3H).

Synthesis of 34.11

To a solution of 34.10 (350 mg, 1.01 mmol) in DCM (20 mL) was added m-CPBA (409 mg, 85%, 2.02 mmol) at 15° C. After stirring at 15° C. for 1 h, the mixture was quenched by NaHCO$_3$ aqueous (50 mL, sat.). The DCM phase was separated and washed with NaHCO$_3$/Na$_2$S$_2$O$_3$ aqueous (1:1, 3×50 mL), brine (50 mL), dried over anhydrous Na$_2$SO$_4$, filtered and concentrated under vacuum to give 34.11 (400 mg). $^1$H NMR (400 MHz, CDCl$_3$) $\delta_H$ 2.92-2.53 (m, 2H), 2.50.2.27 (m, 1H), 2.08-1.69 (m, 2H), 1.35 (s, 11H), 1.25 (br s, 7H), 1.10 (s, 5H), 0.89 (br d, J=4.8 Hz, 7H), 0.82-0.77 (m, 1H), 0.80 (s, 1H), 0.73-0.65 (m, 3H).

Synthesis of 34 & 35

To a solution of 34.11 (400 mg, 1.10 mmol) in DMF (15 mL) were added Cs$_2$CO$_3$ (1.07 mg, 3.30 mmol) and 1H-pyrazole-4-carbonitrile (204 mg, 2.20 mmol). After stirring at 130° C. for 12 h, the mixture was added into NH$_4$Cl (50 Ml, sat.) and extracted with EtOAc (3×50 mL). The combined organic layer was washed with LiCl (100 mL, 5% in water), brine (2×100 mL), dried over anhydrous Na$_2$SO$_4$, filtered and concentrated. The residue was purified by flash column (0~50% of EtOAc in PE) to give product (450 mg), which was purified by SFC (Column: DAICEL CHIRALCEL OD-H (250 mm×30 mm, 5 um); Condition: 0.1% NH$_3$H$_2$O ETOH; Begin B: 30%; End B: 30%) to afford 34 (135.6 mg, 19.5%, Rt=3.132 min) and 35 (23.8 mg, 47.6%, Rt=3.383 min).

34: $^1$H NMR (400 MHz, CDCl$_3$) $\delta_H$ 7.92 (s, 1H), 7.82 (s, 1H), 4.35 (d, J=13.8 Hz, 1H), 4.08 (d, J=13.8 Hz, 1H), 2.54 (s, 1H), 2.07-1.89 (m, 2H), 1.84-1.79 (m, 2H), 1.78-1.71 (m, 3H), 1.68-1.60 (m, 2H), 1.51-1.38 (m, 4H), 1.34-1.15 (m, 7H), 1.09 (s, 4H), 1.08-1.03 (m, 3H), 0.97 (s, 3H), 0.92 (s, 3H), 0.89 (br d, J=4.0 Hz, 5H). LC-ELSD/MS purity 99%, MS ESI calcd. for C$_{28}$H$_{40}$N$_3$ [M−2H$_2$O+H]$^+$ 418.3 found 418.3. SFC 99% de.

35: $^1$H NMR (400 MHz, CDCl$_3$) $\delta_H$ 7.89 (s, 1H), 7.80 (s, 1H), 4.19-4.12 (m, 1H), 4.04-3.97 (m, 1H), 2.29 (s, 1H), 2.08 (br d, J=12.3 Hz, 1H), 1.99-1.89 (m, 2H), 1.82 (br d, J=6.8 Hz, 2H), 1.76-1.60 (m, 5H), 1.52-1.38 (m, 4H), 1.32-1.18 (m, 6H), 1.10 (d, J=3.3 Hz, 10H), 0.93-0.84 (m, 8H). LC-ELSD/MS purity 99%, MS ESI calcd. for C$_{28}$H$_{40}$N$_3$ [M−2H$_2$O+H]$^+$ 418.3 found 418.3. SFC 97% de.

Examples 36 & 37: Synthesis of 1-((S)-2-((3R,5R,8R,9R,10S,13S,14S,17S)-3-hydroxy-13-methyl-3-propylhexadecahydro-1H-cyclopenta[a]phenanthren-17-yl)-2-methoxypropyl)-1H-pyrazole-4-carbonitrile (36) & 1-((R)-2-((3R,5R,8R,9R,10S,13S,14S,17S)-3-hydroxy-13-methyl-3-propylhexadecahydro-1H-cyclopenta[a]phenanthren-17-yl)-2-methoxypropyl)-1H-pyrazole-4-carbonitrile (37)
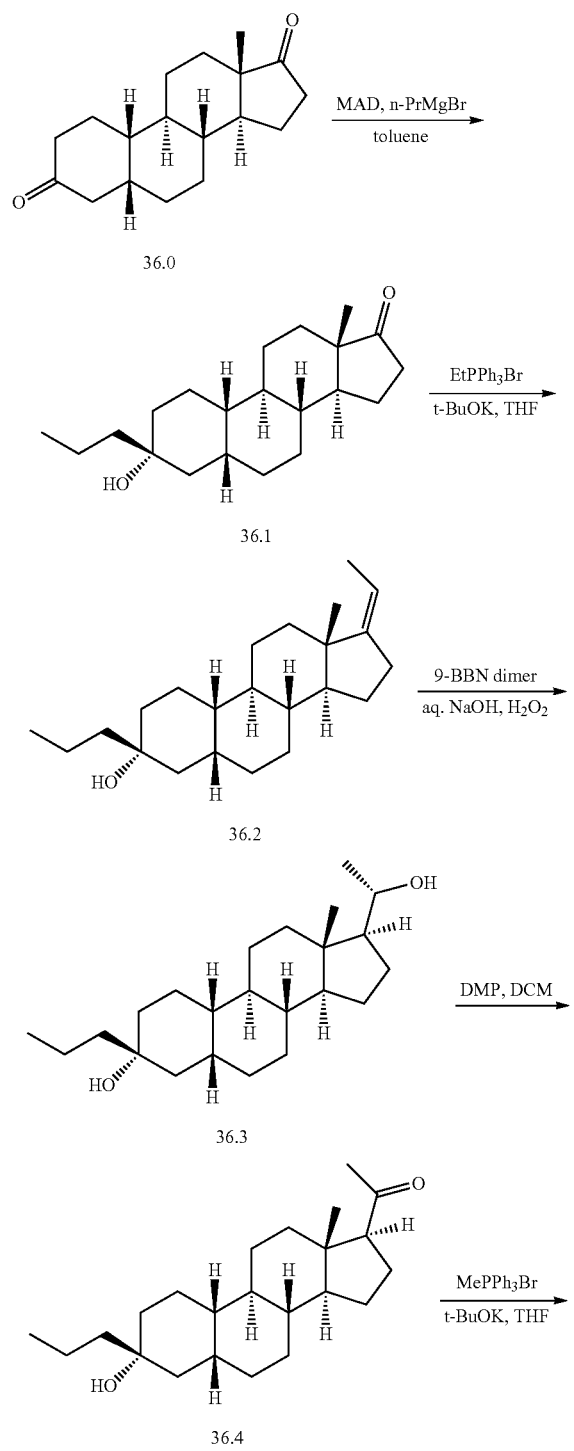
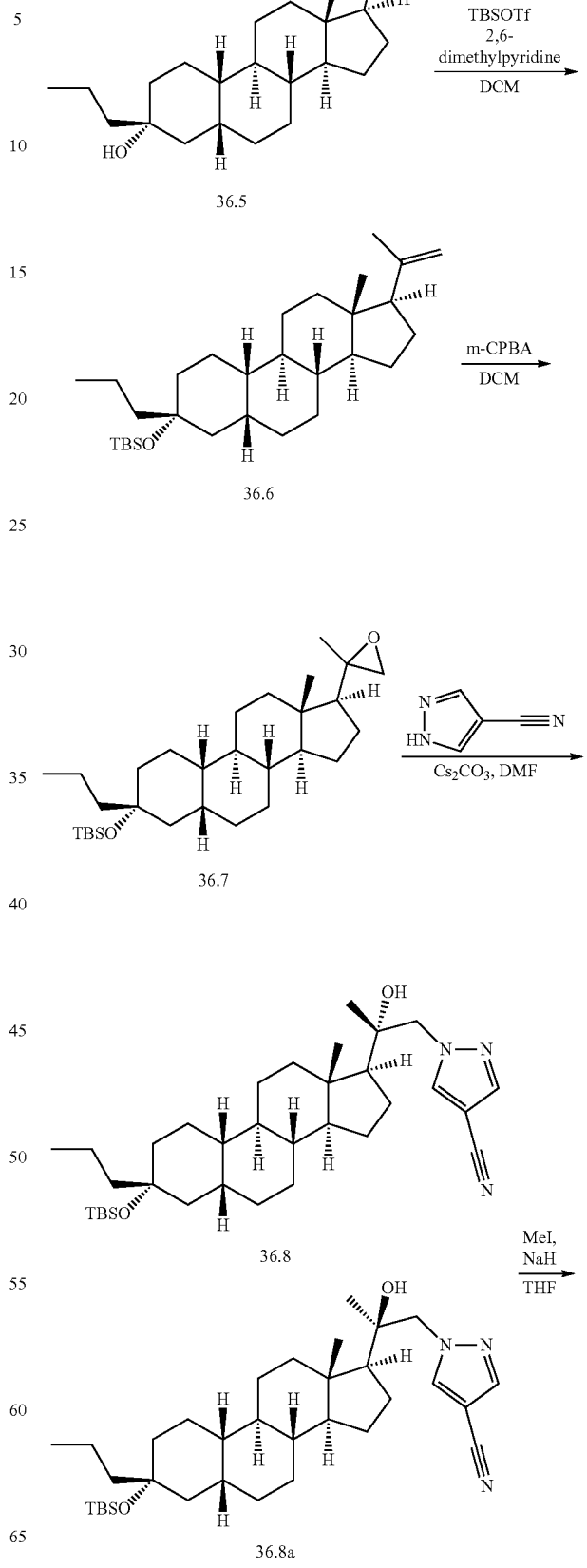

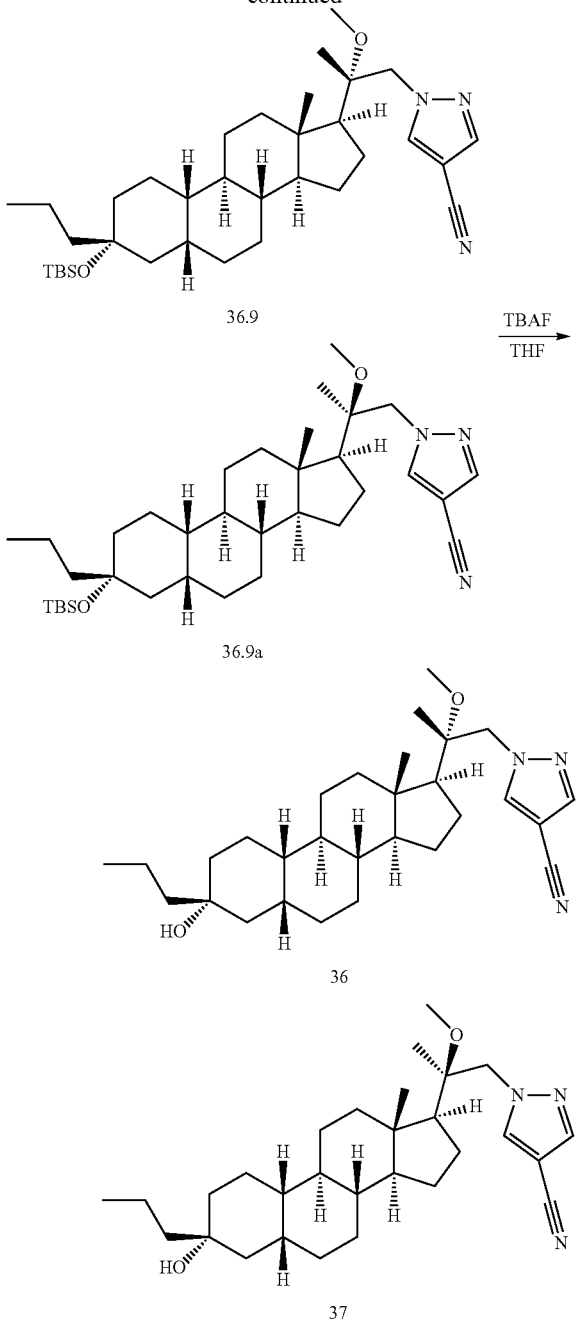

Synthesis of 36.1

To a solution of 2,6-di-tert-butyl-4-methylphenol (24 g, 108 mmol) in toluene (30 mL) under $N_2$ at 0° C. was added $AlMe_3$ (2 M in toluene, 27 mL, 54 mmol) dropwise. After stirring at 25° C. for 1 h, to the MAD (54 mmol in 30 mL toluene) solution was added a solution of 36.0 (5 g, 18.2 mmol) in toluene (20 mL) dropwise at −60° C. After stirring at −60° C. for 1 h under $N_2$, n-prMgBr (27.3 mL, 54.6 mmol, 2M in THF) was added dropwise at −60° C. After stirring at −60° C. for another 4 h, the reaction mixture was poured into aqueous citric acid (100 mL, sat.) at 10° C. and extracted with EtOAc (2×100 mL). The combined organic layer was dried over anhydrous $Na_2SO_4$, filtered and concentrated in vacuum. The residue was purified by silica gel chromatography (PE/EtOAc=0-20% to give 36.1 (3.83 g, 66.1%). H NMR (400 MHz, $CDCl_3$) $\delta_H$ 2.49-2.37 (m, 1H), 2.31-1.98 (m, 2H), 1.97-1.87 (m, 1H), 1.86-1.73 (m, 4H), 1.72-1.60 (m, 2H), 1.55-1.45 (m, 5H), 1.45-1.27 (m, 10H), 1.27-1.00 (m, 4H), 0.93 (t, J=7.2 Hz, 3H), 0.87 (s, 3H).

Synthesis of 36.2

To a mixture of $EtPPh_3Br$ (26.5 g, 71.4 mmol) in THF (50 mL) was added t-BuOK (8.01 g, 71.4 mmol) at 15° C. under $N_2$. After stirring at 50° C. for 30 min, 36.1 (3.8 g, 11.9 mmol) was added in portions below 40° C. After stirring at 40° C. for 1 h, the reaction mixture was quenched with 10% $NH_4Cl$ aqueous (100 mL) at 15° C. and extracted with EtOAc (500 mL). The combined organic layer was dried over anhydrous $Na_2SO_4$, filtered and concentrated under vacuum. The residue was purified by trituration with MeOH/$H_2O$ (1:1, 300 mL) at reflux to give 36.2 (4.5 g). $^1$H NMR (400 MHz, $CDCl_3$) $\delta_H$ 5.10 (d, J=7.2 Hz, 1H), 2.41-2.09 (m, 4H), 1.78-1.71 (m, 3H), 1.66-1.63 (m, 3H), 1.56-1.51 (m, 3H), 1.50-1.42 (m, 3H), 1.37-1.29 (m, 6H), 1.21-1.00 (m, 6H), 0.93 (t, J=7.28 Hz, 3H), 0.87 (s, 3H).

Synthesis of 36.3

To a solution of 36.2 (4.5 g, 13.6 mmol) in THF (50 mL) was added 9-BBN dimer (9.95 g, 40.8 mmol) at 15° C. After stirring at 40° C. for 1 h, the mixture was sequentially treated with EtOH (7.9 mL, 135 mmol) at 15° C., NaOH (27 mL, 5M, 135 mmol) at −10° C., and $H_2O_2$ (13.5 mL, 10 M, 135 mmol) dropwise. After stirring at 80° C. for 1 h, the reaction was quenched with sat. $Na_2S_2O_3$ (50 mL), stirred for 30 mins and extracted with EtOAc (100 mL). The combined organic phase was washed with saturated brine (2×100 mL), dried over anhydrous $Na_2SO_4$, filtered and concentrated under vacuum. The residue was purified by silica gel chromatography (PE/EtOAc=10 to 20%) to give 36.3 (3.2 g, 67.5%). $^1$H NMR (400 MHz, $CDCl_3$) $\delta_H$ 3.74-3.66 (m, 1H), 1.85-1.60 (m, 10H), 1.49-1.29 (m, 13H), 1.22 (d, J=6 Hz, 3H), 1.16-1.00 (m, 7H), 0.93 (t, J=7.2 Hz, 3H), 0.66 (s, 3H). LC-ELSD/MS purity 99%, MS ESI calcd. for $C_{23}H_{40}O_2$ $[M+H-2H_2O]^+$ 313.3, found 313.3.

Synthesis of 36.4

To a solution of 36.3 (3.1 g, 8.89 mmol) in DCM (30 mL) was added Dess-martin (7.5 g, 17.7 mmol) at 25° C. After stirring at 25° C. for 10 mins, the mixture was quenched by $NaHCO_3$/$Na_2S_2O_3$ aqueous (1:1, 375 mL) at 25° C. The organic phase was separated and washed with $NaHCO_3$/$Na_2S_2O_3$ aqueous (1:1, 375 mL), brine (200 mL), dried over anhydrous $Na_2SO_4$, filtered and concentrated under vacuum to give 36.4 (4 g). $^1$H NMR (400 MHz, $CDCl_3$) $\delta_H$ 2.40 (d, J=12.80 Hz, 1H), 2.11 (s, 3H), 1.93-1.81 (m, 4H), 1.72-1.63 (m, 8H), 1.50-1.41 (m, 8H), 1.13-1.02 (m, 6H), 0.94-0.91 (m, 3H), 0.62 (s, 3H).

Synthesis of 36.5

To a mixture of $MePPh_3Br$ (12.3 g, 34.5 mmol) in THF (50 mL) was added t-BuOK (3.87 g, 34.5 mmol) at 15° C. under $N_2$. After stirring at 50° C. for 30 min, 36.4 (4 g, 11.5 mmol) was added in portions below 50° C. After stirring at 50° C. for 1 h, the reaction mixture was quenched with 10% $NH_4Cl$ aqueous (100 mL) at 15° C. and extracted with EtOAc (200 mL). The combined organic phase was dried over anhydrous Na$_2$SO$_4$, filtered and concentrated under vacuum. The residue was purified by silica gel chromatography (PE/EtOAc=0 to 5%) to give 36.5 (600 mg, 15.1%). $^1$H NMR (400 MHz, CDCl$_3$) δ$_H$ 4.84 (s, 1H), 4.69 (s, 1H) 2.04-1.99 (m, 2H), 1.86-1.76 (m, 3H), 1.75 (s, 3H), 1.74-1.57 (m, 6H), 1.56-1.50 (m, 2H), 1.49-1.28 (m, 10H), 1.23-0.97 (m, 6H), 0.93 (t, J=7.2 Hz, 3H), 0.56 (s, 3H).

Synthesis of 36.6

To a solution of 36.5 (1.7 g, 4.93 mmol) and 2, 6-dimethylpyridine (1.57 g, 14.7 mmol) in DCM (10 mL) was added TBSOTf (1.56 g, 5.91 mmol) at 0° C. After stirring at 25° C. for 16 h, the mixture was poured into water (20 mL) and extracted with EtOAc (2×50 mL). The combined organic phase was washed with brine (20 mL), dried over anhydrous Na$_2$SO$_4$, filtered and concentrated. The residue was purified by flash column (100% of PE) to give 36.6 (2 g, 88.4%).

Synthesis of 36.7

To a solution of 36.6 (2 g, 4.35 mmol) in DCM (50 mL) was added m-CPBA (1.31 g, 6.52 mmol, 85%) at 25° C. After stirring at 25° C. for 2 h, the mixture was poured into NaHCO$_3$ aqueous (100 mL, sat.) and extracted with EtOAc (2×100 mL). The combined organic phase was washed with brine (2×100 mL), dried over Na$_2$SO$_4$, filtered and concentrated to give 36.7 (1.8 g). $^1$H NMR (400 MHz, CDCl$_3$) δ$_H$ 2.96-2.86 (m, 0.7H), 2.62-2.54 (m, 0.7H), 2.52-2.48 (m, 0.3H), 2.52-2.47 (m, 0.3H), 2.34-2.29 (m, 1H), 2.10-1.91 (m, 2H), 1.81-1.58 (m, 7H), 1.52-1.34 (m, 11H), 1.32-0.96 (m, 13H), 0.86 (d, J=1.2 Hz, 9H), 0.83-0.75 (m, 1H), 0.68 (s, 2H), 0.07 (s, 6H).

Synthesis of 36.8 & 36.8a

To a solution of 36.7 (900 mg, 1.89 mmol) in DMF (10 mL) were added Cs$_2$CO$_3$ (1.48 g, 5.67 mmol) and 1H-pyrazole-4-carbontrile (527 mg, 5.67 mmol). After stirring at 130° C. for 16 h, the mixture was added into NH$_4$Cl (100 mL, sat.) and extracted with EtOAc (3×100 mL). The combined organic layer was washed with water (100 mL), brine (100 mL), dried over anhydrous Na$_2$SO$_4$, filtered and concentrated. The residue was purified by flash column (0-15% of EtOAc in PE) to give product (780 mg). The residue was purified by flash column (0-10% of EtOAc in PE) to give 36.8 (350 mg) and 36.8a (230 mg).

36.8: $^1$H NMR (400 MHz, CDCl$_3$) δ$_H$ 7.92 (s, 1H), 7.84-7.80 (m, 1H), 4.37 (d, J=13.6 Hz, 1H), 4.09 (d, J=13.6 Hz, 1H), 2.48 (s, 1H), 2.08-1.96 (m, 1H), 1.83-1.58 (m, 8H), 1.49-1.21 (m, 16H), 1.20-1.01 (m, 6H), 0.96 (s, 3H), 0.92 (s, 3H), 0.86 (s, 14H), 0.07 (s, 6H).

36.8a: $^1$H NMR (400 MHz, CDCl$_3$) δ$_H$ 7.92 (s, 1H), 7.89 (s, 1H), 4.22-4.11 (m, 1H), 4.06-3.95 (m, 1H), 2.26 (s, 1H), 2.14-2.02 (m, 1H), 1.95-1.87 (m, 1H), 1.81-1.61 (m, 7H), 1.50-1.24 (m, 18H), 1.20-0.99 (m, 10H), 0.91-0.87 (m, 9H), 0.07 (d, J=1.2 Hz, 6H).

Synthesis of 36.9

To a solution of 36.8 (350 mg, 0.6162 mmol) in THF (10 mL) was added NaH (123 mg, 3.08 mmol, 60%) at 0° C. under N$_2$. After stirring for 0.5 h, MeI (874 mg, 6.16 mmol) was added into the reaction mixture at 25° C. After stirring at 25° C. for another 16 h, the reaction mixture was quenched by ammonia (1 mL), poured into water (50 mL) and extracted with EtOAc (2×50 mL). The combined organic phase was washed with brine (2×50 mL), dried over anhydrous Na$_2$SO$_4$, filtered and concentrated. The residue was purified by flash column (0-20% of EtOAc in PE) to give 36.9 (350 mg). $^1$H NMR (400 MHz, CDCl$_3$) δ$_H$ 7.91 (s, 1H), 7.75 (s, 1H), 4.34-4.18 (m, 2H), 3.18 (s, 3H), 2.00-1.93 (m, 1H), 1.83-1.58 (m, 11H), 1.48-1.25 (m, 19H), 1.22-0.97 (m, 15H), 0.86 (s, 22H), 0.07 (s, 6H).

Synthesis of 36.9a

To a solution of 36.8a (230 mg, 0.4049 mmol) in THF (5 mL) was added NaH (80.6 mg, 2.02 mmol, 60%) at 0° C. under N$_2$. After stirring for 0.5 h, MeI (573 mg, 4.04 mmol) was added into the reaction mixture at 25° C. After stirring at 25° C. for another 16 h, the reaction mixture was quenched by ammonia (1 mL), poured into water (50 mL) and extracted with EtOAc (2×50 mL). The combined organic phase was washed with brine (2×50 mL), dried over anhydrous Na$_2$SO$_4$, filtered and concentrated. The residue was purified by flash column (0-20% of EtOAc in PE) to give 36.9a (230 mg). $^1$H NMR (400 MHz, CDCl$_3$) δ$_H$ 7.90 (s, 1H), 4.35-4.03 (m, 3H), 3.21-3.05 (m, 3H), 2.11-1.94 (m, 3H), 1.80-1.61 (m, 11H), 1.47-1.27 (m, 18H), 1.21-0.98 (m, 18H), 0.86-0.73 (m, 16H), 0.07 (br s, 6H)

Synthesis of 36

To a solution of 36.9 (350 mg, 0.5993 mmol) in THF (3.5 mL) was added TBAF (5.99 mL, 5.99 mmol, 1M in THF). After stirring at 80° C. for 16 h, the reaction mixture was quenched with NH$_4$Cl solution (30 mL, sat.) and extracted with EtOAc (2×20 mL). The combined organic phase was washed with brine (50 mL), dried over anhydrous Na$_2$SO$_4$, filtered and concentrated to the product (120 mg). The product (130 mg, 0.2779 mmol) was purified by SFC (Column: DAICEL CHIRALPAK AD-H (250 mm*30 mm, 5 um); Condition: 0.1% NH$_3$H$_2$O IPA; Begin B 35 End B 35; Flow Rate (ml/min) 60) to give 36 (95.4 mg, 73.9%, Rt=1.459 min). $^1$H NMR (400 MHz, CDCl$_3$) δ$_H$ 7.99-7.86 (m, 1H), 7.80-7.67 (m, 1H), 4.35-4.13 (m, 2H), 3.25-3.12 (m, 3H), 1.95 (br d, J=12.8 Hz, 1H), 1.83-1.57 (m, 9H), 1.49-1.23 (m, 12H), 1.07 (s, 10H), 0.93 (t, J=7.2 Hz, 3H), 0.85 (s, 3H). LC-ELSD/MS purity 99%, MS ESI calcd for C$_{28}$H$_{41}$N$_3$ [M−CH$_3$OH-H$_2$O+H]$^+$ 418.3, found 418.3. SFC 99% de.

Synthesis of 37

To a solution of 36.9a (230 mg, 0.3938 mmol) in THF (2.3 mL) was added TBAF (1.96 mL, 1.96 mmol, 1M in THF). After stirring at 80° C. for 16 h, the reaction mixture was quenched with NH$_4$Cl solution (30 mL, sat.) and extracted with EtOAc (2×20 mL). The combined organic phase was washed with brine (50 mL), dried over anhydrous Na$_2$SO$_4$, filtered and concentrated to give the product (50 mg). The product was purified by SFC (Column: DAICEL CHIRALPAK AD-H (250 mm*30 mm, 5 um); Condition: 0.1% NH$_3$H$_2$O IPA; Begin B 35 End B 35; Flow Rate (ml/min) 60) to afford 37 (39.2 mg, 78.5%, Rt=1.703 min). $^1$H NMR (400 MHz, CDCl$_3$) δ$_H$ 7.90 (s, 1H), 7.75 (s, 1H), 4.24 (s, 2H), 3.14 (s, 3H), 2.04 (br d, J=12.4 Hz, 1H), 1.84-1.59 (m, 9H), 1.49-1.05 (m, 18H), 1.02 (s, 4H), 0.93 (t, J=7.2 Hz, 3H), 0.82 (s, 3H). LC-ELSD/MS purity 99%, MS ESI calcd for C$_{28}$H$_{41}$N$_3$ [M−CH$_3$OH-H$_2$O+H]$^+$ 418.3, found 418.3. SFC 99% de.

Example 38: Synthesis of 1-(2,2-difluoro-2-((3R, 5R,8R,9R,10S,13S,14S,17S)-3-hydroxy-3-(methoxymethyl)-13-methylhexadecahydro-1H-cyclopenta[a]phenanthren-17-yl)ethyl)-1H-pyrazole-4-carbonitrile (38)

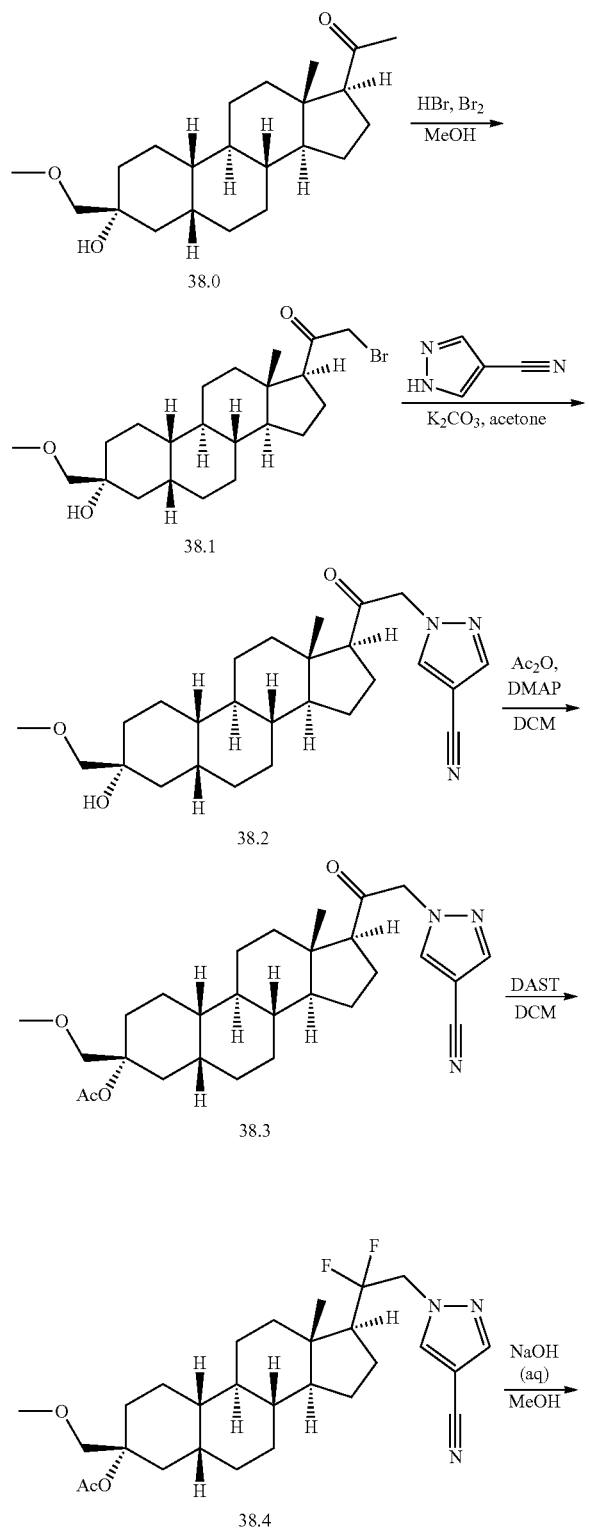

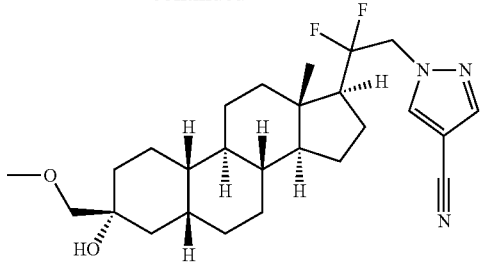

Synthesis of 38.1

To a solution of 38.0 (1.70 g, 4.87 mmol) in MeOH (20 ml) were added HBr (196 mg, 974 μmol, 40% in water) and Br$_2$ (934 mg, 5.84 mmol) at 25° C. After stirring at 25° C. for 2 h, the mixture was quenched by NaHCO$_3$(10 mL, sat.aq.), treated with water (20 mL), and extracted with EtOAc (2×30 mL). The combined organic phase was washed with brine (30 mL), dried over anhydrous Na$_2$SO$_4$, filtered and concentrated in vacuum to afford 38.1 (2.1 g), which was used directly for the next step. $^1$H NMR (400 MHz, CDCl$_3$) $\delta_H$ 3.96-3.86 (m, 2H), 3.43-3.34 (m, 6H), 2.85-2.76 (m, 1H), 2.62 (s, 1H), 2.22-2.11 (m, 1H), 1.95-1.87 (m, 1H), 1.86-1.67 (m, 7H), 1.58-1.33 (m, 9H), 1.21-0.97 (m, 4H), 0.63 (s, 3H).

Synthesis of 38.2

To a solution of 38.1 (2.1 g, 4.91 mmol) in acetone (30 mL) were added 1H-pyrazole-4-carbonitrile (685 mg, 7.36 mmol) and K$_2$CO$_3$ (2.02 g, 14.7 mmol). After stirring at 15° C. for 12 h, the mixture was treated with water (30 mL) and extracted with EtOAc (2×30 mL). The combined organic phase was washed with brine (30 mL), dried over anhydrous Na$_2$SO$_4$, filtered and concentrated. The residue was purified by flash column (0-50% of EtOAc in PE) to give 38.2 (1.6 g, 74.4%). $^1$H NMR (400 MHz, CDCl$_3$) $\delta_H$ 7.85 (s, 1H), 7.81 (s, 1H), 5.05-4.86 (m, 2H), 3.44-3.38 (m, 5H), 2.67-2.56 (m, 2H), 2.25-2.14 (m, 1H), 2.07-2.02 (m, 1H), 1.87-1.72 (m, 6H), 1.67-1.59 (m, 2H), 1.53-1.34 (m, 8H), 1.31-1.26 (m, 2H), 1.18-1.05 (m, 3H), 0.67 (s, 3H).

Synthesis of 38.3

To a solution of 38.2 (1.6 g, 3.63 mmol) in DCM (30 mL) were added DMAP (442 mg, 3.63 mmol) and acetyl acetate (1.47 g, 14.5 mmol). After stirring at 25° C. for 16 h, the mixture was poured into ice-water (100 mL), stirred for 10 mins. and extracted with DCM (2×50 mL). The combined organic phase was washed with brine (2×100 mL), dried over anhydrous Na$_2$SO$_4$, filtered and concentrated. The residue was purified by flash column (0-20% of EtOAc in PE) to give 38.3 (590 mg, 33.9%). $^1$H NMR (400 MHz, CDCl$_3$) $\delta_H$ 7.85 (s, 1H), 7.81 (s, 1H), 5.04-4.86 (m, 2H), 3.86-3.74 (m, 2H), 3.40-3.34 (m, 4H), 2.55-2.66 (m, 1H), 2.25-2.15 (m, 2H), 2.03-1.98 (m, 4H), 1.90-1.68 (m, 10H), 1.56-1.49 (m, 2H), 1.44-1.31 (m, 6H), 1.15-0.98 (m, 4H), 0.67 (s, 3H).

Synthesis of 38.4

To a solution of 38.3 (290 mg, 600 μmol) in chloroform (4 mL) was added dropwise DAST (1.58 ml, 12 mmol, 1.22 g/ml) at 0° C. under N₂. After stirring at 60° C. for 12 h, the mixture was quenched with NaHCO₃(30 mL) carefully and extracted with EtOAc (2×30 mL). The combined organic phase was washed with brine (20 mL), dried over Na₂SO₄, filtered and concentrated. The residue was purified by flash column (0-30% of EtOAc in PE) to give 38.4 (34 mg, 11.2%). $^1$H NMR (400 MHz, CDCl₃) $\delta_H$ 7.92 (s, 1H), 7.82 (s, 1H), 4.50-4.37 (m, 1H), 3.84-3.75 (m, 2H), 3.36 (s, 3H), 2.02-1.93 (m, 5H), 1.86-1.63 (m, 8H), 1.53-1.26 (m, 7H), 1.24-1.00 (m, 7H), 0.86 (m, 4H).

Synthesis of 38

To a solution of 38.4 (24 mg, 47.6 μmol) in MeOH (1 ml) was added LiOH(1.99 ml, 9.99 mmol, 5M) at 15° C. After stirring at 15° C. for 20 h, the mixture was poured into water (20 mL), stirred for 10 min, and extracted with EtOAc (3×5 mL). The combined organic phase was washed with brine (2×5 mL), dried over anhydrous Na₂SO₄, filtered and concentrated. The residue was purified by flash column (0~30% of EtOAc in PE) to give 38 (10 mg). $^1$H NMR (400 MHz, CDCl₃) $\delta_H$ 7.92 (s, 1H), 7.83 (s, 1H), 4.52-4.37 (m, 2H), 3.42-3.36 (m, 5H), 2.58 (s, 1H), 2.02-1.96 (m, 1H), 1.83-1.67 (m, 8H), 1.50-1.34 (m, 7H), 1.25 (s, 3H), 1.15-1.06 (m, 5H), 0.86 (d, J=3.0 Hz, 3H). LC-ELSD/MS 30-90AB_2min_E, purity>99%, MS ESI calcd. for C₂₆H₃₇F₂N₃O₂ [M−H₂O+H]⁺ 444.2, found 444.2.

Example 39: Synthesis of 1-((1-((3R,5R,8R,9R,10S,13S,14S,17S)-3-hydroxy-3,13-dimethylhexadecahydro-1H-cyclopenta[a]phenanthren-17-yl)cyclopropyl)methyl)-1H-pyrazole-4-carbonitrile (39)

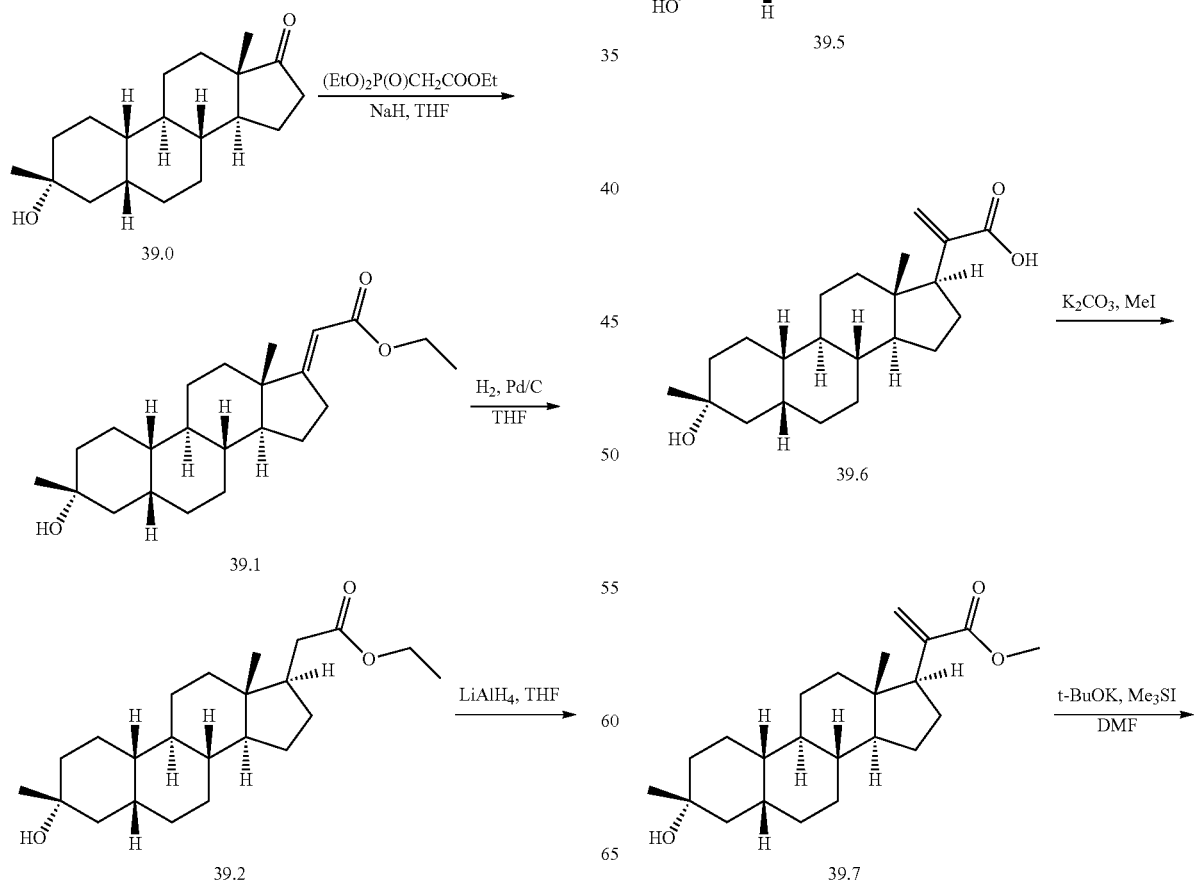

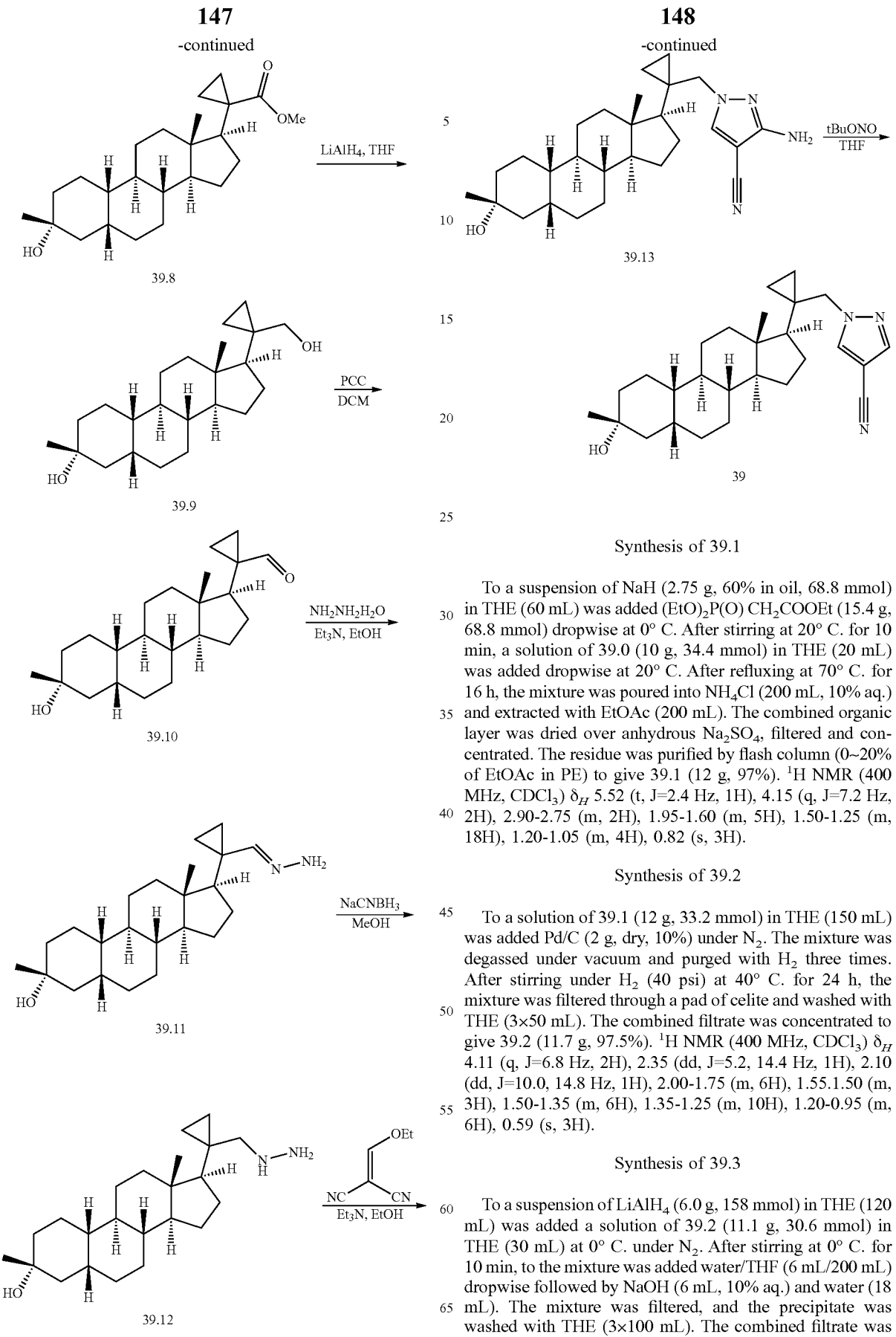

Synthesis of 39.1

To a suspension of NaH (2.75 g, 60% in oil, 68.8 mmol) in THF (60 mL) was added (EtO)$_2$P(O) CH$_2$COOEt (15.4 g, 68.8 mmol) dropwise at 0° C. After stirring at 20° C. for 10 min, a solution of 39.0 (10 g, 34.4 mmol) in THF (20 mL) was added dropwise at 20° C. After refluxing at 70° C. for 16 h, the mixture was poured into NH$_4$Cl (200 mL, 10% aq.) and extracted with EtOAc (200 mL). The combined organic layer was dried over anhydrous Na$_2$SO$_4$, filtered and concentrated. The residue was purified by flash column (0~20% of EtOAc in PE) to give 39.1 (12 g, 97%). $^1$H NMR (400 MHz, CDCl$_3$) $\delta_H$ 5.52 (t, J=2.4 Hz, 1H), 4.15 (q, J=7.2 Hz, 2H), 2.90-2.75 (m, 2H), 1.95-1.60 (m, 5H), 1.50-1.25 (m, 18H), 1.20-1.05 (m, 4H), 0.82 (s, 3H).

Synthesis of 39.2

To a solution of 39.1 (12 g, 33.2 mmol) in THF (150 mL) was added Pd/C (2 g, dry, 10%) under N$_2$. The mixture was degassed under vacuum and purged with H$_2$ three times. After stirring under H$_2$ (40 psi) at 40° C. for 24 h, the mixture was filtered through a pad of celite and washed with THF (3×50 mL). The combined filtrate was concentrated to give 39.2 (11.7 g, 97.5%). $^1$H NMR (400 MHz, CDCl$_3$) $\delta_H$ 4.11 (q, J=6.8 Hz, 2H), 2.35 (dd, J=5.2, 14.4 Hz, 1H), 2.10 (dd, J=10.0, 14.8 Hz, 1H), 2.00-1.75 (m, 6H), 1.55.1.50 (m, 3H), 1.50-1.35 (m, 6H), 1.35-1.25 (m, 10H), 1.20-0.95 (m, 6H), 0.59 (s, 3H).

Synthesis of 39.3

To a suspension of LiAlH$_4$ (6.0 g, 158 mmol) in THF (120 mL) was added a solution of 39.2 (11.1 g, 30.6 mmol) in THF (30 mL) at 0° C. under N$_2$. After stirring at 0° C. for 10 min, to the mixture was added water/THF (6 mL/200 mL) dropwise followed by NaOH (6 mL, 10% aq.) and water (18 mL). The mixture was filtered, and the precipitate was washed with THF (3×100 mL). The combined filtrate was concentrated and triturated from DCM (50 mL) to give 39.3

(9 g, 92%). $^1$H NMR (400 MHz, CDCl$_3$) $\delta_H$ 3.75-3.55 (m, 2H), 1.90-1.60 (m, 9H), 1.50-1.15 (m, 16H) 1.15-0.90 (m, 6H), 0.59 (s, 3H).

Synthesis of 39.4

To a solution of 39.3 (3 g, 9.3 mmol) in DCM (80 mL) was added DMP (7.92 g, 18.7 mmol). After stirring at 30° C. for 1 h, the mixture was washed with a mixed solution of NaHCO$_3$ (160 mL, aq. sat.) and Na$_2$S$_2$O$_3$ (80 mL, aq. sat.) twice, dried over Na$_2$SO$_4$, filtered and concentrated. The residue was purified by flash column (10~30% of EtOAc in PE) to give 39.4 (2.2 g, 74%). $^1$H NMR (400 MHz, CDCl$_3$) $\delta_H$ 9.76 (t, J=2.4 Hz, 1H), 2.55-2.45 (m, 1H), 2.30-2.20 (m, 1H), 2.00-1.80 (m, 5H), 1.55.1.55 (m, 4H), 1.50-1.20 (m, 13H), 1.30-1.00 (m, 6H), 0.60 (s, 3H).

Synthesis of 39.5

A solution of 39.4 (2 g, 6.27 mmol), HCHO (5.05 g, 37%, 62.6 mmol), Et$_3$N (1.90 g, 18.8 mmol) in water (10 mL) and dioxane (20 mL) was stirred at 70° C. for 16 hs. The mixture was added into water (50 mL) and extracted with EtOAc (3×20 mL). The combined organic layer was washed with brine (50 mL), dried over anhydrous Na$_2$SO$_4$, filtered and concentrated to give 39.5 (1.5 g). $^1$H NMR (400 MHz, CDCl$_3$) $\delta_H$ 9.55 (s, 1H), 6.27 (s, 1H), 6.11 (s, 1H), 2.85-2.75 (m, 1H), 1.90-1.59 (m, 9H), 1.52-1.28 (m, 11H), 1.26 (s, 3H), 1.20-0.85 (m, 4H), 0.52 (s, 3H).

Synthesis of 39.6

To a mixture of 39.5 (1.5 g, 4.53 mmol) and 2-methyl-2-butene (10 mL) in acetone (50 mL) were added a solution of NaClO$_2$ (2.04 g, 22.6 mmol) and NaH$_2$PO$_4$ (2.71 g, 22.6 mmol) in H$_2$O (25 mL) at 0° C. After stirring at 20° C. for 16 h, the reaction mixture was diluted with H$_2$O (100 mL) and extracted with EtOAc (3×50 mL). The combined organic phase was washed with brine (20 mL), dried over anhydrous Na$_2$SO$_4$, filtered and concentrated to give 39.6 (1.9 g). $^1$H NMR (400 MHz, CDCl$_3$) $\delta_H$ 6.38 (s, 1H), 5.64 (s, 1H), 2.81 (t, J=9.2 Hz, 1H), 1.90-1.59 (m, 10H), 1.52-1.28 (m, 9H), 1.26 (s, 3H), 1.24-0.90 (m, 6H), 0.55 (s, 3H).

Synthesis of 39.7

To a solution of 39.6 (1.9 g, 5.48 mmol) in DMF (30 mL) was added K$_2$CO$_3$ (1.52 g, 10.9 mmol) at 20° C. After stirring at 20° C. for 1 h, MeI (1.16 g, 8.22 mmol) was added at 20° C. After stirring at 20° C. for another 2 h, the mixture was added into NH$_4$Cl (150 mL, sat.) and extracted with EtOAc (3×50 mL). The combined organic layer was washed with water (2×100 mL), brine (150 mL), dried over anhydrous Na$_2$SO$_4$, filtered and concentrated. The residue was purified by flash column (0-15% of EtOAc in PE) to give 39.7 (1.26 g, 64%). $^1$H NMR (400 MHz, CDCl$_3$) $\delta_H$ 6.19 (s, 1H), 5.50 (s, 1H), 3.73 (s, 3H), 2.80 (t, J=9.2 Hz, 1H), 1.90-1.59 (m, 8H), 1.52-1.28 (m, 11H), 1.26 (s, 3H), 1.24-0.90 (m, 5H), 0.52 (s, 3H).

Synthesis of 39.8

To a solution of 39.7 (1.25 g, 3.46 mmol) in DMF (30 mL) were added Me$_3$SI (2.10 g, 10.3 mmol) and t-BuOK (1.15 g, 10.3 mmol). After stirring at 20° C. for 16 h, the mixture was added into water (200 mL) and extracted with EtOAc (3×50 mL). The combined organic layer was washed with brine (200 mL), dried over anhydrous Na$_2$SO$_4$, filtered and concentrated. The residue was purified by flash column (0-15% of EtOAc in PE) to give 39.8 (350 mg, 27%). $^1$H NMR (400 MHz, CDCl$_3$) $\delta_H$ 3.63 (s, 3H), 2.45-2.35 (m, 1H), 1.92-1.78 (m, 3H), 1.75-1.59 (m, 5H), 1.52-1.28 (m, 9H), 1.26 (s, 3H), 1.25-0.80 (m, 9H), 0.68-0.55 (m, 5H). LC-ELSD/MS 30-90AB_2min_E, purity 99%, MS ESI calcd. for C$_{24}$H$_{37}$O$_2$ [M−H$_2$O+H]$^+$ 357.3, found 357.3.

Synthesis of 39.9

To a solution of 39.8 (350 mg, 0.93 mmol) in THF (10 mL) was added LiAlH$_4$ (70.5 mg, 1.86 mmol) at 20° C. After stirring at 20° C. for 1 h, water (70 mg) was added to the mixture. The mixture was filtered, and the mother liquid was concentrated to give 39.9 (320 mg, 99%). $^1$H NMR (400 MHz, CDCl$_3$) $\delta_H$ 3.96 (d, J=10.8 Hz, 1H), 3.00 (d, J=11.2 Hz, 1H), 2.10-2.00 (m, 2H), 1.92-1.75 (m, 3H), 1.74-1.59 (m, 3H), 1.52-1.28 (m, 11H), 1.26 (s, 3H), 1.25-0.95 (m, 7H), 0.72 (s, 3H), 0.71-0.65 (m, 1H), 0.35-0.25 (m, 2H), 0.24-0.11 (m, 1H). LC-ELSD/MS purity 99%, MS ESI calcd. for C$_{23}$H$_{35}$ [M−2H$_2$O+H]$^+$ 311.3, found 311.3.

Synthesis of 39.10

To a solution of 39.9 (1.7 g, 4.90 mmol) in DCM (50 mL) were added silica gel (2.10 g) and PCC (2.10 g, 9.80 mmol) at 25° C. After stirring at 25° C. for 1 h, the mixture was concentrated. The residue was purified by flash column (0-20% of EtOAc in PE) to give 39.10 (1.28 g, 76.1%). $^1$H NMR (400 MHz, CDCl$_3$) $\delta_H$ 9.48 (s, 1H), 2.01 (t, J=8 Hz, 1H), 1.72-1.87 (m, 5H), 1.62-1.69 (m, 5H), 1.36-1.50 (m, 8H), 1.26 (s, 4H), 0.91-1.17 (m, 8H), 0.79-0.84 (m, 1H), 0.68 (s, 3H).

Synthesis of 39.11

To a solution of 39.10 (1.28 g, 3.71 mmol) in EtOH (30 mL) was added NH$_2$NH$_2$H$_2$O (1.11 g, 22.2 mmol) and Et$_3$N (749 mg, 7.42 mmol) at 25° C. After stirring at 75° C. for 5 h, the mixture was added into water (50 mL) and extracted with EtOAc (3×30 mL). The combined organic layer was washed with brine (50 mL), dried over anhydrous Na$_2$SO$_4$, filtered and concentrated to give 39.11 (1.3 g). $^1$H NMR (400 MHz, CDCl$_3$) $\delta_H$ 7.32 (s, 1H), 1.77-1.81 (m, 4H), 1.56-1.66 (m, 12H), 1.35-1.42 (m, 6H), 1.00-1.11 (m, 9H), 0.68 (s, 4H), 0.60-0.63 (m, 1H), 0.49-0.54 (m, 1H).

Synthesis of 39.12

To a solution of 39.11 (1.3 g, 3.62 mmol) in MeOH (20 mL) was added NaCNBH$_3$ (2.27 g, 36.2 mmol) at 25° C. After stirring at 70° C. for 16 h, the mixture was added into water (100 mL) and extracted with EtOAc (3×30 mL). The combined organic layer was washed with brine (100 mL), dried over anhydrous Na$_2$SO$_4$, filtered and concentrated to give 39.12 (1.5 g). $^1$H NMR (400 MHz, CDCl$_3$) $\delta_H$ 2.51-2.99 (m, 4H), 2.28-2.40 (m, 1H), 2.04 (s, 3H), 1.80 (br s, 3H), 1.53-1.72 (m, 4H), 1.29-1.50 (m, 8H), 0.98-1.15 (m, 5H), 0.97-1.18 (m, 5H), 0.74-0.92 (m, 4H), 0.72 (s, 1H), 0.44 (br s, 2H), 0.07 (s, 4H).

Synthesis of 39.13

To a solution of 39.12 (350 mg, 970 µmol) in EtOH (5 mL) were added Et$_3$N (979 mg, 9.70 mmol) and 2-(ethoxymethylidene) propanedinitrile (236 mg, 1.94 mmol). After stirring at 75° C. for 16 h, the mixture was added into water (30 mL) and extracted with EtOAc (3×20 mL). The combined organic layer was washed with brine (2×50 mL), dried over anhydrous Na$_2$SO$_4$, filtered and concentrated. The residue was purified by flash column (20-40% of EtOAc in PE) to give 39.13 (85 mg). $^1$H NMR (400 MHz, CDCl$_3$) δ$_H$ 7.46 (s, 1H), 4.27 (s, 2H), 3.93-3.97 (m, 1H), 1.92-2.00 (m, 2H), 1.77-1.80 (m, 5H), 1.38-1.42 (m, 9H), 1.04-1.11 (m, 10H), 0.78 (s, 3H), 0.55.0.74 (m, 3H), 0.59 (s, 1H), 0.39-0.43 (m, 2H), 0.10-0.13 (m, 1H).

Synthesis of 39

To a solution of 39.13 (50 mg, 114 μmol) in THF (2 mL) was added —BuONO (25 mg, 242 μmol). After stirring at 70° C. for 16 h, the mixture was added into water (20 mL) and extracted with EtOAc (3×20 mL). The combined organic layer was washed with brine (50 mL), dried over anhydrous Na$_2$SO$_4$, filtered and concentrated. The residue was purified by flash column (15-30% of EtOAc in PE) to give 39 (4.4 mg, 3.23%). $^1$H NMR (400 MHz, CDCl$_3$) δ$_H$ 7.94 (s, 1H), 7.79 (s, 1H), 4.69 (d, J=12.0 Hz, 1H), 3.54 (d, J=12.0 Hz, 1H), 1.97-2.02 (m, 1H), 1.65-1.87 (m, 7H), 1.34-1.47 (m, 8H), 1.25 (s, 5H), 0.98-1.12 (m, 7H), 0.87-0.90 (m, 1H), 0.76 (s, 3H), 0.46-0.55 (m, 2H), 0.36-0.42 (m, 1H). LC-ELSD/MS purity>99%, MS ESI calcd. For C$_{27}$H$_{39}$N$_3$O [M−H$_2$O+H]$^+$ 404.3, found 404.3.

Example 40: Synthesis of 1-((3-((3R,5R,8R,9R,10S, 13S,14S,17S)-3-hydroxy-3-(methoxymethyl)-13-methylhexadecahydro-1H-cyclopenta[a] phenanthren-17-yl)oxetan-3-yl)methyl)-1H-pyrazole-4-carbonitrile (40)

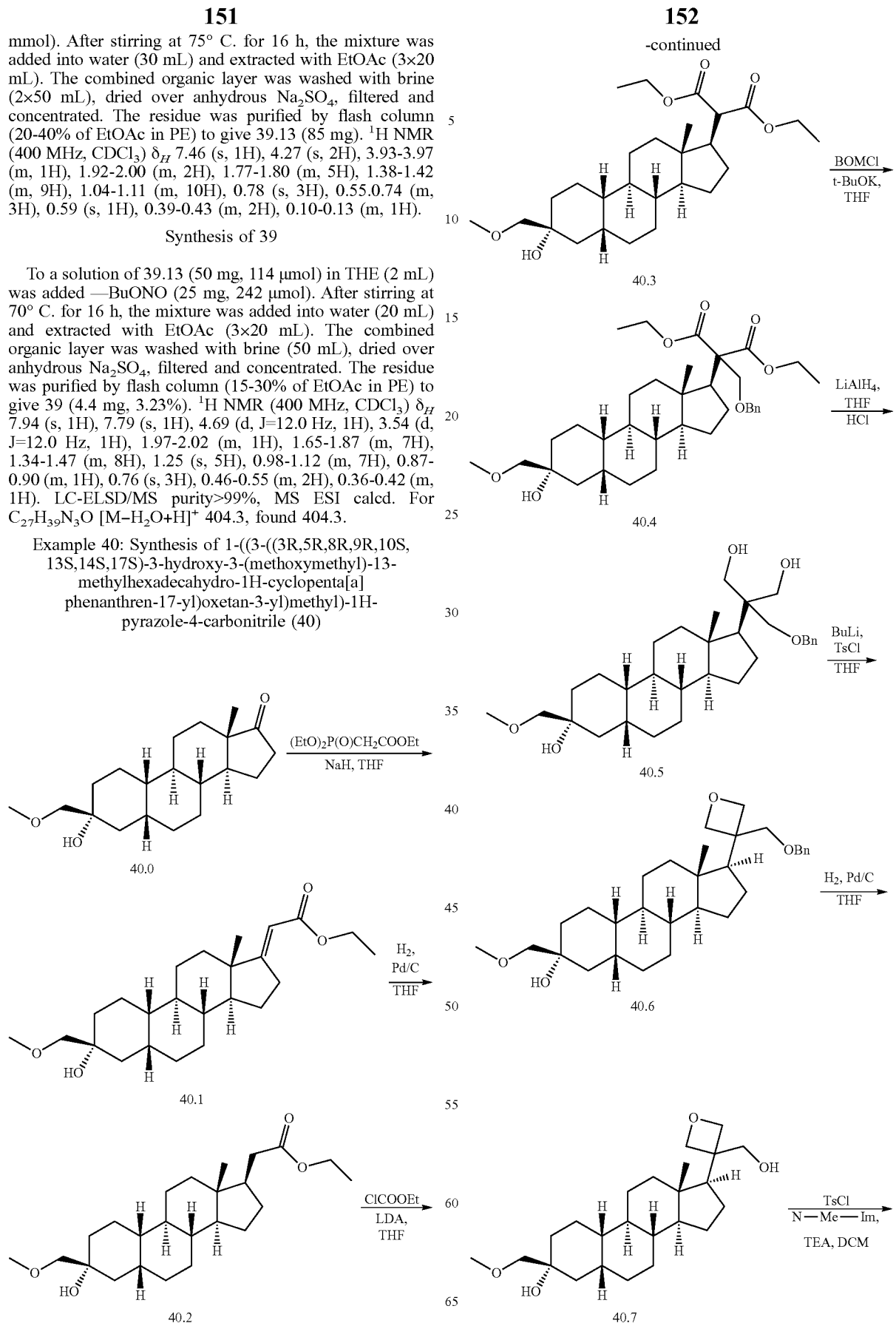

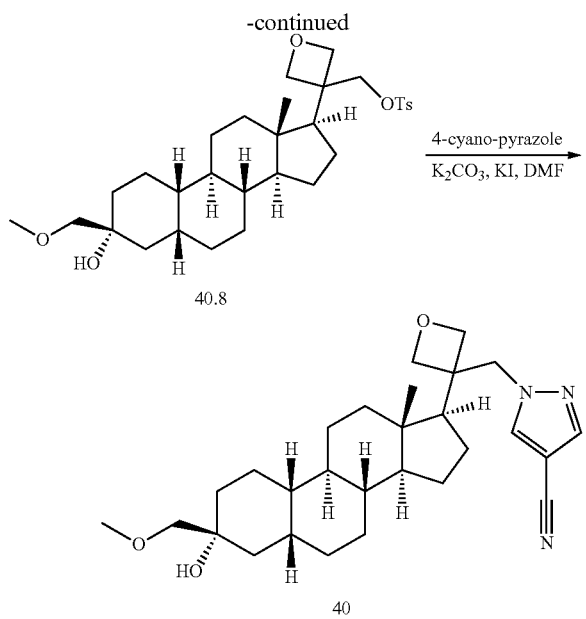

40.8

40

Synthesis of 40.1

To a suspension of NaH (2.23 g, 56.0 mmol, 60% in oil) in THF (50 mL) was added $(EtO)_2P(O)CH_2COOEt$ (12.5 g, 56.0 mmol) dropwise at 0° C. After stirring at 20° C. for 10 min, a solution of 40.0 (9 g, 28.0 mmol) in THF (90 mL) was added dropwise at 20° C. After refluxing at 70° C. for 16 h, the mixture was poured into 10% $NH_4Cl$ (200 mL, aq.) and extracted with EtOAc (200 mL×3). The organic layer was washed with brine (100 mL×2), dried over $Na_2SO_4$, filtered and concentrated. The residue was purified by flash column (0~20% of EtOAc in PE) to give 40.1 (9.5 g, 87.1%). $^1H$ NMR (400 MHz, $CDCl_3$)) $\delta_H$ 5.46-5.57 (m, 1H), 3.86-4.40 (m, 3H), 3.27-3.51 (m, 5H), 2.71-2.97 (m, 2H), 2.53-2.62 (m, 1H), 1.61-1.95 (m, 7H), 1.34-1.53 (m, 6H), 1.32-1.09 (m, 10H), 0.81 (s, 3H).

Synthesis of 40.2

To a solution of 40.1 (9.5 g, 24.3 mmol) in THF (100 mL) was added Pd/C (1.5 g, dry, 10%) under $N_2$. The suspension was degassed under vacuum and purged with $H_2$ for three times. After stirring under $H_2$ (40 psi) at 40° C. for 24 h, the mixture was filtered through a pad of celite and washed with THF (3×100 mL). The combined filtrate was concentrated to give 40.2 (9.3 g, 97.5%). $^1H$ NMR (400 MHz, $CDCl_3$) $\delta_H$ 4.00-4.25 (m, 2H), 3.39 (s, 4H), 3.31-3.46 (m, 1H), 2.58 (s, 1H), 2.29-2.40 (m, 1H), 2.03-2.15 (m, 1H), 1.60-1.94 (m, 9H), 1.28-1.58 (m, 8H), 1.27-1.23 (m, 4H), 0.97-1.17 (m, 6H), 0.59 (s, 3H).

Synthesis of 40.3

To a solution of $i-Pr_2NH$ (7.16 g, 70.8 mmol) in THF (60 mL) was added n-BuLi (28.3 mL, 2.5 M in hexane, 70.8 mmol) at −70° C. To the mixture was added a solution of 40.2 (9.3 g, 23.6 mmol) in THF (90 mL) at −70° C. After stirring at −70° C. for 1 h, to the mixture was added ClCOOEt (7.68 g, 70.8 mmol). After stirring at −70° C. for 1 h, the mixture was quenched by $NH_4Cl$ (200 mL, 10%) and extracted with EtOAc (3×150 mL). The combined organic layer was washed with brine (2×100 mL), dried over anhydrous $Na_2SO_4$, filtered and concentrated in vacuum. The residue was purified by flash column (0~40% of EtOAc in PE) twice to give 40.3 (9.2 g). $^1H$ NMR (400 MHz, $CDCl_3$) $\delta_H$ 4.11-4.19 (m, 4H), 3.34-3.45 (m, 5H), 3.32-3.24 (m, 1H), 2.57 (s, 1H), 2.13-2.27 (m, 1H), 1.86-2.00 (m, 1H), 1.61-1.85 (m, 5H), 1.31-1.57 (m, 8H), 1.23-1.29 (m, 8H), 0.82-1.20 (m, 7H), 0.70 (s, 3H).

Synthesis of 40.4

To a suspension of t-BuOK (11.1 g, 99.0 mmol) in THF (110 mL) was added a solution of 40.3 (9.2 g, 19.8 mmol) in THF (90 mL) at 0° C. After stirring at 20° C. for 1 h, BOMCl (18.4 g, 118 mmol) was added at 0° C. After stirring at 0° C. for 1 h, the mixture was poured into $NH_4Cl$ (250 mL, sat.) and extracted with EtOAc (100 mL×3). The combined organic layer was dried over anhydrous $Na_2SO_4$, filtered and concentrated to give 40.4 (20.7 g).

Synthesis of 40.5

To a suspension of LAH (7.51 g, 198 mmol) in THF (200 mL) was added a solution of 40.4 (11.5 g, 19.8 mmol) in THF (100 mL) dropwise at 0° C. After stirring at 0° C. for 1 h, the mixture was quenched sequentially with water/THF (7.5 mL/150 mL), NaOH (7.5 mL, 10%) and water (22.5 mL). The mixture was filtered and the solid was washed with THF (3×100 mL). The combined filtrate was concentrated to 150 mL and HCl (2 M, 40 mL) was added. After stirring at 50° C. for 1 h, to the mixture was added $NaHCO_3$(200 mL, sat) and extracted with EtOAc (150 mL×3). The combined organic layer was dried over $Na_2SO_4$, filtered and concentrated. The residue was purified by flash column (30-100% of EtOAc in PE) twice to give 40.5 (4.8 g). $^1H$ NMR (400 MHz, $CDCl_3$) $\delta_H$ 7.27-7.40 (m, 5H), 4.50 (s, 2H), 3.59-3.97 (m, 6H), 3.38 (s, 5H), 2.53-2.81 (m, 3H), 1.66-1.94 (m, 5H), 1.29-1.61 (m, 12H), 0.85-1.23 (m, 7H), 0.73 (s, 3H).

Synthesis of 40.6

To a solution of 40.5 (1 g, 1.99 mmol) in THF (20 mL) was added n-BuLi (0.952 mL, 2.5 M in hexane, 2.38 mmol) at 0° C. After stirring at 0° C. for 10 min, to the mixture was added a solution of TsCl (453 mg, 2.38 mmol) in THF (5 mL). After stirring at 0° C. for 1 h, to the mixture was added n-BuLi (952 μL, 2.5 M in hexane, 2.38 mmol) at 0° C. After stirring at 15° C. for 2 h, the mixture was quenched by $NH_4Cl$ (20 mL, sat.) and extracted with EtOAc (2×30 mL). The combined organic layer was dried over anhydrous $Na_2SO_4$, filtered and concentrated under vacuum. The residue was purified by flash column (0~15% of EtOAc in PE) to give 40.6 (600 mg, 62.5%). $^1H$ NMR (400 MHz, $CDCl_3$) $\delta_H$ 7.27-7.41 (m, 5H), 4.78-4.88 (m, 1H), 4.41-4.67 (m, 4H), 4.20-4.27 (m, 1H), 3.85-3.94 (m, 1H), 3.61-3.71 (m, 1H), 3.39 (s, 5H), 2.59 (s, 1H), 2.05-2.17 (m, 1H), 1.58.1.99 (m, 7H), 0.95-1.50 (m, 16H), 0.51 (s, 3H).

Synthesis of 40.7

To a solution of 40.6 (550 mg, 1.13 mmol) in THF (20 mL) was added Pd/C (0.5 g, 10%, wet) under $N_2$. The mixture was degassed under vacuum and purged with $H_2$ for three times. After stirring under $H_2$ (40 psi) at 30° C. for 20 h, the mixture was filtered and the solid was washed with THF (20 mL). The combined filtrate was concentrated and purified by flash column (40~70% of EtOAc in PE) to give 40.7 (300 mg, 67.7%). $^1$H NMR (400 MHz, CDCl$_3$) $\delta_H$ 4.85 (d, J=6.4 Hz, 1H), 4.55 (d, J=6.0 Hz, 1H), 4.46 (d, J=6.0 Hz, 1H), 4.24 (d, J=6.8 Hz, 1H), 4.09 (dd, J=6.4, 10.8 Hz, 1H), 3.82 (dd, J=4.8, 11.2 Hz, 1H), 3.39 (s, 5H), 2.59 (s, 1H), 2.04-2.21 (m, 1H), 1.59-2.02 (m, 10H), 0.98-1.50 (m, 14H), 0.53 (s, 3H). LC-ELSD/MS purity: 99%, MS ESI calcd. for C$_{24}$H$_{40}$O$_4$ [M+H]$^+$ 393.2, found C$_{24}$H$_{40}$O$_4$ [M+H]$^+$ 393.3.

Synthesis of 40.8

To a solution of 40.7 (150 mg, 0.3820 mmol) in DCM (5 mL) were added N-Me-imidazole (31.3 mg, 0.382 mmol), TEA (193 mg, 1.91 mmol) and TsCl (217 mg, 1.14 mmol). After stirring at 20° C. for 1 h, the mixture was concentrated to give 40.8 (340 mg).

Synthesis of 40

To a solution of 40.8 (250 mg, 0.4572 mmol) in DMF (5 mL) were added 4-cyano-pyrazole (85.1 mg, 0.9144 mmol), KI (75.8 mg, 0.4572 mmol) and K$_2$CO$_3$ (128 mg, 0.9144 mmol). After stirring at 80° C. for 16 h, the mixture was washed with water (5 mL) and extracted with EtOAc (50 mL×3). The combined organic layer was washed with brine (30 mL×2), dried over anhydrous Na$_2$SO$_4$, filtered and concentrated under vacuum. The residue was purified by Pre-HPLC (column: Welch Xtimate C18 150*25 mm*5 um; Mobile phase: A: CO$_2$ B: water (0.225% FA)-ACN; gradient: from 55% to 85% of B, Flow Rate (ml/min): 25) to give 40 (10 mg, 3.44%). $^1$H NMR (400 MHz, CDCl$_3$) $\delta_H$ 7.88 (s, 1H), 7.84 (s, 1H), 4.70-4.55 (d, J=6.8 Hz, 1H), 4.56-4.70 (m, 2H), 4.55-4.45 (m, 2H), 4.38-4.28 (m, 1H), 3.39 (s, 5H), 2.57 (s, 1H), 1.60-2.15 (m, 11H), 0.98-1.50 (m, 13H), 0.69 (s, 3H). LC-ELSD/MS purity: 99%, MS ESI calcd. for C$_{28}$H$_{41}$N$_3$O$_3$ [M+H]$^+$ 468.3, found C$_{28}$H$_{41}$N$_3$O$_3$ [M+H]$^+$ 468.3.

Example 41: Synthesis of 1-(2-((3R,5R,8R,9R,10S,13S,14S,17S)-3-hydroxy-3,13-dimethylhexadecahydro-1H-cyclopenta[a]phenanthren-17-yl)-2-methylpropyl)-1H-pyrazole-4-carbonitrile (41)

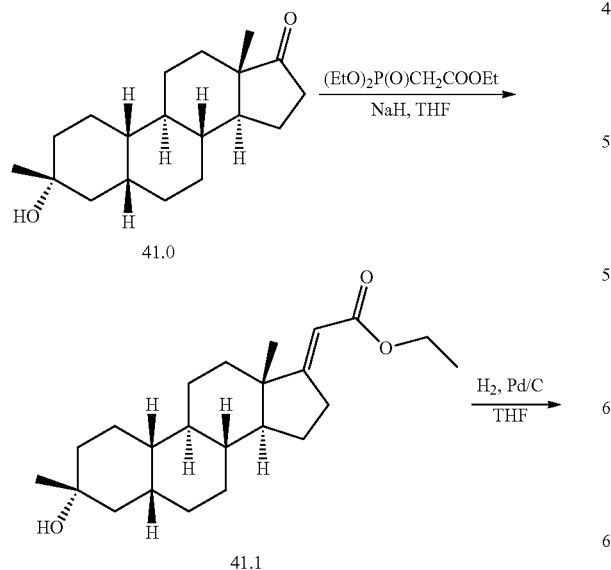
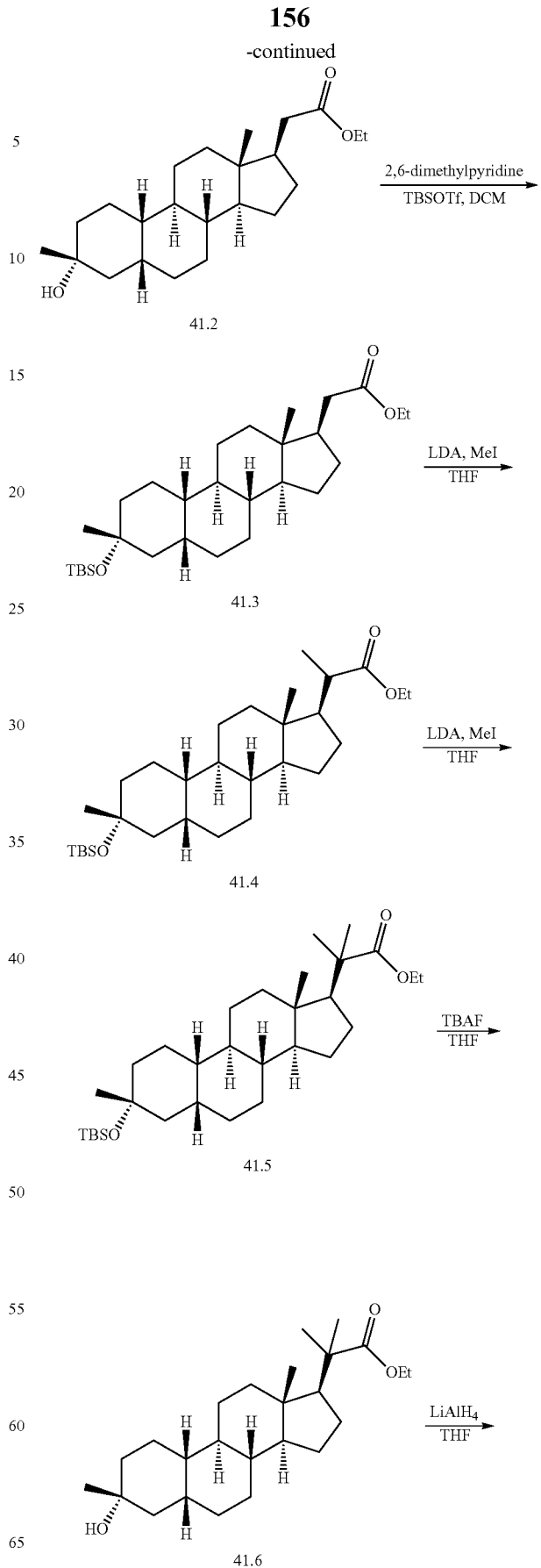

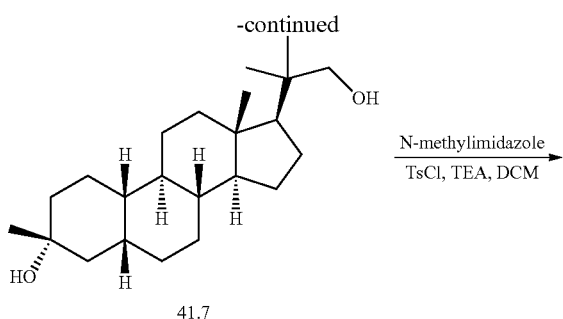

41.7

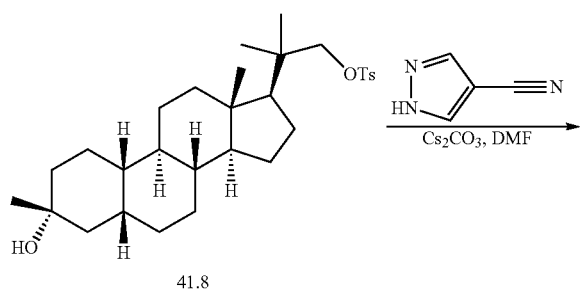

41.8

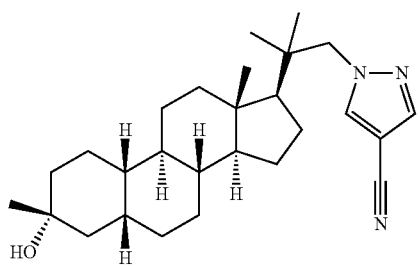

41

Synthesis of 41.1

To a suspension of NaH (2.75 g, 60%, 68.8 mmol) in THF (60 mL) was added (EtO)$_2$P(O)CH$_2$COOEt (15.4 g, 68.8 mmol) dropwise at 0° C. under N$_2$. After stirring at 20° C. for 10 mins, a solution of 41.0 (10 g, 34.4 mmol) in THF (20 mL) was added dropwise at 20° C. After refluxing at 70° C. for 16 h, the mixture was poured into NH$_4$Cl (200 mL, 10% aq) and extracted with EtOAc (200 mL). The organic layer was separated, dried over Na$_2$SO$_4$, filtered, concentrated. The residue was purified by flash column (0~20% EtOAc in PE) to give 41.1 (12 g, 97%). $^1$H NMR (400 MHz, CDCl$_3$) δ$_H$ 5.52 (t, J=2.4 Hz, 1H), 4.15 (q, J=7.2 Hz, 2H), 2.90-2.75 (m, 2H), 1.95-1.60 (m, 5H), 1.50-1.25 (m, 18H), 1.20-1.05 (m, 4H), 0.82 (s, 3H).

Synthesis of 41.2

To a solution of 41.1 (12 g, 33.2 mmol) in THF (150 mL) was added Pd/C (2 g, dry, 10%) at 20° C. under N$_2$. After stirring at 40° C. under H$_2$ (40 psi) for 24 h, the mixture was filtered though a pad of celite and washed with THF (3×50 mL). The combined filtrate was concentrated to give 41.2 (11.7 g, 97.5%). $^1$H NMR (400 MHz, CDCl$_3$) δ$_H$ 4.11 (q, J=6.8 Hz, 2H), 2.35 (dd, J=5.2, 14.4 Hz, 1H), 2.10 (dd, J=10.0, 14.8 Hz, 1H), 2.00-1.75 (m, 6H), 1.70-1.50 (m, 3H), 1.50-1.35 (m, 6H), 1.35-1.25 (m, 10H), 1.20-0.95 (m, 6H), 0.59 (s, 3H).

Synthesis of 41.3

To a solution of 41.2 (2.3 g, 6.3 mmol), 2,6-dimethylpyridine (1.69 g, 15.8 mmol) in DCM (20 mL) was added dropwise tert-butyldimethylsilyl trifluoromethanesulfonate (3.33 g, 12.6 mmol) at 0° C. After stirring at 15° C. for 18 h, the reaction mixture was quenched with water (30 mL) and extracted with DCM (2×20 mL). The combined organic phase washed with brine (50 mL), dried over Na$_2$SO$_4$, filtered and concentrated under vacuum. The residue was purified by flash column (0~10% of EtOAc in PE) to afford 41.3 (2.9 g). $^1$H NMR (400 MHz, CDCl$_3$) δ$_H$ 4.14-4.08 (m, 2H), 2.40-2.32 (m, 1H), 2.15-2.03 (m, 1H), 1.95-1.59 (m, 9H), 1.46-1.28 (m, 6H), 1.27-1.21 (m, 8H), 1.20-0.92 (m, 7H), 0.86-0.85 (m, 9H), 0.59 (s, 3H), 0.09-0.05 (m, 6H)

Synthesis of 41.4

To a solution of i-Pr$_2$NH (2.34 g, 23.2 mmol) in THF (20 mL) was added n-BuLi (11.1 mL, 2.5 M, 27.8 mmol) at −70° C. under N$_2$. The mixture was warmed to 0° C. and stirred at 0° C. for 30 mins. To the mixture was added to a stirred solution of 41.3 (3.7 g, 7.7 mmol) in THF (20 mL) at −70° C. After stirring at −70° C. for 1 h, methyl iodide (6.60 g, 46.5 mmol) was added. After stirring at 20° C. for 16 h, the reaction was diluted with water (50 mL) and extracted with EtOAc (3×30 mL). The combined organic layers were washed with brine (100 mL), dried over anhydrous Na$_2$SO$_4$, filtered and concentrated. The residue was purified by flash column (0-5% of EtOAc in PE) to give 41.4 (2.7 g, 71%). $^1$H NMR (400 MHz, CDCl$_3$) δ$_H$ 4.20-4.11 (m, 2H), 2.36-2.26 (m, 1H), 1.90-1.56 (m, 10H), 1.51-1.29 (m, 8H), 1.28-1.27 (m, 3H), 1.21 (s, 3H), 1.10 (d, J=6.8 Hz, 3H), 1.07-0.87 (m, 6H), 0.86 (s, 9H), 0.69 (s, 3H), 0.06 (s, 6H)

Synthesis of 41.5

To a solution of i-Pr$_2$NH (1.15 g, 11.4 mmol) in THF (10 mL) under N$_2$ was added n-BuLi (5.4 mL, 2.5 M, 13.6 mmol) at −70° C. The mixture was warmed to 0° C. and stirred at 0° C. for 30 min. To the mixture was added to a stirred solution of 41.4 (2.8 g, 5.7 mmol) in THF (10 mL) at −78° C. After stirring at −0° C. for 1 h, methyl iodide (4.85 g, 34.2 mmol) was added. After stirring at 20° C. for 16 h, the reaction was diluted with water (20 mL) and extracted with EtOAc (3×30 mL). The combined organic layers were washed with brine (50 mL), dried over anhydrous Na$_2$SO$_4$, filtered and concentrated. The residue was purified by flash column (0-5% of EtOAc in PE) to give 41.5 (1.7 g). $^1$H NMR (400 MHz, CDCl$_3$) δ$_H$ 4.19-3.98 (m, 1H), 1.80-1.58 (m, 9H), 1.45-1.29 (m, 9H), 1.23-1.18 (m, 8H), 1.13-0.89 (m, 11H), 0.86 (s, 9H), 0.72-0.58 (m, 3H), 0.08-0.06 (m, 6H)

Synthesis of 41.6

To the mixture of 41.5 (1.7 g, 3.4 mmol) in THF (10 mL) was added TBAF (6.7 ml, 1 M, 6.7 mmol). After stirring at 80° C. for 18 h, the mixture cooled to 20° C., diluted with water (10 mL), and extracted with EtOAc (3×20 mL). The combined organic phase was washed with brine (2×30 mL), dried over anhydrous Na$_2$SO$_4$, filtered, concentrated. The residue was purified by flash column (0~30% of EtOAc in PE) to give 41.6 (870 mg). $^1$H NMR (400 MHz, CDCl$_3$) δ$_H$ 4.09-3.99 (m, 1H), 1.80-1.61 (m, 9H), 1.48-1.29 (m, 11H), 1.26-1.24 (m, 4H), 1.19 (d, J=5.6 Hz, 3H), 1.15-0.90 (m, 10H), 0.83 (d, J=7.2 Hz, 1H), 0.72-0.58 (m, 3H)

Synthesis of 41.7

To a solution of 41.6 (870 mg, 2.3 mmol) in THF (20 mL) was added LiAlH$_4$ (175 mg, 4.6 mmol) at 25° C. After stirring at 25° C. for 16 h, the reaction was quenched with H$_2$O (0.2 ml) and then HCl (50 mL, 1 M). The mixture was poured into water (30 mL), stirred for 5 min and filtered. The filter cake was washed with water (2×20 mL) and dried to give 41.7 (240 mg, 30%). $^1$H NMR (400 MHz, CDCl$_3$) δ$_H$ 3.42-3.28 (m, 2H), 2.01-1.95 (m, 1H), 1.87-1.78 (m, 3H), 1.64-1.57 (m, 4H), 1.52-1.26 (m, 12H), 1.26 (s, 3H), 1.25-1.19 (m, 2H), 1.11-1.01 (m, 4H), 0.99 (s, 3H), 0.90 (s, 3H), 0.77 (s, 3H). LC-ELSD/MS: purity >99%; MS ESI calcd. for C$_{23}$H$_{40}$O$_2$ [M–H$_2$O+H]$^+$ 331.3, found 331.3, MS ESI calcd. for C$_{23}$H$_{40}$O$_2$ [M–H$_2$O—H$_2$O+H]$^+$ 313.3, found 313.3, Synthesis of 41.8

To a solution of 41.7 (100 mg, 0.3 mmol) in DCM (3 mL) were added N-methylimidazole (35.3 mg, 0.4 mmol), TEA (87.0 mg, 0.8 mmol) and TsCl (164 mg, 0.8 mmol). After stirring at 25° C. for 2 h, the mixture was poured into water (20 mL) and extracted with EtOAc (2×30 mL). The combined organic phase was washed with water (2×20 mL), dried over anhydrous Na$_2$SO$_4$, filtered and concentrated a 41.8 (200 mg). $^1$H NMR (400 MHz, CDCl$_3$) δ$_H$ 7.79 (d, J=8.0 Hz, 2H), 7.35 (d, J=8.0 Hz, 2H), 3.79-3.66 (m, 2H), 2.46 (s, 3H), 1.85-1.77 (m, 4H), 1.66-1.49 (m, 5H), 1.45-1.27 (m, 9H), 1.26 (s, 3H), 1.23-0.99 (m, 7H), 0.97 (s, 3H), 0.88 (s, 3H), 0.70 (s, 3H)

Synthesis of 41

To a solution of 41.8 (200 mg, 0.4 mmol) in DMF (5 mL) were added 1H-pyrazole-4-carbonitrile (55.5 mg, 0.6 mmol) and Cs$_2$CO$_3$ (645 mg, 2.0 mmol) at 25° C. under N$_2$. After stirring at 120° C. for 16 h, the mixture was added into water (20 mL), stirred at 25° C. for 5 mins and extracted with EtOAc (3×30 mL). The combined organic layer was washed with brine (2×100 mL), dried over anhydrous Na$_2$SO$_4$, filtered and concentrated. The residue was purified by flash column (0-40% of EtOAc in PE) to give 41 (130 mg).

41 (130 mg) was further purified by HPLC (Method: SAGE-TJF-242-P1A; Column: Welch Xtimate C18 150*25 mm*5 um; Condition: water (0.04% NH$_3$H$_2$O)-ACN; Begin B: 70; End B: 100) to afford 41 (15.2 mg, 12%). $^1$H NMR (400 MHz, CDCl$_3$) δ$_H$ 7.78 (s, 1H), 7.74 (s, 1H), 4.09 (d, J=13.6 Hz, 1H), 3.92 (d, J=13.6 Hz, 1H), 2.00-1.94 (m, 1H), 1.87-1.56 (m, 9H), 1.52-1.29 (m, 9H), 1.26 (s, 3H), 1.23-1.02 (m, 6H), 0.99 (s, 3H), 0.94 (s, 3H), 0.82 (s, 3H). LC-ELSD/MS: purity >99%; MS ESI calcd. for C$_{27}$H$_{41}$N$_3$O [M–H$_2$O+H]$^+$ 406.4, found 406.4. MS ESI calcd. for C$_{27}$H$_{41}$N$_3$O [M+H]$^+$ 424.4, found 424.4.

Example 42 & 43: Synthesis of 1-((S)-2-((3R,5R, 8S,9S,10S,13S,14S,17S)-10-ethyl-3-hydroxy-3-(methoxymethyl)-13-methylhexadecahydro-1H-cyclopenta[a]phenanthren-17-yl)-2-hydroxypropyl)-1H-pyrazole-4-carbonitrile (42) & 1-((R)-2-((3R, 5R,8S,9S,10S,13S,14S,17S)-10-ethyl-3-hydroxy-3-(methoxymethyl)-13-methylhexadecahydro-1H-cyclopenta[a]phenanthren-17-yl)-2-hydroxypropyl)-1H-pyrazole-4-carbonitrile (43)

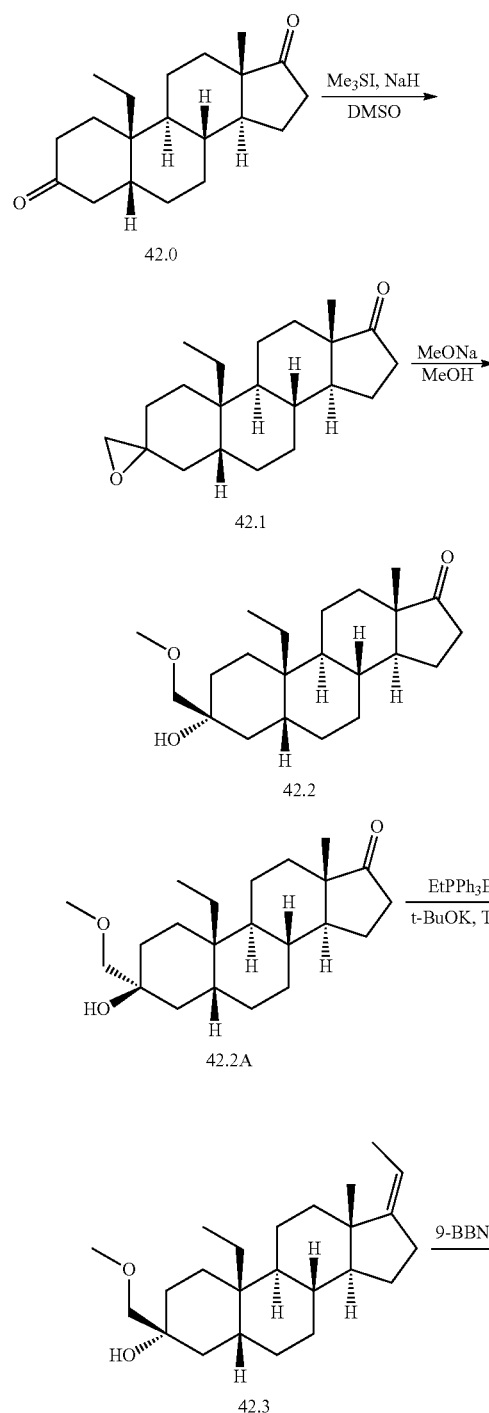

-continued

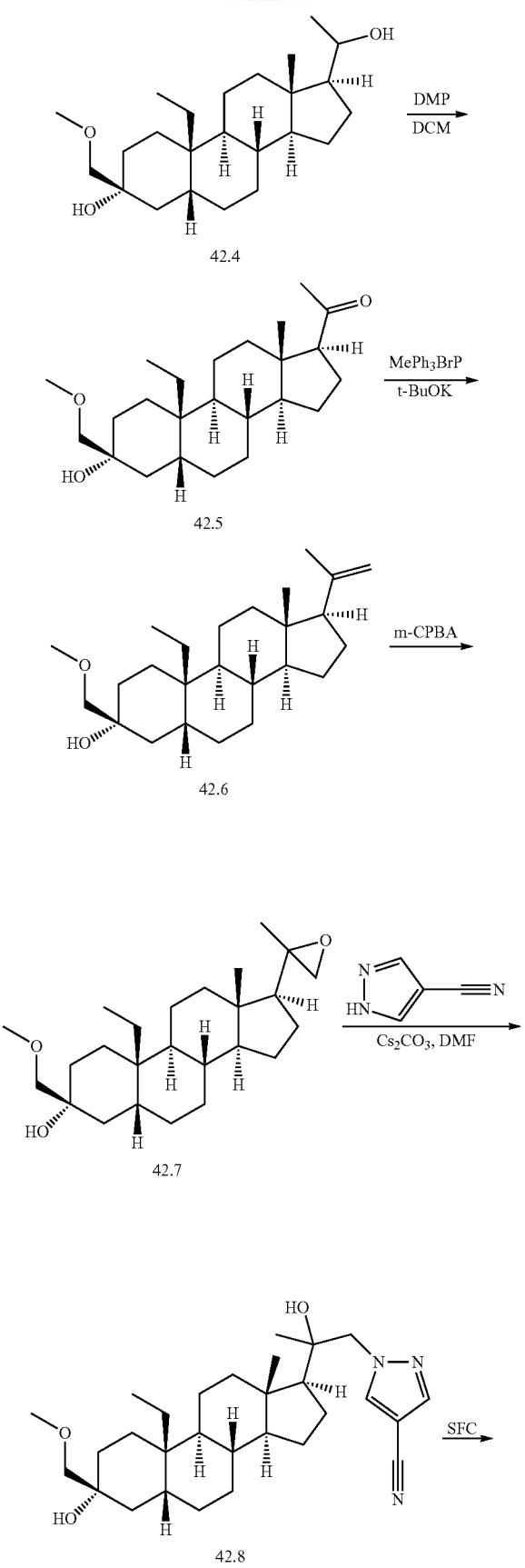

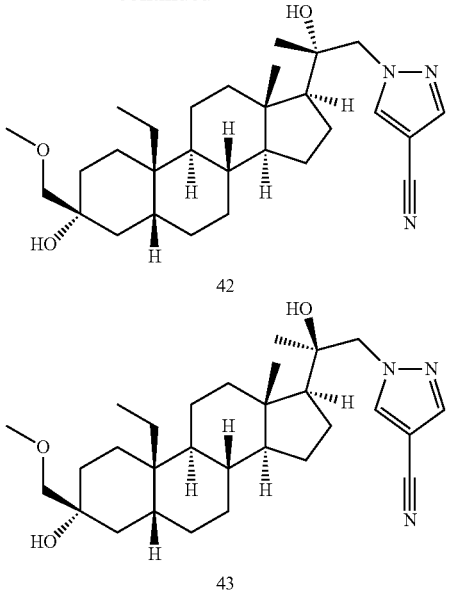

Synthesis of 42.1

To a stirred solution of trimethylsulfonium iodide (6.44 g, 31.6 mmol) in DMSO (40 mL) and THF (20 mL) was added NaH (1.26 g, 31.6 mmol, 60%). After stirring at 0° C. for 1.0 h under $N_2$, the mixture was added to a solution of 42.0 (8 g, 26.4 mmol) in DMSO (20 mL) at 0° C. After stirring at 25° C. for 16 h, the reaction was treated with water (100 mL) and extracted with EtOAc (2×100 mL). The combined organic phase was washed with water (2×100 mL), brine (200 mL), dried over anhydrous $Na_2SO_4$, filtered, and concentrated in vacuum. The residue was purified by column (5%-30% of EtOAc in PE) to give 42.1 (5 g). $^1$H NMR (400 MHz, $CDCl_3$) $\delta_H$ 2.63-2.57 (m, 2H), 2.48-2.33 (m, 2H), 2.13-1.51 (m, 10H), 1.51-0.94 (m, 11H), 0.94-0.80 (m, 7H).

Synthesis of 42.2 & 42.2A

To a solution of 42.1 (6.9 g, 21.8 mmol) in MeOH (50 mL) was added $CH_3ONa$ (11.7 g, 218 mmol). After stirring at 65° C. for 16 h, the reaction mixture was quenched by addition of $H_2O$ (100 mL) and extracted with EtOAc (3×100 mL). The combined organic phase was washed with brine (200 mL), dried over anhydrous $Na_2SO_4$, filtered and concentrated. The residue was purified by column (2~30% of EtOAc in PE) to give 42.2 (3.7 g, 49%) and 42.2A (2 g, 26%).

42.2: $^1$H NMR (400 MHz, $CDCl_3$) $\delta_H$ 3.40-3.34 (m, 5H), 2.59 (s, 1H), 2.46-2.39 (m, 1H), 2.12-1.52 (m, 13H), 1.52-1.14 (m, 10H), 0.84-0.77 (m, 6H). LC-ELSD/MS purity 99%, MS ESI calcd. for $C_{22}H_{33}O$ $[M+H-2H_2O]^+$ 313.2, found 313.2.

42.2A: $^1$H NMR (400 MHz, $CDCl_3$) $\delta_H$ 3.38 (s, 3H), 3.22-3.17 (m, 2H), 2.47-2.40 (m, 2H), 2.10-1.57 (m, 10H), 1.57-1.48 (m, 3H), 1.48-1.06 (m, 10H), 0.87-0.83 (m, 6H). LC-ELSD/MS purity 99%, MS ESI calcd. for $C_{22}H_{33}O$ $[M+H-2H_2O]^+$ 313.2, found 313.2.

Synthesis of 42.3

To a suspension of $Ph_3PEtBr$ (10.8 g, 29.2 mmol) in anhydrous THF (100 mL) was added t-BuOK (3.27 g, 29.2 mmol) at 25° C. under N$_2$. After stirring at 60° C. for 30 mins, a solution of 42.2 (3.4 g, 9.75 mmol) in anhydrous THF (50 mL) was added. After stirring at 60° C. for 16 h, the mixture was poured into saturated NH$_4$Cl (100 mL) and extracted with EtOAc (2×100 mL). The combine organic phase was washed with brine (200 mL), filtered and concentrated. The residue was purified by column (0~3% of EtOAc in PE) to give 42.3 (3.5 g). $^1$H NMR (400 MHz, CDCl$_3$) δ$_H$ 5.12-4.98 (m, 1H), 3.41-3.34 (m, 5H), 2.58 (s, 1H), 2.39-2.09 (m, 3H), 1.96-1.52 (m, 10H), 1.52-1.31 (m, 6H), 1.31-1.03 (m, 8H), 0.84-0.70 (m, 6H).

Synthesis of 42.4

To a solution of 42.3 (3.5 g, 9.71 mmol) in anhydrous THF (50 mL) was added 9-BBN dimer (7.04 g, 29.1 mmol) at 25° C. under N$_2$. After stirring at 60° C. for 16 h, the mixture was cooled and sequentially treated at 0° C. with EtOH (20 mL) and NaOH (9.7 mL, 5M, 48.5 mmol) dropwise. After addition, H$_2$O$_2$ (9.7 mL, 97.1 mmol, 10 M in water) was added slowly until the inner temperature no longer rises and the inner temperature was maintained below 30° C. The mixture was stirred at 60° C. for 2 h. Then the mixture was cooled and quenched with Na$_2$S$_2$O$_3$ (100 mL, sat. aq.). The mixture was extracted with EtOAc (2×100 mL) and the organic layer was dried over Na$_2$SO$_4$, filtered and concentrated in vacuum. The residue was purified by column (20% of EtOAc in PE) to give 42.4 (2.2 g). $^1$H NMR (400 MHz, CDCl$_3$) δ$_H$ 3.72-3.58 (m, 1H), 3.41-3.34 (m, 4H), 2.59 (s, 1H), 2.03-1.46 (m, 16H), 1.46-1.02 (m, 16H), 0.79-0.63 (m, 4H).

Synthesis of 42.5

To a solution of 42.4 (2.1 g, 5.54 mmol) in DCM (30 mL) was added DMP (4.66 g, 11 mmol). After stirring at 25° C. for 1 h, the mixture was quenched with NaHCO$_3$ (50 mL) and extracted with EtOAc (3×30 mL). The combined organic layer was washed with Na$_2$S$_2$O$_3$ (3×30 mL, sat.), brine (50 mL), dried over Na$_2$SO$_4$, filtered and concentrated in vacuum to give 42.5 (2.1 g). $^1$H NMR (400 MHz, CDCl$_3$) δ$_H$ 3.40-3.34 (m, 5H), 2.67-2.50 (m, 2H), 2.04-1.59 (m, 10H), 1.59-1.32 (m, 7H), 1.32-1.08 (m, 10H), 0.77 (t, J=7.6 Hz, 3H), 0.58 (s, 3H).

Synthesis of 42.6

To a suspension of MePh$_3$BrP (6.93 g, 19.4 mmol) in anhydrous THF (50 mL) was added t-BuOK (2.17 g, 19.4 mmol) at 25° C. under N$_2$. After stirring at 60° C. for 30 mins, a solution of 42.5 (2.1 g, 5.57 mmol) in anhydrous THF (20 mL) was added at 25° C. After stirring at 60° C. for 16 h, the mixture was poured into saturated NH$_4$Cl (50 mL) and extracted with EtOAc (2×100 mL). The combined organic phase was washed with brine (200 mL), filtered and concentrated. The residue was purified by column (0~10% of EtOAc in PE) to give 42.6 (1.1 g, 53%). $^1$H NMR (400 MHz, CDCl$_3$) δ$_H$ 4.83 (s, 1H), 4.69 (s, 1H), 3.41-3.34 (m, 5H), 2.58 (s, 1H), 2.04-1.55 (m, 8H), 1.55-1.30 (m, 10H), 1.30-1.07 (m, 10H), 0.77 (t, J=7.2 Hz, 3H), 0.54 (s, 3H).

Synthesis of 42.7

To a solution of 42.6 (400 mg, 1.06 mmol) in DCM (10 mL) was added m-CPBA (454 mg, 2.12 mmol, 80%) at 25° C. After stirring at 25° C. for 1 h, the mixture was quenched with sat. NaHCO$_3$ and Na$_2$S$_2$O$_3$ (40 mL, v:v=1:1) and extracted with DCM (2×20 mL). The combined organic phase was washed with sat. NaHCO$_3$ and Na$_2$S$_2$O$_3$ (100 mL, v:v=1:1), dried over Na$_2$SO$_4$, filtered and concentrated to give 42.7 (430 mg). $^1$H NMR (400 MHz, CDCl$_3$) δ$_H$ 3.40-3.34 (m, 5H), 2.88 (d, J=4.4 Hz, 0.6H), 2.62-2.47 (m, 2H), 2.31 (d, J=4.8 Hz, 0.4H), 2.04-1.55 (m, 9H), 1.55-1.29 (m, 10H), 1.29-0.99 (m, 10H), 0.77 (t, J=7.6 Hz, 3H), 0.65 (s, 2H).

Synthesis of 42.8

To a solution of 42.7 (430 mg, 1.1 mmol) in DMF (5 mL) were added Cs$_2$CO$_3$ (1.07 g, 3.3 mmol) and 1H-pyrazole-4-carbonitrile (255 mg, 2.75 mmol). After stirring at 120° C. for 48 h, the mixture was added into saturated NH$_4$Cl (50 mL) and extracted with EtOAc (3×50 mL). The combined organic layer was washed with LiCl (100 mL, 5% in water), brine (2×100 mL), dried over anhydrous Na$_2$SO$_4$, filtered and concentrated. The residue was purified by column (10~30% of EtOAc in PE) to afford 42.8 (410 mg).

Separation of 42 & 43

42.8 was separated by SFC (Column: DAICEL CHIRAL-PAK AD-H (250 mm×30 mm, 5 um), Condition: 0.1% NH$_3$H$_2$O, ETOH, Begin B: 45%, End B: 45%) to give 42 (201.7 mg, 92%, Rt=2.165 min) and 43 (100 mg, Rt=5.035 min). 43 (100 mg) was further purified by HPLC separation (column: Xtimate C18 150×25 mm×5 um, condition: water (0.225% FA)-ACN, Begin B: 90, End B: 100) to give 43 (53.4 mg, 53.4%, Rt=5.016 min).

42: $^1$H NMR (400 MHz, CDCl$_3$) δ$_H$ 7.92 (s, 1H), 7.82 (s, 1H), 4.35-4.05 (m, 2H), 3.40-3.34 (m, 5H), 2.61-2.53 (m, 2H), 2.02-1.57 (m, 10H), 1.57-1.18 (m, 10H), 1.18-0.75 (m, 14H). LC-ELSD/MS purity 99%, MS ESI calcd. for C$_{29}$H$_{42}$N$_3$O [M+H-H$_2$O]$^+$ 448.3, found 448.3. analytic SFC 100% de.

43: $^1$H NMR (400 MHz, CDCl$_3$) δ$_H$ 7.88 (s, 1H), 7.79 (s, 1H), 4.17-3.98 (m, 2H), 3.40-3.34 (m, 5H), 2.62 (s, 1H), 2.34 (s, 1H), 2.07-1.59 (m, 10H), 1.59-1.14 (m, 13H), 1.14-1.03 (m, 5H), 0.84-0.75 (m, 6H). LC-ELSD/MS purity 99%, MS ESI calcd. for C$_{29}$H$_{42}$N$_3$O [M+H-H$_2$O]$^+$ 448.3, found 448.3. analytic SFC 100% de.

Example 44 & 45: Synthesis of 1-((S)-2-((3R,5R,8S,9S,10S,13S,14S,17S)-10-ethyl-3-hydroxy-13-methyl-3-propylhexadecahydro-1H-cyclopenta[a]phenanthren-17-yl)-2-hydroxypropyl)-1H-pyrazole-4-carbonitrile (44) & 1-((R)-2-((3R,5R,8S,9S,10S,13S,14S,17S)-10-ethyl-3-hydroxy-13-methyl-3-propylhexadecahydro-1H-cyclopenta[a]phenanthren-17-yl)-2-hydroxypropyl)-1H-pyrazole-4-carbonitrile (45)

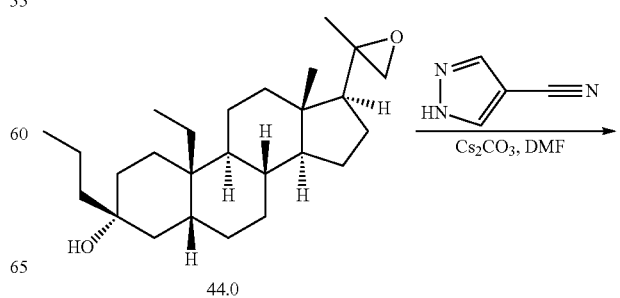

44.0

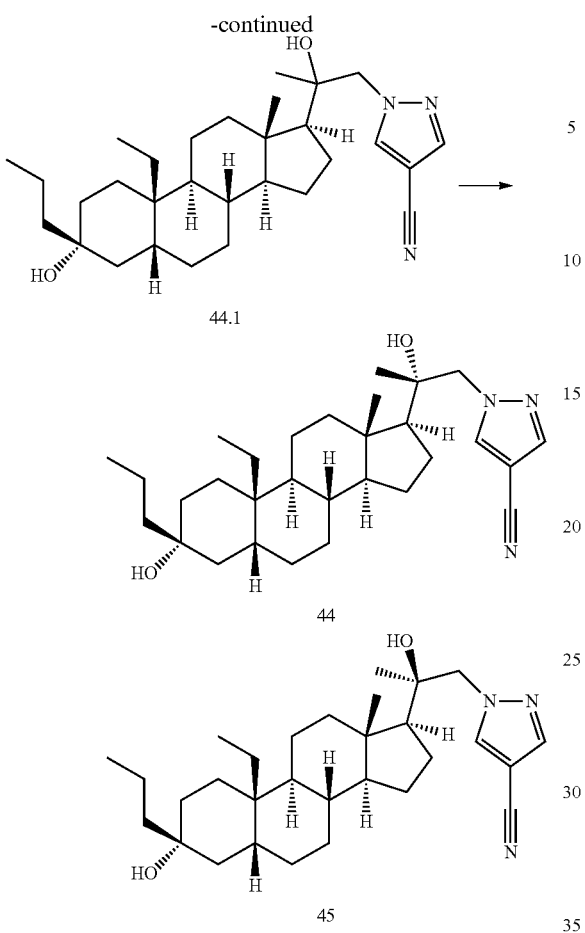

44.1

44

45

Synthesis of 44.1

To a solution of 44.0 (400 mg, 1.02 mmol) in DMF (10 mL) were added 1H-pyrazole-4-carbonitrile (237 mg, 2.55 mmol) and Cs$_2$CO$_3$ (1.66 g, 5.10 mmol) at 20° C. under N$_2$. After stirring at 120° C. for 16 h, the reaction mixture was poured into water (20 mL) and extracted with ethyl acetate (3×50 mL). The combined organic layers were washed with 5% LiCl (3×100 mL), dried over anhydrous Na$_2$SO$_4$, filtered and concentrated under vacuum. The residue was purified by flash column (0~15% of EtOAc in PE) to give 44.1 (600 mg).

Separation of 44 & 45

44.1 (600 mg, 1.24 mmol) was separated by SFC (Column: DAICEL CHIRALCEL OD (250 mm*30 mm, 10 um; Condition: 0.1% NH$_3$H$_2$O ETOH; Begin B: 55; End B: 55; FlowRate(ml/min): 80) to give 44 (233.8 mg, Rt=0.641 min) and 45 (107.5 mg, Rt=1.929 min).

44: $^1$H NMR (400 MHz, CDCl$_3$) δ$_H$ 7.92 (s, 1H), 7.81 (s, 1H), 4.35-4.31 (m, 1H), 4.08-4.05 (m, 1H), 2.52 (s, 1H), 2.04-1.97 (m, 1H), 1.90-1.57 (m, 10H), 1.57-1.30 (m, 10H), 1.30-1.00 (m, 9H), 1.00-0.85 (m, 9H), 0.78 (t, J=7.6 Hz, 3H). LC-ELSD/MS purity 99%, MS ESI calcd. for C$_{30}$H$_{44}$N$_3$ [M+H−2H$_2$O]$^+$ 446.3, found 446.3. SFC 100% de.

45: $^1$H NMR (400 MHz, CDCl$_3$) δ$_H$ 7.88 (s, 1H), 7.80 (s, 1H), 4.17-4.13 (m, 1H), 4.02-3.99 (m, 1H), 2.30 (s, 1H), 2.07-2.00 (m, 1H), 1.94-1.52 (m, 10H), 1.52-1.23 (m, 13H), 1.23-1.02 (m, 9H), 0.94 (t, J=7.2 Hz, 3H), 0.85 (s, 3H), 0.78 (t, J=7.6 Hz, 3H). LC-ELSD/MS purity 99%, MS ESI calcd. for C$_{30}$H$_{44}$N$_3$ [M+H−2H$_2$O]$^+$ 446.3, found 446.4. SFC 100% de.

Example 46 & 47: Synthesis of 1-((R)-2-((3R,5R,8R,9R,10S,13S,14S,15S,17S)-15-cyclopropyl-3-hydroxy-3,13-dimethylhexadecahydro-1H-cyclopenta[a]phenanthren-7-yl)-2-hydroxypropyl)-1H-pyrazole-4-carbonitrile (46) & 1-((S)-2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-hydroxypropyl)-1H-pyrazole-4-carbonitrile (47)

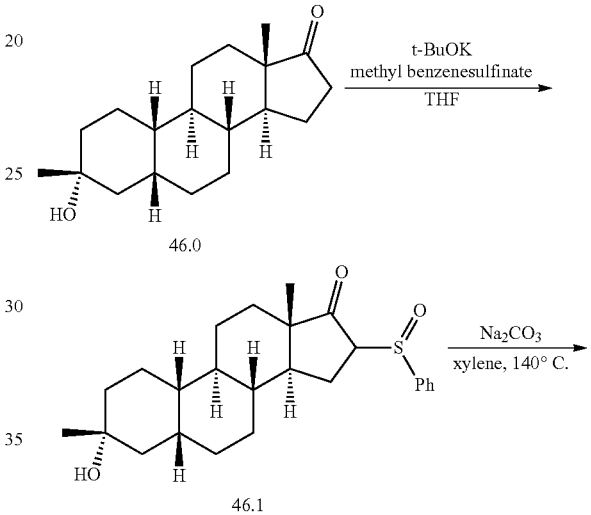

46.0

46.1

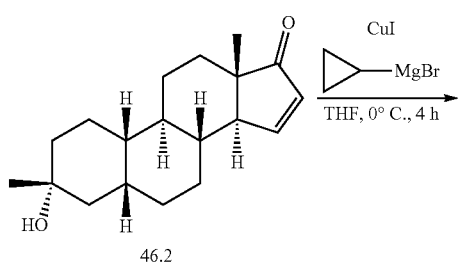

46.2

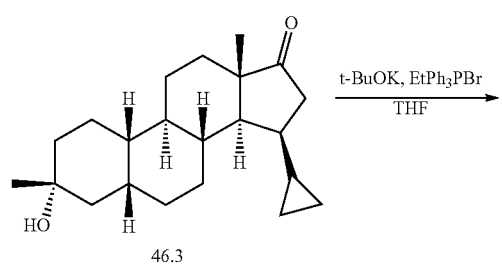

46.3

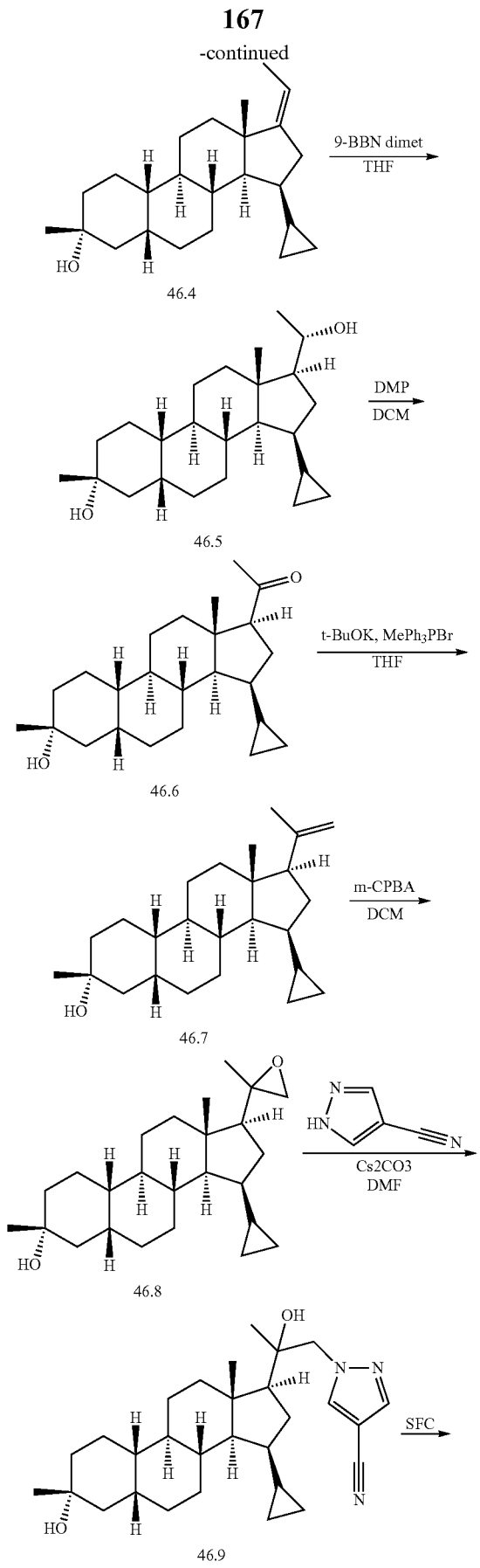

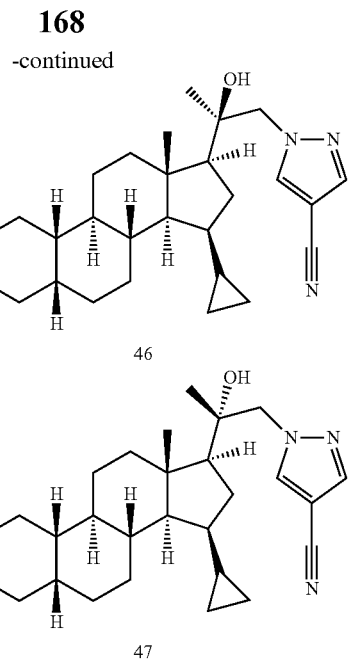

Synthesis of 46.1

To a solution of t-BuOK (6.17 g, 55.0 mmol) in THF (150 mL) was added 46.0 (8 g, 27.5 mmol) at 25° C. under $N_2$. After stirring at 25° C. for 10 min, methyl benzenesulfinate (8.59 g, 55.0 mmol) was added. After stirring at 30° C. for another 30 min, the mixture was quenched with $H_2O$(200 mL) and extracted with EtOAc (200×3 mL). The organic layer was dried over $Na_2SO_4$, filtered and concentrated in vacuum to give 46.1 (16 g). $^1$H NMR (400 MHz, $CDCl_3$) $\delta_H$ 7.74-7.44 (m, 8H), 3.53-3.44 (m, 1H), 3.26 (dd, J=8.2, 9.9 Hz, 1H), 2.41-2.35 (m, 1H), 1.81 (br s, 1H), 1.56-1.30 (m, 15H), 1.23-1.01 (m, 4H), 0.98 (s, 1H), 0.93 (s, 2H).

Synthesis of 46.2

To a mixture of 46.1 (16 g, 38.5 mmol) in xylene (200 mL) was added $Na_2CO_3$ (61.1 g, 577 mmol) in portions. After stirring at 140° C. under $N_2$ for 12 h, the mixture was filtered and concentrated. The residue was purified by flash column (0~15% of EtOAc in PE) to give 46.2 (4.3 g). $^1$H NMR (400 MHz, $CDCl_3$) $\delta_H$ 7.55-7.51 (m, 1H), 6.03 (dd, J=3.1, 5.9 Hz, 1H), 2.37 (br d, J=10.3 Hz, 1H), 1.85 (br s, 5H), 1.72 (br s, 2H), 1.62-1.34 (m, 9H), 1.33-1.23 (m, 6H), 1.08 (s, 3H).

Synthesis of 46.3

To a solution of bromo (cyclopropyl) magnesium (6.14 g, 84.6 ml, 42.3 mmol, 0.5 M in THF) in THF (150 mL) was added CuI (8.05 g, 42.3 mmol) at 0° C. under $N_2$. After stirring at 0° C. for 1 h, 46.2 (3.5 g, 12.1 mmol) was added. After stirring at 0° C. for another 3 h, the residue was poured into $NH_4Cl$ (50 mL) and extracted with EtOAc (3×50 mL). The combined organic phase was washed with brine (2×50 mL), dried over anhydrous $Na_2SO_4$, filtered, concentrated. The residue was purified by flash column (0~30% of EtOAc in PE) to give 46.3 (3.8 g). $^1$H NMR (400 MHz, $CDCl_3$) $\delta_H$ 2.47-2.39 (m, 1H), 2.38-2.27 (m, 1H), 1.96-1.69 (m, 8H), 1.63-1.48 (m, 6H), 1.45-1.43 (m, 1H), 1.40-1.31 (m, 3H), 1.30-1.27 (m, 4H), 1.26-1.18 (m, 1H), 1.11 (s, 4H), 0.95 (br d, J=8.3 Hz, 1H), 0.70-0.62 (m, 1H), 0.47 (s, 1H), 0.24-0.03 (m, 2H). LC-ELSD/MS purity 99%, MS ESI calcd. for $C_{22}H_{33}N_3O[M-H_2O+H]^+$ 313.3, found 313.3.

Synthesis of 46.4

To a mixture of EtPPh$_3$Br (20.6 g, 55.5 mmol) in THF (100 mL) was added t-BuOK (6.22 g, 55.5 mmol) at 25° C. under N$_2$. After stirring at 45° C. for 30 min, 46.3 (3.7 g, 11.1 mmol) was added below 45° C. After stirring at 45° C. for another 16 h, the reaction mixture was quenched with 10% NH$_4$Cl aqueous (40 mL) at 25° C. and extracted with EtOAc (2×30 mL). The combined organic phase was dried over Na$_2$SO$_4$, filtered, concentrated. The residue was purified by flash column (0~20% of EtOAc in PE) to give 46.4 (3.7 g). $^1$H NMR (400 MHz, CDCl$_3$) $\delta_H$ 5.18-5.07 (m, 1H), 2.46-2.36 (m, 1H), 2.31-2.15 (m, 2H), 1.84 (br d, J=6.8 Hz, 4H), 1.77-1.63 (m, 4H), 1.59-1.30 (m, 12H), 1.29-1.27 (m, 4H), 1.19-1.08 (m, 5H), 0.86-0.77 (m, 1H), 0.58-0.49 (m, 1H), 0.40-0.31 (m, 1H), 0.13-0.00 (m, 2H).

Synthesis of 46.5

To a solution of 46.4 (700 mg, 2.04 mmol) in anhydrous THF (15 mL) was added BH$_3$.Me$_2$S (1.01 ml, 10.2 mmol) at 25° C. under N$_2$. After stirring at 25° C. for 12 h, the resulting mixture was treated sequentially with ethanol (3.09 mL, 61.2 mmol) at 25° C., NaOH aqueous (12.2 mL, 5.0 M, 61.2 mmol) and H$_2$O$_2$ (6.13 mL, 30% in water, 61.2 mmol) dropwise at 0° C. After stirring at 50° C. for 1 h, the mixture was cooled, poured into Na$_2$S$_2$O$_3$ (50 mL, sat. aq.) and extracted with EtOAc (2×50 mL). The combined organic phase was washed with brine (30 mL), dried over anhydrous Na$_2$SO$_4$, filtered and concentrated in vacuum. The residue was purified by flash column (15~25% of EtOAc in PE) to give 46.5 (560 mg). $^1$H NMR (400 MHz, CDCl$_3$) $\delta_H$ 3.82-3.74 (m, 1H), 2.24 (td, J=9.2, 13.5 Hz, 1H), 2.02 (s, 1H), 1.85 (br d, J=6.5 Hz, 5H), 1.92-1.58 (m, 1H), 1.92-1.58 (m, 1H), 1.41 (br d, J=3.3 Hz, 9H), 1.28 (s, 5H), 1.24 (d, J=6.3 Hz, 4H), 1.18-1.01 (m, 4H), 0.92-0.78 (m, 4H), 0.57 (br dd, J=3.9, 7.7 Hz, 1H), 0.42-0.32 (m, 1H), 0.16-0.02 (m, 2H). LC-ELSD/MS purity 99%, MS ESI calcd. for $C_{24}H_{37}[M-2H_2O+H]^+$ 325.3, found 325.3.

Synthesis of 46.6

To a mixture of 46.5 (460 mg, 1.27 mmol) in DCM (30 mL) was added DMP (1.61 g, 3.81 mmol) in portions. After stirring at 20° C. for 30 min, the mixture was quenched with NaHCO$_3$(20 mL) and Na$_2$S$_2$O$_3$ (20 mL) and extracted with DCM (2×30 mL) The organic phase was washed with Na$_2$S$_2$O$_3$ (2×20 mL, sat.), brine (30 mL, sat), dried over Na$_2$SO$_4$, filtered and concentrated. The residue was purified by flash column (0~15% of EtOAc in PE) to give 46.6 (310 mg). $^1$H NMR (400 MHz, CDCl$_3$) $\delta_H$ 2.44 (dd, J=8.8, 10.5 Hz, 1H), 2.14 (s, 4H), 2.02-1.92 (m, 3H), 1.85 (br d, J=6.8 Hz, 2H), 1.76-1.65 (m, 2H), 1.38 (br s, 12H), 1.29 (s, 4H), 1.17-1.04 (m, 2H), 0.87-0.77 (m, 1H), 0.85 (s, 3H), 0.62-0.52 (m, 1H), 0.46-0.35 (m, 1H), 0.17-0.01 (m, 2H). LC-ELSD/MS purity 99%, MS ESI calcd. for $C_{24}H_{37}O[M-H_2O+H]^+$ 341.3, found 341.3.

Synthesis of 46.7

To a suspension of Ph$_3$PMeBr (3.08 g, 8.64 mmol) in THF (20 mL) was added t-BuOK (969 mg, 8.64 mmol) at 20° C. under N$_2$. After stirring for 30 min at 50° C., a solution of 46.6 (310 mg, 0.864 mmol) in TH (5 mL) was added dropwise to the resulting suspension. After stirring at 50° C. for 2 h under N$_2$, the reaction mixture was poured into 10% NH$_4$Cl (50 mL) and extracted with EtOAc (40 mL×3). The combined organic phase was washed with brine (40 mL), dried over anhydrous Na$_2$SO$_4$, filtered and concentrated. The residue was purified by flash column (0~10% of EtOAc in PE) to give 46.7 (300 mg). $^1$H NMR (400 MHz, CDCl$_3$) $\delta_H$ 4.86 (s, 1H), 4.74 (s, 1H), 2.03-1.79 (m, 7H), 1.78 (s, 3H), 1.76-1.60 (m, 3H), 1.51-1.27 (m, 13H), 1.23-0.98 (m, 4H), 0.78 (s, 4H), 0.58 (br s, 1H), 0.45-0.32 (m, 1H), 0.17-0.03 (m, 1H), 0.17-0.03 (m, 1H).

Synthesis of 46.8

To a solution of 46.7 (200 mg, 0.560 mmol) in DCM (20 mL) was added m-CPBA (223 mg, 1.11 mmol, 85%) at 0° C. After stirring at 0° C. for 1 h to give colorless suspension, the mixture was quenched with NaHCO$_3$ and Na$_2$S$_2$O$_3$ (40 mL, v:v=1:1, sat.) and extracted with DCM (2×40 mL). The combined organic phase was washed with NaHCO$_3$ and Na$_2$S$_2$O$_3$ (60 mL, v:v=1:1, sat.), dried over Na$_2$SO$_4$, filtered and concentrated to give 46.8 (250 mg). $^1$H NMR (400 MHz, CDCl$_3$) $\delta_H$ 3.01-2.62 (m, 1H), 2.59-2.30 (m, 1H), 2.03-1.60 (m, 3H), 1.51-1.34 (m, 12H), 1.33-1.24 (m, 10H), 1.16-1.04 (m, 3H), 1.01 (s, 1H), 0.95-0.72 (m, 4H), 0.61-0.51 (m, 1H), 0.41-0.30 (m, 1H), 0.14-0.06 (m, 3H).

Synthesis of 46.9

To solution of 46.8 (250 mg, 0.670 mmol) in DMF (5 mL) were added Cs$_2$CO$_3$ (655 mg, 2.01 mmol) and 1H-pyrazole-4-carbonitrile (155 mg, 1.67 mmol). After stirring at 130° C. for 12 h, the mixture was added into saturated NH$_4$Cl (50 mL) and extracted with EtOAc (3×20 mL). The combined organic layer was washed with LiCl (50 mL, 5% in water), brine (2×20 mL), dried over anhydrous Na$_2$SO$_4$, filtered, concentrated and purified by column (0~30% of EtOAc in PE) to afford 46.9 (300 mg).

Separation of 46 & 47

46.9 was separated by SFC (Column: DAICEL CHIRALCEL OD-H (250 mm*30 mm, 5 um); Condition: 0.1% NH$_3$H$_2$O ETOH; Begin B: 35%; End B: 35%) to afford 46 (24.4 mg, 7.82%, Rt=1.708 min) and 47 (83.7 mg, 26.8%, Rt=1.847 min).

46: $^1$H NMR (400 MHz, CDCl$_3$) $\delta_H$ 7.92 (s, 1H), 7.81 (s, 1H), 4.28-3.97 (m, 1H), 4.28-3.97 (m, 1H), 2.30 (s, 1H), 1.84 (br d, J=6.5 Hz, 7H), 1.76-1.60 (m, 2H), 1.40 (br d, J=4.8 Hz, 9H), 1.32-1.23 (m, 6H), 1.22-1.16 (m, 1H), 1.09 (d, J=1.5 Hz, 8H), 0.90-0.78 (m, 1H), 0.65-0.55 (m, 1H), 0.46-0.36 (m, 1H), 0.19-0.02 (m, 2H). LC-ELSD/MS purity 99%, MS ESI calcd. for $C_{29}H_{40}N_3$ $[M-2H_2O+H]^+$ 430.3, found 430.3. SFC 100% de 47: $^1$H NMR (400 MHz, CDCl$_3$) $\delta_H$ 7.94 (s, 1H), 7.83 (s, 1H), 4.37-4.06 (m, 2H), 2.59 (s, 1H), 2.01 (br d, J=12.0 Hz, 3H), 1.84 (br d, J=6.8 Hz, 6H), 1.52-1.33 (m, 8H), 1.32-1.14 (m, 9H), 1.12 (s, 3H), 1.03 (s, 4H), 0.89-0.79 (m, 1H), 0.64-0.55 (m, 1H), 0.46-0.35 (m, 1H), 0.19-0.03 (m, 2H). LC-ELSD/MS purity 99%, MS ESI calcd. for $C_{29}H_{40}N_3$ $[M-2H_2O+H]^+$ 430.3, found 430.3. SFC 99% de.

Example 48 & 49: Synthesis of 1-((S)-2-hydroxy-2-((3R,5R,8R,9R,10S,13S,14S,15R,17S)-3-hydroxy-3,13,15-trimethylhexadecahydro-1H-cyclopenta[a]phenanthren-17-yl)propyl)-1H-pyrazole-4-carbonitrile (48) & 1-((R)-2-hydroxy-2-((3R,5R,8R,9R,10S,13S,14S,15R,17S)-3-hydroxy-3,13,15-trimethylhexadecahydro-1H-cyclopenta[a]phenanthren-17-yl)propyl)-1H-pyrazole-4-carbonitrile (49)

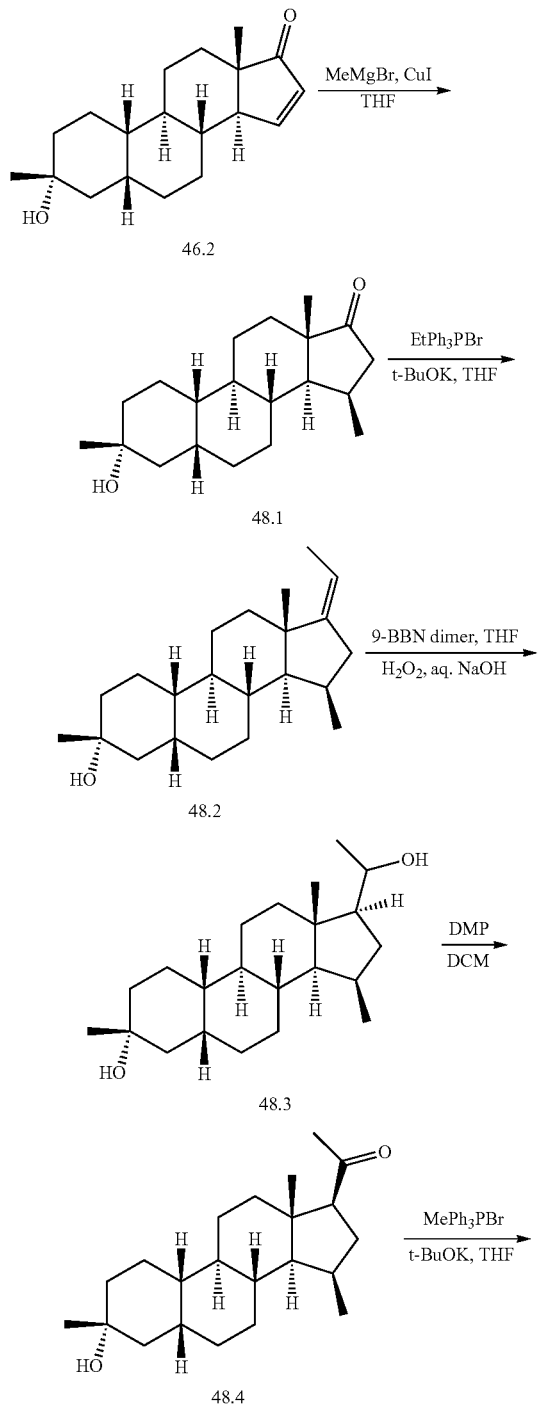

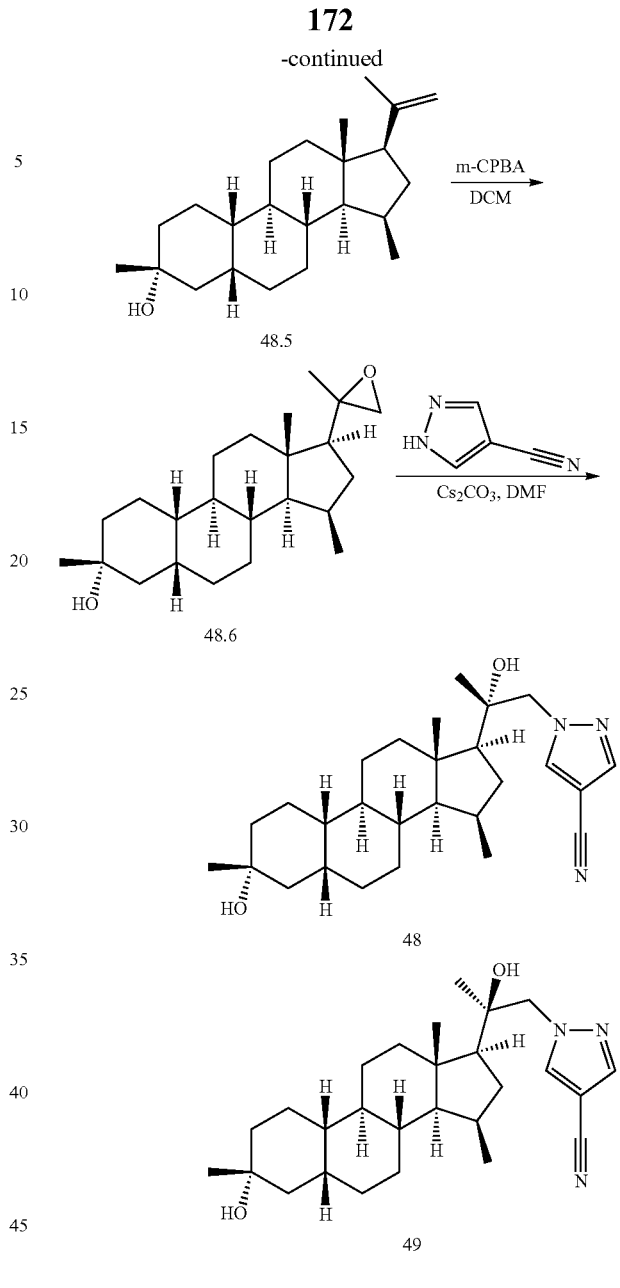

Synthesis of 48.1

To a solution of MeMgBr (2.3 mL, 6.92 mmol, 3M) in THF (10 mL) was added CuI (988 mg, 5.19 mmol) at 0° C. After stirring at 0° C. for 1 h, 46.2 (500 mg, 1.73 mmol) in THF (5 mL) was added at 0° C. After stirring at 0° C. for 3 h, the mixture was poured into saturated NH$_4$Cl (20 mL) and extracted with EtOAc (3×30 mL). The combined organic layer was washed with brine (20 mL), dried over anhydrous Na$_2$SO$_4$, filtered and concentrated. The residue was purified by flash column (10%25% of EtOAc in PE) to give 48.1 (360 mg, 68.4%, 35.2 mg). $^1$H NMR (400 MHz, CDCl$_3$) $\delta_H$ 2.51-2.39 (m, 2H), 2.29-2.19 (m, 1H), 1.91-1.80 (m, 3H), 1.78-1.62 (m, 4.5H), 1.53-1.46 (m, 2.5H), 1.44-1.31 (m, 7H), 1.28 (s, 5H), 1.24-1.20 (m, 1H), 1.10 (d, J=7.6 Hz, 3H), 1.03 (s, 3H). LC-ELSD/MS purity 99%, MS ESI calcd. for C$_{20}$H$_{31}$O [M−H$_2$O+H]$^+$ 287.2, found 287.2.

Synthesis of 48.2

To a mixture of EtPPh$_3$Br (18.2 g, 49.2 mmol) in THF (40 mL) was added t-BuOK (5.52 g, 49.2 mmol) at 20° C. under N$_2$. After stirring at 40° C. for 30 min, 48.1 (2.5 g, 8.21 mmol) in THF (30 mL) was added in portions below 40° C. After stirring at 40° C. for 16 h, the reaction mixture was quenched with 10% NH$_4$Cl aqueous (200 mL) at 15° C. and extracted with EtOAc (3×200 mL). The combined organic phase was washed with brine (2×150 mL), filtered, concentrated under vacuum. The residue was purified by flash column (0~30% ethyl acetate in PE) to give 48.2 (3.1 g). $^1$H NMR (400 MHz, CDCl$_3$) $\delta_H$ 5.18-5.07 (m, 1H), 2.63-2.50 (m, 1H), 2.33-2.23 (m, 3H), 2.22-2.06 (m, 3H), 1.91-1.79 (m, 3H), 1.66 (s, 7H), 1.61-1.31 (m, 11H), 1.25-1.13 (m, 7H), 1.09 (s, 3H), 0.93 (m, 3H).

Synthesis of 48.3

To a solution of 48.2 (2.6 g, 8.21 mmol) in anhydrous THF (30 mL) was added 9-BBN dimer (4.00 g, 16.4 mmol) at 25° C. under N$_2$. After stirring at 40° C. for 16 h, to the resulting mixture was added ethanol (4.53 g, 98.5 mmol) at 25° C., followed by NaOH aqueous (19.7 mL, 5.0 M, 98.5 mmol) and H$_2$O$_2$ (9.85 mL, 10 M, 98.5 mmol) dropwise at 0° C. After stirring at 80° C. for 1 h, the mixture was cooled, poured into Na$_2$S$_2$O$_3$ (100 mL, sat. aq.) and extracted with EtOAc (2×150 mL). The organic phase was washed with brine (2×100 mL), dried over anhydrous Na$_2$SO$_4$, filtered and concentrated in vacuum. The residue was purified by flash column (15~40% EtOAc in PE) to give 48.3 (2.6 g, 94.8%) $^1$H NMR (400 MHz, CDCl$_3$) $\delta_H$ 3.86-3.65 (m, 1H), 2.38-2.26 (m, 1H), 2.20-2.07 (m, 1H), 1.91-1.52 (m, 11H), 1.50-1.37 (m, 6H), 1.29-1.24 (m, 8H), 1.19-0.98 (m, 5H), 0.93 (m, 3H), 0.82 (s, 3H).

Synthesis of 48.4

To a solution of 48.3 (2.6 g, 7.77 mmol) in DCM (30 mL) was added Dess-martin (6.57 g, 15.5 mmol) at 25° C. After stirring at 25° C. for 10 min, the mixture was quenched with saturated NaHCO$_3$ aqueous (100 mL) at 10° C. The DCM phase was separated and washed with saturated NaHCO$_3$/Na$_2$S$_2$O$_3$ aqueous (1:1, 3×100 mL), brine (2×50 mL), dried over Na$_2$SO$_4$, filtered and concentrated under vacuum. The residue was purified by flash column (0~30% of EtOAc in PE) to give 48.4 (1 g, 38.7%). $^1$H NMR (400 MHz, CDCl$_3$) $\delta_H$ 2.49 (dd, J=8.8, 10.8 Hz, 1H), 2.22-2.13 (m, 1H), 2.11 (s, 3H), 2.09-2.00 (m, 1H), 1.97-1.79 (m, 5H), 1.75-1.59 (m, 3H), 1.51-1.29 (m, 9H), 1.28 (s, 4H), 1.25-0.99 (m, 3H), 0.96 (d, J=7.2 Hz, 3H), 0.78 (s, 3H). LC-ELSD/MS purity: 99%, MS ESI calcd. for C$_{22}$H$_{36}$O$_2$ [M–H$_2$O+H]$^+$ 315.3, found C$_{22}$H$_{36}$O$_2$ [M–H$_2$O+H]$^+$ 315.2.

Synthesis of 48.5

To a mixture of MePPh$_3$Br (2.24 g, 6.30 mmol) in THF (27 mL) was added t-BuOK (706 mg, 6.30 mmol) at 20° C. under N$_2$. After stirring at 50° C. for 30 min, 48.4 (700 mg, 2.10 mmol) in THF (3 mL) was added in portions below 50° C. After stirring at 50° C. for 16 h, the reaction mixture was quenched with 10% NH$_4$Cl aqueous (20 mL) at 15° C. and extracted with EtOAc (3×20 mL). The combined organic phase was washed with brine (2×20 mL), dried over anhydrous Na$_2$SO$_4$, filtered and concentrated under vacuum. The residue was purified by flash column (0~20% of ethyl acetate in PE) to give 48.5 (620 mg, 89.3%). $^1$H NMR (400 MHz, CDCl$_3$) $\delta_H$ 4.84 (s, 1H), 4.71 (s, 1H), 2.16-1.95 (m, 3H), 1.91-1.77 (m, 4H), 1.76 (s, 3H), 1.69-1.58 (m, 3H), 1.49-1.39 (m, 5H), 1.37-1.28 (m, 4H), 1.27 (s, 4H), 1.24-0.99 (m, 6H), 0.95 (d, J=7.2 Hz, 3H), 0.91-0.82 (m, 2H), 0.72 (s, 3H).

Synthesis of 48.6

To a solution of 48.5 (200 mg, 0.6050 mmol) in DCM (3 ml) was added m-CPBA (194 mg, 0.9074 mmol). After stirring at 20° C. for 20 min, saturated aqueous NaHCO$_3$ (30 mL) and Na$_2$S$_3$O$_3$ (30 mL) were added. After stirring for another 5 min, the aqueous phase was extracted with DCM (3×30 mL). The combined organic phase was washed with brine (20 mL), dried over anhydrous Na$_2$SO$_4$, filtered and concentrated to give 48.6 (240 mg). $^1$H NMR (400 MHz, CDCl$_3$) $\delta_H$ 2.91 (d, J=4.4 Hz, 1H), 2.54 (d, J=4.4 Hz, 1H), 1.76-2.16 (m, 10H), 1.51-1.73 (m, 11H), 1.39-1.49 (m, 6H), 1.34-1.37 (m, 4H), 1.27 (s, 5H), 1.00-1.24 (m, 8H), 0.95 (s, 1H), 0.94-0.96 (m, 1H), 0.88-0.93 (m, 5H), 0.85 (s, 3H).

Synthesis of 48 & 49

To a solution of 48.6 (340 mg, 0.9810 mmol) in DMF (5 mL) were added 1H-pyrazole-4-carbonitrile (273 mg, 2.94 mmol) and Cs$_2$CO$_3$ (963 mg, 2.94 mmol) at 25° C. After stirring at 120° C. for 16 h, the mixture was added water (20 mL) and extracted with EtOAc (120 mL). The combined organic solution was washed with brine (70 mL), dried over anhydrous Na$_2$SO$_4$, filtered, concentrated in vacuum. The residue was purified by column (0%-55% of EtOAc in PE) to give a mixture of diastereomers, which was separated by SFC (column: DAICEL CHIRALPAK AS (250 mm*30 mm, 10 um); Mobile phase: A: CO$_2$ B: 0.1% NH$_3$H$_2$O ETOH; gradient: from 25% to 25% of B, Flow Rate (ml/min): 70) to give 48 (158.2 mg, 93%) and 49 (73.8 mg, 43%).

48: $^1$H NMR (400 MHz, CDCl$_3$) $\delta_H$ 7.92 (s, 1H), 7.82 (s, 1H), 4.44-3.93 (m, 2H), 2.54 (s, 1H), 2.25-2.07 (m, 2H), 2.00-1.92 (m, 1H), 1.90-1.77 (m, 3H), 1.74-1.56 (m, 3H), 1.54-1.29 (m, 9H), 1.27 (s, 4H), 1.26-1.25 (m, 1H), 1.25-1.09 (m, 4H), 1.06 (s, 4H), 1.00 (s, 3H), 0.96 (d, J=6.8 Hz, 3H). LC-ELSD/MS purity: 99%, MS ESI calcd. for C$_{27}$H$_{41}$N$_3$O$_2$ [M–2H$_2$O+H]$^+$ 404.3, found C$_{27}$H$_{41}$N$_3$O$_2$ [M–2H$_2$O+H]$^+$ 404.3.

49: $^1$H NMR (400 MHz, CDCl$_3$) $\delta_H$ 7.89 (s, 1H), 7.80 (s, 1H), 4.28-3.96 (m, 2H), 2.27 (s, 1H), 2.22-1.96 (m, 3H), 1.91-1.78 (m, 3H), 1.75-1.56 (m, 4H), 1.53-1.30 (m, 8H), 1.27 (s, 4H), 1.26-1.10 (m, 4H), 1.07 (s, 4H), 1.03 (s, 3H), 0.97 (d, J=6.4 Hz, 3H) LC-ELSD/MS purity: 99%, MS ESI calcd. for C$_{27}$H$_{41}$N$_3$O$_2$ [M–2H$_2$O+H]$^+$ 404.3, found C$_{27}$H$_{41}$N$_3$O$_2$ [M–2H$_2$O+H]$^+$ 404.3.

Example 50 & 51: Synthesis of 1-((S)-2-hydroxy-2-((2S,3S,5R,8R,9R,10S,13S,14S,17S)-3-hydroxy-2,3,13-trimethylhexadecahydro-1H-cyclopenta[a]phenanthren-17-yl)propyl)-1H-pyrazole-4-carbonitrile (50) & 1-((R)-2-hydroxy-2-((2S,3S,5R,8R,9R,10S,13S,14S,17S)-3-hydroxy-2,3,13-trimethylhexadecahydro-1H-cyclopenta[a]phenanthren-17-yl)propyl)-1H-pyrazole-4-carbonitrile (51)

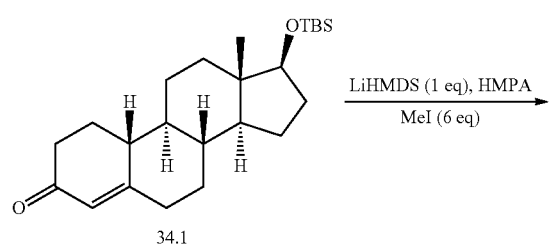
34.1 → LiHMDS (1 eq), HMPA / MeI (6 eq)

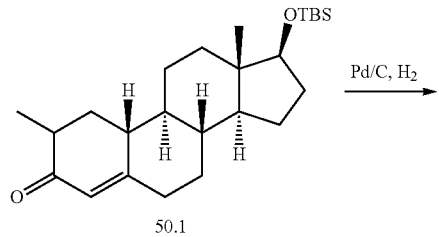
50.1 → Pd/C, H₂

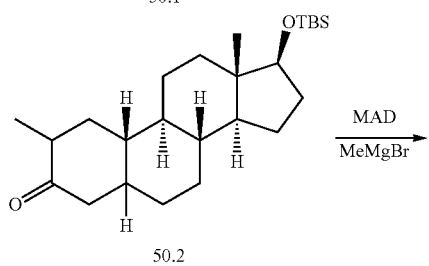
50.2 → MAD / MeMgBr 50.3 → TBAF

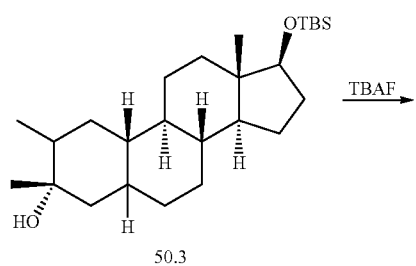
50.3

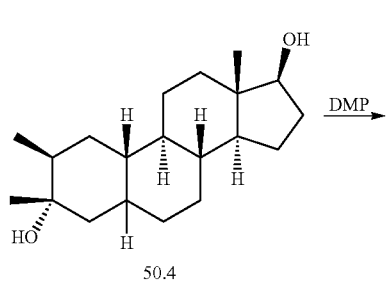
50.4 → DMP

-continued

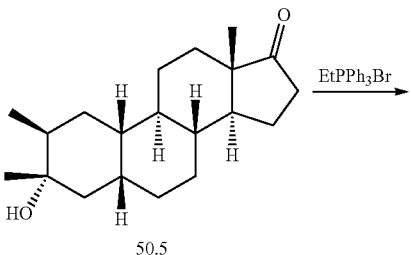
50.5 → EtPPh₃Br

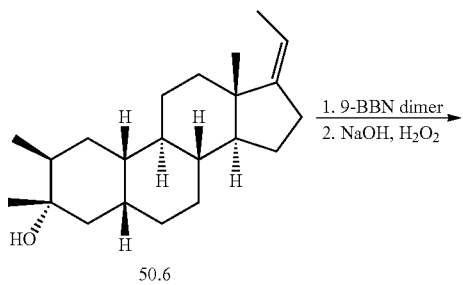
50.6 → 1. 9-BBN dimer  2. NaOH, H₂O₂

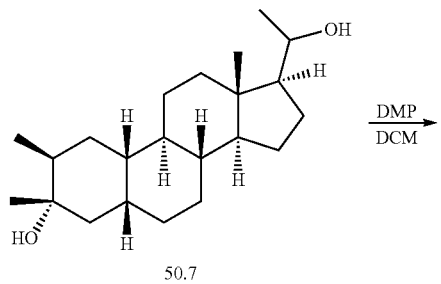
50.7 → DMP / DCM

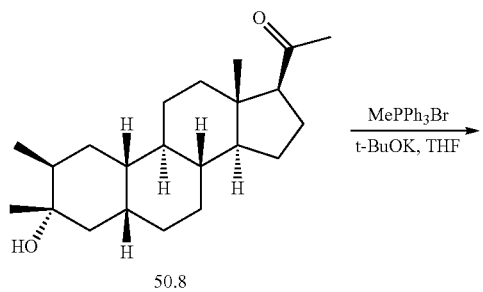
50.8 → MePPh₃Br / t-BuOK, THF

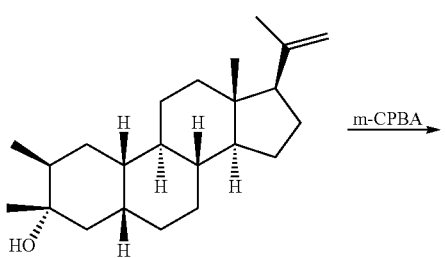
50.9 → m-CPBA

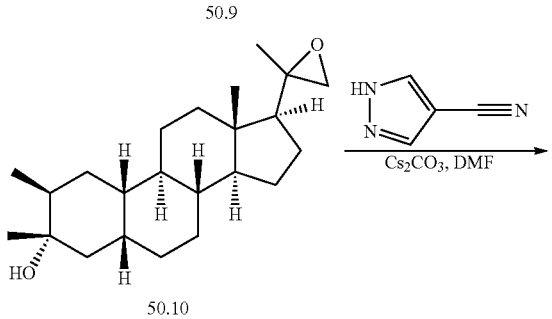
50.10 → Cs₂CO₃, DMF

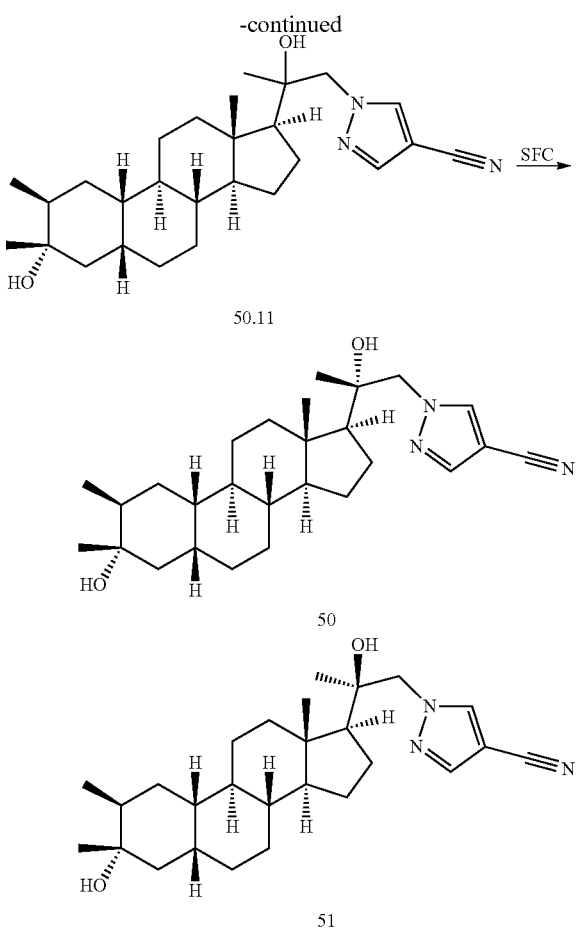

Synthesis of 50.1

To a solution of 34.1 (50 g, 128 mmol) in TH (300 mL) was added LiMDS (115 mL, 1 M in THF, 115 mL) at −70° C. under N₂. After stirring at −70° C. for 1 h, HMPA (27.4 g, 153 mmol) was added. After stirring at −70° C. for 30 minutes, MeI (109 g, 768 mmol) was added. After stirring at 25° C. for 1 h, the mixture was quenched with NH₄Cl (200 mL, sat.) and extracted with EtOAc (300 mL). The combined organic layer was separated, dried over Na₂SO₄, filtered and concentrated. The residue was purified by flash column (0-3% of EtOAc in PE) to give 50.1 (6 g, 11.6%). ¹H NMR (400 MHz, CDCl₃) δ$_H$ 5.73 (s, 1H), 3.57 (t, J=8.4 Hz, 1H), 2.47-2.34 (m, 2H), 2.29-2.19 (m, 1H), 2.17-2.09 (m, 1H), 1.99-1.74 (m, 5H), 1.58-1.40 (m, 2H), 1.35-1.25 (m, 4H), 1.10 (d, J=7.2 Hz, 3H), 1.05-0.91 (m, 4H), 0.88 (s, 9H), 0.76 (s, 3H), 0.01 (d, J=2.8 Hz, 6H).

Synthesis of 50.2

To a mixture of 50.1 (16 g, 2.48 mmol) in pyridine (200 mL) was added Pd/C (2 g, 10%). After hydrogenating under 15 psi of hydrogen at 25° C. for 24 h, the reaction mixture was filtered through a pad of Celite and washed with pyridine (3×150 mL). The filtrate was concentrated and washed with 1M HCl (200 mL). The aqueous phase was extracted with EtOAc (2×150 mL). The combined organic phase was washed with brine (20 mL), dried over anhydrous Na₂SO₄, filtered and concentrated to give 50.2 (16 g). ¹H NMR (400 MHz, CDCl₃) δ$_H$ 3.58 (t, J=8.8 Hz, 1H), 2.66-2.57 (m, 1H), 2.38-2.30 (m, 1H), 2.22-2.14 (m, 2H), 2.09-2.04 (m, 1H), 1.94-1.84 (m, 1H), 1.82-1.77 (m, 1H), 1.76-1.63 (m, 2H), 1.53-1.13 (m, 9H), 1.13-0.99 (m, 4H), 0.97 (d, J=6.8 Hz, 3H), 0.88 (s, 9H), 0.74 (s, 3H), 0.01 (d, J=2.8 Hz, 6H).

Synthesis of 50.3

To a solution of BHT (30 g, 136 mmol) in toluene (150 mL) under nitrogen at −70° C. in three-necked flask (1000 mL) was added trimethylaluminum (34 mL, 2 M in toluene, 68 mmol) dropwise. After stirring at −70° C. for 1 h, to the MAD (56.7 g in toluene, 118 mmol) solution was added a solution of 50.2 (16 g, 39.5 mmol) in toluene (100 mL) and DCM (100 mL) dropwise at −70° C. under N₂. After stirring at −70° C. for 1 h, MeMgBr (39.3 mL, 3M, 118 mmol) was added dropwise at −70° C. After stirring for 2 h, the reaction mixture was poured slowly into saturated aqueous citric acid (500 mL) at 10° C. The aqueous phase was extracted with DCM (2×400 mL). The combined organic phase was washed with brine (300 mL), dried over anhydrous Na₂SO₄, filtered, and concentrated. The residue was purified by flash column (0-2% of EtOAc in PE) to give 50.3 (7.87 g, 44.7%). ¹H NMR (400 MHz, CDCl₃) δ$_H$ 3.55 (t, J=8.0 Hz, 1H), 1.92-1.79 (m, 3H), 1.77-1.71 (m, 2H), 1.68-1.63 (m, 1H), 1.62-1.58 (m, 1H), 1.53-1.48 (m, 1H), 1.47-1.36 (m, 4H), 1.30-1.23 (m, 5H), 1.10 (s, 3H), 1.07-0.95 (m, 6H), 0.87 (s, 9H), 0.86-0.84 (m, 3H), 0.69 (s, 3H), 0.00 (d, J=2.4 Hz, 6H).

Synthesis of 50.4

To a solution of 50.3 (12.25 g, 30.1 mmol) in THF (150 mL) was added TBAF (3.93 g, 120 mmol). After stirring at 80° C. for 3 h, the mixture was poured into water (200 mL) and extracted with EtOAc (2×200 mL). The combined organic phase was washed with brine (200 mL), dried over anhydrous Na₂SO₄, filtered, and concentrated. The residue was purified by flash column (0~15% of EtOAc in PE) to give 50.4 (8 g, 91.5%). ¹H NMR (400 MHz, CDCl₃) δ$_H$ 3.64 (t, J=8.0 Hz, 1H), 2.10-2.02 (m, 1H), 1.83-1.68 (m, 3H), 1.51-1.45 (m, 2H), 1.44-1.36 (m, 4H), 1.32-1.23 (m, 7H), 1.10 (s, 3H), 1.08-1.02 (m, 5H), 0.86 (d, J=6.8 Hz, 5H), 0.74 (s, 3H).

Synthesis of 50.5

To a solution of 50.4 (6.2 g, 20.2 mmol) in DCM (100 mL) was added DMP (17.1 g, 40.4 mmol) at 25° C. under N₂. After stirring at 25° C. for 2 h, the mixture was quenched with NaHCO₃/NaS₂SO₃ (v:v=1:1) (200 mL) and extracted with DCM (2×100 mL). The combined organic phase was washed with brine (100 mL), dried over anhydrous Na₂SO₄, filtered, and concentrated. The residue was purified by flash column (0~10%-20% of EtOAc in PE) to give 50.5 (5.9 g, 95.9%). ¹H NMR (400 MHz, CDCl₃) δ$_H$ 2.44 (dd, J=8.4, 19.6 Hz, 1H), 2.13-2.03 (m, 1H), 1.97-1.89 (m, 1H), 1.84-1.71 (m, 4H), 1.69-1.61 (m, 1H), 1.53-1.40 (m, 3H), 1.38-1.24 (m, 7H), 1.23-1.15 (m, 2H), 1.11 (s, 3H), 0.90-0.83 (m, 9H).

Synthesis of 50.6

To a solution EtPPh₃Br (21.4 g, 57.9 mmol) in THF (50 mL) was added t-BuOK (6.49 g, 57.9 mmol) at 25° C. under N₂. After stirring at 25° C. for 30 min, 50.5 (5.9 g, 19.3 mmol) in THF (50 mL) was added. After stirring at 45° C.

for 16 h, the mixture was poured into NH₄Cl (100 mL) and extracted with EtOAc (2×150 mL). The combined organic phase was washed with brine (100 mL), dried over anhydrous Na$_2$SO$_4$, filtered and concentrated. The residue was purified by flash column (0~8% of EtOAc in PE) to give 50.6 (7 g). $^1$H NMR (400 MHz, CDCl$_3$) $\delta_H$ 5.15-5.07 (m, 1H), 2.41-2.31 (m, 1H), 2.28-2.13 (m, 2H), 1.84-1.80 (m, 2H), 1.78-1.68 (m, 3H), 1.67-1.62 (m, 4H), 1.55-1.50 (m, 2H), 1.49-1.45 (m, 1H), 1.42 (s, 1H), 1.40-1.29 (m, 3H), 1.26 (t, J=7.2 Hz, 3H), 1.21-1.14 (m, 2H), 1.10 (s, 3H), 1.09-1.06 (m, 2H), 0.87-0.85 (m, 6H).

Synthesis of 50.7

To a solution of 50.6 (7 g, 22.1 mmol) in THF (100 mL) was added 9-BBN dimer (10.6 g, 44.2 mmol) under N$_2$. After stirring at 40° C. for 1 h, the mixture was cooled to room temperature, and sequentially treated with EtOH (12.6 mL, 221 mmol) and NaOH (44.2 mL, 5M, 221 mmol). H$_2$O$_2$ (22.1 mL, 10M, 221 mmol) was then added very slowly, keeping the inner temperature below 15° C. After diluting with saturated aqueous Na$_2$S$_2$O$_3$ (150 mL), the mixture was stirred at 25° C. for 1 h. The reaction was checked by potassium iodide-starch test paper to confirm excess H$_2$O$_2$ was destroyed. The reaction mixture was filtered to give 50.7 (12.3 g). $^1$H NMR (400 MHz, CDCl$_3$) $\delta_H$ 3.75-3.65 (m, 1H), 1.95-1.80 (m, 4H), 1.76-1.70 (m, 1H), 1.66-1.60 (m, 3H), 1.58-1.45 (m, 4H), 1.43-1.32 (m, 3H), 1.30 (s, 2H), 1.24-1.21 (m, 4H), 1.16-1.11 (m, 2H), 1.10 (s, 4H), 1.08-0.96 (m, 4H), 0.86 (d, J=6.8 Hz, 3H), 0.66 (s, 3H).

Synthesis of 50.8

To a solution of 50.7 (12.3 g, 36.7 mmol) in DCM (200 mL) was added DMP (46.6 g, 110 mmol) in portions. After stirring at 25° C. for 3 h, the mixture was poured into NaS$_2$SO$_3$/NaHCO$_3$ (v:v, 1:1, 1000 mL) and extracted with DCM (2×500 mL). The combined organic phase was washed with brine (200 mL), dried over anhydrous Na$_2$SO$_4$, filtered and concentrated to give 50.8 (4.6 g, 37.7%). $^1$H NMR (400 MHz, CDCl$_3$) $\delta_H$ 2.53 (t, J=9.2 Hz, 1H), 2.20-2.12 (m, 1H), 2.11 (s, 3H), 2.04-1.97 (m, 1H), 1.82 (d, J=6.4 Hz, 2H), 1.76-1.68 (m, 2H), 1.67-1.52 (m, 6H), 1.44-1.37 (m, 3H), 1.36-1.28 (m, 2H), 1.26-1.13 (m, 3H), 1.11 (s, 3H), 1.09-1.01 (m, 3H), 0.87 (d, J=6.8 Hz, 3H), 0.61 (s, 3H).

Synthesis of 50.9

To a solution of MePPh$_3$Br (14.7 g, 41.4 mmol) in THF (30 mL) was added t-BuOK (4.64 g, 41.4 mmol) at 25° C. under N$_2$. After stirring at 25° C. for 1 h, a solution of 50.8 (4.6 g, 13.8 mmol) in THF (20 mL) was added. After stirring at 40° C. for 2 h, the reaction was poured into water (20 mL) and extracted with EtOAc (2×50 mL). The combined organic phase was washed with brine (20 mL), dried over anhydrous Na$_2$SO$_4$, filtered and concentrated. The residue was purified by flash column (0~10% of EtOAc in PE) to give 50.9 (2.7 g, 39.9%). $^1$H NMR (400 MHz, CDCl$_3$) $\delta_H$ 4.84 (s, 1H), 4.70 (s, 1H), 2.07-1.99 (m, 1H), 1.88-1.80 (m, 3H), 1.75 (s, 4H), 1.73-1.48 (m, 8H), 1.47-1.13 (m, 8H), 1.11-1.09 (m, 3H), 1.07-0.98 (m, 3H), 0.86 (d, J=6.8 Hz, 3H), 0.57 (s, 3H).

Synthesis of 50.10

To a solution of 50.9 (250 mg, 0.7563 mmol) in DCM (5 mL) was added m-CPBA (260 mg, 1.51 mmol) at 25° C. After stirring at 25° C. for 1 h, the mixture was poured into water (20 mL) and extracted with DCM (2×20 mL). The combined organic phase was washed with NaHCO$_3$/NaS$_2$SO$_3$ (1:1) (2×20 mL), dried over anhydrous Na$_2$SO$_4$, filtered and concentrated. The residue was purified by flash column (5%15% of EtOAc in PE) to give 50.10 (290 mg). $^1$H NMR (400 MHz, CDCl$_3$) $\delta_H$ 2.88 (d, J=4.8 Hz, 1H), 2.55 (d, J=4.0 Hz, 1H), 2.49 (d, J=4.8 Hz, 0.5H), 2.32 (d, J=4.8 Hz, 0.5H), 1.96-1.85 (m, 2H), 1.76-1.61 (m, 5H), 1.51-1.45 (m, 2H), 1.35 (s, 3H), 1.31-1.24 (m, 4H), 1.23-1.13 (m, 3H), 1.10 (s, 4H), 1.08-1.01 (m, 5H), 0.86 (d, J=6.8 Hz, 4H), 0.68 (s, 3H).

Synthesis of 50.11

To a solution of 50.10 (290 mg, 0.8368 mmol) in DMF (5 mL) were added 1H-pyrazole-4-carbonitrile (155 mg, 1.67 mmol) and Cs$_2$CO$_3$ (817 mg, 2.51 mmol) at 20° C. under N$_2$. After stirring at 130° C. for 16 h, the mixture was poured into saturated H$_2$O (10 mL) and extracted with EtOAc (2×20 mL). The combined organic layer was washed with brine (20 mL), dried over anhydrous Na$_2$SO$_4$, filtered, and concentrated. The residue was purified by flash column (0~20% of EtOAc in PE) to give 50.11 (250 mg, 68.1%). $^1$H NMR (400 MHz, CDCl$_3$) $\delta_H$ 7.93 (s, 1H), 7.82 (s, 1H), 4.35 (d, J=14.0 Hz, 1H), 4.08 (d, J=13.6 Hz, 1H), 2.51 (s, 1H), 2.04-1.98 (m, 1H), 1.83-1.79 (m, 2H), 1.78-1.60 (m, 3H), 1.53-1.45 (m, 3H), 1.44-1.35 (m, 4H), 1.33-1.24 (m, 3H), 1.22-1.13 (m, 3H), 1.10 (s, 4H), 1.09-1.03 (m, 1H), 0.97 (s, 3H), 0.91 (s, 3H), 0.86 (d, J=6.4 Hz, 6H).

Separation of 50 & 51

50.11 (250 mg, 0.5686 mmol) was separated by SFC (Column: DAICEL CHIRALPAK AD 250 mm×30 mm, 10 um; Condition: 0.1% NH$_3$H$_2$O ETOH; Gradient: from 45% to 45% of B; Flow rate: 80 mL/min; Column temperature: 40° C.) and then further purified by HPLC (Column: Phenomenex Gemini-NX 80 mm×40 mm, 3 um; Condition: water(0.05% NH$_3$H$_2$O+10 mM NH$_4$HCO$_3$)-ACN); Gradient: from 57% to 87% of B in 8 min and hold 100% for 1.4 min; Flow rate: 30 mL/min) to afford 51 (10.3 mg, 10.3%) and 50 (76.3 mg, 30.6%).

50: $^1$H NMR (400 MHz, CDCl$_3$) $\delta_H$ 7.93 (s, 1H), 7.82 (s, 1H), 4.35 (d, J=13.2 Hz, 1H), 4.08 (d, J=14.0 Hz, 1H), 2.50 (s, 1H), 2.04-1.98 (m, 1H), 1.84-1.79 (m, 2H), 1.77-1.60 (m, 6H), 1.52-1.35 (m, 5H), 1.31-1.17 (m, 5H), 1.10 (s, 4H), 1.09-1.03 (m, 4H), 0.97 (s, 3H), 0.91 (s, 3H), 0.86 (d, J=6.8 Hz, 3H). LC-ELSD/MS purity 99%, MS ESI calcd. for C$_{27}$H$_{38}$N$_3$ [M−2H$_2$O+H]$^+$ 404.3, found 404.3. SFC 99% de.

51: $^1$H NMR (400 MHz, CDCl$_3$) $\delta_H$ 7.89 (s, 1H), 7.80 (s, 1H), 4.19-4.13 (m, 1H), 4.04-3.98 (m, 1H), 2.30 (s, 1H), 2.09-2.02 (m, 1H), 1.96-1.86 (m, 1H), 1.84-1.79 (m, 2H), 1.75-1.61 (m, 5H), 1.53-1.45 (m, 3H), 1.43-1.35 (m, 2H), 1.32-1.14 (m, 5H), 1.11-1.03 (m, 11H), 0.88-0.85 (m, 6H). LC-ELSD/MS purity 99%, MS ESI calcd. for C$_{27}$H$_{38}$N$_3$ [M−2H$_2$O+H]$^+$ 404.3, found 404.3 SFC 100% de.

Examples 52 & 53: Synthesis of 1-((S)-2-hydroxy-2-((2R,3S,5R,8R,9R,10S,13S,14S,17S)-3-hydroxy-2,3,13-trimethylhexadecahydro-1H-cyclopenta[a]phenanthren-17-yl)propyl)-1H-pyrazole-4-carbonitrile (52) & 1-((R)-2-hydroxy-2-((2R,3S,5R,8R,9R,10S,13S,14S,17S)-3-hydroxy-2,3,13-trimethylhexadecahydro-1H-cyclopenta[a]phenanthren-17-yl)propyl)-1H-pyrazole-4-carbonitrile (53)
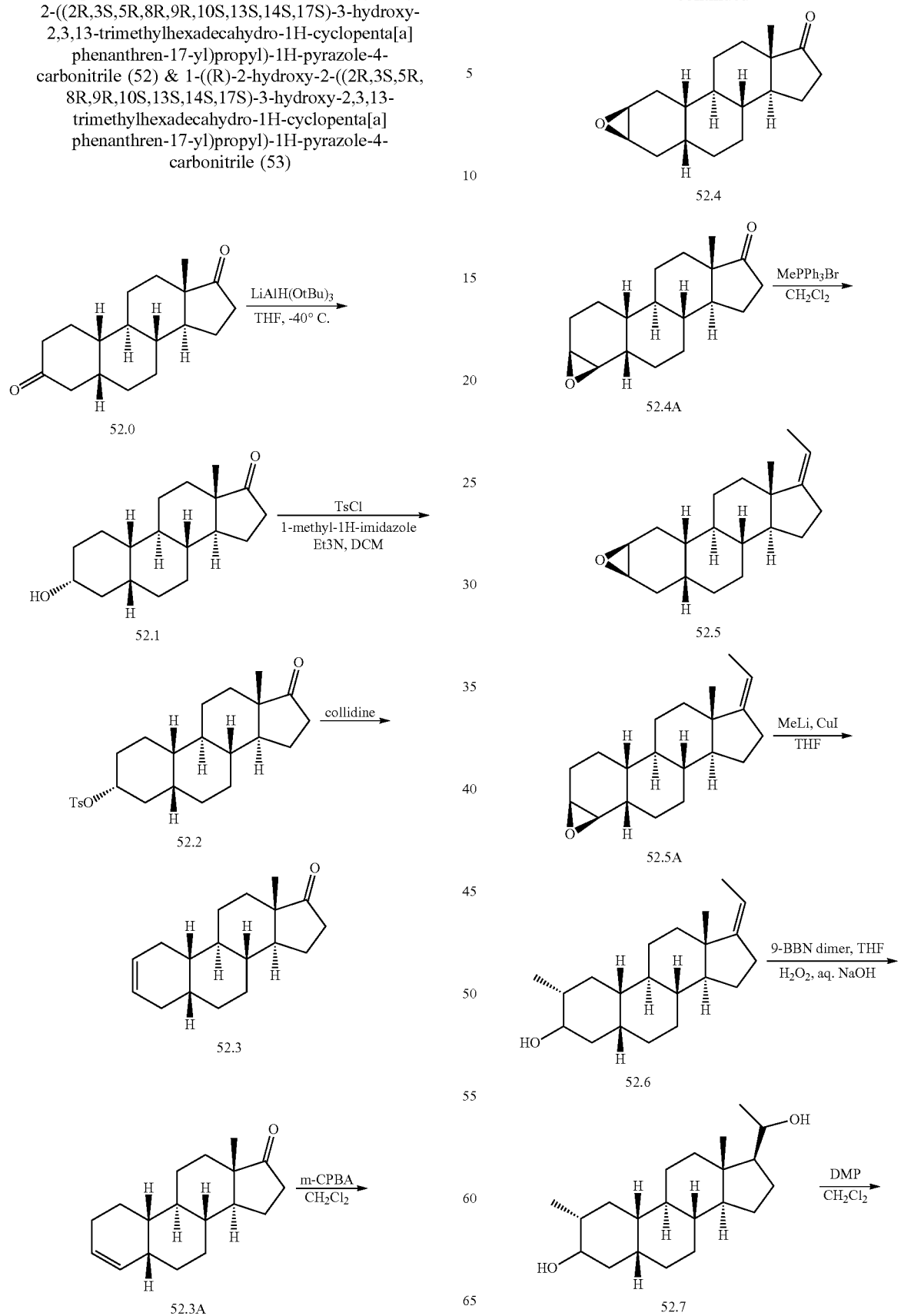

-continued

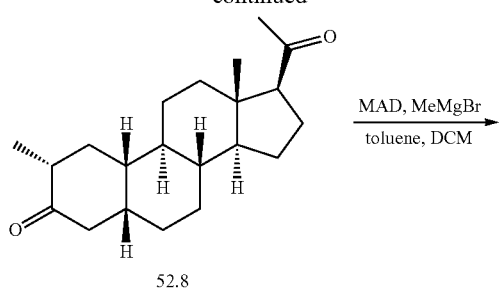
52.8

MAD, MeMgBr
toluene, DCM

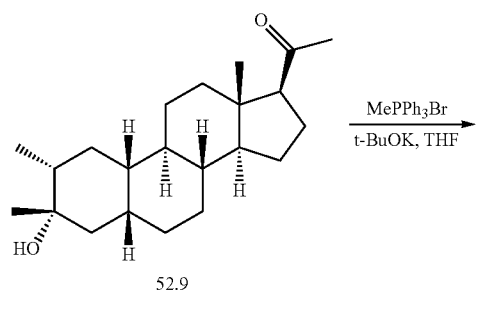
52.9

MePPh₃Br
t-BuOK, THF

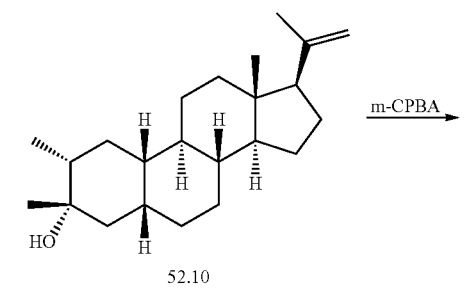
52.10 m-CPBA

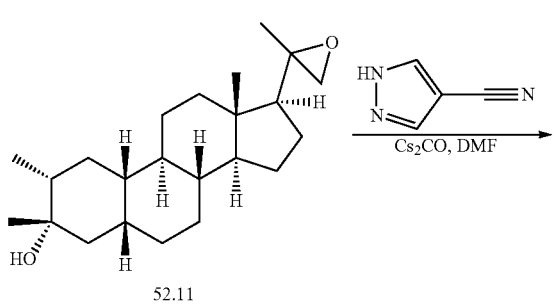
52.11

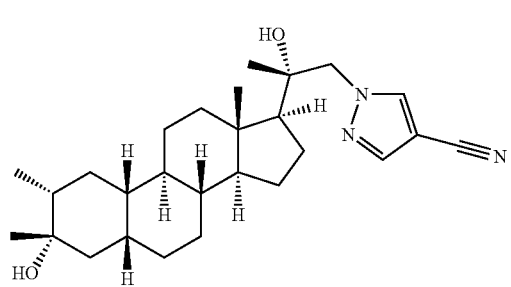
52

-continued

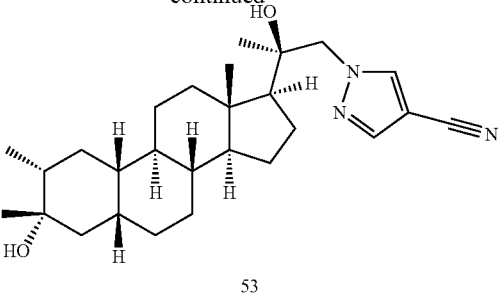
53

Synthesis of 52.1

To a solution of 52.0 (14.0 g, 51.0 mmol) in anhydrous THF (140 mL) was added a solution of LiAlH(OtBu)₃ (23.3 g, 91.8 mmol) in anhydrous THF (70 mL) dropwise at −40° C. over a period of 30 mins under N₂. After stirring at −40° C. for 2 h a suspension resulted, and the reaction mixture was poured into saturated NH₄Cl (150 mL) at 0° C., stirred for 30 mins and extracted with EtOAc (3×150 mL). The combined organic phase was washed with brine (300 mL), dried over anhydrous Na₂SO₄, filtered and concentrated to give 52.1 (13.92 g). ¹H NMR (400 MHz, CDCl₃) δ$_H$ 0.87 (s, 3H) 1.00-1.33 (m, 8H) 1.33-1.49 (m, 4H) 1.52-1.58 (m, 3H) 1.66-1.72 (m, 2H) 1.75-1.84 (m, 3H) 1.89-1.98 (m, 2H) 2.05-2.14 (m, 1H) 2.39-2.49 (m, 1H) 3.63 (br s, 1H).

Synthesis of 52.2

To a solution of 52.1 (13.0 g, 47.0 mmol) in DCM (130 mL) was added 1-methyl-1H-imidazole (7.70 g, 94.0 mmol) and TEA (9.49 g, 94.0 mmol) at 25° C., followed by TsCl (17.9 g, 94.0 mmol). After stirring at 25° C. for 2 h, the residue was poured into ice-water (250 mL) and stirred for 20 mins. The aqueous phase was extracted with EtOAc (2×200 mL). The combined organic phase was washed with brine (2×250 mL), dried over anhydrous Na₂SO₄, filtered and concentrated under vacuum to give 52.2 (16.0 g). ¹H NMR (400 MHz, CDCl₃) δ$_H$ 0.84 (s, 3H) 0.93-0.93 (m, 1H) 0.95-1.16 (m, 3H) 1.17-1.36 (m, 5H) 1.38-1.58 (m, 4H) 1.76-2.00 (m, 4H) 2.02-2.27 (m, 3H) 2.36-2.37 (m, 1H) 2.39-2.43 (m, 1H) 2.44 (s, 3H) 2.45-2.63 (m, 1H) 4.40-4.55 (m, 1H) 7.32 (d, J=8.13 Hz, 2H) 7.74-7.84 (m, 2H).

Synthesis of 52.3 & 52.3A

To 52.2 (16.0 g, 37.1 mmol) was added collidine (150 mL, 37.1 mmol) at 25° C. under N₂. After stirring at 140° C. for 16 h a solution resulted. The mixture was poured into water (500 mL), extracted with EtOAc (3×400 mL). The combined organic phase was washed with water (3×100 mL), brine (200 mL), dried over anhydrous Na₂SO₄, filtered and concentrated under vacuum. The residue was purified by flash column (0-20% of EtOAc in PE) to give a mixture of 52.3 and 52.3A (8.6 g). ¹H NMR (400 MHz, CDCl₃) δ$_H$ 0.87 (s, 1H) 0.91 (s, 1H) 0.94-1.10 (m, 2H) 1.10-1.33 (m, 6H) 1.53 (br dd, J=6.02, 2.76 Hz, 7H) 1.67-1.83 (m, 3H) 1.83-1.97 (m, 3H) 2.28-2.72 (m, 3H) 5.31-5.55 (m, 1H) 5.60 (br s, 1H).

Synthesis of 52.4 & 52.4A

To a mixed solution of 52.3 and 52.3A (7.5 g, 29.0 mmol) in DCM (90 mL) was added m-CPBA (8.8 g, 43.5 mmol) at 0° C. under N$_2$. After stirring at 25° C. for 2 h, the mixture was quenched with saturated NaHCO$_3$(100 mL) and the mixture was extracted with DCM (2×150 mL). The organic layer was washed with Na$_2$S$_2$O$_3$ (2×100 mL, sat.), brine (2×100 mL), dried over anhydrous Na$_2$SO$_4$, filtered and concentrated in vacuum. The residue was purified by flash column (0~20% of EtOAc in PE) to give a mixture of 52.4 and 52.4A (7 g). $^1$H NMR (400 MHz, CDCl$_3$) δ$_H$ 3.34-2.78 (m, 2H), 2.54-2.33 (m, 1H), 2.20-2.02 (m, 2H), 1.96-1.49 (m, 11H), 1.39-0.97 (m, 7H), 0.91-0.81 (m, 3H)

Synthesis of 52.5 & 52.5A

To a suspension of Ph$_3$PEtBr (24.2 g, 65.3 mmol) in anhydrous THF (100 mL) was added t-BuOK (7.32 g, 65.3 mmol) at 15° C. under N$_2$ and the mixture was stirred at 45° C. for 30 min. A mixture of 52.4 and 52.4A (6.0 g, 21.8 mmol) in anhydrous THF (15 mL) was then added dropwise. After stirring for 16 h the mixture was cooled and poured into ice-water (50 mL) and stirred for 10 min. The aqueous phase was extracted with EtOAc (2×50 mL) and the combined organic phase was washed with brine (2×50 mL), filtered, concentrated and purified by flash column (0~10% of EtOAc in PE) to give a mixture of 52.5 and 52.5A (5.5 g, 88%).

Synthesis of 52.6

To a suspension of CuI (1.80 g, 9.48 mmol) in THF (10 mL) was added MeLi (7.75 mL, 1.6 M, 12.4 mmol) at 0° C. After stirring at 0° C. for 1 h, a mixture of 52.5 and 52.5A (0.3 g, 1.04 mmol) in THF (10 mL) was added at 0° C. After stirring at 15° C. for 16 h the mixture was poured into water (50 mL) and the aqueous phase was extracted with EtOAc (2×50 mL). The combined organic phase was washed with brine (50 mL), dried over anhydrous Na$_2$SO$_4$, filtered, concentrated and purified by flash column (0~15% of EtOAc in PE) to give 52.6 (100 mg, 31.8%). $^1$H NMR (400 MHz, CDCl$_3$) δ$_H$ 5.12 (q, J=7.0 Hz, 1H), 3.55 (br s, 1H), 2.48-2.10 (m, 4H), 1.98-1.68 (m, 4H), 1.68-1.65 (m, 4H), 1.55-1.11 (m, 13H), 1.06-0.97 (m, 4H), 0.89 (s, 3H).

Synthesis of 52.7

To a solution of 52.6 (100 mg, 0.3305 mmol) in THF (10 mL) was added 9-BBN dimer (159 mg, 0.661 mmol) under N$_2$. The reaction mixture was stirred at 50° C. under N$_2$ for 2 h to give a colorless mixture. The mixture was cooled to 0° C., where ethanol (0.288 mL, 4.95 mmol) and NaOH (0.99 mL, 5 M, 4.95 mmol) were added, resulting in the mixture turning clear. H$_2$O$_2$ (560 mg, 30%, 4.95 mmol) was added dropwise at 15° C. After stirring at 50° C. for 2 h saturated aqueous Na$_2$S$_2$O$_3$ (50 mL) was added and the mixture was stirred at 0° C. for another 1 h. The reaction was checked by potassium iodide-starch test paper to confirm excess H$_2$O$_2$ was destroyed (did not changed to blue). The aqueous phase was extracted with EtOAc (3×40 mL) and the combined organic phase was washed with brine (2×50 mL), dried over anhydrous Na$_2$SO$_4$, filtered and concentrated to give 52.7 (800 mg).

Synthesis of 52.8

To a solution of 52.7 (900 mg, 2.80 mmol) in DCM (40 mL) was added DMP (4.74 g, 12.4 mmol) under N$_2$. After stirring at 15° C. under N$_2$ for 2 h a colorless mixture resulted, and saturated aqueous NaHCO$_3$(50 mL) and saturated aqueous Na$_2$S$_2$O$_3$ (50 mL) were added. The aqueous phase was extracted with DCM (3×40 mL). The combined organic phase was washed with brine (2×50 mL), dried over anhydrous Na$_2$SO$_4$, filtered, concentrated and purified by flash column (0~20% of EtOAc in PE) to give 52.8 (550 mg, 62%). $^1$H NMR (400 MHz, CDCl$_3$) δ$_H$ 2.62-2.31 (m, 4H), 2.12-1.95 (m, 7H), 1.90-1.56 (m, 3H), 1.53-1.39 (m, 2H), 1.33-1.09 (m, 6H), 1.05 (d, J=6.8 Hz, 3H), 1.03-0.85 (m, 4H), 0.66 (s, 3H)

Synthesis of 52.9

To a solution of BHT (2.26 g, 10.3 mmol) in toluene (10 mL) under nitrogen at 0° C. was added AlMe$_3$ (2 M in toluene, 2.57 mL, 5.15 mmol) dropwise. The mixture was stirred at 20° C. for 1 h to give the MAD solution. To the MAD solution (4.71 mmol in 10 mL toluene) was added a solution of 52.8 (500 mg, 1.57 mmol) in anhydrous DCM (5 mL) dropwise at −70° C. After stirring at −70° C. for 1 h under N$_2$, MeMgBr (4.16 mL, 12.5 mmol, 3 M in ethyl ether) was added drop wise at −70° C. The resulting solution was stirred at −70° C. for 3 h. The reaction mixture was poured into citric acid (30 mL, 20% aq.) at below 10° C. and extracted with EtOAc (2×30 mL). The combined organic layer was dried over Na$_2$SO$_4$, filtered, concentrated and purified by silica gel chromatography (0-30% of EtOAc in PE) to give 52.9 (300 mg, 57.4%). $^1$H NMR (400 MHz, CDCl$_3$) δ$_H$ 2.54 (br t, J=8.9 Hz, 1H), 2.23-2.13 (m, 1H), 2.12 (s, 3H), 2.05-1.94 (m, 1H), 1.89-1.56 (m, 12H), 1.52-1.36 (m, 3H), 1.28 (s, 3H), 1.25-1.09 (m, 6H), 1.08-0.94 (m, 5H), 0.63 (s, 3H).

Synthesis of 52.10

To a solution of MePPh$_3$Br (1.61 g, 4.51 mmol) in THF (40 mL) was added t-BuOK (0.506 g, 4.51 mmol) at 15° C. under N$_2$. After stirring at 15° C. for 1 h, 52.9 (0.3 g, 0.9021 mmol) in THF (10 mL) was added. After stirring at 40° C. for 2 h, the mixture was poured into water (20 mL) and the aqueous phase was extracted with EtOAc (2×50 mL). The combined organic phase was washed with brine (20 mL), dried over anhydrous Na$_2$SO$_4$, filtered, concentrated and purified by flash column (0~10% of EtOAc in PE) to give 52.10 (180 mg, 60.4%). $^1$H NMR (400 MHz, CDCl$_3$) δ$_H$ 4.85 (s, 1H), 4.71 (s, 1H), 2.10-1.99 (m, 1H), 1.87-1.78 (m, 4H), 1.76 (s, 3H), 1.73-1.57 (m, 7H), 1.49-1.38 (m, 2H), 1.28 (s, 3H), 1.24-1.07 (m, 7H), 1.02 (d, J=7.0 Hz, 3H), 0.99-0.80 (m, 3H), 0.58 (s, 3H).

Synthesis of 52.11

To a solution of 52.10 (90 mg, 0.2722 mmol) in DCM (10 mL) was added m-CPBA (110 mg, 0.54 mmol, 85%) at 0° C. under N$_2$. After stirring at 15° C. for 2 h, the mixture was quenched with saturated NaHCO$_3$(10 mL). The mixture was extracted with DCM (2×10 mL), the organic layer was washed with Na$_2$S$_2$O$_3$ (2×10 mL, sat.), brine (2×10 mL), dried over anhydrous Na$_2$SO$_4$, filtered and concentrated to give 52.11 (100 mg).

Synthesis of 52 & 53

To a solution of 52.11 (100 mg, 0.2885 mmol) in DMF (5 mL) was added 1H-pyrazole-4-carbonitrile (53.7 mg, 0.577 mmol) and Cs$_2$CO$_3$ (187 mg, 0.577 mmol) at 20° C. under N$_2$. After stirring at 130° C. for 16 h, the mixture was poured into H$_2$O (10 mL) and extracted with EtOAc (2×20 mL). The combined organic layer was washed with brine (20 mL), dried over anhydrous Na$_2$SO$_4$, filtered, concentrated and purified by SFC (Column DAICEL CHIRALPAK AS(250 mm*30 mm, 10 um) Condition 0.1% NH$_3$H$_2$O ETOH Begin B 20 End B 20 Gradient Time(min) 100% B Hold Time(min) FlowRate(ml/min) 60 Injections 170) to afford 52 (19.1 mg, 15.1%) and 53 (14.7 mg, 11.6%).

52: $^1$H NMR (400 MHz, CDCl$_3$) $\delta_H$ 7.93 (s, 1H), 7.82 (s, 1H), 4.36 (d, J=13.8 Hz, 1H), 4.09 (d, J=13.8 Hz, 1H), 2.51 (s, 1H), 2.01 (br d, J=11.3 Hz, 1H), 1.87-1.56 (m, 11H), 1.42 (br t, J=9.7 Hz, 5H), 1.28 (s, 3H), 1.25-1.04 (m, 7H), 1.00 (br d, J=7.0 Hz, 3H), 0.98 (s, 3H), 0.93 (s, 3H). LC-ELSD/MS purity 99%, MS ESI calcd. For C$_{27}$H$_{38}$N$_3$ [M−2H$_2$O+H]$^+$ 404.3, found 404.3.

53: ~1H NMR (400 MHz, CDCl$_3$) $\delta_H$ 7.82 (s, 1H), 7.73 (s, 1H), 4.13-4.03 (m, 1H), 3.99-3.87 (m, 1H), 2.20 (s, 1H), 2.02-1.93 (m, 1H), 1.80-1.53 (m, 9H), 1.44-1.25 (m, 9H), 1.20 (s, 3H), 1.15 (br s, 4H), 1.02 (s, 3H), 0.93 (br d, J=7.3 Hz, 3H), 0.81 (s, 3H). LC-ELSD/MS purity 99%, MS ESI calcd. For C$_{27}$H$_{38}$N$_3$ [M−2H$_2$O+H]$^+$ 404.3, found 404.3.

Examples 54 & 55: Synthesis of 1-((S)-2-((3R,5R,8R,9S,10S,13S,14S,17S)-3-hydroxy-3-(methoxymethyl)-10,13-dimethylhexadecahydro-1H-cyclopenta[a]phenanthren-17-yl)-2-methoxypropyl)-1H-pyrazole-4-carbonitrile (54) & 1-((R)-2-((3R,5R,8R,9S,10S,13S,14S,17S)-3-hydroxy-3-(methoxymethyl)-10,13-dimethylhexadecahydro-1H-cyclopenta[a]phenanthren-17-yl)-2-methoxypropyl)-1H-pyrazole-4-carbonitrile (55)

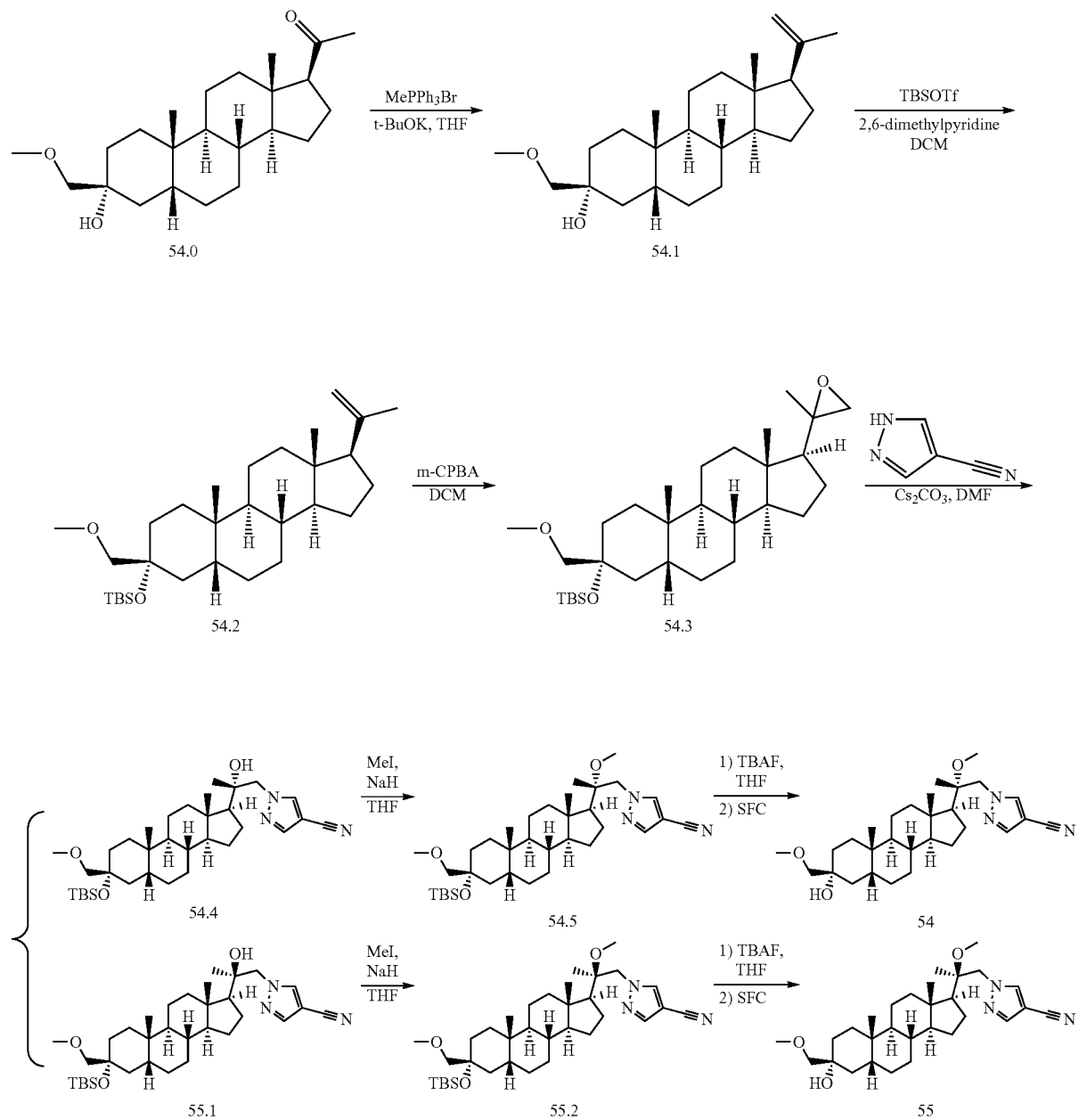

Synthesis of 54.1

To a mixture of MePPh$_3$Br (10.4 g, 28.8 mmol) in THF (20 mL) was added t-BuOK (3.7 g, 33.0 mmol) at 25° C. under N$_2$. The resulting mixture was stirred at 45° C. for 30 min. 54.0 (8.0 g, 22.0 mmol) was added in portions below 45° C. After stirring at 55° C. for 3 h a suspension resulted. The reaction mixture was quenched with 10% NH$_4$Cl aqueous (40 mL) at 25° C. The aqueous layer was extracted with EtOAc (2×40 mL) and the combined organic phase was separated, dried over Na$_2$SO$_4$, filtered, concentrated and purified by flash column (15~35% of EtOAc in PE) to give 54.1 (3.1 g, 39%). $^1$H NMR (400 MHz, CDCl$_3$) $\delta_H$ 4.82-4.89 (m, 1H), 4.50-4.73 (m, 1H), 3.36-3.42 (m, 4H), 2.56-2.61 (m, 1H), 1.77-2.03 (m, 4H), 1.74 (s, 3H), 1.63-1.72 (m, 3H), 1.31-1.60 (m, 9H), 1.09-1.29 (m, 7H), 0.91-0.95 (m, 3H), 0.78-0.89 (m, 1H), 0.54 (s, 2H).

Synthesis of 54.2

To a solution of 54.1 (710 mg, 1.96 mmol), 2,6-dimethylpyridine (1.04 g, 9.79 mmol) in DCM (7 mL) was added drop-wise tertbutyldimethylsilyl trifluoromethanesulfonate (2.07 g, 7.84 mmol) at 0° C. After stirring at 25° C. for 36 h the reaction mixture was quenched with water (15 mL) and extracted with DCM (2×15 mL). The combined organic phase washed with brine (15 mL), dried over Na$_2$SO$_4$, filtered and concentrated under vacuum. The residue was purified by flash column (0~5% of EtOAc in PE) to afford 54.2 (290 mg, 31%). $^1$H NMR (400 MHz, CDCl$_3$), $\delta_H$ 4.85 (s, 1H), 4.70 (s, 1H), 3.38-3.42 (m, 1H), 3.35 (s, 3H), 3.28-3.31 (m, 1H), 1.65-1.85 (m, 12H), 1.31-1.47 (m, 10H), 1.09-1.28 (m, 9H), 0.92 (s, 3H), 0.86-0.87 (m, 9H), 0.55 (s, 3H), 0.07-0.10 (m, 7H),

Synthesis of 54.3

To a solution of 54.2 (700 mg, 1.47 mmol) in DCM (10 mL) was added m-CPBA (596 mg, 85%, 2.94 mmol). After stirring at 15° C. for 0.5 h a colorless solution resulted. The mixture was quenched with saturated aq. NaHCO$_3$(100 mL). The DCM phase was separated and washed with saturated NaHCO$_3$/Na$_2$S$_2$O$_3$ aqueous (1:1, 3×100 mL), brine (100 mL), dried over Na$_2$SO$_4$, filtered and concentrated under vacuum to give 54.3 (800 mg). $^1$H NMR (400 MHz, CDCl$_3$), $\delta_H$ 3.42-3.28 (m, 5H), 2.88-2.87 (m, 0.6H), 2.56-2.49 (m, 1H), 2.32-2.31 (m, 0.4H), 2.06-1.51 (m, 4H), 1.49-1.31 (m, 10H), 1.26-0.91 (m, 12H), 0.86-0.66 (m, 15H), 0.08-0.07 (m, 6H).

Synthesis of 54.4 & 55.1

To a solution of 54.3 (800 mg, 1.62 mmol) in DMF (20 mL), was added 1H-pyrazole-4-carbonitrile (451 mg, 4.86 mmol) and Cs$_2$CO$_3$ (1.58 g, 4.86 mmol). After stirring at 130° C. for 16 h the reaction mixture was diluted with water (100 mL) and extracted with EtOAc (3×100 mL). The combined organic layer was washed with 5% LiCl (3×100 mL) and concentrated. The residue was purified by flash column (0~12% of EtOAc in PE) to give 54.4 (340 mg) and 55.1 (380 mg).

54.4: $^1$H NMR (400 MHz, CDCl$_3$), $\delta_H$ 7.92 (s, 1H), 7.81 (s, 1H), 4.37-4.34 (m, 1H), 4.11-4.07 (m, 1H), 3.41-3.27 (m, 5H), 2.49 (s, 1H), 2.03-2.01 (m, 1H), 1.85-1.62 (m, 7H), 1.56-1.26 (m, 8H), 1.23-0.94 (m, 13H), 0.91-0.86 (m, 8H), 0.85-0.82 (m, 4H), 0.08-0.07 (m, 6H).

55.1: $^1$H NMR (400 MHz, CDCl$_3$), $\delta_H$ 7.86-7.81 (m, 1H), 7.74-7.72 (m, 1H), 4.11-3.91 (m, 2H), 3.34-3.20 (m, 5H), 2.02-1.56 (m, 8H), 1.44-1.07 (m, 13H), 1.06-0.78 (m, 15H), 0.77-0.69 (m, 6H), 0.01-0.00 (m, 6H).

Synthesis of 54.5

To a solution of 54.4 (310 mg, 0.530 mmol) in THF (10 mL) was added NaH (211 mg, 5.30 mmol, 60%) at 0° C. under N$_2$ in 100 mL three-neck flask. After stirring at 25° C. for 0.5 h, MeI (752 mg, 5.30 mmol) was added into the reaction mixture. After stirring at 25° C. for 16 h, the reaction mixture was quenched by ammonia (1 mL) and poured into water (50 mL). The aqueous phase was extracted with EtOAc (2×50 mL). The combined organic layer was washed with brine (2×50 mL), dried over anhydrous Na$_2$SO$_4$, filtered and concentrated to give 54.5 (470 mg). $^1$H NMR (400 MHz, CDCl$_3$), $\delta_H$ 7.91 (s, 1H), 7.75 (s, 1H), 4.30-4.18 (m, 2H), 3.41-3.27 (m, 5H), 3.17 (s, 3H), 1.98-1.59 (m, 10H), 1.41-1.29 (m, 7H), 1.25-1.17 (m, 5H), 1.14-1.05 (m, 4H), 0.91-0.83 (m, 15H), 0.07-0.06 (m, 6H).

Synthesis of 54

To a solution of 54.5 (470 mg, 0.786 mmol) in THF (20 mL) was added TBAF (1.63 g, 6.28 mmol). After stirring at 80° C. for 16 h a solution resulted, and the reaction mixture was quenched with saturated aq. NH$_4$Cl solution (30 mL) and extracted with EtOAc (2×50 mL). The combined organic layer was washed with saturated brine (100 mL), dried over anhydrous Na$_2$SO$_4$, filtered and concentrated to give a residue, which was purified by flash column (0~50% of EtOAc in PE) to give 54 (150 mg), which was further purified by SFC (Column DAICEL CHIRALCEL OD-H (250 mm*30 mm, 5 um); Condition 0.1% NH$_3$H$_2$O EtOH; Begin B 50%; End B 50%; Flow Rate (ml/min) 80; Injections 45) to provide 54 (95.9 mg, 64%). $^1$H NMR (400 MHz, CDCl$_3$), $\delta_H$ 7.90 (s, 1H), 7.75 (s, 1H), 4.28-4.17 (m, 2H), 3.41-3.34 (m, 5H), 3.17 (s, 3H), 2.56 (s, 1H), 1.98-1.58 (m, 6H), 1.50-1.10 (m, 13H), 1.09-0.93 (m, 10H), 0.82 (s, 3H). LC-ELSD/MS purity 99%, MS ESI calcd. For C$_{27}$H$_{37}$N$_3$ [M−2MeOH−H$_2$O+H]$^+$ 402.3 found 402.3.

Synthesis of 55.2

To a solution of 55.1 (310 mg, 0.530 mmol) in THF (10 mL) was added NaH (211 mg, 5.30 mmol, 60%) at 0° C. under N$_2$ in 100 mL three-neck flask. After stirring at 25° C. for 0.5 h, MeI (752 mg, 5.30 mmol) was added into the reaction mixture. After stirring at 25° C. for 16 h, the reaction mixture was quenched by ammonia (1 mL) and poured into water (50 mL). The aqueous phase was extracted with EtOAc (2×50 mL) and the combined organic phase was washed with brine (2×50 mL), dried over anhydrous Na$_2$SO$_4$, filtered and concentrated to give 55.2 (500 mg). $^1$H NMR (400 MHz, CDCl$_3$), $\delta_H$ 7.90 (s, 1H), 7.75 (s, 1H), 4.35-4.24 (m, 2H), 3.41-3.27 (m, 5H), 3.15 (s, 3H), 2.07-1.60 (m, 7H), 1.39-1.25 (m, 8H), 1.24-1.07 (m, 7H), 1.05-0.90 (m, 4H), 0.89-0.83 (m, 7H), 0.82-0.78 (m, 8H), 0.08-0.07 (m, 6H).

Synthesis of 55

To a solution of 55.2 (500 mg, 0.836 mmol) in THF (20 mL) was added TBAF (1.74 g, 6.68 mmol). After stirring at 80° C. for 16 h a solution resulted, and the reaction mixture was quenched with saturated aq. NH$_4$Cl solution (30 mL)

and extracted with EtOAc (2×50 mL). The combined organic phase was washed with saturated brine (100 mL), dried over anhydrous Na$_2$SO$_4$, filtered and concentrated to give a residue, which was purified by flash column (0~50% of EtOAc in PE) to give 55 (250 mg), which was further purified by SFC (Column DAICEL CHIRALCEL OD-H (250 mm*30 mm, 5 um); Condition 0.1% NH$_3$H$_2$O ETOH; Begin B 50%; End B 50%; Flow Rate (ml/min) 80; Injections 60), to provide 55 (71.2 mg, 28.5%). $^1$H NMR (400 MHz, CDCl$_3$), $\delta_H$ 7.90 (s, 1H), 7.75 (s, 1H), 4.27-4.20 (m, 2H), 3.42-3.35 (m, 5H), 2.58 (s, 3H), 2.05-1.57 (m, 7H), 1.51-1.06 (m, 15H), 1.00-0.93 (m, 8H), 0.79 (s, 3H). LC-ELSD/MS purity 99%, MS ESI calcd. For C$_{27}$H$_{37}$N$_3$ [M−2MeOH-H$_2$O+H]$^+$ 402.3 found 402.3.

Example 56: Synthesis of 1-(2-((3R,5R,8R,9R,10S, 13S,14S,17S)-3-hydroxy-3-(methoxymethyl)-13-methylhexadecahydro-1H-cyclopenta[a]phenanthren-17-yl)-2-methylpropyl)-1H-pyrazole-4-carbonitrile (56)

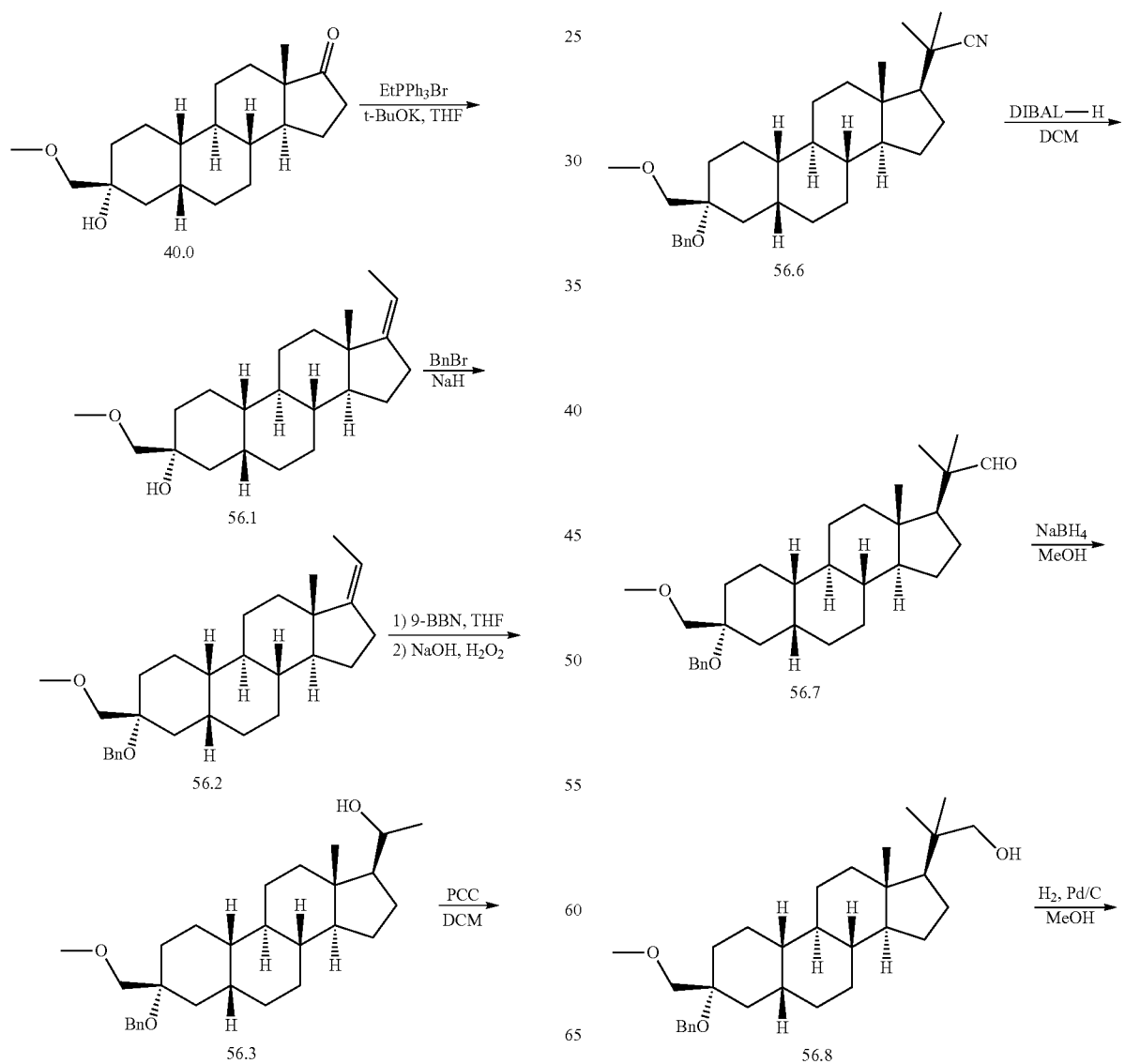

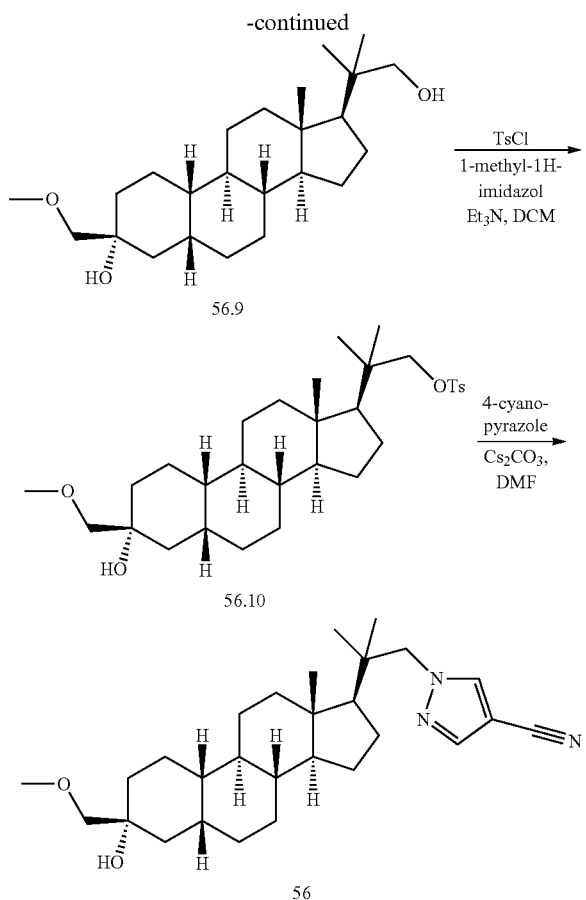

Synthesis of 56.1

To a solution of EtPh₃PBr (41.5 g, 112 mmol) in THF (110 mL) was added t-BuOK (12.5 g, 112 mmol) at 25° C. The mixture was stirred at 50° C. for 1 h where a solution of 40.0 (12.0 g, 37.4 mmol) in THF (50 mL) was added into the reaction mixture below 50° C. After stirring at 40° C. for 16 h the mixture was added into saturated NH₄Cl (100 mL). The aqueous layer was extracted with EtOAc (3×150 mL) and the combined organic layer was washed with saturated brine (100 mL), dried over anhydrous Na₂SO₄, filtered and concentrated. The residue was purified by flash column (0~30% of EtOAc in PE) to give 56.1 (14.0 g). ¹H NMR (400 MHz, CDCl₃) $\delta_H$ 5.15-5.05 (m, 1H), 3.42-3.37 (m, 5H), 2.41-2.30 (m, 1H), 2.27-2.11 (m, 2H), 1.88-1.80 (m, 1H), 1.74-1.68 (m, 1H), 1.66-1.63 (m, 3H), 1.63-1.59 (m, 2H), 1.56-1.53 (m, 1H), 1.52-1.45 (m, 2H), 1.44-1.35 (m, 5H), 1.35-1.18 (m, 5H), 1.17-1.02 (m, 4H), 0.87 (s, 3H)

Synthesis of 56.2

To a mixture of 56.1 (14.0 g, 42.1 mmol) in DMF (150 mL) was added NaH (6.71 g, 168 mmol, 60% in mineral oil) at 0° C. The mixture was stirred at 25° C. for 1 h and BnBr (28.7 g, 168 mmol) was added. After stirring at 60° C. for 20 h triethylamine (50 mL) was added and the mixture was stirred at 60° C. for another 30 min. The mixture was added into NH₄Cl (100 mL) and the aqueous phase was extracted with EtOAc (3×100 mL). The combined organic phase was washed with saturated brine (2×100 mL), dried over anhydrous Na₂SO₄, filtered and concentrated. The residue was purified by flash column (0-20% of EtOAc in PE) to give 56.2 (18.8 g). ¹H NMR (400 MHz, CDCl₃) $\delta_H$ 7.37-7.37 (m, 1H), 7.36 (s, 1H), 7.33 (s, 1H), 7.31 (s, 1H), 7.29 (s, 1H), 5.17-5.05 (m, 1H), 4.57 (s, 2H), 3.58 (d, J=4.0 Hz, 2H), 3.38 (s, 3H), 2.42-2.31 (m, 1H), 2.28-2.11 (m, 2H), 1.94-1.83 (m, 1H), 1.79-1.70 (m, 2H), 1.69-1.63 (m, 4H), 1.62-1.57 (m, 2H), 1.54-1.51 (m, 1H), 1.50-1.37 (m, 4H), 1.37-1.31 (m, 1H), 1.30-1.21 (m, 3H), 1.18-0.99 (m, 4H), 0.88 (s, 3H).

Synthesis of 56.3

To a solution of 56.2 (18.8 g, 44.4 mmol) in THF (200 mL) was added 9-BBN dimer (32.4 g, 133 mmol) at 25° C. The mixture was stirred at 40° C. for 1 h. To the resulting mixture was added ethanol (10.2 g, 222 mmol) at 0° C. Then aqueous NaOH (44.4 mL, 5M) was added at 0° C. followed by H₂O₂ (22.2 mL, 10M, 222 mmol) dropwise. After the addition, the mixture was stirred at 80° C. for 1 h. Sat. Na₂S₂O₃ (100 mL) was added and the mixture stirred for 30 mins. The aqueous layer was extracted with EtOAc (200 mL), washed with saturated brine (2×100 mL), dried over anhydrous Na₂SO₄ and the combined organic phase was concentrated under vacuum to give 56.3 (13.0 g).

Synthesis of 56.4

To a solution of 56.3 (3.0 g, 6.8 mmol) in DCM (30 mL) was added silica gel (6.6 g) and PCC (4.38 g, 20.4 mmol) at 25° C. After stirring at 25° C. for 25 min the suspension was filtered, and the filter cake was washed with DCM (2×50 mL). The combined filtrate was concentrated, and the residue was purified by silica gel chromatography (0-20% of EtOAc in PE) to give 56.4 (2.6 g, 87.2%). ¹H NMR (400 MHz, CDCl₃) $\delta_H$ 7.40-7.29 (m, 4H), 7.25-7.21 (m, 1H), 4.58 (s, 2H), 3.59 (d, J=3.6 Hz, 2H), 3.38 (s, 3H), 2.55 (t, J=8.4 Hz, 1H), 2.19-2.13 (m, 1H), 2.11 (s, 3H), 2.03-1.96 (m, 1H), 1.92-1.79 (m, 3H), 1.77-1.59 (m, 5H), 1.54-1.32 (m, 7H), 1.31-1.03 (m, 6H), 0.61 (s, 3H).

Synthesis of 56.5

To a stirred solution of t-BuOK (1.01 g, 9.08 mmol) in t-BuOH (10 mL) was added a solution of 56.4 (1.0 g, 2.27 mmol) in DME (10 mL) and a solution of Tosmic (886 mg, 4.54 mmol) in DME (10 mL) under N₂. After stirring at 25° C. for 72 h the mixture was quenched by aq.NH₄Cl (40 mL, sat.) and extracted with EtOAc (2×50 mL). The combined organic layer was dried over Na₂SO₄, filtered, concentrated and purified by flash column chromatography on silica gel (0-15% EtOAc in PE) to give 56.5 (1.0 g, 98%). ¹H NMR (400 MHz, CDCl₃) $\delta_H$ 7.29-7.39 (m, 4H) 7.20-7.25 (m, 1H) 4.58 (s, 2H) 3.53-3.64 (m, 2H) 3.38 (s, 3H) 2.25-2.70 (m, 2H) 1.60-2.08 (m, 10H) 1.26-1.45 (m, 9H) 0.89-1.22 (m, 7H) 0.73 (d, J=2.00 Hz, 3H)

Synthesis of 56.6

To a solution of DIPEA (3.12 mL, 22.2 mmol) in THF (50 mL) under N₂ was added n-BuLi (10.6 mL, 2.5 M in hexane, 26.6 mmol) at −70° C. The mixture was warmed to 0° C. and stirred for 0.5 h under N₂. The freshly prepared LDA (2.37 g, 22.2 mmol) was added to a stirred solution of 56.5 (1.0 g, 2.22 mmol) in THF (50 mL) at −70° C. The mixture was stirred at −70° C. for 1 h where methyl iodide (3.15 g, 22.2 mmol) was added under N₂ and the mixture was then warmed to 20° C. for 16 h. Water (50 mL) was added and the aqueous phase was extracted with EtOAc (3×50 mL). The combined organic layers were washed with brine (50 mL), dried over anhydrous Na$_2$SO$_4$, filtered, concentrated and purified by flash column (0~2% of EtOAc in PE) to afford 56.6 (900 mg). $^1$H NMR (400 MHz, CDCl$_3$) δ$_H$ 7.35-7.20 (m, 4H), 7.20-7.05 (m, 1H), 4.55-4.45 (m, 2H), 3.55-3.45 (m, 2H), 3.30 (s, 3H), 2.00-1.90 (m, 1H), 1.90-1.65 (m, 9H), 1.65-1.50 (m, 3H), 1.50-1.40 (m, 2H), 1.36-1.27 (m, 13H), 1.27-1.15 (m, 6H), 1.15-0.95 (m, 2H), 0.87-0.80 (m, 4H), 0.80-0.75 (m, 3H).

Synthesis of 56.7

To a solution of 56.6 (900 mg, 1.88 mmol) in DCM (10 mL) a solution of DIBAL-H (9.40 mL, 9.40 mmol, 1 M in toluene) was added slowly at −70° C. After stirring for 30 mins at −70° C., HCl (4 ml, 0.468 M, 1.88 mmol) was added. After stirring at 25° C. for another 10 mins the mixture was carefully poured into H$_2$O (30 mL), extracted with EtOAc (2×30 mL), dried over Na$_2$SO$_4$, filtered and concentrated to give 56.7 (800 mg). $^1$H NMR (400 MHz, CDCl$_3$) δ$_H$ 9.70 (s, 1H), 7.45-7.30 (m, 4H), 7.30-7.20 (m, 1H), 4.65-4.50 (m, 2H), 3.65-3.50 (m, 2H), 3.40 (s, 3H), 2.00-1.85 (m, 2H), 1.85-1.60 (m, 10H), 1.60-1.55 (m, 2H), 1.56-1.35 (m, 5H), 1.34-1.21 (m, 14H), 1.20-1.15 (m, 3H), 1.14-0.95 (m, 8H), 0.90-0.88 (m, 8H), 0.87-0.75 (m, 6H), 0.70 (s, 2H).

Synthesis of 56.8

To a suspension of 56.7 (800 mg, 1.71 mmol) in anhydrous MeOH (20 mL) was added NaBH$_4$ (323 mg, 8.55 mmol) slowly at 0° C. After stirring at 20° C. for 30 min a colorless mixture resulted. The mixture was poured into H$_2$O (20 mL) slowly and extracted with EtOAc (2×20 mL). The combined organic layers were washed with brine (10 mL), dried over Na$_2$SO$_4$, filtered, concentrated and purified by flash column (0~7% of EtOAc in PE) to give 56.8 (500 mg, 62%). $^1$H NMR (400 MHz, CDCl$_3$) δ$_H$ 7.40-7.30 (m, 4H), 7.25-7.20 (m, 1H), 4.55-4.50 (m, 2H), 3.70-3.55 (m, 2H), 3.45-3.25 (m, 5H), 2.05-1.95 (m, 1H), 1.90-1.75 (m, 4H), 1.70-1.52 (m, 7H), 1.50-1.35 (m, 5H), 1.32-1.20 (m, 6H), 1.20-0.95 (m, 5H), 0.99 (s, 3H), 0.90 (s, 3H).

Synthesis of 56.9

To a solution of 56.8 (500 mg, 1.06 mmol) in MeOH (20 mL) was added Pd/C (50 mg) under N$_2$. After hydrogenation at 50° C. under 50 psi for 16 h, the reaction mixture was filtered through a pad of Celite and washed with EtOAc (3×50 mL). The filtrate was concentrated to give 56.9 (270 mg). $^1$H NMR (400 MHz, CDCl$_3$) δ$_H$ 3.50-3.35 (m, 7H), 2.58 (s, 1H), 2.10-1.95 (m, 1H), 1.90-1.75 (m, 4H), 1.70-1.55 (m, 3H), 1.50-1.35 (m, 8H), 1.30-1.20 (m, 4H), 1.15-1.10 (m, 4H), 1.01 (s, 3H), 0.92 (s, 3H), 0.78 (s, 3H).

Synthesis of 56.10

To a solution of 56.9 (50 mg, 0.132 mmol) in DCM (10 mL) was added 1-methyl-1H-imidazol (21.6 mg, 0.264 mmol), TEA (0.0365 ml, 0.264 mmol) and TsCl (25.1 mg, 0.132 mmol). After stirring at 20° C. for 1 h, the mixture was washed with water (5 mL) and the aqueous layer was extracted with DCM (3×20 mL). The combined organic layer was washed with brine (50 mL), dried over anhydrous Na$_2$SO$_4$, filtered and concentrated to give 56.10 (50 mg).

Synthesis of 56

To a solution of 56.10 (200 mg, 0.375 mmol) in DMF (20 mL) was added Cs$_2$CO$_3$ (244 mg, 0.750 mmol) and 4-cyano-pyrazole (104 mg, 1.12 mmol) at 25° C. After stirring at 120° C. for 12 h, the mixture was washed with water (10 mL) and the aqueous phase was extracted with EtOAc (2×10 mL). The combined organic phase was washed with brine (2×10 mL), dried over anhydrous Na$_2$SO$_4$, filtered, concentrated and purified by HPLC (Column: Chiralcel OD-3 150×4.6 mm I.D., 3 um); Condition: water(0.05% NH$_3$H$_2$O+10 mM NH$_4$HCO$_3$)-ACN; Gradient: from 64% to 94% of B; Flow rate: 30 mL/min; Injections: 4; Column temperature: 35° C.) to afford 56 (50 mg, 20.0%). The compound 56 (50 mg, 0.110 mmol) was purified by flash column (0~20% of EtOAc in PE) to give 56 (7.8 mg, 15.6%). $^1$H NMR (400 MHz, CDCl$_3$) δ$_H$ 7.80 (s, 1H), 7.40 (s, 1H), 4.15-4.00 (m, 1H), 3.95-3.85 (m, 1H), 3.45-3.30 (m, 6H), 2.56 (s, 1H), 2.00-1.90 (m, 1H), 1.85-1.65 (m, 4H), 1.64-1.55 (m, 5H), 1.54-1.45 (m, 1H), 1.44-1.30 (m, 5H), 1.29-1.15 (m, 4H), 1.14-1.00 (m, 4H), 0.98 (s, 3H), 0.93 (s, 3H), 0.82 (s, 3H). LC-ELSD/MS purity 99%, MS ESI calcd. For C$_{28}$H$_{42}$N$_3$O [M−H$_2$O+H]$^+$ 436.4 found 436.4.

Example 57: Synthesis of 1-((S)-2-cyano-2-((3R, 5R,8R,9R,10S,13S,14S,17S)-3-hydroxy-3,13-dimethylhexadecahydro-1H-cyclopenta[a]phenanthren-17-yl)propyl)-1H-pyrazole-4-carbonitrile (57)

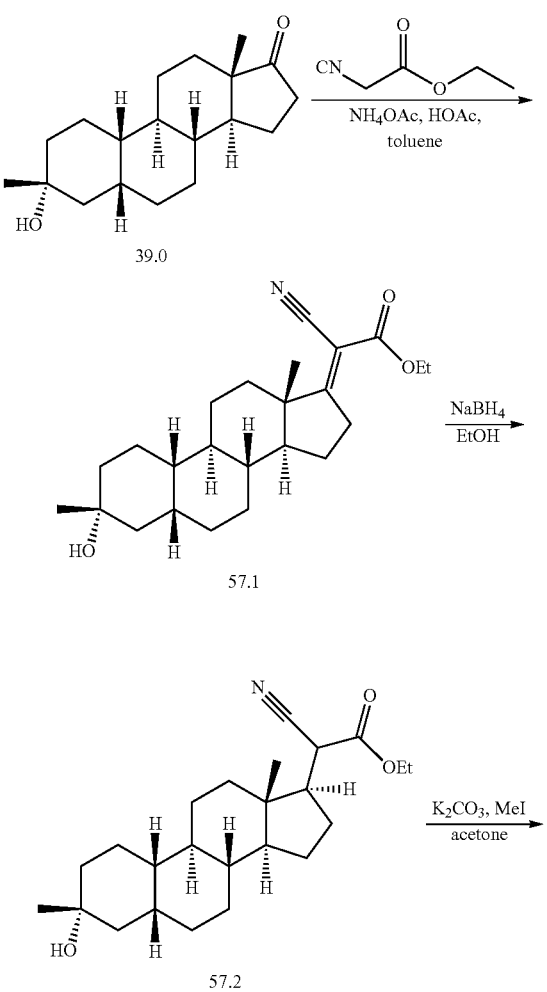

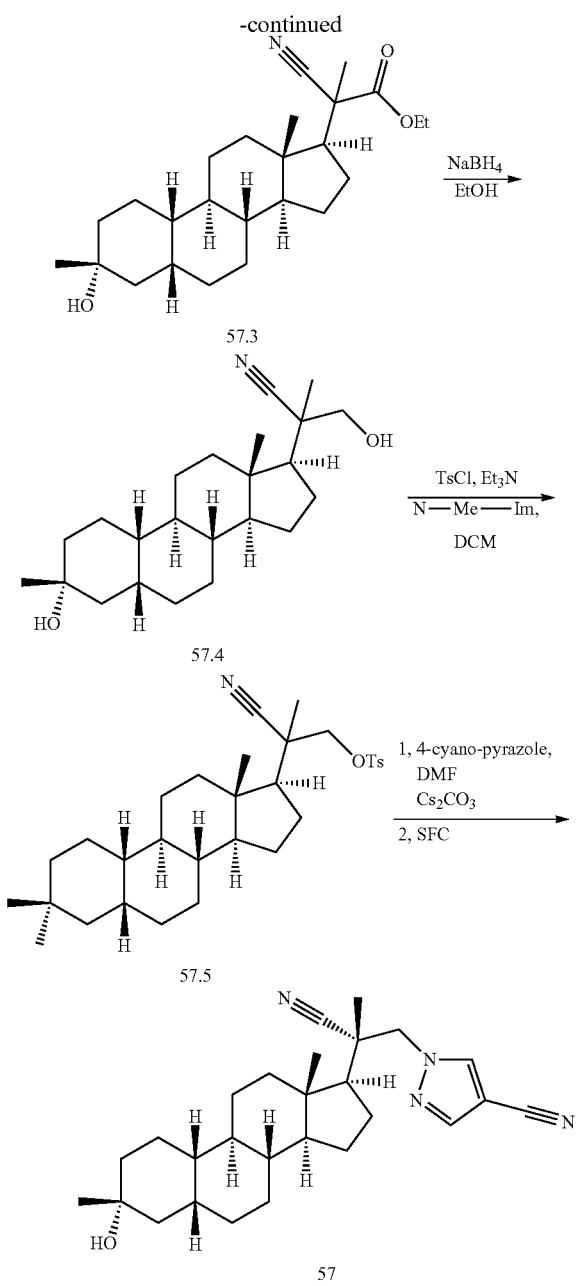

Synthesis of 57.1

To a solution of 39.0 (3 g, 10.3 mmol) in toluene (50 mL) was added acetic acid amine (2.38 g, 30.9 mmol), acetic acid (6.18 g, 103 mmol) and ethyl-1,2-isocyanoacetate (2.33 g, 20.6 mmol) at 25° C. under $N_2$. After stirring at 140° C. for 18 h the reaction mixture was quenched with saturated $NH_4Cl$ aqueous (50 mL) at 20° C. The aqueous was extracted with EtOAc (2×50 mL) and the combined organic phase were concentrated. The residue was purified by flash column (020% of EtOAc in PE) to give 57.1 (3.5 g). $^1$H NMR (400 MHz, CDCl$_3$) $\delta_H$ 4.20-4.31 (m, 2H), 3.07-3.23 (m, 1H), 2.68-3.02 (m, 2H), 1.72-1.92 (m, 5H), 1.38-1.69 (m, 11H), 1.23-1.36 (m, 12H), 1.10-1.22 (m, 3H), 1.01 (s, 3H),

Synthesis of 57.2

To a solution of 57.1 (500 mg, 1.29 mmol) in EtOH (5 mL) was added $NaBH_4$ (12.2 mg, 0.3225 mmol) at 0° C. under $N_2$. After stirring at 0° C. for 0.5 h the reaction mixture was quenched with saturated aqueous $NH_4Cl$ (10 mL). The aqueous was extracted with EtOAc (2×10 mL) and the combined organic phase was concentrated. The residue was purified by flash column (0~20% of EtOAc in PE) to give 57.2 (500 mg). $^1$H NMR (400 MHz, CDCl$_3$) $\delta_H$ 4.09-4.29 (m, 2H), 3.23-3.42 (m, 1H), 1.98-2.24 (m, 2H), 1.63-1.89 (m, 6H), 1.36-1.51 (m, 7H), 1.26 (m, 10H), 0.95-1.23 (m, 6H), 0.76 (d, J=4.4 Hz, 3H).

Synthesis of 57.3

To a solution of 57.2 (400 mg, 1.03 mmol) in acetone (10 mL), MeI (2.93 mL, 46.3 mmol) and $K_2CO_3$ (1.44 g, 10.3 mmol) were added into the reaction mixture at 25° C. After stirring for 16 h at 25° C. the residue was poured into water (20 mL). The aqueous phase was extracted with EtOAc (2×20 mL) and the combined organic phase was washed with water (2×20 mL), dried over anhydrous $Na_2SO_4$, filtered and concentrated to give 57.3 (350 mg, 85%). $^1$H NMR (400 MHz, CDCl$_3$) $\delta_H$ 4.18-4.28 (m, 2H), 1.76-2.01 (m, 8H), 1.63-1.72 (m, 3H), 1.46-1.51 (m, 2H), 1.35 (m, 9H), 1.26 (m, 7H), 1.00-1.10 (m, 5H), 0.94 (s, 3H).

Synthesis of 57.4

To a solution of 57.3 (350 mg, 0.8715 mmol) in EtOH (10 mL) was added $NaBH_4$ (491 mg, 13.0 mmol) at 25° C. under $N_2$. After stirring at 25° C. for 18 h the reaction mixture was quenched with saturated $NH_4Cl$ aqueous (20 mL) at 25° C. The aqueous was extracted with EtOAc (2×20 mL) and the combined organic phase was concentrated. The residue was purified by flash column (0~20% of EtOAc in PE) to give 57.4 (310 mg, 99%). $^1$H NMR (400 MHz, CDCl$_3$) $\delta_H$ 3.91-3.99 (m, 1H), 3.51-3.60 (m, 1H), 1.58-1.98 (m, 11H), 1.36-1.44 (m, 8H), 1.21-1.30 (m, 8H), 1.01-1.16 (m, 5H), 0.94 (s, 3H).

Synthesis of 57.5

To a solution of 57.4 (310 mg, 0.8621 mmol) in DCM (20 mL) was added N-Me-Im (87.2 mg, 0.8621 mmol), TEA (436 mg, 4.31 mmol) and TsCl (985 mg, 5.17 mmol). After stirring at 20° C. for 2 h the mixture was washed with water (40 mL), dried over $Na_2SO_4$, filtered and concentrated. The residue was purified by column (0%-40% of EtOAc in PE) to give 57.5 (260 mg, 58.8%). $^1$H NMR (400 MHz, CDCl$_3$) $\delta_H$ 7.79-7.85 (m, 2H), 7.36-7.40 (m, 2H), 4.19-4.24 (m, 1H), 3.95-4.00 (m, 1H), 2.47 (s, 3H), 1.59-1.90 (m, 10H), 1.54 (s, 3H), 1.33-1.50 (m, 12H), 0.98-1.15 (m, 6H), 0.84 (s, 3H).

Synthesis of 57

To a solution of 57.5 (260 mg, 0.51 mmol) in DMF (5 mL) was added $Cs_2CO_3$ (331 mg, 1.00 mmol), 4-cyano-pyrazole (94.0 mg, 1.01 mmol) and KI (83.9 mg, 0.51 mmol) at 25° C. After stirring at 120° C. for 18 h the mixture was washed with water (10 mL) and the aqueous phase was extracted with EtOAc (2×10 mL). The combined organic phase was washed with saturated brine (2×10 mL), dried over anhydrous $Na_2SO_4$, filtered, concentrated and purified by flash column (60-80% of EtOAc in PE) to give 57 (130 mg, 59%). 57 (110 mg, 0.2530 mmol, SFC spectra: SAGE-LXM-138-

P1A K3) was purified by SFC (Phenomenex-Cellulose-2 (250 mm*30 mm, 10 um)); Mobile phase: A: $CO_2$ B: 0.1% $NH_3H_2O$ EtOH; gradient: from 55% to 55% of B, FlowRate (ml/min): 80) providing 57 (68.0 mg, 62%). $^1$H NMR (400 MHz, $CDCl_3$) $\delta_H$ 8.10 (s, 1H), 7.83 (s, 1H), 4.66 (d, J=13.6 Hz, 1H), 4.16 (d, J=14.0 Hz, 1H), 1.95-2.03 (m, 2H), 1.64-1.88 (m, 7H), 1.54 (s, 3H), 1.44-1.45 (m, 1H), 1.38-1.52 (m, 5H), 1.24-1.32 (m, 7H), 1.18 (s, 3H), 1.08-1.14 (m, 3H), 1.04 (s, 3H). LC-ELSD/MS 30-90AB_2min_E, purity 99%; MS ESI calcd. for $C_{27}H_{38}N_4O$ [M+H]$^+$ 435.3, found 435.3.

Examples 58 & 59: Synthesis of 1-((S)-2-hydroxy-2-((2R,3S,5R,8R,9R,10S,13S,14S,17S)-3-hydroxy-2-(methoxymethyl)-3,13-dimethylhexadecahydro-1H-cyclopenta[a]phenanthren-17-yl)propyl)-1H-pyrazole-4-carbonitrile (58) & 1-((R)-2-hydroxy-2-((2R,3S,5R,8R,9R,10S,13S,14S,17S)-3-hydroxy-2-(methoxymethyl)-3,13-dimethylhexadecahydro-1H-cyclopenta[a]phenanthren-17-yl)propyl)-1H-pyrazole-4-carbonitrile (59) & 1-((S)-2-hydroxy-2-((2S,3S,5R,8R,9R,10S,13S,14S,17S)-3-hydroxy-2-(methoxymethyl)-3,13-dimethylhexadecahydro-1H-cyclopenta[a]phenanthren-17-yl)propyl)-1H-pyrazole-4-carbonitrile (58A) &1-((R)-2-hydroxy-2-((2S,3S,5R,8R,9R,10S,13S,14S,17S)-3-hydroxy-2-(methoxymethyl)-3,13-dimethylhexadecahydro-1H-cyclopenta[a]phenanthren-17-yl)propyl)-1H-pyrazole-4-carbonitrile (59A)

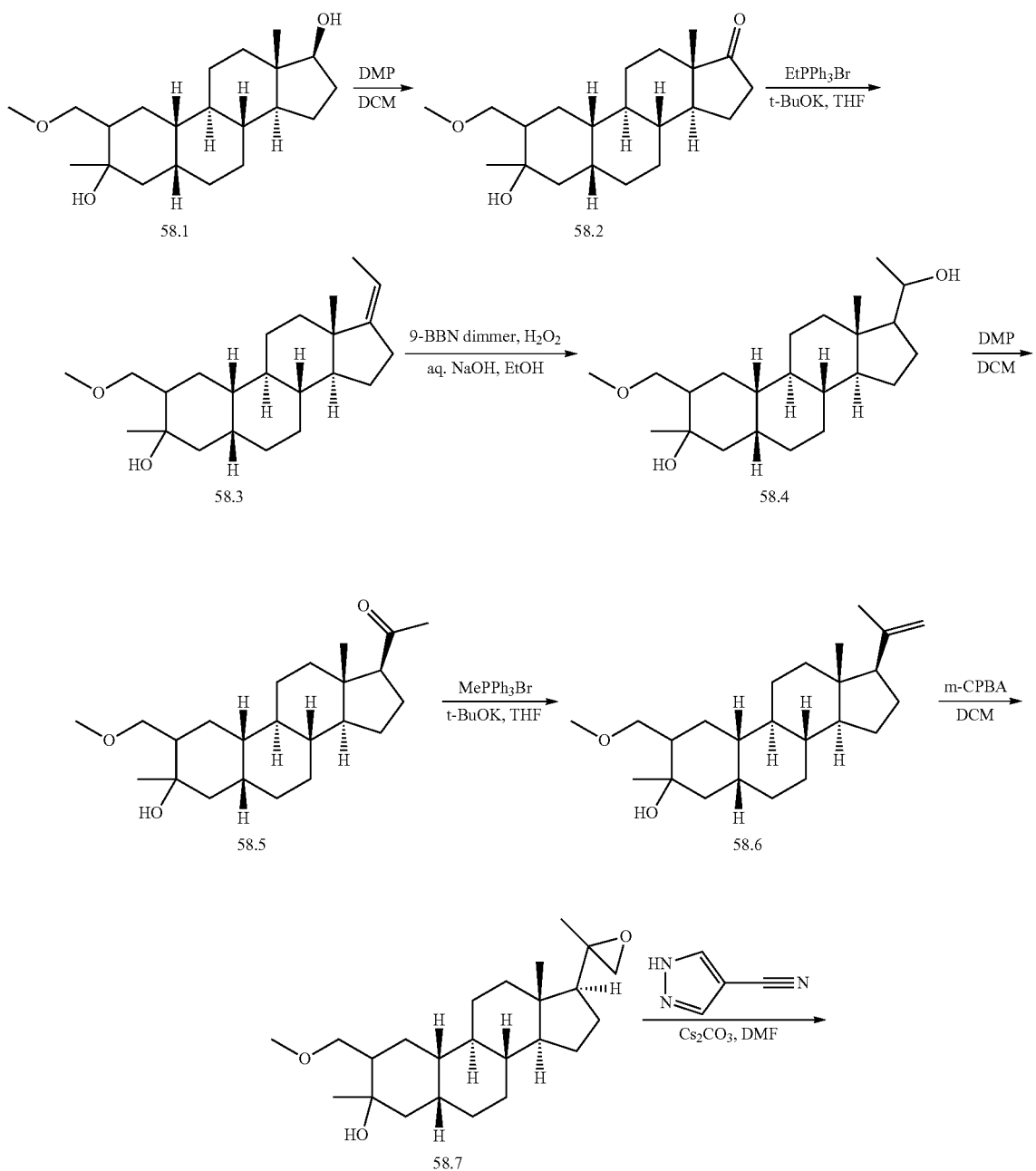

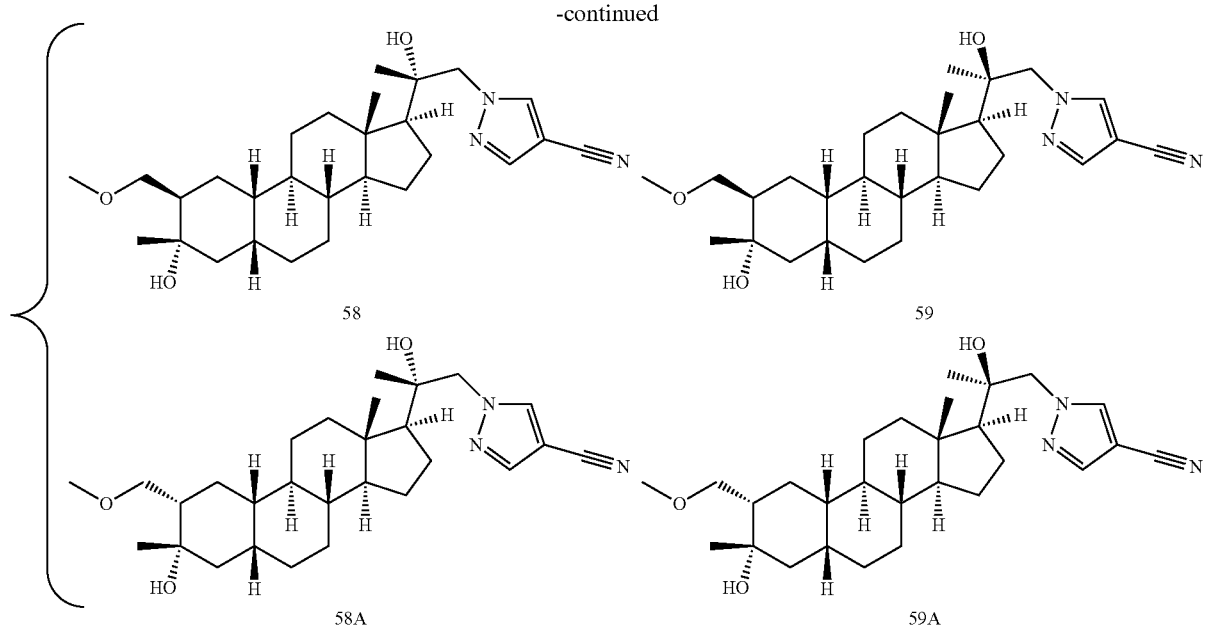

Synthesis of 58.2

To a mixture of 58.1 (380 mg, 1.12 mmol) in DCM (10 mL) was added DMP (950 mg, 2.24 mmol) in portions. After stirring at 20° C. for 2 h, the mixture was quenched with NaHCO$_3$(30 mL) and Na$_2$S$_2$O$_3$ (30 mL) then extracted with DCM (2×20 mL). The organic layer was washed with Na$_2$S$_2$O$_3$ (2×100 mL, sat.), brine (300 mL, sat.), dried over Na$_2$SO$_4$, filtered and concentrated to give 58.2 (600 mg). $^1$H NMR (400 MHz, CDCl$_3$) $\delta_H$ 3.70-3.66 (m, 1H), 3.42-3.23 (m, 4H), 2.47-2.40 (m, 1H), 2.18-1.60 (m, 8H), 1.57-1.14 (m, 14H), 1.13-0.86 (m, 6H).

Synthesis of 58.3

To a suspension of Ph$_3$PEtBr (3.97 g, 10.7 mmol) in THF (20 mL) was added t-BuOK (1.20 g, 10.7 mmol). After stirring at 40° C. for 30 min under N$_2$, 58.2 (600 mg, 1.79 mmol) in THF (20 mL) was added, then the resulting mixture was stirred at 40° C. for 16 h under N$_2$. The reaction mixture was poured into water (90 mL). The aqueous phase was extracted with EtOAc (2×100 mL). The combined organic phase was washed with brine (100 mL), dried over anhydrous Na$_2$SO$_4$, filtered and concentrated. The product was purified by flash column (0-10% EtOAc in PE) to give 58.3 (350 mg). $^1$H NMR (400 MHz, CDCl$_3$) $\delta_H$ 5.14-5.09 (m, 1H), 3.84-3.74 (m, 1H), 3.42-3.29 (m, 5H), 2.38-2.13 (m, 3H), 1.96-1.51 (m, 7H), 1.49-1.03 (m, 15H), 1.01-0.86 (m, 6H).

Synthesis of 58.4

To a solution of 58.3 (380 mg, 1.09 mmol) in THF (30 mL) was added 9-BBN dimer (797 mg, 3.27 mmol) at 25° C. under N$_2$. After stirring at 40° C. for 16 hours, the reaction mixture was cooled down and quenched with EtOH (0.8 mL, 13.0 mmol) at 0° C., followed by slow addition of NaOH (2.6 mL, 5M, 13.0 mmol). Then H$_2$O$_2$ (1.63 mL, 16.3 mmol, 10 M in water) was added slowly maintaining the temperature below 30° C. The mixture was stirred at 70° C. for another 1 h. The aqueous phase was extracted with ethyl acetate (3×100 mL). The combine organic phase was washed with saturated Na$_2$S$_2$O$_3$ (2×100 mL), brine (100 mL), drive over anhydrous Na$_2$SO$_4$, filtered and concentrated in vacuum to give a residue, which was purified by flash column (0~20% of EtOAc in PE) to give 58.4 (250 mg). $^1$H NMR (400 MHz, CDCl$_3$) $\delta_H$ 3.84-3.67 (m, 2H), 3.41-3.29 (m, 5H), 1.95-1.59 (m, 8H), 1.53-1.18 (m, 13H), 1.16-0.75 (m, 9H), 0.66-0.65 (m, 3H).

Synthesis of 58.5

To a solution of 58.4 (250 mg, 0.685 mmol) in DCM (10 mL) was added DMP (576 mg, 1.36 mmol) at 25° C. After stirring at 25° C. for 60 min, the mixture was quenched with NaHCO$_3$(300 mL) and Na$_2$S$_2$O$_3$ (300 mL) then extracted with DCM (2×100 mL). The organic layer was washed with Na$_2$S$_2$O$_3$ (2×100 mL, sat.), brine (300 mL, sat.), dried over Na$_2$SO$_4$, filtered and concentrated in vacuum to give 58.5 (400 mg). $^1$H NMR (400 MHz, CDCl$_3$) $\delta_H$ 3.78-3.71 (m, 1H), 3.45-3.32 (m, 5H), 2.56-2.50 (m, 2H), 2.26-1.85 (m, 7H), 1.83-1.54 (m, 6H), 1.53-1.29 (m, 6H), 1.25-0.79 (m, 7H), 0.63-0.60 (m, 4H).

Synthesis of 58.6

To a suspension of Ph$_3$PMeBr (1.57 g, 4.40 mmol) in THF (20 mL) was added t-BuOK (493 mg, 4.40 mmol) at 25° C. under N$_2$. After stirring at 50° C. for 30 min, a solution of 58.5 (400 mg, 1.10 mmol) in THF (20 mL) was added dropwise to the resulting suspension, and then the mixture was stirred at 50° C. for 2 h under N$_2$. The reaction mixture was poured into 10% aq. NH$_4$Cl (100 mL). The aqueous phase was extracted with EtOAc (3×100 mL). The combined organic phase was washed with brine (100 mL), dried over anhydrous Na$_2$SO$_4$, filtered and concentrated. The product was purified by flash column (0~10% of EtOAc in PE) to give 58.6 (200 mg). $^1$H NMR (400 MHz, CDCl$_3$) $\delta_H$ 4.84 (s, 1H), 4.70 (s, 1H), 3.87-3.75 (m, 1H), 3.42-3.31 (m, 5H), 2.04-1.56 (m, 9H), 1.51-1.18 (m, 12H), 1.15-0.83 (m, 8H), 0.57 (s, 3H).

Synthesis of 58.7

To a solution of 58.6 (170 mg, 0.471 mmol) in DCM (10 mL) was added m-CPBA (190 mg, 85%, 0.94 mmol) at 15° C. and stirred for 0.5 h. The mixture was quenched with saturated aq. $NaHCO_3$ (100 mL). The DCM phase was separated and washed with saturated aq. $NaHCO_3/Na_2S_2O_3$ (1:1, 3×100 mL), brine (100 mL), dried over $Na_2SO_4$, filtered and concentrated under vacuum to give 58.7 (250 mg). $^1$H NMR (400 MHz, $CDCl_3$) $\delta_H$ 3.92-3.72 (m, 1H), 3.42-3.30 (m, 5H), 2.88-2.87 (m, 0.7H), 2.56-2.49 (m, 1H), 2.32-2.31 (m, 0.3H), 2.05-1.52 (m, 7H), 1.48-1.20 (m, 12H), 1.18-0.81 (m, 10H), 0.79-0.67 (m, 3H).

Synthesis of 58 & 59 & 58A & 59A

To a solution of 58.7 (250 mg, 0.663 mmol) in DMF (10 mL) was added 1H-pyrazole-4-carbonitrile (184 mg, 1.98 mmol) and $Cs_2CO_3$ (645 mg, 1.98 mmol). After stirring at 130° C. for 16 hours, the reaction mixture was diluted with water (100 mL) and extracted with EtOAc (3×100 mL). The combined organic layer was washed with 5% LiCl (3×100 mL) and concentrated. The residue was purified by flash column (0~12% of EtOAc in PE) to give 200 mg of compound, which was purified by SFC (Column DAICEL CHIRALPAK IG (250 mm*30 mm, 10 um); Condition 0.1% $NH_3H_2O$ ETOH; Begin B 60%; End B 60%) to give 58 (8.9 mg, 6%), 59 (10.1 mg, 6%), 58A (46.7 mg, 31%), 59A (22.2 mg, 14%).

58: $^1$H NMR (400 MHz, $CDCl_3$) $\delta_H$ 7.92 (s, 1H), 7.81 (s, 1H), 4.36-4.33 (m, 1H), 4.09-4.06 (m, 1H), 3.84 (s, 1H), 3.40-3.29 (m, 4H), 2.49 (s, 1H), 2.02-1.56 (m, 8H), 1.49-1.12 (m, 12H), 1.11-0.91 (m, 13H). LC-ELSD/MS purity 99%, MS ESI calcd. for $C_{27}H_{36}N_3$ $[M-2H_2O-MeOH+H]^+$ 402.3 found 402.3.

59: $^1$H NMR (400 MHz, $CDCl_3$) $\delta_H$ 7.88 (s, 1H), 7.80 (s, 1H), 4.18-4.15 (m, 1H), 4.02-3.99 (m, 1H), 3.85 (s, 1H), 3.40-3.29 (m, 6H), 2.32 (s, 1H), 2.07-1.58 (m, 5H), 1.50-1.18 (m, 11H), 1.16-0.85 (m, 15H). LC-ELSD/MS purity 99%, MS ESI calcd. for $C_{27}H_{36}N_3$ $[M-2H_2O-MeOH+H]^+$ 402.3 found 402.3.

58A: $^1$H NMR (400 MHz, $CDCl_3$) $\delta_H$ 7.92 (s, 1H), 7.81 (s, 1H), 4.36-4.32 (m, 1H), 4.10-4.07 (m, 1H), 3.71 (t, J=9.2 Hz, 1H), 3.41-3.34 (m, 4H), 3.22 (s, 1H), 2.50 (s, 1H), 2.04-2.00 (m, 1H), 1.88-1.57 (m, 9H), 1.46-1.14 (m, 10H), 1.11-0.85 (m, 12H). LC-ELSD/MS purity 99%, MS ESI calcd. for $C_{27}H_{36}N_3$ $[M-2H_2O-MeOH+H]^+$ 402.3 found 402.3.

59A: $^1$H NMR (400 MHz, $CDCl_3$) $\delta_H$ 7.88 (s, 1H), 7.80 (s, 1H), 4.18-4.14 (m, 1H), 4.02-3.99 (m, 1H), 3.71 (t, J=8.8 Hz, 1H), 3.41-3.34 (m, 4H), 3.24 (s, 1H), 2.28 (s, 1H), 2.08-1.57 (m, 9H), 1.52-1.12 (m, 11H), 1.09-0.88 (m, 12H). LC-ELSD/MS purity 99%, MS ESI calcd. for $C_{27}H_{36}N_3$ $[M-2H_2O-MeOH+H]^+$ 402.3 found 402.3.

Examples 60 & 61: Synthesis of 1-((S)-2-hydroxy-2-((2R,3S,5R,8R,9R,10S,13S,14S,17S)-3-hydroxy-2-methoxy-3,13-dimethylhexadecahydro-1H-cyclopenta[a]phenanthren-17-yl)propyl)-1H-pyrazole-4-carbonitrile (60) & 1-((R)-2-hydroxy-2-((2R,3S,5R,8R,9R,10S,13S,14S,17S)-3-hydroxy-2-methoxy-3,13-dimethylhexadecahydro-1H-cyclopenta[a]phenanthren-17-yl)propyl)-1H-pyrazole-4-carbonitrile (61)

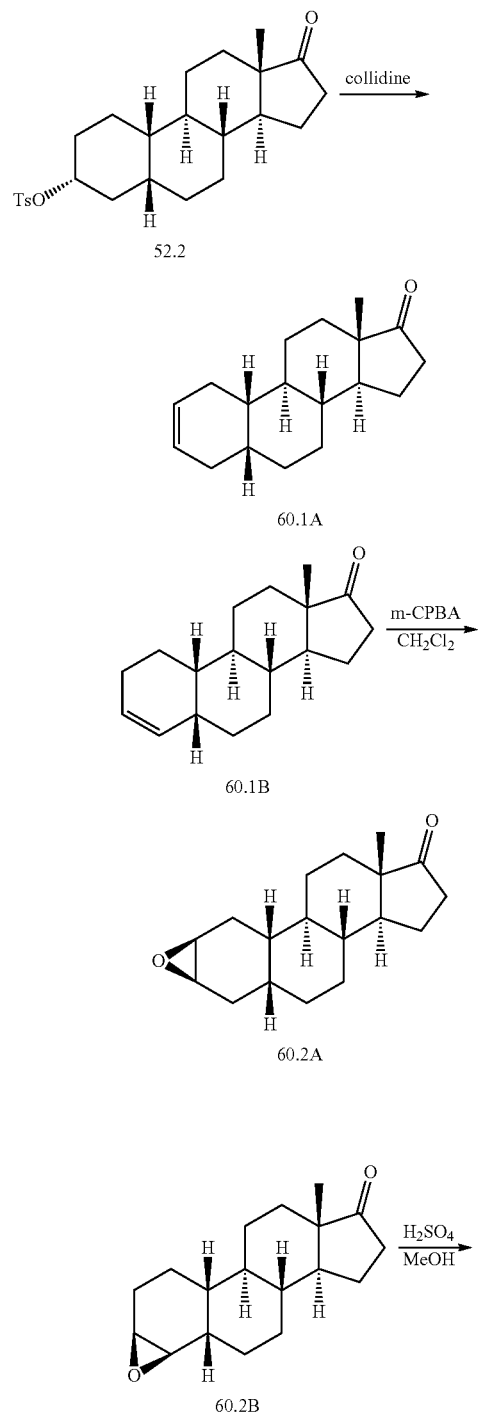

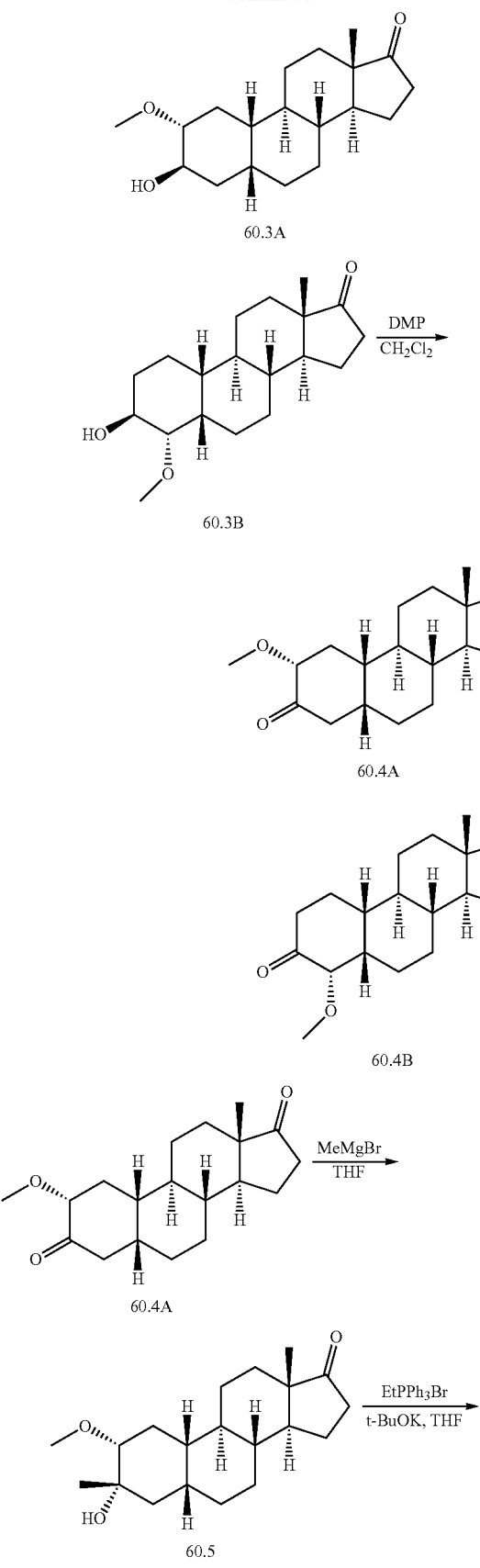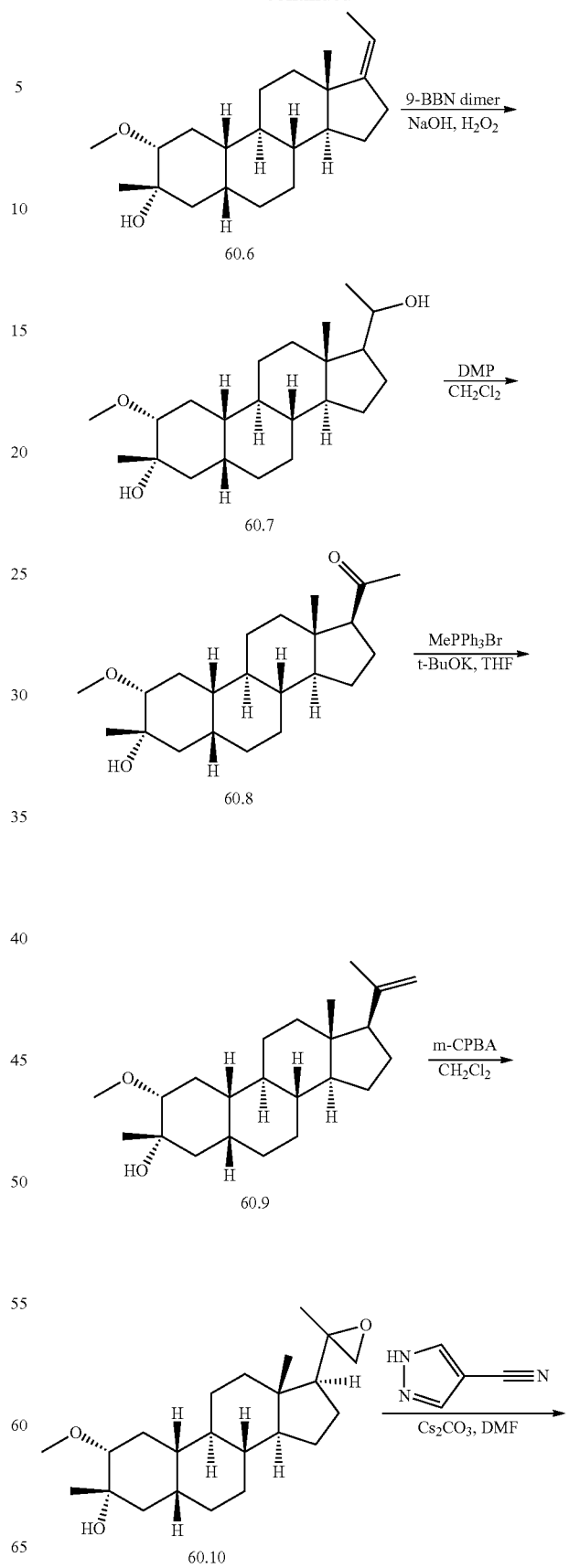

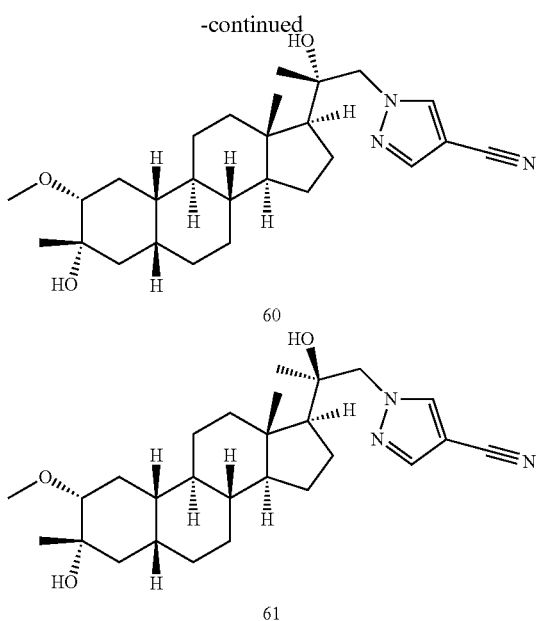

60

61

Synthesis of 60.1A & 60.1B

Compound 52.2 (16.0 g, 37.1 mmol) was added to collidine (150 mL, 37.1 mmol) at 25° C. under $N_2$. The mixture was stirred at 140° C. for 16 hours to give a solution. The mixture was poured into water (500 mL), extracted with EtOAc (3×400 mL). The combined organic phase was washed with water(3×100 mL), brine (200 mL), dried over anhydrous $Na_2SO_4$, filtered and concentrated under vacuum. The residue was purified by flash column (0-0% of EtOAc in PE) to give 60.1A and 60.1B (8.60 g). $^1$H NMR (400 MHz, CDCl$_3$) $\delta_H$ 0.87 (s, 1H) 0.91 (s, 1H) 0.94-1.10 (m, 2H) 1.10-1.33 (m, 6H) 1.53 (br dd, J=6.02, 2.76 Hz, 7H) 1.67-1.83 (m, 3H) 1.83-1.97 (m, 3H) 2.28-2.72 (m, 3H) 5.31-5.55 (m, 1H) 5.60 (br s, 1H).

Synthesis of 60.2A & 60.2B

To a mixed solution 60.1A and 60.1B (8.60 g, 33.2 mmol) in DCM (90 mL) was added m-CPBA (10.0 g, 49.8 mmol) at 0° C. under $N_2$. After stirring at 25° C. for 2 h, the mixture was quenched with saturated NaHCO$_3$(100 mL) and extracted with DCM (2×150 mL). The organic layer was washed with $Na_2S_2O_3$ (2×100 mL, sat.), brine (2×100 mL), dried over anhydrous $Na_2SO_4$, filtered and concentrated in vacuum. The residue was purified by flash column (0-20% of EtOAc in PE) to give 60.2A and 60.2B (4.60 g). $^1$H NMR (400 MHz, CDCl$_3$) $\delta_H$ 30.64-0.82 (m, 1H) 0.71-0.89 (m, 1H) 0.82-0.86 (m, 1H) 0.87 (br s, 1H) 0.9-1.12 (m, 2H) 1.12-1.33 (m, 4H) 1.30-1.44 (m, 3H) 1.44-1.65 (m, 3H) 1.65-1.76 (m, 2H) 1.76-1.89 (m, 2H) 1.89-2.09 (m, 3H) 2.09-2.74 (m, 2H) 2.76-3.31 (m, 1H).

Synthesis of 60.3A & 60.3B

To a solution of the mixture of 60.2A and 60.2B (4.80 g, 17.4 mmol) in MeOH (50 mL) was treated with 0.5 mL of $H_2SO_4$ (98%) at 25° C. for 3 hours. The reaction mixture was treated with saturated NaHCO$_3$(200 mL). The mixture was extracted with EtOAc (2×300 mL). The organic layer was washed with brine (2×200 mL), dried over anhydrous $Na_2SO_4$, filtered and concentrated. The product was purified by flash column chromatography on silica gel (0~15% of EtOAc in PE) to give 60.3A and 60.3B (4.30 g). $^1$H NMR (400 MHz, CDCl$_3$) $\delta_H$ 0.87 (s, 3H) 0.87-0.89 (m, 1H) 0.91-1.13 (m, 3H) 1.14-1.35 (m, 6H) 1.35-1.60 (m, 4H) 1.70-2.01 (m, 4H) 2.06-2.65 (m, 3H) 2.96-3.24 (m, 1H) 3.33 (s, 1H) 3.37 (s, 1H) 3.40 (s, 2H) 3.60-3.77 (m, 1H).

Synthesis of 60.4A & 60.4B

To a solution of 60.3A and 60.3B (500 mg, 1.63 mmol) in DCM (10 mL) was added DMP (1.38 g, 3.26 mmol) at 25° C. under $N_2$. After stirring at 25° C. for 1 h, another batch of DMP (1.38 g, 3.26 mmol) was added to the reaction mixture at 25° C. under $N_2$. After stirring at 35° C. for 2 h, the mixture was quenched with saturated aqueous NaHCO$_3$ and saturated aqueous $Na_2S_2O_3$ (50 mL, 1:1). The mixture was extracted with DCM (2×100 mL). The combined organic phase was washed with a mixture of saturated aqueous NaHCO$_3$ and saturated aqueous $Na_2S_2O_3$ (150 mL, 1:1), The combined organic phase was washed with brine (2×100 mL), dried over anhydrous $Na_2SO_4$, filtered and concentrated. The residue was purified by pre-HPLC (Column: Welch Xtimate C18 150*25 mm*5 um; Condition: water (0.225% FA)-ACN; Begin B: 70%; End B: 100%) to afford 60.4A (50 mg, 10.0%) and 60.4B (430 mg).

60.4A: $^1$H NMR (400 MHz, CDCl$_3$) $\delta_H$ 5.70-5.65 (m, 1H), 5.42-5.36 (m, 1H), 3.93-3.89 (m, 1H), 3.60-3.56 (m, 1H), 2.58-2.48 (m, 2H), 2.24-1.90 (m, 6H), 1.80-1.10 (m, 16H), 1.00-0.87 (m, 1H), 0.60 (s, 3H). LC-ELSD/MS purity 99%, MS ESI calcd. for $C_{19}H_{29}O_3$ [M+H]$^+$ 305.2 found 305.2.

60.4B: $^1$H NMR (400 MHz, CDCl$_3$) $\delta_H$ 0.70 (s, 1H) 0.83-0.91 (m, 3H) 0.92-1.08 (m, 1H) 1.08-1.26 (m, 1H) 1.26-1.50 (m, 4H) 1.65-1.76 (m, 3H) 1.76-1.90 (m, 2H) 1.90-2.02 (m, 2H) 2.05 (br d, J=8.78 Hz, 2H) 2.12-2.27 (m, 1H) 2.27-2.36 (m, 1H) 2.45 (br dd, J=19.20, 8.66 Hz, 1H) 2.66-2.80 (m, 1H) 3.01 (t, J=13.80 Hz, 1H) 3.25 (s, 1H) 3.26 (s, 1H) 3.27-3.28 (m, 1H) 3.48 (br d, J=3.51 Hz, 1H).

Synthesis of 60.5

To a solution of 60.4A (350 mg, 1.14 mmol) in THE (10 mL) was added MeMgBr (1.9 mL, 3 M in ethyl ether, 5.70 mmol) dropwise at –70° C. and the mixture was stirred for 2 h. The reaction mixture was slowly poured into saturated aqueous citric acid (20 mL) at below 10° C. The aqueous phase was extracted with EtOAc (2×20 mL). The combined organic phase was washed with brine (30 mL), dried over anhydrous $Na_2SO_4$, filtered and concentrated to afford 60.5 (450 mg). $^1$H NMR (400 MHz, CDCl$_3$) $\delta_H$ 3.37 (s, 3H), 3.05 (s, 1H), 3.01 (br s, 1H), 2.43 (dd, J=8.2, 19.2 Hz, 1H), 2.28-2.17 (m, 1H), 2.13-2.06 (m, 1H), 1.92-1.75 (m, 5H), 1.55-1.33 (m, 8H), 1.22 (s, 3H), 1.21-1.03 (m, 5H), 0.87 (s, 3H).

Synthesis of 60.6

To a suspension of EtPh$_3$PBr (2.59 g, 7.00 mmol) in anhydrous THE (20 mL) was added t-BuOK (784 mg, 7.00 mmol) at 25° C. under $N_2$ and stirred at 45° C. for 30 min. Then a solution of 60.5 (450 mg, 1.40 mmol) in anhydrous THE (10 mL) was added dropwise. The reaction mixture was stirred for 16 h. The mixture was cooled and poured into water (25 mL) and stirred for 10 min. The aqueous phase was extracted with EtOAc (2×30 mL). The combine organic phase was washed with brine (2×50 mL), filtered, dried over anhydrous Na$_2$SO$_4$, and concentrated. The residue was purified by flash column (0~15% of EtOAc in PE) to give 60.6 (350 mg, 75.2%). $^1$H NMR (400 MHz, CDCl$_3$) $\delta_H$ 5.21-5.02 (m, 1H), 3.39 (s, 3H), 3.09 (s, 1H), 3.00 (br s, 1H), 2.45-2.09 (m, 4H), 1.98-1.87 (m, 1H), 1.86-1.77 (m, 2H), 1.70-1.57 (m, 6H), 1.54-1.31 (m, 6H), 1.22 (s, 3H), 1.20-1.04 (m, 4H), 0.97-0.89 (m, 1H), 0.88 (s, 3H).

Synthesis of 60.7

To a solution of 60.6 (350 mg, 1.05 mmol) in THF (20 mL) was added 9-BBN (8.4 ml, 4.20 mmol, 0.5 M in THF) under N$_2$. The reaction mixture was stirred at 50° C. under N$_2$ for 2 h. The mixture was cooled to 0° C. Then ethanol (0.902 mL, 15.7 mmol) and NaOH (3.13 mL, 5 M, 15.7 mmol) were added to the reaction mixture. Subsequently, H$_2$O$_2$ (1.56 mL, 10 M, 15.7 mmol) was added dropwise at 0° C. The mixture was stirred at 50° C. for 2 hours. Saturated aqueous Na$_2$S$_2$O$_3$ (50 mL) was added and the mixture was stirred at 0° C. for another 1 hour. The reaction was checked with potassium iodide-starch test paper to confirm excess H$_2$O$_2$ was destroyed. The aqueous phase was extracted with EtOAc (3×20 mL). The combined organic layer was washed with brine (2×50 mL), dried over anhydrous Na$_2$SO$_4$, filtered and concentrated to give 60.7 (350 mg).

Synthesis of 60.8

To a solution of 60.7 (350 mg, 0.998 mmol) in DCM (30 mL) was added DMP (1.69 g, 3.99 mmol) at 25° C. under N$_2$. After stirring at 25° C. for 0.5 h, the resulting mixture was quenched with NaHCO$_3$ and Na$_2$S$_2$O$_3$ (50 mL, 1:1). The mixture was extracted with DCM (2×50 mL). The combined organic phase was washed with a mixture of NaHCO$_3$ and Na$_2$S$_2$O$_3$ (50 mL, 1:1). The combined organic layer was washed with brine (2×30 mL), dried over anhydrous Na$_2$SO$_4$, filtered and concentrated. The residue was purified by flash column (0-30% of EtOAc in PE) to give 60.8 (260 mg, 74.9%). $^1$H NMR (400 MHz, CDCl$_3$) $\delta_H$ 3.40 (s, 3H), 3.07 (s, 1H), 3.02 (br s, 1H), 2.54 (br t, J=8.7 Hz, 1H), 2.30-2.13 (m, 2H), 2.12 (s, 3H), 2.04-1.97 (m, 1H), 1.92-1.77 (m, 3H), 1.68-1.59 (m, 3H), 1.51-1.26 (m, 7H), 1.22 (s, 3H), 1.20-1.00 (m, 4H), 0.96-0.81 (m, 1H), 0.61 (s, 3H).

Synthesis of 60.9

To a suspension of MePh$_3$PBr (675 mg, 1.89 mmol) in anhydrous THF (15 mL) was added t-BuOK (212 mg, 1.89 mmol) at 15° C. under N$_2$ and stirred at 60° C. for 30 min. Then a solution of 60.8 (220 mg, 0.63 mmol) in anhydrous THF (5 mL) was added dropwise. The reaction mixture was stirred for 1 h. The mixture was cooled and poured into ice-water (50 mL) stirred for 10 min. The aqueous phase was extracted with EtOAc (2×50 mL). The combine organic phase was washed with brine (2×50 mL), filtered and concentrated. The residue was purified by flash column (0~10% of EtOAc in PE) to give 60.9 (200 mg, 91.7%). $^1$H NMR (400 MHz, CDCl$_3$) $\delta_H$ 4.84 (s, 1H), 4.70 (s, 1H), 3.40 (s, 3H), 3.09 (s, 1H), 3.00 (br s, 1H), 2.30-2.18 (m, 1H), 1.96-1.77 (m, 4H), 1.76 (s, 3H), 1.73-1.59 (m, 3H), 1.53-1.31 (m, 6H), 1.22 (s, 3H), 1.20-1.00 (m, 5H), 0.91-0.78 (m, 3H), 0.57 (s, 3H).

Synthesis of 60.10

To a solution of 60.9 (110 mg, 0.3174 mmol) in DCM (10 mL) was added m-CPBA (128 mg, 0.64 mmol, 85%) and NaHCO$_3$ (53.3 mg, 0.64 mmol) at 0° C. under N$_2$. Then the mixture was stirred at 15° C. for 2 h. The mixture was quenched with saturated NaHCO$_3$ (10 mL) and extracted with DCM (2×10 mL). The organic layer was washed with Na$_2$S$_2$O$_3$ (2×10 mL, sat.), brine (2×10 mL), dried over anhydrous Na$_2$SO$_4$, filtered and concentrated to give 60.10 (100 mg).

Synthesis of 60 & 61

To a solution of 60.10 (100 mg, 0.28 mmol) in DMF (5 mL) was added 1H-pyrazole-4-carbonitrile (51.3 mg, 0.55 mmol) and Cs$_2$CO$_3$ (179 mg, 0.55 mmol) at 20° C. under N$_2$. After stirring at 130° C. for 16 hours, the mixture was poured into H$_2$O (10 mL) and extracted with EtOAc (2×20 mL). The combined organic layer was washed with brine (20 mL), dried over anhydrous Na$_2$SO$_4$, filtered and concentrated. The residue was purified by flash column (0~30% of EtOAc in PE), which was purified by SFC (Column: DAICEL CHIRALPAK AD(250 mm*30 mm, 10 um); Condition: 0.1% NH$_3$H$_2$ IPA; Begin B: 60%; End B: 60%) to afford 60 (26.1 mg, Rt=2.091 min, 26.1%) and 61 (7.2 mg, Rt=2.275 min, 7.22%).

60: $^1$H NMR (400 MHz, CDCl$_3$) $\delta_H$ 7.94 (d, J=2.5 Hz, 1H), 7.83 (d, J=2.5 Hz, 1H), 4.42-4.02 (m, 2H), 3.39 (d, J=2.8 Hz, 3H), 3.11-2.95 (m, 2H), 2.53 (d, J=2.8 Hz, 1H), 2.30-1.99 (m, 1H), 2.30-1.99 (m, 2H), 1.97-1.80 (m, 2H), 1.70-1.32 (m, 9H), 1.23 (br s, 10H), 0.99 (d, J=2.5 Hz, 3H), 0.93 (d, J=2.3 Hz, 4H). LC-ELSD/MS purity 99%, MS ESI calcd. for C$_{27}$H$_{38}$N$_3$O [M−2H$_2$O+H]$^+$ 420.3 found 420.3.

61: $^1$H NMR (400 MHz, CDCl$_3$) $\delta_H$ 7.90 (s, 1H), 7.81 (s, 1H), 4.24-3.93 (m, 2H), 3.39 (s, 3H), 3.14-2.94 (m, 2H), 2.29 (s, 4H), 1.95-1.60 (m, 4H), 1.54-1.28 (m, 8H), 1.24-1.06 (m, 11H), 0.91-0.86 (m, 1H), 0.89 (s, 4H). LC-ELSD/MS purity 99%, MS ESI calcd. for C$_{27}$H$_{38}$N$_3$O [M−2H$_2$O+H]$^+$ 420.3 found 420.3.

Steroid Inhibition of TBPS Binding

[$^{35}$S]-t-Butylbicyclophosphorothionate (TBPS) binding assays using rat brain cortical membranes in the presence of 5 mM GABA has been described (Gee et al, J. Pharmacol. Exp. Ther. 1987, 241, 346-353; Hawkinson et al, *Mol. Pharmacol.* 1994, 46, 977-985; Lewin, A. H et al., *Mol. Pharmacol.* 1989, 35, 189-194).

Briefly, cortices are rapidly removed following decapitation of carbon dioxide-anesthetized Sprague-Dawley rats (200-250 g). The cortices are homogenized in 10 volumes of ice-cold 0.32 M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na—K phosphate pH 7.4 buffer and centrifuged at 10,000×g for 10 min at 4° C. This washing procedure is repeated twice and the pellets are resuspended in 10 volumes of buffer. Aliquots (100 mL) of the membrane suspensions are incubated with 3 nM [35S]-TBPS and 5 mL aliquots of test drug dissolved in dimethyl sulfoxide (DMSO) (final 0.5%) in the presence of 5 mM GABA. The incubation is brought to a final volume of 1.0 mL with buffer. Nonspecific binding is determined in the presence of 2 mM unlabeled TBPS and ranged from 15 to 25%. Following a 90 min incubation at room temp, the assays are terminated by filtration through glass fiber filters (Schleicher and Schuell No. 32) using a cell harvester (Brandel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition ($IC_{50}$) of specific binding and the maximal extent of inhibition ($I_{max}$) are determined for the individual experiments with the same model used for the overall data and then the means±SEM.s of the individual experiments are calculated. Picrotoxin serves as the positive control for these studies as it has been demonstrated to robustly inhibit TBPS binding.

Various compounds are or can be screened to determine their potential as modulators of [$^{35}$S]-TBPS binding in vitro. These assays are or can be performed in accordance with the above In Table 2 below, A indicates a TBPS $IC_{50}$ (μM) <0.1 μM, B indicates a TBPS $IC_{50}$ (μM) of 0.1 μM to <1.0 μM, C indicates a TBPS $IC_{50}$ (μM) of ≥1.0 μM.

TABLE 2

| Compound No. | Structure | $IC_{50}$ |
|---|---|---|
| 1 | 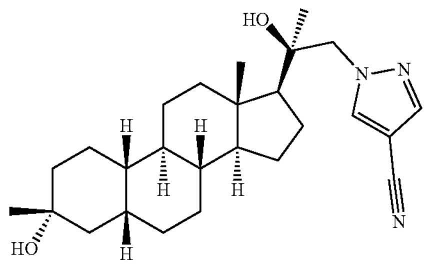 | A |
| 2 | 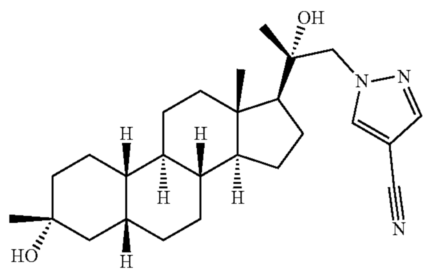 | A |
| 3 | 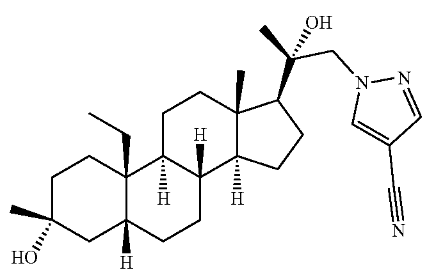 | A |
| 4 | 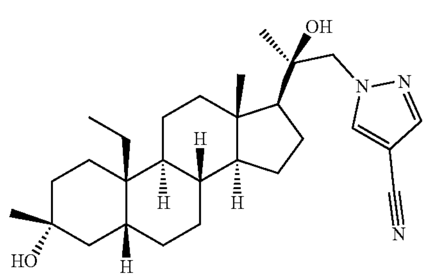 | A |

TABLE 2-continued

| Compound No. | Structure | IC$_{50}$ |
|---|---|---|
| 5 | 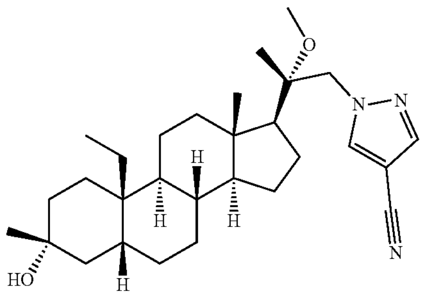 | A |
| 6 | 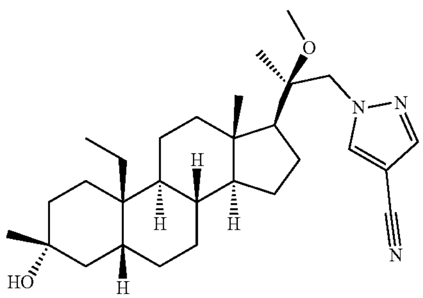 | A |
| 7 | 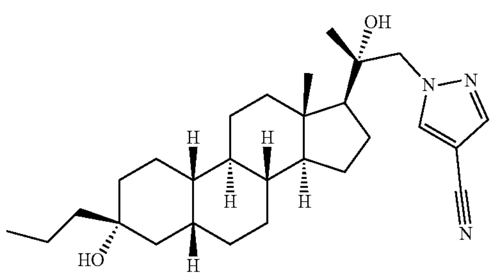 | A |
| 8 | 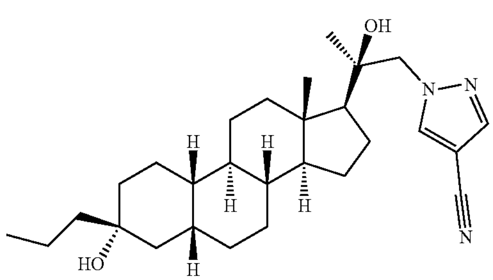 | B |
| 9 | 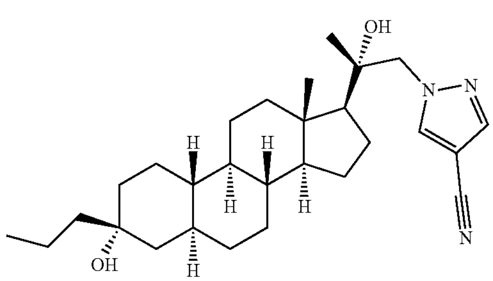 | B |

TABLE 2-continued
| Compound No. | Structure | IC$_{50}$ |
|---|---|---|
| 10 | 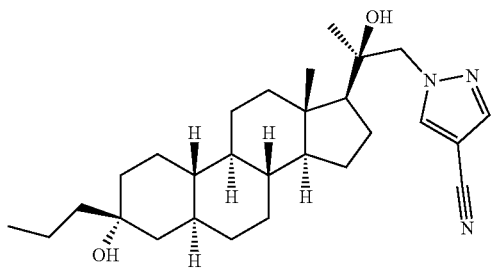 | C |
| 11 | 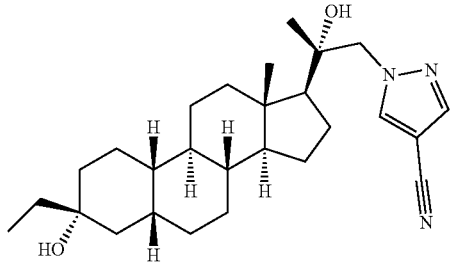 | A |
| 12 | 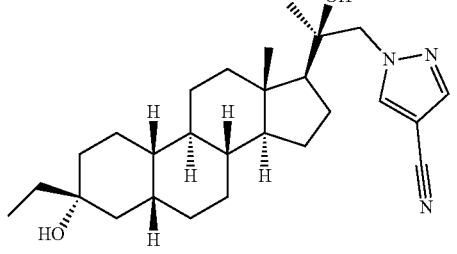 | B |
| 13 | 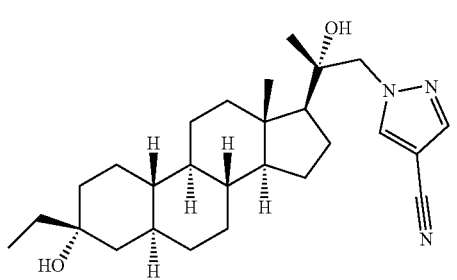 | B |
| 14 | 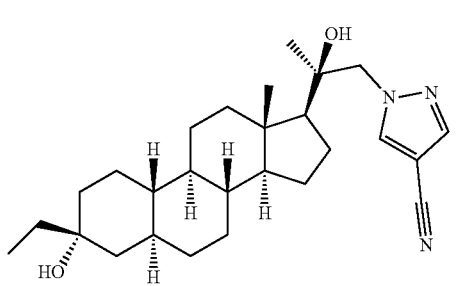 | C |

TABLE 2-continued

| Compound No. | Structure | IC$_{50}$ |
|---|---|---|
| 15 | 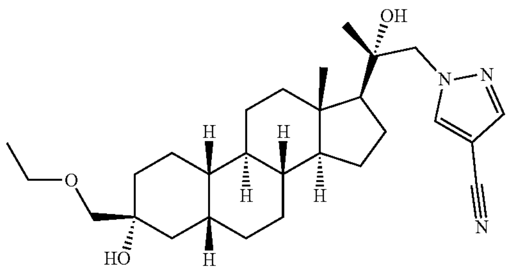 | A |
| 16 | 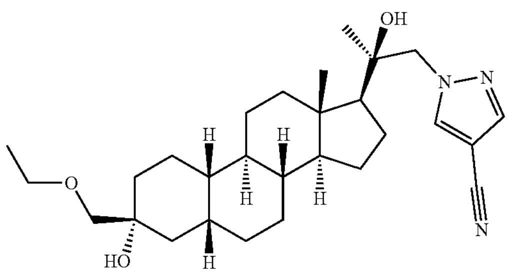 | A |
| 17 | 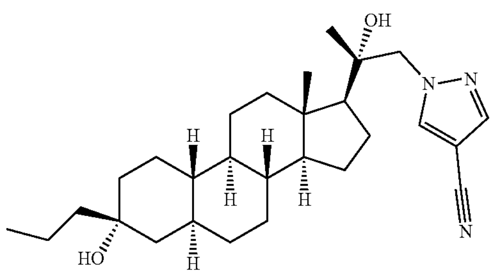 | B |
| 18 | 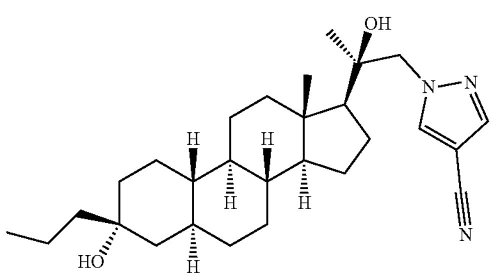 | A |
| 19 | 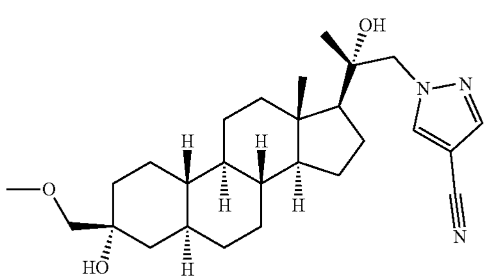 | A |

TABLE 2-continued

| Compound No. | Structure | IC$_{50}$ |
|---|---|---|
| 20 | 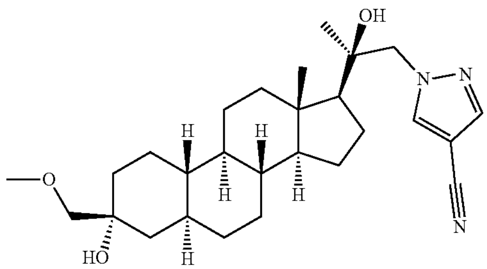 | B |
| 21 | 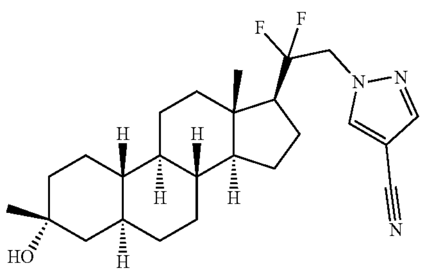 | A |
| 22 | 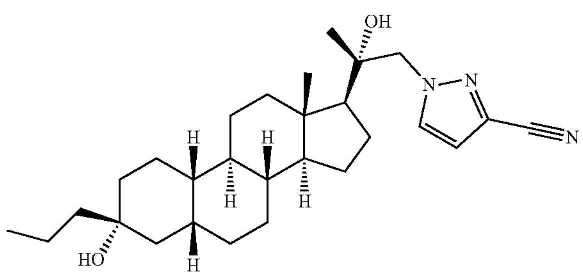 | A |
| 23 | 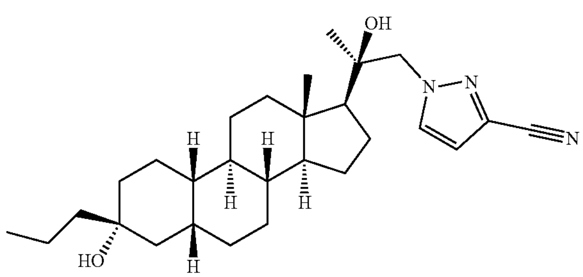 | B |
| 24 | 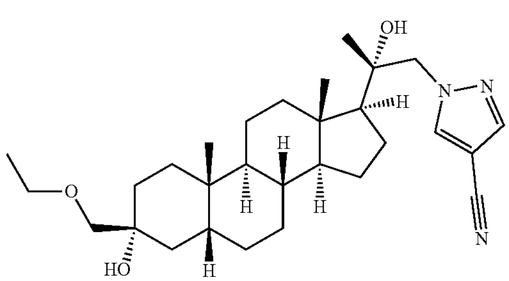 | A |

TABLE 2-continued

| Compound No. | Structure | IC$_{50}$ |
|---|---|---|
| 25 | 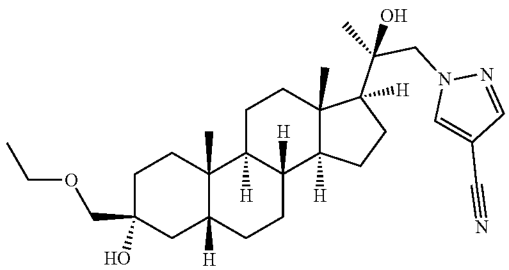 | B |
| 26 | 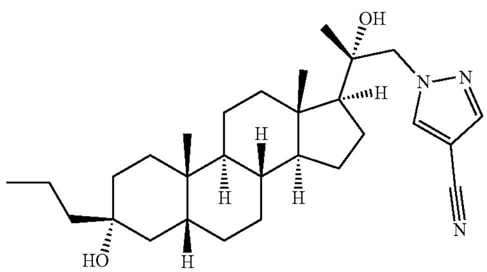 | A |
| 27 | 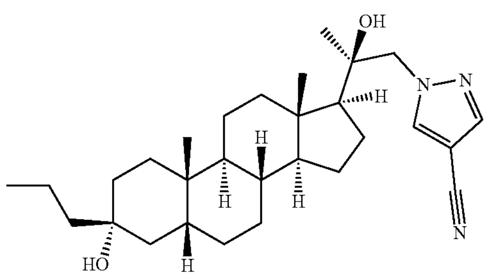 | B |
| 28 | 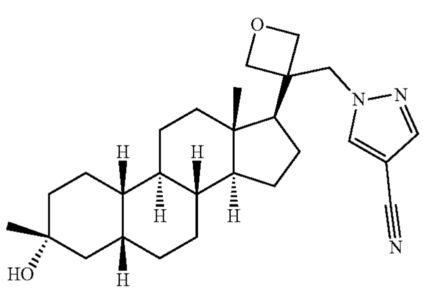 | A |
| 29 | 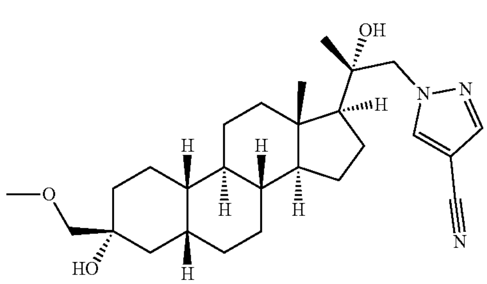 | A |

TABLE 2-continued
| Compound No. | Structure | IC$_{50}$ |
|---|---|---|
| 30 | 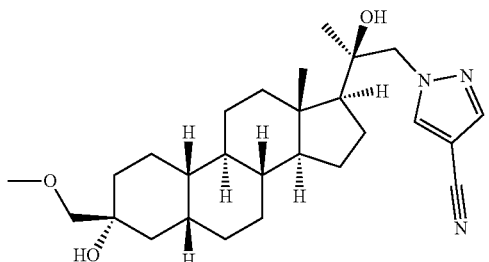 | B |
| 31 | 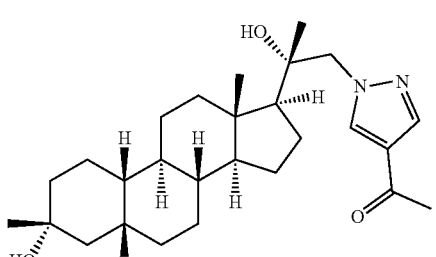 | A |
| 32 | 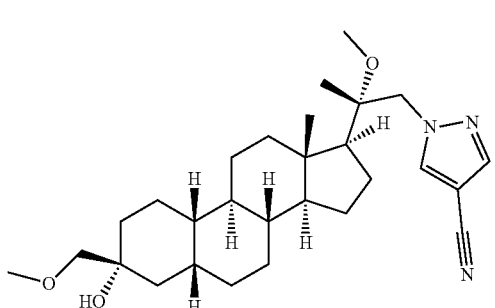 | B |
| 33 | 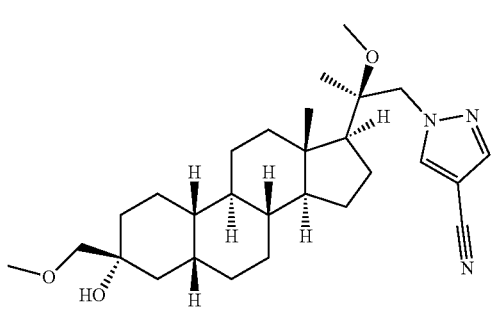 | B |
| 34 | 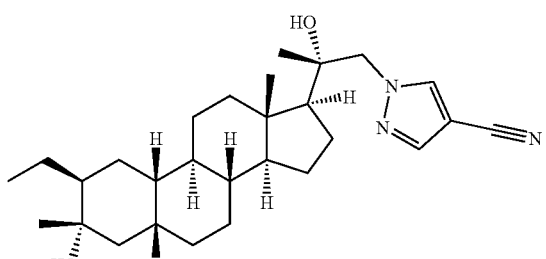 | A |

TABLE 2-continued
| Compound No. | Structure | IC$_{50}$ |
|---|---|---|
| 35 | 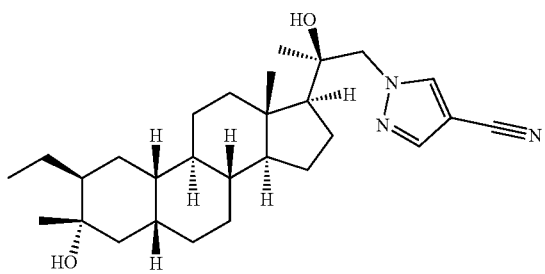 | B |
| 36 | 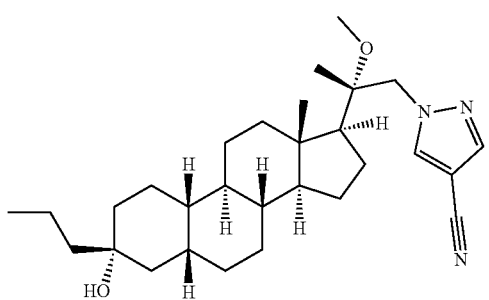 | B |
| 37 | 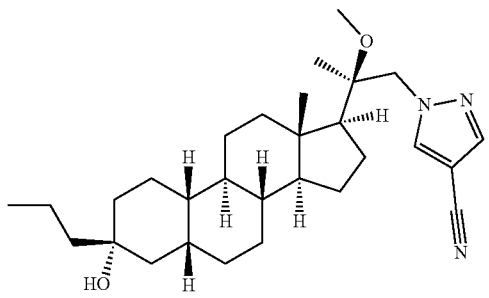 | B |
| 38 | 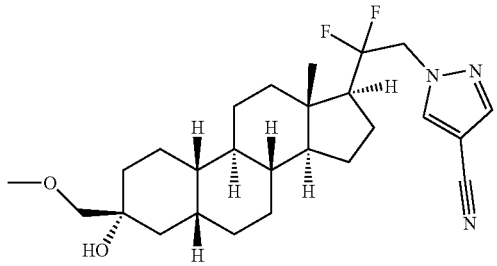 | A |
| 39 | 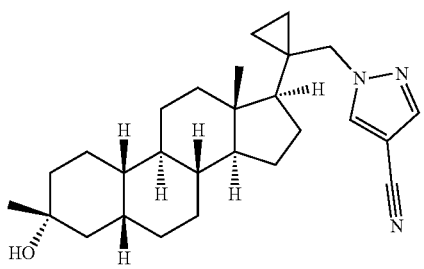 | A |

TABLE 2-continued
| Compound No. | Structure | IC$_{50}$ |
|---|---|---|
| 40 | 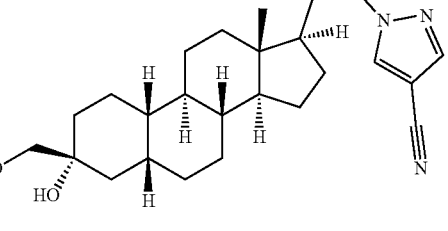 | A |
| 41 | 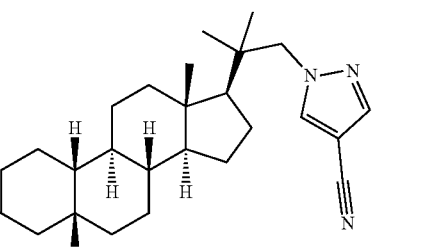 | A |
| 42 | 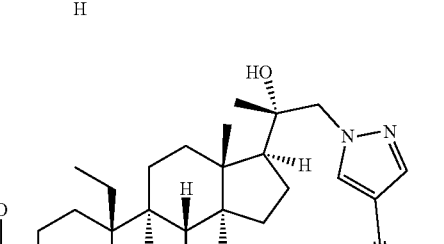 | A |
| 43 | 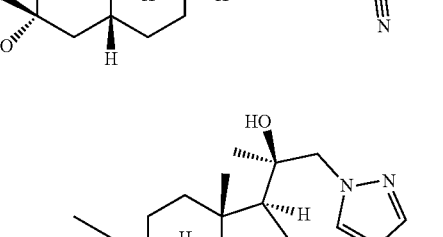 | A |
| 44 | 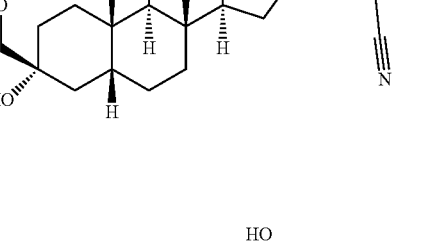 | A |

TABLE 2-continued
| Compound No. | Structure | IC$_{50}$ |
|---|---|---|
| 45 | 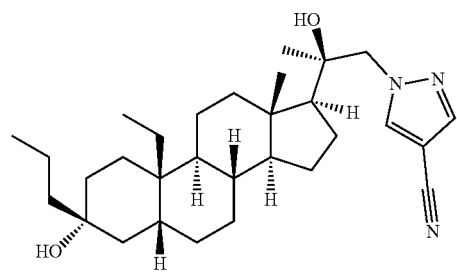 | B |
| 46 | 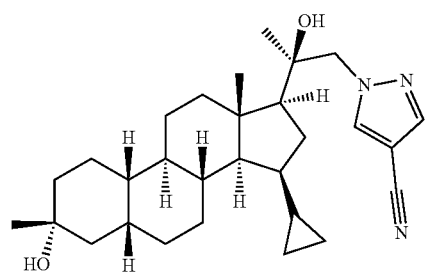 | A |
| 47 | 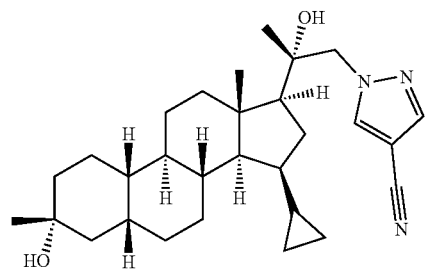 | A |
| 48 | 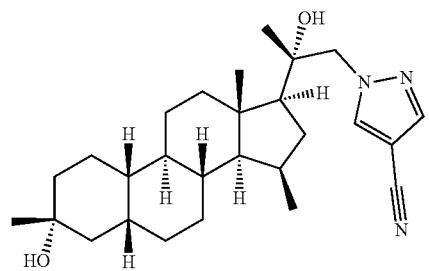 | A |
| 49 | 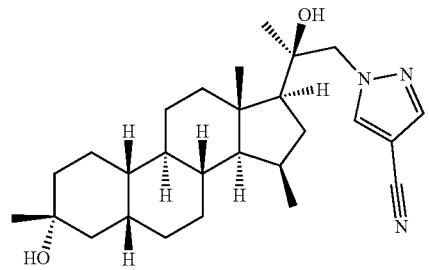 | A |

TABLE 2-continued

| Compound No. | Structure | IC$_{50}$ |
|---|---|---|
| 50 | 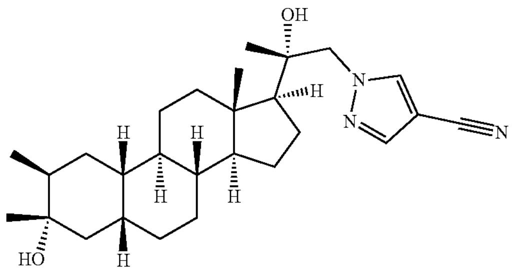 | A |
| 51 | 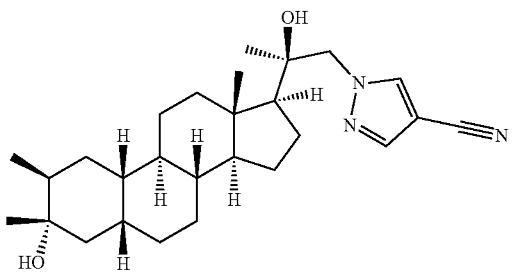 | A |
| 52 | 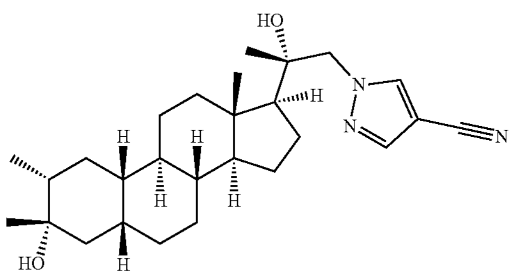 | A |
| 53 | 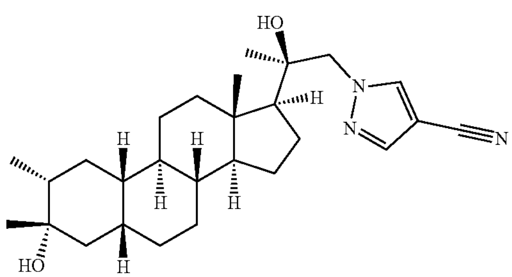 | B |
| 54 | 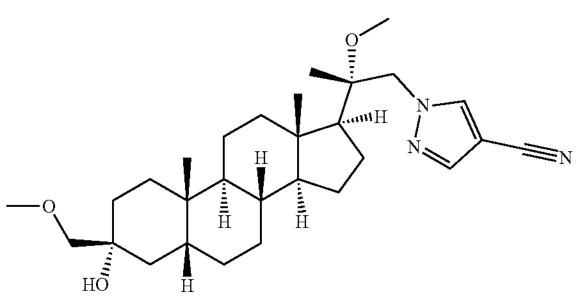 | B |

TABLE 2-continued

| Compound No. | Structure | IC$_{50}$ |
|---|---|---|
| 55 | 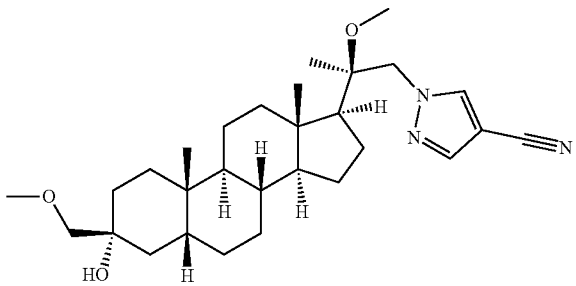 | B |
| 56 | 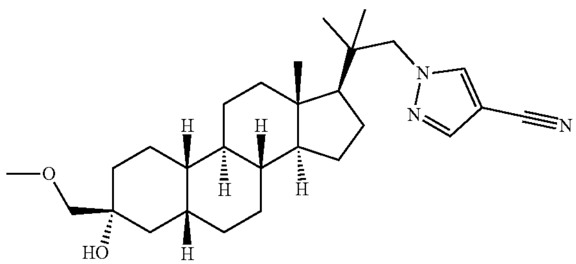 | A |
| 57 | 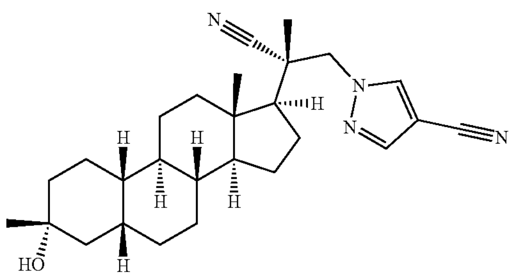 | A |
| 58 | 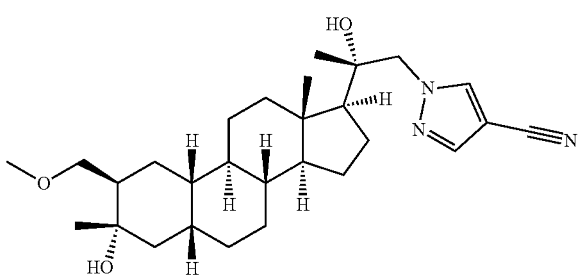 | A |
| 59 | 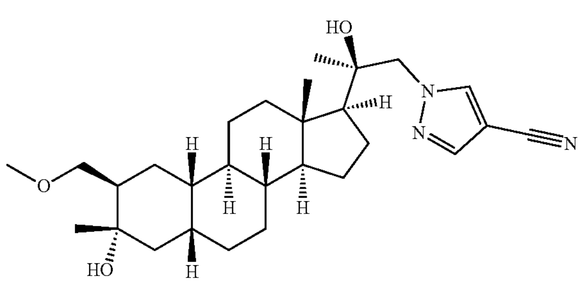 | B |

TABLE 2-continued

| Compound No. | Structure | IC$_{50}$ |
|---|---|---|
| 58A | 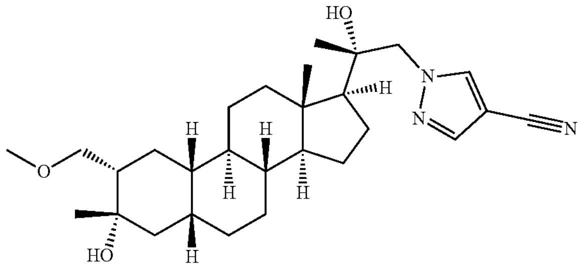 | A |
| 59A | 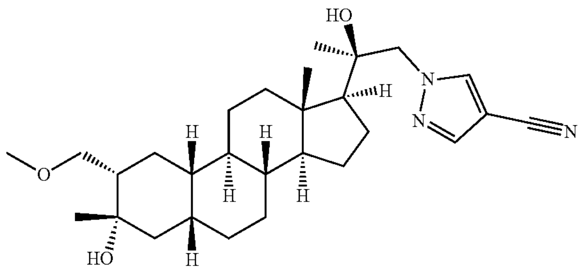 | B |
| 60 | 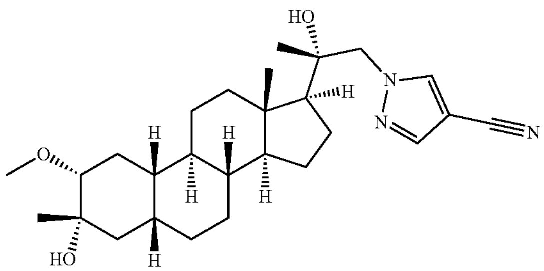 | A |
| 61 | 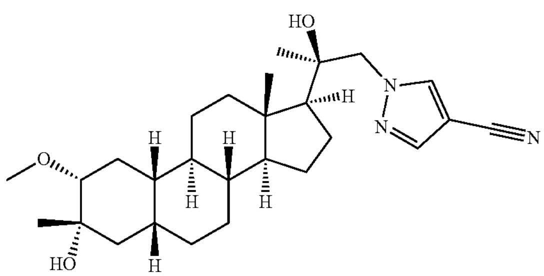 | B |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed:
1. A compound of Formula (I-e6):

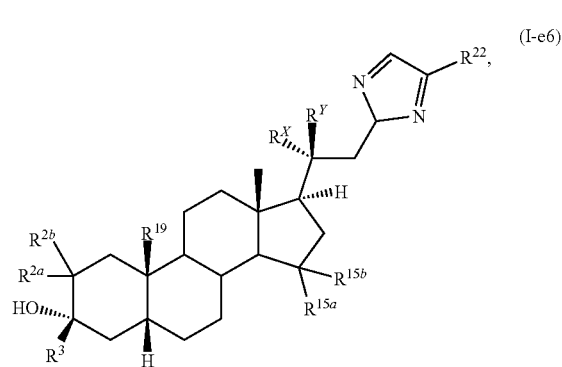

or a pharmaceutically acceptable salt thereof;
wherein:
each of $R^{2a}$, $R^{2b}$, $R^{15a}$, and $R^{15b}$ is hydrogen;
$R^3$ is unsubstituted $C_{1-3}$ alkyl, —$CH_2OCH_3$, or —$CH_2OCH_2CH_3$;
$R^{19}$ is hydrogen, methyl, or ethyl;
$R^X$ is —OH;
$R^Y$ is methyl; and
$R^{22}$ is —CN.

2. The compound or pharmaceutically acceptable salt of claim 1, wherein $R^3$ is methyl, ethyl, or propyl.

3. The compound or pharmaceutically acceptable salt of claim 2, wherein $R^3$ is methyl.

4. The compound or pharmaceutically acceptable salt of claim 2, wherein $R^3$ is ethyl.

5. The compound or pharmaceutically acceptable salt of claim 2, wherein $R^3$ is propyl.

6. The compound or pharmaceutically acceptable salt of claim 1, wherein $R^3$ is —$CH_2OCH_3$.

7. The compound or pharmaceutically acceptable salt of claim 1, wherein $R^3$ is —$CH_2OCH_2CH_3$.

8. The compound or pharmaceutically acceptable salt of claim 1, wherein $R^{19}$ is hydrogen.

9. The compound or pharmaceutically acceptable salt of claim 1, wherein $R^{19}$ is methyl.

10. The compound or pharmaceutically acceptable salt of claim 1, wherein $R^{19}$ is ethyl.

11. A compound selected from

| Compound No. | Structure |
|---|---|
| 2 | 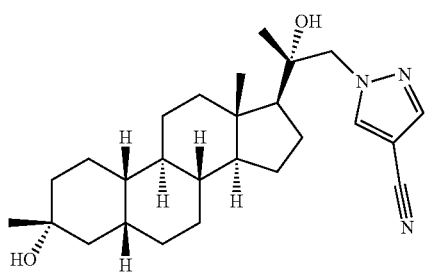 |
| 3 | 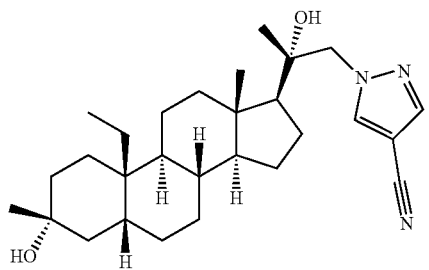 |
| 7 | 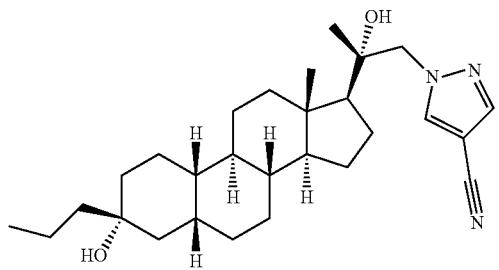 |
| 11 | 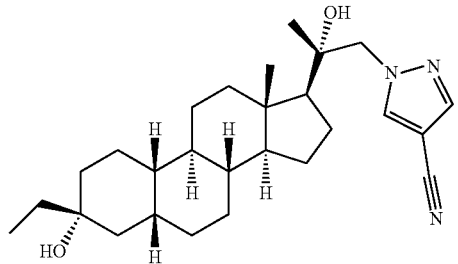 |

| Compound No. | Structure |
|---|---|
| 15 | 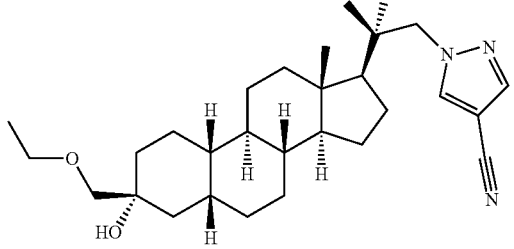 |
| 24 | 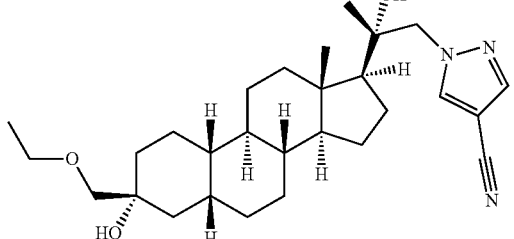 |
| 26 | 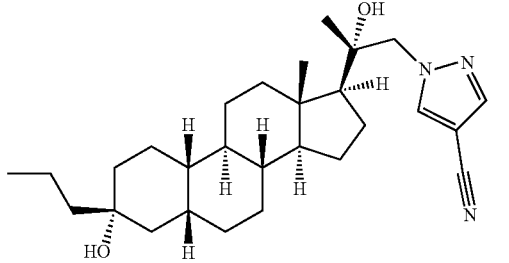 | or a pharmaceutically acceptable salt thereof.

12. A compound selected from

| Compound No. | Structure |
|---|---|
| 29 | 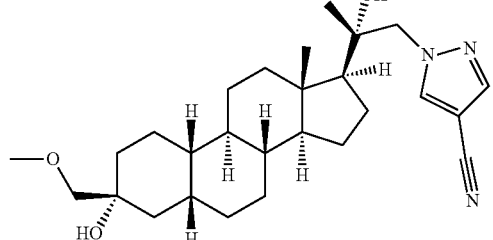 |
| 42 | 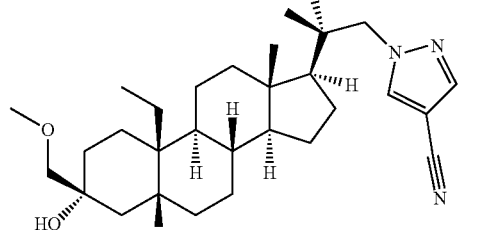 |
| 44 | 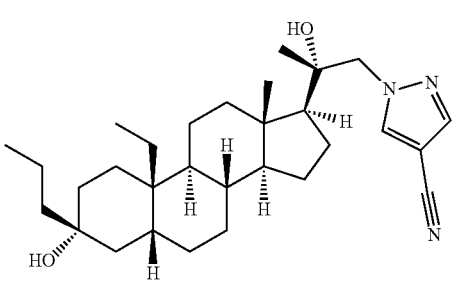 | or a pharmaceutically acceptable salt thereof.

13. A pharmaceutical composition comprising a compound or pharmaceutically acceptable salt of claim 1 and a pharmaceutically acceptable excipient.

14. A pharmaceutical composition comprising a compound or pharmaceutically acceptable salt of claim 11 and a pharmaceutically acceptable excipient.

15. A pharmaceutical composition comprising a compound or pharmaceutically acceptable salt of claim 12 and a pharmaceutically acceptable excipient.

16. A compound of the formula

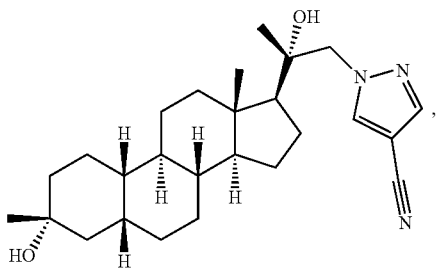

or a pharmaceutically acceptable salt thereof.

17. A compound of the formula

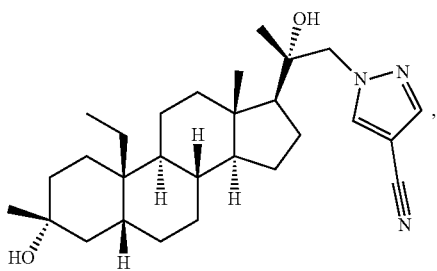

or a pharmaceutically acceptable salt thereof.

18. A compound of the formula

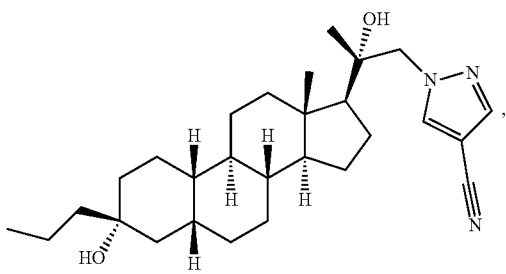

or a pharmaceutically acceptable salt thereof.

19. A compound of the formula

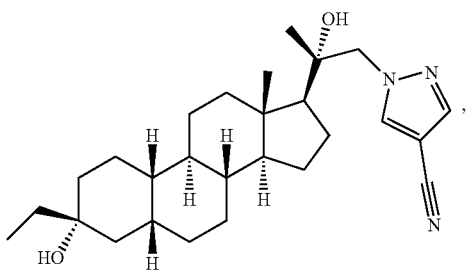

or a pharmaceutically acceptable salt thereof.

20. A compound of the formula

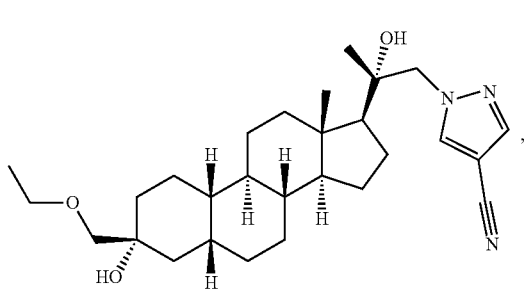

or a pharmaceutically acceptable salt thereof.

21. A compound of the formula

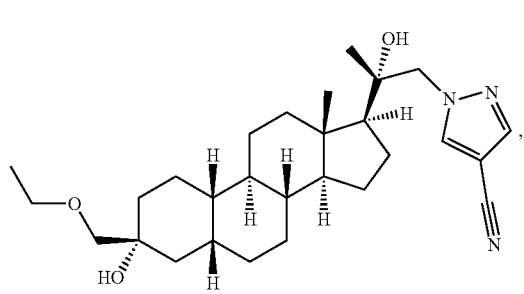

or a pharmaceutically acceptable salt thereof.

22. A compound of the formula

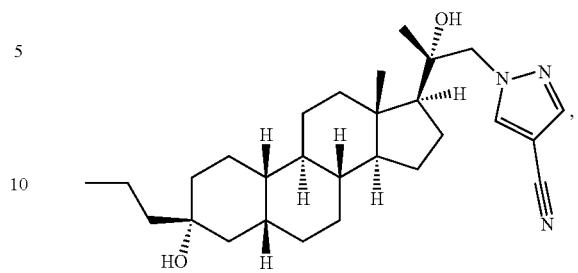

or a pharmaceutically acceptable salt thereof.

23. A compound of the formula

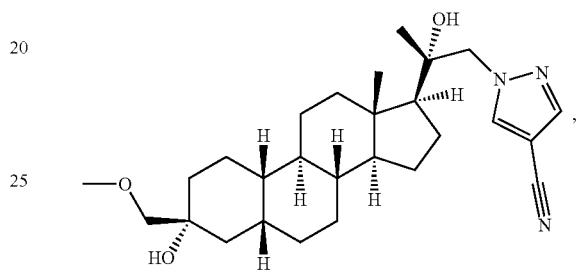

or a pharmaceutically acceptable salt thereof.

24. A compound of the formula

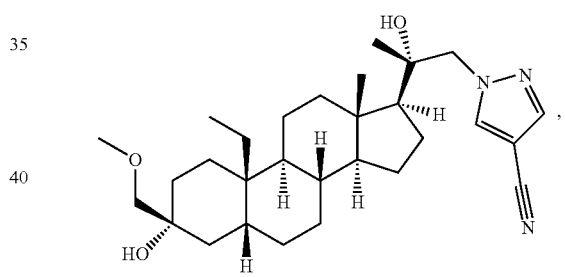

or a pharmaceutically acceptable salt thereof.

25. A compound of the formula

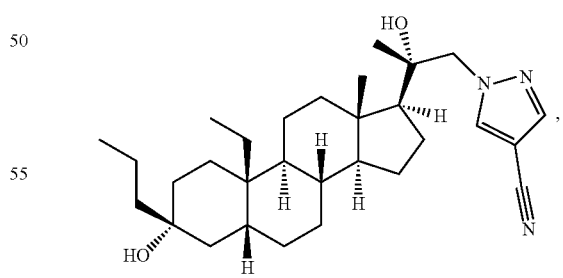

or a pharmaceutically acceptable salt thereof.

* * * * *

UNITED STATES PATENT AND TRADEMARK OFFICE
CERTIFICATE OF CORRECTION

PATENT NO. : 11,643,434 B2
APPLICATION NO. : 16/887887
DATED : May 9, 2023
INVENTOR(S) : Francesco G. Salituro, Maria Jesus Blanco-Pillado and Marshall Lee Morningstar It is certified that error appears in the above-identified patent and that said Letters Patent is hereby corrected as shown below:

In the Claims

In Column 237, Claim 1, Lines 34-51, please delete:
"1. A compound of Formula (I-e6):

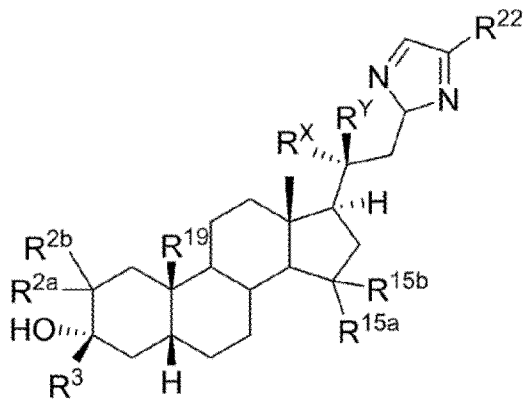

(I-e6),
or a pharmaceutically acceptable salt thereof;"

Signed and Sealed this
Fifteenth Day of April, 2025

Coke Morgan Stewart
*Acting Director of the United States Patent and Trademark Office*

CERTIFICATE OF CORRECTION (continued)
U.S. Pat. No. 11,643,434 B2

And replace with:
--1. A compound of Formula (I-e6):

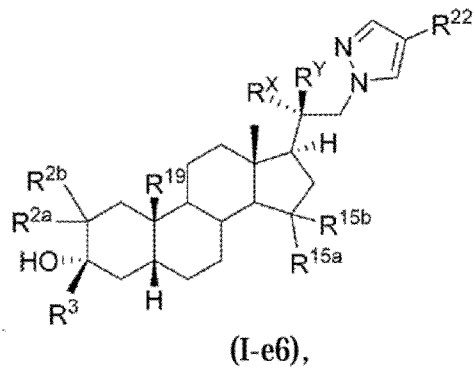

(I-e6), or a pharmaceutically acceptable salt thereof;--

In Column 239, Claim 11, Lines 1-38, please delete:

"
| Compound No. | Structure |
|---|---|
| 15 | 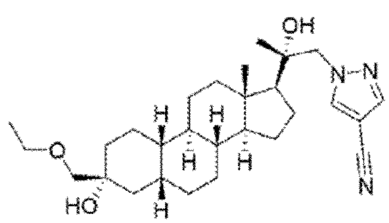 |
| 24 | 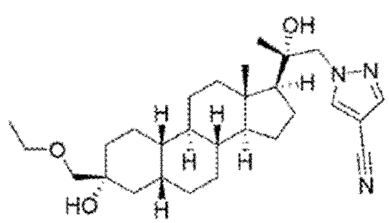 |
| 26 | 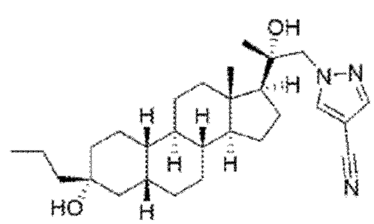 |
"

And replace with:
| Compound No. | Structure |
|---|---|
| 15 | 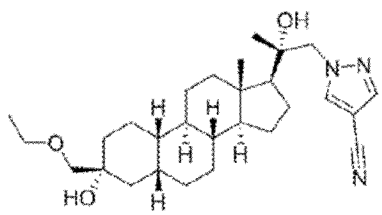 |
| 24 | 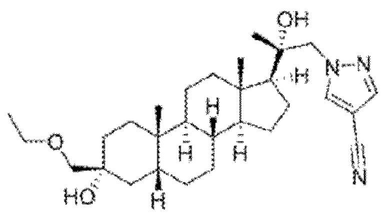 |
| 26 | 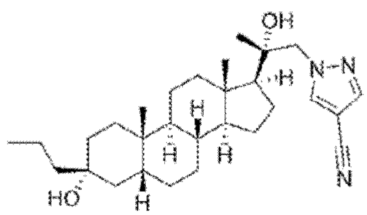 |
In Column 241, Claim 21, Lines 48-62, please delete:
"21. A compound of the formula
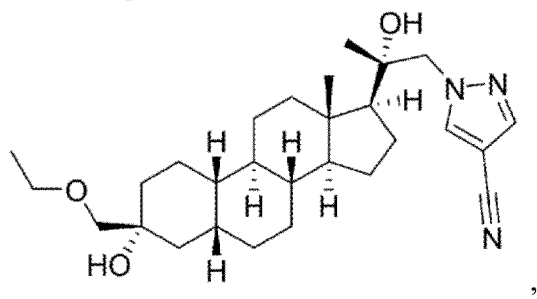
or a pharmaceutically acceptable salt thereof."

And replace with:
--21. A compound of the formula
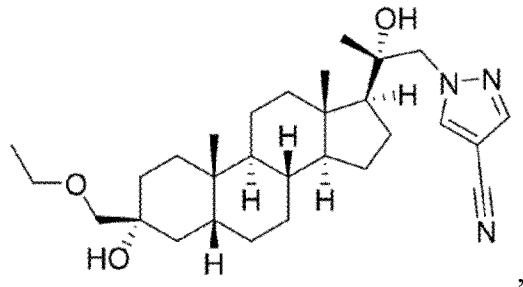
or a pharmaceutically acceptable salt thereof.--